(12) United States Patent
Guzi et al.

(10) Patent No.: US 8,211,854 B2
(45) Date of Patent: *Jul. 3, 2012

(54) METHODS FOR INHIBITING PROTEIN KINASES

(75) Inventors: Timothy J. Guzi, Sudbury, MA (US); Kamil Paruch, Tisnov (CZ); Michael P. Dwyer, Scotch Plains, NJ (US); David A. Parry, Mountain View, CA (US)

(73) Assignee: Schering Corporation, Kenilworth, NJ (US)

( * ) Notice: Subject to any disclaimer, the term of this patent is extended or adjusted under 35 U.S.C. 154(b) by 297 days.

This patent is subject to a terminal disclaimer.

(21) Appl. No.: 12/688,664

(22) Filed: Jan. 15, 2010

(65) Prior Publication Data

US 2010/0125068 A1    May 20, 2010

Related U.S. Application Data

(62) Division of application No. 11/542,801, filed on Oct. 4, 2006, now abandoned.

(60) Provisional application No. 60/724,158, filed on Oct. 6, 2005.

(51) Int. Cl.
*A61K 31/54* (2006.01)
*A61K 31/519* (2006.01)
*A61K 31/535* (2006.01)
*A01N 43/90* (2006.01)

(52) U.S. Cl. .... 514/2; 514/228.5; 514/259.3; 514/233.2

(58) Field of Classification Search ........... 514/2, 228.5, 514/259.3, 233.2
See application file for complete search history.

*Primary Examiner* — Marcos Sznaidman
(74) *Attorney, Agent, or Firm* — Peter Haeberli; David A. Muthard

(57) ABSTRACT

The present invention provides methods for inhibiting protein kinases selected from the group consisting of AKT, Checkpoint kinase, Aurora kinase, Pim kinases, and tyrosine kinase using pyrazolo[1,5-a]pyrimidine compounds and methods of treatment, prevention, inhibition, or amelioration of one or more diseases associated with protein kinases using such compounds.

2 Claims, No Drawings

METHODS FOR INHIBITING PROTEIN KINASES

RELATED APPLICATIONS

This application is a divisional of application Ser. No. 11/542,801 filed Oct. 4, 2006, currently under prosecution, which is incorporated herein by reference and which claims priority to U.S. provisional patent application Ser. Nos. 60/724,158 filed Oct. 6, 2005.

FIELD OF THE INVENTION

The present invention relates to methods for inhibiting, regulating or modulating Akt kinases, Checkpoint kinases, Aurora kinases, Pim kinases, and/or tyrosine kinases using pyrazolo[1,5-a]pyrimidine compounds or pharmaceutical compositions containing the compounds, and methods of treatment using the compounds or compositions to treat diseases such as, for example, cancer, inflammation, arthritis, viral diseases, neurodegenerative diseases such as Alzheimer's disease, cardiovascular diseases, and fungal diseases. This application claims the benefit of priority from U.S. Provisional Patent Application Ser. No. 60/724,158, filed on Oct. 6, 2005.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways making stimulatory genes hyperactive or inhibitory genes inactive. Protein kinase inhibitors, regulators or modulators alter the function of kinases such as Akt kinases, Checkpoint (CHK) kinases (e.g., CHK-1, CHK-2 etc.), Aurora kinases, Pim kinases (e.g., Pim-1, Pim-2, Pim-3 etc.), tyrosine kinases and the like.

Checkpoint kinases prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G2 arrest induced by DNA damage inflicted by either anticancer agents or endogenous DNA damage, as well as result in preferential killing of the resulting checkpoint defective cells. See, e.g., Peng et al., *Science,* 277, 1501-1505 (1997); Sanchez et al., Science, 277, 1497-1501 (1997), Nurse, *Cell,* 91, 865-867 (1997); Weinert, *Science,* 277, 1450-1451 (1997); Walworth et al., Nature, 363, 368-371 (1993); and Al-Khodairy et al., *Molec. Biol. Cell.,* 5, 147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., Nature, 395, 507-510 (1998); Matsuoka, *Science,* 282, 1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1(FLK-1), fetal liver kinase-4 (FLK-4) and the fms-like tyrosine kinase-(flt-1). For detailed discussion of the receptor-type tyrosine kinases, see Plowman et al., DN&P 7(6): 334-339, 1994.

At least one of the non-receptor protein tyrosine kinases, namely. LCK, is believed to mediate the transduction in T-cells of a signal from the interaction of a cell-surface protein (Cd4) with a cross-linked anti-Cd4 antibody. Amore detailed discussion of non-receptor tyrosine kinases is provided in Bolen. *Oncogene,* 8, 2025-2031 (1993). The non-receptor type of tyrosine kinases is also comprised of numerous subfamilies, including Svc, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993).

In addition to its role in cell-cycle control, protein kinases also playa crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Research*, 56, 3540-3545 (1996)), as has been shown with mutants of VEGF-R2 which fail to mediate signal transduction. Millauer et al, Cancer Research, 56, 1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly. FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17, 5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., Science, 277, 55-60 (1997).

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa-Tom. 616, (Aug. 30, 2005), http://kirjasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

References of interest in regard to the present invention are: A. Bullock et al., *J. Med. Chem.*, 48 (2005), 7604-7614; A. Bullock et al., *J. Biol. Chem.*, 280 No. 50 (2005), 41675-41682; D. Williamson et al, *J. Bioorg. Med. Chem. Lett.*, 15 (2005), 863-867; and patents and patent publications: US2006/0135526; WO2003/095455; WO2006/044958; US2006/0135514; US2004/081013; US2006/0053568; WO2001/23388; WO2004/087707; WO2003/093297; WO2002/070494; U.S. Pat. No. 6,313,124; FR2874821; WO2005/070431; US2005/0222171; US2005/0107386; and JP2006/160628.

Pyrazolopyrimidines are known. For example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest include: U.S. Pat. Nos. 5,688,949 and 6,313,124, WO 98/54093, WO 03/101993, WO 03/091256, WO 04/089416 and DE 10223917.

The following patents and patent applications disclose several types of pyrazolopyrimidines and are incorporated herein in their entirety by reference: (i) Ser. No. 11/245,401 filed Oct. 6, 2005 and published as US 2006/0128725 on Jun. 15, 2006), (ii) Ser. No. 10/654,546, filed Feb. 11, 2004, and published as US 2004/0209878 on Oct. 21, 2004, (iii) Ser. No. 11/244,772, filed Oct. 6, 2005, and published as US 2006/0041131 on Feb. 23, 2006, (iv) Ser. No. 11/244,776, filed Oct. 6, 2005, and published as US 2006/0040958 on Feb. 23, 2006, (v) Ser. No. 10/654,163 filed Sep. 3, 2003, published as US 2004/0102452 on May 27, 2004, and granted as U.S. Pat. No. 7,084,271 on Aug. 1, 2006, and (vi) Ser. No. 10/653,868 filed Sep. 3, 2003, published as US 2004/0116442 on Jun. 17, 2004, and granted as U.S. Pat. No. 7,074,924 on Jul. 11, 2006. Additionally, (vii) U.S. application Ser. Nos. 11/542,920, (vii) 11/542,921, (ix) 11/542,833, and (x) 11/543,182, all four commonly owned and being filed of even date herewith, are also incorporated herein in their entirety by reference. The disclosures in the foregoing references (i) through (x) cited above in this paragraph should be considered part of the present invention.

There is a need for methods to inhibit protein kinases to treat or prevent disease states associated with abnormal cell proliferation. Moreover, it is desirable for such methods to use kinase inhibitors that possess both high affinity for the target kinase as well as high selectivity versus other protein kinases. Useful small-molecule compounds that may be readily synthesized and are potent inhibitors of cell proliferation are those, for example, that are inhibitors of one or more protein kinases, such as Akt (e.g., Akt-1, Akt-2, Akt-3), CHK1, CHK2, VEGF (VEGF-R2), Aurora (e.g., Aurora-1, Aurora-2, Aurora-3 etc), Pim-1 and both receptor and non-receptor tyrosine kinases.

SUMMARY OF THE INVENTION

In its many embodiments, the present invention provides methods for inhibiting, regulating or modulating Akt kinases, Checkpoint kinases, Aurora kinases, Pim-1 and/or tyrosine kinases using pyrazolo[1,5-a]pyrimidine compounds or pharmaceutical compositions including such compounds and methods of treatment, prevention, inhibition or amelioration of one or more diseases associated with such protein kinases using such compounds or pharmaceutical compositions.

In one aspect, the present invention provides a method of inhibiting activity of one or more kinases in a patient, wherein the kinases are selected from the group consisting of Akt kinases, Checkpoint kinases (e.g., CHK-1, CHK-2 etc), Pim kinases and Aurora kinases (e.g., Aurora-1, Aurora-2, Aurora-3 etc), the method comprising: administering a therapeutically effective amount of at least one compound, or a pharmaceutically acceptable salt, solvate, ester, isomer or prodrug of the compound, to a patient in need thereof, the compound being represented by any of the structural following formulas I through VI, as well as the various compounds in the patents and patent applications cited for the compounds of formulas I through VI, as well as the compounds disclosed in copending patent application Ser. Nos. 11/542,920, 11/542,833, and 11/543,182 filed of even date herewith:

I. from application Ser. No. 11/245,401 filed Oct. 6, 2005 and published as US 2006/0128725 on Jun. 15, 2006), a compound or pharmaceutically acceptable salts, solvates, esters, isomers or prodrugs of said compound, said compound having the general structure shown in Formula I:

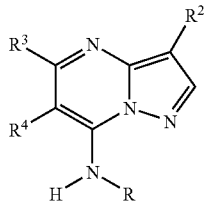

Formula I wherein:

R is H, alkyl, alkenyl, alkynyl, arylalkyl, arylalkenyl, cycloalkyl, cycloalkylalkyl, alkenylalkyl, alkynylalkyl, heterocyclyl, heterocyclylalkyl, heteroarylalkyl (including N-oxide of said heteroaryl), —(CHR$^5$)$_n$-aryl, —(CHR$^5$)$_n$— heteroaryl,

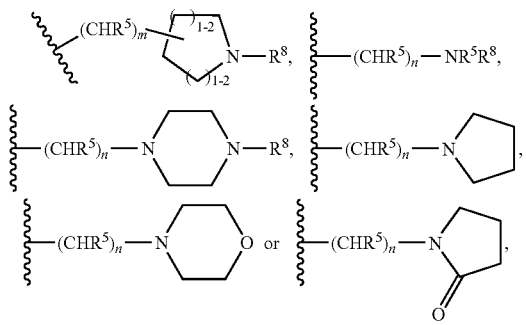

wherein each of said alkyl, alkenyl, alkynyl, aryl, cycloalkyl, heterocyclyl, and heteroaryl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^2$ is selected from the group consisting of H, R$^9$, alkyl, alkenyl, alkynyl, CF$_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 R$^9$ groups which can be the same or different and are independently selected from the list of R$^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

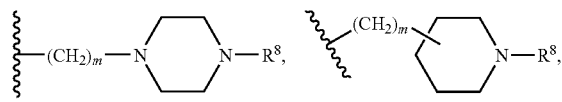

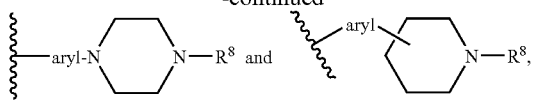

wherein one or more of the aryl and/or one or more of the heteroaryl in the above-noted definitions for R$^2$ can be unsubstituted or optionally substituted with one or more moieties which can be the same or different, each moiety being independently selected from the group consisting of halogen, —CN, —OR$^5$, —SR$^5$, —S(O$_2$)R$^6$, —S(O$_2$)NR$^5$R$^6$, —NR$^5$R$^6$, —C(O)NR$^5$R$^6$, CF$_3$, alkyl, aryl and OCF$_3$;

R$^3$ is selected from the group consisting of H, halogen, —NR$^5$R$^6$, —OR$^6$, —SR$^6$, —C(O)N(R$^5$R$^6$), alkyl, alkynyl, cycloalkyl, aryl, arylalkyl, heterocyclyl, heterocyclylalkyl, heteroaryl and heteroarylalkyl, wherein each of said alkyl, cycloalkyl, aryl, arylalkyl, heterocyclyl, heterocyclylalkyl, heteroaryl and heteroarylalkyl for R$^3$ and the heterocyclyl moieties whose structures are shown immediately above for R$^3$ can be unsubstituted or optionally independently substituted with one or more moieties which can be the same or different, each moiety being independently selected from the group consisting of halogen, alkyl, aryl, cycloalkyl, CF$_3$, CN, —OCF$_3$, —(CR$^4$R$^5$)$_p$OR$^5$, —OR$^5$, —NR$^5$R$^6$, —(CR$^4$R$^5$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$, —N(R$^5$)C(R$^4$R$^5$)$_n$N(R$^5$R$^6$) and —N(R$^5$)C(O)NR$^5$R$^6$, with the proviso that no carbon adjacent to a nitrogen atom on a heterocyclyl ring carries a —OR$^5$ moiety;

R$^4$ is H, halo or alkyl;

R$^5$ is H, alkyl, aryl, heteroaryl, arylalkyl or cycloalkyl;

R$^6$ is selected from the group consisting of H, Boc, alkyl, alkenyl, aryl, arylalkyl, arylalkenyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^4$R$^5$, —C(R$^4$R$^5$)$_p$—R$^9$, —N(R$^5$)Boc, —(CR$^4$R$^5$)$_p$OR$^5$, —C(O$_2$)R$^5$, —C(O)NR$^4$R$^5$, —C(O)R$^5$, —SO$_3$H, —SR$^5$, —S(O$_2$)R$^7$, —S(O$_2$)NR$^4$R$^5$, —N(R$^5$)S(O$_2$)R$^7$, —N(R$^5$)C(O)R$^7$ and —N(R$^5$)C(O)NR$^4$R$^5$;

or optionally (i) R$^5$ and R$^{10}$ in the moiety —NR$^5$R$^{10}$, or (ii) R$^5$ and R$^6$ in the moiety —NR$^5$R$^6$, may be joined together to form a cycloalkyl or heterocyclyl moiety, with each of said cycloalkyl or heterocyclyl moiety being unsubstituted or optionally independently being substituted with one or more R$^9$ groups;

R$^7$ is selected from the group consisting of alkyl, cycloalkyl, aryl, arylalkenyl, heteroaryl, arylalkyl, heteroarylalkyl, heteroarylalkenyl, and heterocyclyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, CF$_3$, OCF$_3$, CN, —OR$^5$, —NR$^5$R$^{10}$, —CH$_2$OR$^5$, —C(O$_2$)R$^5$, —C(O)NR$^5$R$^{10}$, —C(O)R$^5$, —SR$^{10}$, —S(O$_2$)R$^{10}$, —S(O$_2$)NR$^5$R$^{10}$, —N(R$^5$)S(O$_2$)R$^{10}$, —N(R$^5$)C(O)R$^{10}$ and —N(R$^5$)C(O)NR$^5$R$^{10}$;

R$^8$ is selected from the group consisting of R$^6$, —OR$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, and S(O$_2$)R$^7$;

R$^9$ is selected from the group consisting of halogen, —CN, —NR$^5$R$^{10}$, —SCN, —NO$_2$, —C(O)R$^5$, —C(O$_2$)R$^6$, —C(O)NR$^5$R$^{10}$, —OR$^6$, —SR$^6$, —S(O$_2$)R$^7$, —S(O$_2$)NR$^5$R$^{10}$, —N(R$^5$)S(O$_2$)R$^7$, —N(R$^5$)C(O)R$^7$ and N(R$^5$)C(O)NR$^5$R$^{10}$;

m is 0 to 4;
n is 1 to 4; and
p is 1 to 4, with the proviso that when R$^2$ is phenyl, R$^3$ is not alkyl, alkynyl or halogen, and that when R$^2$ is aryl, R is not

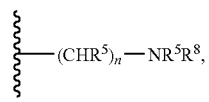

and with the further proviso that when R is arylalkyl, then any heteroaryl substituent on the aryl of said arylalkyl contains at least three heteroatoms;

II. from application Ser. No. 11/244,772, filed Oct. 6, 2005, and published as US 2006/0041131 on Feb. 23, 2006, a compound or pharmaceutically acceptable salts, solvates, esters, isomers or prodrugs of said compound, said compound having the general structure shown in Formula II:

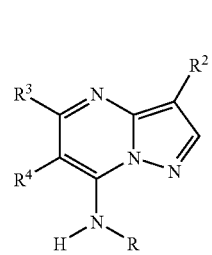

Formula II or a pharmaceutically acceptable salt, solvate, ester or prodrug of said compound, wherein:

R is an aryl, wherein said aryl is either unsubstituted or optionally substituted or fused with one or more heteroaryl;

R$^2$ is selected from the group consisting of R$^9$, alkyl, alkynyl, alkynylalkyl, cycloalkyl, —CF$_3$, —C(O$_2$)R$^6$, aryl, arylalkyl, heteroarylalkyl, heterocyclyl, alkyl substituted with 1-6 R$^9$ groups which groups can be the same or different with each R$^9$ being independently selected, aryl substituted with 1-3 aryl or heteroaryl groups which can be the same or different and are independently selected from phenyl, pyridyl, thiophenyl, furanyl and thiazolo groups,

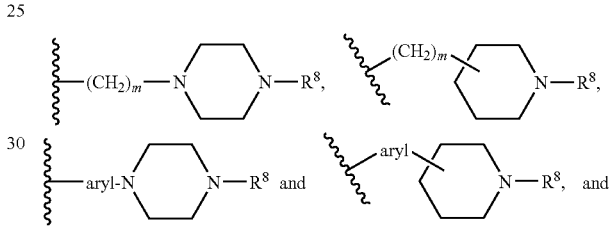

heteroaryl substituted with 0-3 aryl or heteroaryl groups which can be the same or different and are independently selected from alkyl, phenyl, pyridyl, thiophenyl, furanyl and thiazolo groups;

R$^3$ is selected from the group consisting of H, halogen, —NR$^5$R$^6$, —C(O)NR$^5$R$^6$, alkyl, alkynyl, cycloalkyl, aryl, arylalkyl, heterocyclyl, heterocyclylalkyl, heteroaryl and heteroarylalkyl,

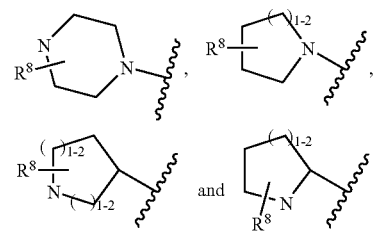

wherein each of said alkyl, cycloalkyl, aryl, arylalkyl, heterocyclyl, heterocyclylalkyl, heteroaryl and heteroarylalkyl for R$^3$ and the heterocyclyl moieties whose structures are shown immediately above for R$^3$ can be substituted or optionally independently substituted with one or more moieties which can be the same or different, each moiety being independently selected from the group consisting of halogen, alkyl, aryl, cycloalkyl, CF$_3$, CN, —OCF$_3$, —(CR$^4$R$^5$, —OR$^5$, —NR$^5$R$^6$, —(CR$^4$R$^5$)$_n$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

$R^4$ is H, halo or alkyl;

$R^5$ is H or alkyl;

$R^6$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^5R^{10}$, $-N(R^5)Boc$, $-(CR^4R^5)_nOR^5$, $-C(O_2)R^5$, $-C(O)R^5$, $-C(O)NR^5R^{10}$, $-SO_3H$, $-SR^{10}$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^4R^5$, $-N(R^5)Boc$, $-(CR^4R^5)_nOR^5$, $-C(O_2)R^5$, $-C(O)NR^4R^5$, $-C(O)R^5$, $-SO_3H$, $-SR^5$, $-S(O_2)R^7$, $-S(O_2)NR^4R^5$, $-N(R^5)S(O_2)R^7$, $-N(R^5)C(O)R^7$ and $-N(R^5)C(O)NR^4R^5$;

or optionally (i) $R^5$ and $R^{10}$ in the moiety $-NR^5R^{10}$, or (ii) $R^5$ and $R^6$ in the moiety $-NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-CH_2OR^5$, $-C(O_2)R^5$, $-C(O)NR^5R^{10}$, $-C(O)R^5$, $-SR^{10}$, $-S(O_2)R^{10}$, $-S(O_2)NR^5R^{10}$, $-N(R^5)S(O_2)R^{10}$, $-N(R^5)C(O)R^{10}$ and $-N(R^5)C(O)NR^5R^{10}$;

$R^8$ is selected from the group consisting of $R^6$, $-C(O)NR^5R^{10}$, $-S(O_2)NR^5R^{10}$, $-C(O)R^7$ and $-S(O_2)R^7$;

$R^9$ is selected from the group consisting of halogen, CN, $-NR^5R^{10}$, $-C(O_2)R^6$, $-C(O)NR^5R^{10}$, $-SR^6$, $-S(O_2)R^7$, $-S(O_2)NR^5R^{10}$, $-N(R^5)S(O_2)R^7$, $-N(R^5)C(O)R^7$ and $N(R^5)C(O)NR^5R^{10}$;

m is 0 to 4, and n is 1 to 4, with the following provisos: (i) that when R is an unsubstituted phenyl, then $R^2$ is not alkyl, $-C(O_2)R^6$, aryl or cycloalkyl, and (ii) that when R is a phenyl substituted with a hydroxyl group, then $R^2$ is halogen only;

III. from application Ser. No. 11/244,776, filed Oct. 6, 2005, and published as US 2006/0040958 on Feb. 23, 2006, a compound or pharmaceutically acceptable salts, solvates, esters, isomers or prodrugs of said compound, said compound having the general structure shown in Formula III:

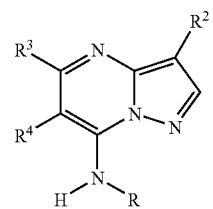

Formula III wherein:

R is heteroaryl, wherein said heteroaryl can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^6$, $-C(R^4R^5)_nOR^5$, $-C(O_2)R^5$, $-C(O)R^5$, $-C(O)NR^5R^6$, $-SR^6$, $-S(O_2)R^7$, $-S(O_2)NR^5R^6$, $-N(R^5)S(O_2)R^7$, $-N(R^5)C(O)R^7$ and $-N(R^5)C(O)NR^5R^6$;

$R^2$ is selected from the group consisting of $R^9$, alkyl, alkynyl, aryl, heteroaryl, $CF_3$, heterocyclylalkyl, alkynylalkyl, cycloalkyl, $-C(O)OR^4$, alkyl substituted with 1-6 $R^9$ groups which can be the same or different and are independently selected from the list of $R^9$ shown later below,

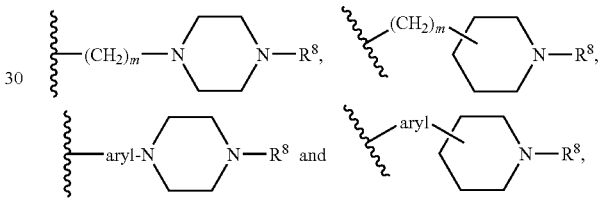

wherein the aryl in the above-noted definitions for $R^2$ can be unsubstituted or optionally substituted with one or more moieties which can be the same or different, each moiety being independently selected from the group consisting of halogen, CN, $-OR^5$, $SR^5$, $-CH_2OR^5$, $-C(O)R^5$, $-SO_3H$, $-S(O_2)R^6$, $-S(O_2)NR^5R^6$, $-NR^5R^6$, $-C(O)NR^5R^6$, $-CF_3$, and $-OCF_3$;

$R^3$ is selected from the group consisting of H, halogen, $-NR^5R^6$, $-C(O)OR^4$, $-C(O)NR^5R^6$, alkyl, alkynyl, cycloalkyl, cycloalkylalkyl, aryl, arylalkyl, heterocyclyl, heterocyclylalkyl, heteroaryl,

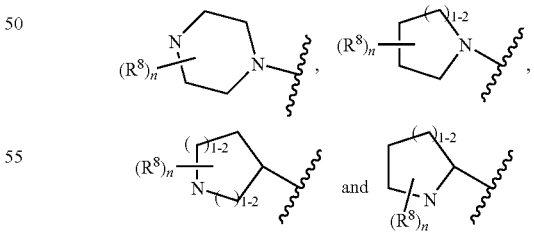

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, $-OCF_3$, $-(CR^4R^5)_nOR^5$, $-OR^5$, —NR⁵R⁶,   —(CR⁴R⁵)ₙNR⁵R⁶,   —C(O₂)R⁵,   —C(O)R⁵,
—C(O)NR⁵R⁶,   —SR⁶,   —S(O₂)R⁶,   —S(O₂)NR⁵R⁶,
—N(R⁵)S(O₂)R⁷,   —N(R⁵)C(O)R⁷  and   —N(R⁵)C(O)NR⁵R⁶;

R⁴ is H, halo or alkyl;

R⁵ is H or alkyl;

R⁶ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, CF₃, OCF₃, CN, —OR⁵, —NR⁵R¹⁰, —N(R⁵)Boc, —(CR⁴R⁵)ₙOR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R¹⁰ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, CF₃, OCF₃, CN, —OR⁵, —NR⁴R⁵, —N(R⁵)Boc, —(CR⁴R⁵)ₙ OR⁵, —C(O₂)R⁵, —C(O)NR⁴R⁵, —C(O)R⁵, —SO₃H, —SR⁵, —S(O₂)R⁷, —S(O₂)NR⁴R⁵, —N(R⁵)S(O₂)R⁷, —N(R⁵)C(O)R⁷ and —N(R⁵)C(O)NR⁴R⁵;

or optionally (i) R⁵ and R¹⁰ in the moiety —NR⁵R¹⁰, or (ii) R⁵ and R⁶ in the moiety —NR⁵R⁶, may be joined together to form a cycloalkyl or heterocyclyl moiety, with each of said cycloalkyl or heterocyclyl moiety being unsubstituted or optionally independently being substituted with one or more R⁹ groups;

R⁷ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl for R⁷ can be unsubstituted or optionally independently substituted with one or more moieties which can be the same or different, each moiety being independently selected from the group consisting of halogen, alkyl, aryl, cycloalkyl, CF₃, OCF₃, CN, —OR⁵, —NR⁵R¹⁰, —CH₂OR⁵, —C(O₂)R⁵, —C(O)NR⁵R¹⁰, —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of R⁶, —C(O)NR⁵R¹⁰, —CH₂OR⁴, —C(O)OR⁶, —C(O)R⁷ and —S(O₂)R⁷;

R⁹ is selected from the group consisting of halogen, —CN, —NR⁵R⁶, —(CH₂)ₙOR⁴, —C(O₂)R⁶, —C(O)NR⁵R⁶, —OR⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶;

m is 0 to 4; and n is 1 to 4;

IV. from application Ser. No. 10/654,163 filed Sep. 3, 2003, published as US 2004/0102452 on May 27, 2004, and granted as U.S. Pat. No. 7,084,271 on Aug. 1, 2006, a compound or pharmaceutically acceptable salts, solvates, esters, isomers or prodrugs of said compound, said compound having the general structure shown in Formula IV:

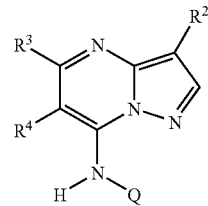

Formula IV wherein:

Q is selected from the group consisting of —S(O₂)NR⁶R⁷—, —C(O)NR⁶R⁷— and —C(O)OR⁷—;

R² is selected from the group consisting of R⁹, alkyl, alkynyl, alkynylalkyl, cycloalkyl, —CF₃, —C(O₂)R⁶, aryl, arylalkyl, heteroarylalkyl, heterocyclyl, alkyl substituted with 1-6 R⁹ groups which can be the same or different and are independently selected from the list of R⁹ shown later below,

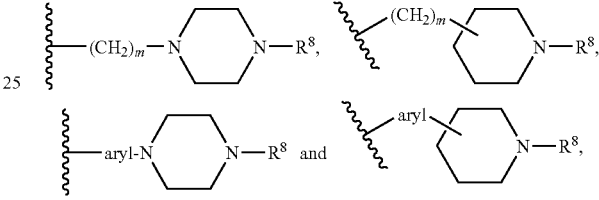

wherein the aryl in the above-noted definitions for R² can be unsubstituted or optionally substituted with one or more moieties which can be the same or different, each moiety being independently selected from the group consisting of halogen, CN, —OR⁵, SR⁵, —S(O₂)R⁶, —S(O₂)NR⁵R⁶, —NR⁵R⁶, —C(O)NR⁵R⁶, CF₃, alkyl, aryl and OCF₃;

R³ is selected from the group consisting of H, halogen, alkyl, alkynyl, —C(O)NR⁵R⁶, —C(O)OR⁴, —NR⁵R⁶, cycloalkyl, cycloalkylalkyl, aryl, arylalkyl, heterocyclyl, heterocyclylalkyl, heteroaryl, heteroarylalkyl,

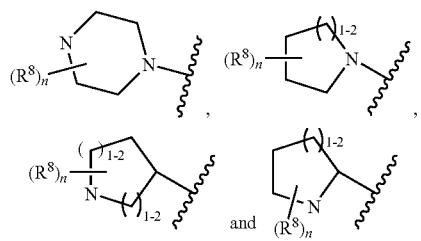

wherein each of said alkyl, cycloalkyl, aryl, arylalkyl, heterocyclyl, heterocyclylalkyl, heteroaryl and heteroarylalkyl for R³ and the heterocyclyl moieties whose structures are shown immediately above for R³ can be substituted or optionally independently substituted with one or more moieties which can be the same or different, each moiety being independently selected from the group consisting of halogen, alkyl, aryl, cycloalkyl, CF₃, CN, —OCF₃, —(CR⁴R⁵)ₙOR⁵, —OR⁵, —NR⁵R⁶, —(CR⁴R⁵)ₙNR⁵R⁶, —C(O₂)R⁵, —C(O)R⁵, —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶;

R⁴ is H, halo or alkyl;

R⁵ is H or alkyl;

$R^6$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, —$OR^5$, —$NR^5R^{10}$, —$N(R^5)Boc$, —$(CR^4R^5)_nOR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, —$OR^5$, —$NR^4R^5$, —$N(R^5)Boc$, —$(CR^4R^5)_nOR^5$, —$C(O_2)R^5$, —$C(O)NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$;

or optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$ and —$N(R^5)C(O)NR^5R^{10}$;

$R^8$ is selected from the group consisting of $R^6$, —$C(O)NR^5R^{10}$, —$S(O_2)NR^5R^{10}$, —$C(O)R^7$ and —$S(O_2)R^7$;

$R^9$ is selected from the group consisting of halogen, CN, —$NR^5R^{10}$, —$C(O_2)R^6$, —$C(O)NR^5R^{10}$, —$OR^6$, —$SR^6$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

m is 0 to 4, and n is 1 to 4;

V. from application Ser. No. 10/653,868 filed Sep. 3, 2003, published as US 2004/0116442 on Jun. 17, 2004, and granted as U.S. Pat. No. 7,074,924 on Jul. 11, 2006, a compound or pharmaceutically acceptable salts, solvates, esters, isomers or prodrugs of said compound, said compound having the general structure shown in Formula V:

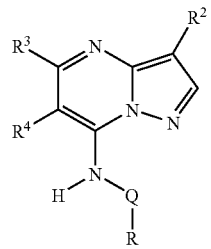

Formula V wherein:

Q is —$S(O_2)$— or —$C(O)$—;

R is aryl or heteroaryl, wherein said aryl or heteroaryl can be unsubstituted or optionally independently substituted with one or more moieties which can be the same or different, each moiety being independently selected from the group consisting of halogen, CN, $SR^5$, —$S(O_2)R^6$, —$S(O_2)NR^5R^6$, —$NR^5R^6$, —$C(O)NR^5R^6$, $CF_3$, alkyl, aryl and $OCF_3$;

$R^2$ is selected from the group consisting of CN, $NR^5R^6$, —$C(O_2)R^6$, —$C(O)NR^5R^6$, —$SR^6$, —$S(O_2)R^7$, —$S(O_2)NR^5R^6$, —$N(R^5)S(O_2)R^7$, —$N(R^5)C(O)R^7$ and —$N(R^5)C(O)NR^5R^6$; alkynyl, heteroaryl, $CF_3$, heterocyclyl, alkynylalkyl, cycloalkyl, alkyl substituted with 1-6 $R^9$ groups which can be the same or different and are independently selected from the list of $R^9$ shown below,

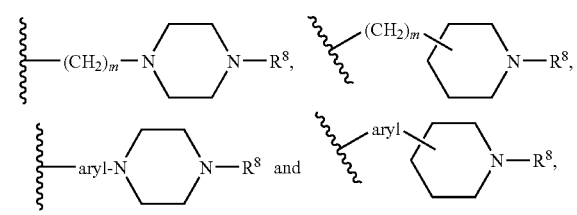

$R^3$ is selected from the group consisting of H, halogen, —$NR^5R^6$, —$C(O)NR^5R^6$, alkyl, alkynyl, cycloalkyl, aryl, arylalkyl, heterocyclyl, heterocyclylalkyl, heteroaryl and heteroarylalkyl,

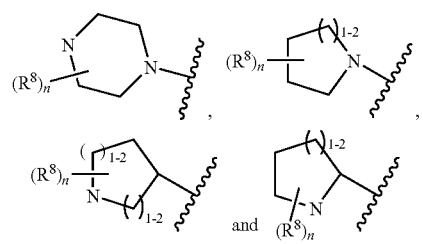

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, —$OCF_3$, —$(CR^4R^5)_nOR^5$, —$NR^5R^6$, —$(CR^4R^5)_nNR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$;

R⁴ is H, halo or alkyl;

R⁵ is H or alkyl;

R⁶ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF₃, OCF₃, CN, —OR⁵, —NR⁵R¹⁰, —N(R⁵)Boc, —(CR⁴R⁵)ₙOR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R¹⁰ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF₃, OCF₃, CN, —OR⁵, —NR⁴R⁵, —N(R⁵)Boc, —(CR⁴R⁵)ₙOR⁵, —C(O₂)R⁵, —C(O)NR⁴R⁵, —C(O)R⁵, —SO₃H, —SR⁵, —S(O₂)R⁷, —S(O₂)NR⁴R⁵, —N(R⁵)S(O₂)R⁷, —N(R⁵)C(O)R⁷ and —N(R⁵)C(O)NR⁴R⁵;

or optionally (i) R⁵ and R¹⁰ in the moiety —NR⁵R¹⁰, or (ii) R⁵ and R⁶ in the moiety —NR⁵R⁶, may be joined together to form a cycloalkyl or heterocyclyl moiety, with each of said cycloalkyl or heterocyclyl moiety being unsubstituted or optionally independently being substituted with one or more R⁹ groups;

R⁷ is selected from the group consisting of alkyl, cycloalkyl, aryl, heteroaryl, arylalkyl and heteroarylalkyl, wherein each of said alkyl, cycloalkyl, heterocyclylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, CF₃, OCF₃, CN, —OR⁵, —NR⁵R¹⁰, —CH₂OR⁵, —C(O₂)R⁵, —C(O)NR⁵R¹⁰, —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of R⁶, —C(O)NR⁵R¹⁰, —S(O₂)NR⁵R¹⁰, —C(O)R⁷ and —S(O₂)R⁷;

R⁹ is selected from the group consisting of halogen, CN, —NR⁵R¹⁰, —C(O₂)R⁵, —C(O)NR⁵R¹⁰, —OR⁶, —SR⁶, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

m is 0 to 4, and n is 1 to 4; and

VI. from copending application Ser. No. 11/542,921 filed of even date herewith, a compound or pharmaceutically acceptable salts, solvates, esters, isomers or prodrugs of said compound, said compound having the general structure shown in Formula VI:

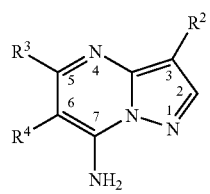

Formula VI or a pharmaceutically acceptable salt, solvate, ester or prodrug thereof, wherein:

R² is selected from the group consisting of halo; —CF₃; —CN; —SR⁶; —NO₂; —NR⁵R⁶ᵃ; —C(O)R⁶; —S(O₂)R⁷; —S(O₂)NR⁵R¹⁰; —N(R⁵)S(O₂)R⁷; —N(R⁵)C(O)NR⁵R¹⁰; alkyl; alkenyl; alkynyl; heterocyclyl; heterocyclylalkyl; halo; haloalkyl; cycloalkyl; aryl; arylalkyl; arylalkenyl; arylalkynyl; heteroarylalkyl; alkynylalkyl; aryl fused with an aryl or heteroaryl group; heteroaryl; heteroaryl fused with an aryl or heteroaryl group;

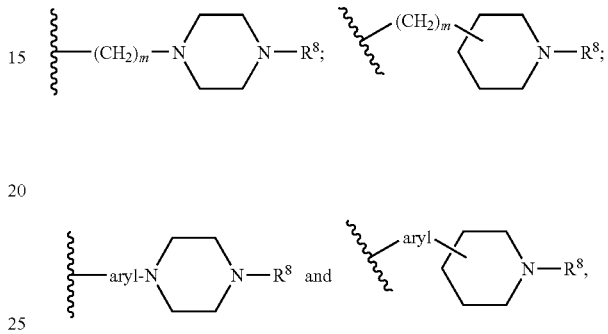

wherein each of the alkyl, alkenyl, alkynyl, heterocyclyl, heterocyclylalkyl, haloalkyl, cycloalkyl, aryl, arylalkyl, arylalkenyl, arylalkynyl, heteroarylalkyl, and alkynylalkyl groups and the heterocyclic moieties shown immediately above for R² can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)ₚOR⁵, —OR⁵, —NR⁵R⁶, —(CR⁵R¹¹)ₚNR⁵R⁶, —C(O₂)R⁵, —C(O)R⁵, —C(O)NR⁵R⁶, —SR⁶, —S(O₂)R⁶, —S(O₂)NR⁵R⁶, —N(R⁵)S(O₂)R⁷, —C(═N—OH), —N(R⁵)C(O)R⁷ and —N(R⁵)C(O)NR⁵R⁶, with the proviso that no carbon adjacent to a nitrogen atom on a heterocyclyl ring carries a —OR⁵ moiety;

R³ is selected from the group consisting of H; —NR⁵R⁶ᵃ; —OR⁶ᵇ; —SR⁶; CF₃; —C(O)N(R⁵R⁶); alkyl; alkenyl, alkynyl; cycloalkyl; aryl; arylalkyl; heterocyclyl; heterocyclylalkyl; heteroaryl; heteroarylalkyl;

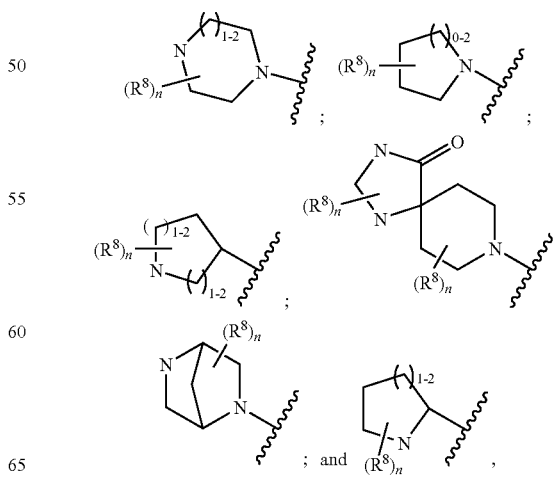

wherein each of the alkyl, alkynyl; cycloalkyl, aryl, arylalkyl, heterocyclyl, heterocyclylalkyl, heteroaryl, heteroarylalkyl, and the heterocyclic moieties whose structures are shown immediately above for R³ can be unsubstituted or optionally independently substituted with one or more moieties which can be the same or different, each moiety being independently selected from the group consisting of halo, alkyl, aryl, cycloalkyl, —CF₃, —CN, —OCF₃, —(CR¹¹R¹¹)$_p$OR⁵, —OR⁵, —NR⁵R⁶, —(CR⁵R¹¹)$_p$NR⁵R⁶, —C(O₂)R⁵, —C(O)R⁵, —C(O)NR⁵R⁶, —C(=N—OH), —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, with the proviso that no carbon adjacent to a nitrogen atom on a heterocyclyl ring carries a —OR⁵ moiety;

R⁴ is selected from the group consisting of —CF₃; —CN; —NR⁶R⁶ᵃ; (CR⁵R¹¹)$_p$C(O₂)R⁶; —(CR⁵R¹¹)$_p$C(O)NR⁵R¹⁰; —C(O)—N(R⁵R¹⁰); —OR⁶ᵇ; —SR⁶; —S(O₂)R⁷; —S(O₂)NR⁵R¹⁰; —C(O)R⁶; —N(R⁵)S(O₂)R⁷; —N(R⁵)C(O)R⁷; —N(R⁵)C(O)NR⁵R¹⁰; alkenyl; alkenyl (substituted with alkoxy); hydroxyalkyl; alkynyl; heterocyclyl; heterocyclylalkyl; aryl; aryl fused with an aryl or heteroaryl group; heteroaryl; heteroaryl fused with an aryl or heteroaryl group; substituted alkyl; cycloalkyl;

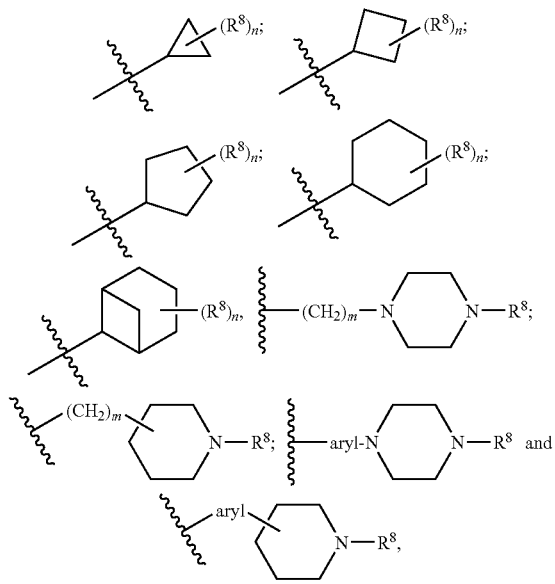

wherein each of the alkyl, cycloalkyl; heterocyclyl, heterocyclylalkyl, aryl, fused aryl, heteroaryl and fused heteroaryl groups of R⁴ can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$NR⁵R⁶, —C(O₂)R⁵, —C(O)R⁵, —C(R⁵)(=N—OR⁵), —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, with the proviso that no carbon adjacent to a nitrogen atom on a heterocyclyl ring carries a —OR⁵ moiety, and wherein the substituted alkyl group of R⁴ is independently substituted with one or more of the above moieties;

R⁵ is H, alkyl, aryl or cycloalkyl;

R⁶ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, CF₃, OCF₃, CN, —OR⁵, —NR⁵R¹⁰, —C(R⁵R¹¹)$_p$—R⁹, —N(R⁵)Boc, —(CR⁵R¹¹)$_p$OR⁵, —C(O₂)R⁵, —C(O)R⁵, —C(=N—OH), —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁶ᵃ is selected from the group consisting of alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, CF₃, OCF₃, CN, —OR⁵, —NR⁵R¹⁰, —C(R⁵R¹¹)$_p$—R⁹, —N(R⁵)Boc, —(CR⁵R¹¹)$_p$OR⁵, —C(O₂)R⁵, —C(O)R⁵, —C(=N—OH), —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁶ᵇ is selected from the group consisting of alkenyl, aryl, arylalkyl, arylalkenyl, cycloalkyl, heterocyclyl, heterocyclylalkyl, heteroaryl, and heteroarylalkyl, wherein each of the alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF₃, —OCF₃, —CN, —OR⁵, —NR⁵R¹⁰, —C(R⁵R¹¹)$_p$—R⁹, —N(R⁵)Boc, —(CR⁵R¹¹)$_p$OR⁶, —C(O₂)R⁶, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷, —C(=N—OH), and —N(R⁵)C(O)NR⁵R¹⁰;

R⁷ is selected from the group consisting of alkyl, cycloalkyl, aryl, arylalkenyl, heteroaryl, arylalkyl, heteroarylalkyl, heteroarylalkenyl, and heterocyclyl, wherein each of the alkyl, cycloalkyl, heteroarylalkyl, aryl, arylalkenyl, heteroaryl, arylalkyl, heteroarylalkyl, heteroarylalkenyl, and heterocyclyl can be unsubstituted or optionally independently substituted with one or more moieties which can be the same or different, each moiety being independently selected from the group consisting of halo, alkyl, aryl, cycloalkyl, CF₃, OCF₃, CN, —OR⁵, —NR⁵R¹⁰, —CH₂OR⁵, —C(O₂)R⁵, —C(O)NR⁵R¹⁰, —C(=N—OH), —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of R⁶, —OR⁶, —NR⁵R⁶, —C(O)NR⁵R¹⁰, —S(O₂)NR⁵R¹⁰, —C(O)R⁷, —C(=N—CN)—NH₂, —C(=NH)—NHR⁶, heterocyclyl, —S(O₂)R⁷, and

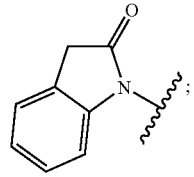

R⁹ is selected from the group consisting of halo, —CN, —NR⁵R¹⁰, —C(O₂)R⁶, —C(O)NR⁵R¹⁰, —C(=N—OH), —OR⁶, —SR⁶, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰; and R¹⁰ is selected from the group consisting of H, alkyl, aryl, arylalkyl, cycloalkyl, heterocyclyl, heterocyclylalkyl, heteroaryl, and heteroarylalkyl, wherein each of the alkyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, CF₃, OCF₃, CN, —OR⁵, —NR⁵R¹¹, —C(R⁵R¹¹)ₚ—R⁹, —N(R⁵)Boc, —(CR⁵R¹¹)ₚOR⁵, —C(O₂)R⁵, —C(O)NR⁵R¹¹, —C(O)R⁵, —C(=N—OH), —SO₃H, —SR⁵, —S(O₂)R⁷, —S(O₂)NR⁵R¹¹, —N(R⁵)S(O₂)R⁷, —N(R⁵)C(O)R⁷ and —N(R⁵)C(O)NR⁵R¹¹;

or optionally (i) R⁵ and R¹⁰ in the moiety NR⁵R¹⁰, or (ii) R⁵ and R⁶ in the moiety NR⁵R⁶, may be joined together to form a cycloalkyl or heterocyclyl moiety, with each of the cycloalkyl or heterocyclyl moiety being unsubstituted or optionally independently being substituted with one or more R⁹ groups;

R¹¹ is H, halo or alkyl;
m is 0 to 4;
n is 1 to 4; and
p is 1 to 4;

with the provisos that (1) when R² is alkyl, carboxyl, phenyl or cycloalkyl, then R³ is selected from the group consisting of —NR⁵R⁶ᵃ; —C(O)N(R⁵R⁶); alkynyl; arylalkyl; heterocyclyl; heterocyclylalkyl; heteroaryl; heteroarylalkyl;

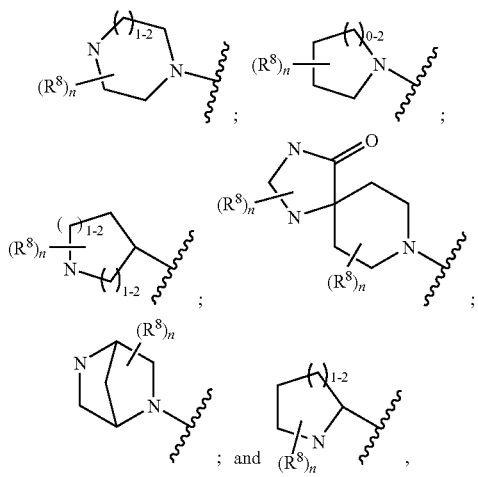

wherein each of the alkynyl, arylalkyl, heterocyclyl, heterocyclylalkyl, heteroaryl, heteroarylalkyl, and the heterocyclic moieties whose structures are shown immediately above for R³ is unsubstituted or independently substituted with one or more moieties which can be the same or different, each moiety being independently selected from the group consisting of —CN, —NR⁵R⁶, —(CR⁵R¹¹)ₚNR⁵R⁶, —C(O)NR⁵R⁶, —S(O₂)NR⁵R⁶, —N(R⁵)S(O₂)R⁷, —N(R⁵)C(O)R⁷ and —N(R⁵)C(O)NR⁵R⁶;

(2) when R² is halo, then R³ is selected from the group consisting of R⁶ᵇ; —SR⁶; —C(O)N(R⁶R⁶); cycloalkyl; heterocyclyl; heterocyclylalkyl;

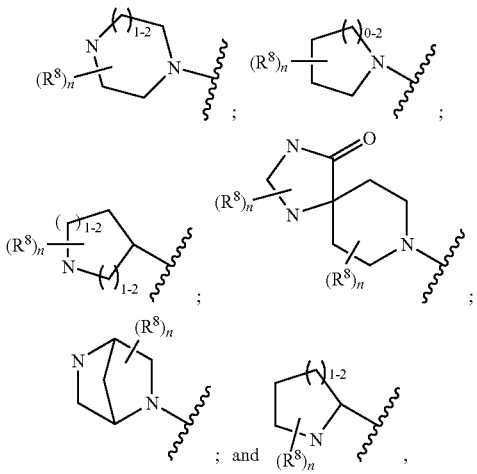

wherein each of the cycloalkyl, heterocyclyl, heterocyclylalkyl, and the heterocyclic moieties whose structures are shown immediately above for R³ can be unsubstituted or optionally independently substituted with one or more moieties which can be the same or different, each moiety being independently selected from the group consisting of halo, alkyl, aryl, cycloalkyl, —CF₃, —CN, —OCF₃, —(CR¹¹R¹¹)ₚOR⁵, —OR⁵, —NR⁵R⁶, —(CR⁵R¹¹)ₚNR⁵R⁶, —C(O₂)R⁵, —C(O)R⁵, —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, with the proviso that no carbon adjacent to a nitrogen atom on a heterocyclyl ring carries a —OR⁵ moiety; and (3) when R² is NH₂, R³ is not methyl.

The compounds disclosed in copending patent application Ser. No. 11/542,920 filed of even date herewith generically fall within Formula I. The compounds disclosed in copending patent application Ser. No. 11/542,833 filed of even date herewith generically fall within Formula II. The compounds disclosed in copending patent application Ser. No. 11/543,182 filed of even date herewith generically fall within Formula III.

The various embodiments and preferred embodiments described in the patents and patent applications described above for the compounds of Formulas I through VI, as well as for the compounds disclosed in copending patent application Ser. Nos. 11/542,920, 11/542,833 and 11/543,182 filed of even date herewith, are equally applicable in the practice of the present inventive methods.

In another aspect, the present invention provides a method of treating, or slowing the progression of, a disease associated with one or more one or more kinases in a patient in need of treatment, wherein the kinases are selected from the group consisting of Akt, Checkpoint kinases, Pim kinases and Aurora kinases, the method comprising administering a therapeutically effective amount of at least one compound of any of Formula I through VI above, or a pharmaceutically acceptable salt, solvate, isomer or ester thereof.

In another aspect, the present invention provides a method of treating one or more diseases associated with a kinase selected from the group consisting of Akt kinases, Checkpoint kinases, Pim kinases and Aurora kinases, comprising administering to a patient in need of such treatment an amount of a first compound of any of Formula I through VI above or a pharmaceutically acceptable salt, solvate, ester, isomer or prodrug thereof;

and an amount of at least one second compound, said second compound being an anti-cancer agent;

wherein the amounts of the first compound and said second compound result in a therapeutic effect.

In another aspect, the present invention provides a method of treating, or slowing the progression of, a disease associated with a kinase selected from the group consisting of Akt kinases, Checkpoint kinases, Pim kinases and Aurora kinases in a patient in need thereof, comprising administering a therapeutically effective amount of a pharmaceutical composition comprising in combination at least one pharmaceutically acceptable carrier and at least one compound of any of Formula I through VI above or a pharmaceutically acceptable salt, solvate, ester, isomer or prodrug thereof.

In another aspect, the present invention provides a method of inhibiting activity of at least one tyrosine kinase in a patient, the method comprising administering a therapeutically effective amount of at least one compound, or a pharmaceutically acceptable salt, solvate, ester, isomer or prodrug thereof to a patient in need thereof, the compound being represented by any of the structural formulas Formula I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith.

In another aspect, the present invention provides a method of treating, or slowing the progression of, a disease associated with tyrosine kinase in a patient in need of said inhibition, said method comprising administering a therapeutically effective amount of at least one compound, or a pharmaceutically acceptable salt, solvate, ester, isomer or prodrug thereof to a patient in need thereof, the compound being represented by any of the structural formulas Formula I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith.

In another aspect, the present invention provides a method of treating one or more diseases associated with tyrosine kinases, comprising administering to a mammal in need of such treatment an amount of a first compound, which is a compound of any of the structural formulas Formula I through VI, or a pharmaceutically acceptable salt, solvate, ester, isomer or prodrug thereof;

and an amount of at least one second compound, said second compound being an anti-cancer agent;

wherein the amounts of the first compound and said second compound result in a therapeutic effect.

In another aspect, the present invention provides a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one compound of any of the structural formulas Formula I through VI, or a pharmaceutically acceptable salt, solvate, ester, isomer or prodrug thereof.

The methods of the present invention can be useful in the treatment and prevention of proliferative diseases, for example, cancer, inflammation and arthritis, neurodegenerative diseases such Alzheimer's disease, cardiovascular diseases, viral diseases and fungal diseases.

DETAILED DESCRIPTION

The present invention provides methods for inhibiting, regulating or modulating Akt kinases, Checkpoint kinases, Aurora kinases, Pim kinases, and/or tyrosine kinases using pyrazolo[1,5-a]pyrimidine compounds of Formulas any of the structural formulas Formula I through VI or pharmaceutical compositions including such compounds, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith, and methods of treatment, prevention, inhibition or amelioration of one or more diseases associated with Akt kinases, Checkpoint kinases, Aurora kinases, Pim kinases and/or tyrosine kinases using such compounds or pharmaceutical compositions, as discussed above and in further detail below.

The above methods can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, incorporated by reference herein.

More specifically, the compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The methods of the present invention also may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith may also be useful in the treatment of Alzheimer's disease.

The compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith, may induce or inhibit apoptosis. The apoptotic response is aberrant in a variety of human diseases. The compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith, as modulators of apoptosis, can be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith, may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith, may also be useful in inhibiting tumor angiogenesis and metastasis.

A preferred dosage is about 0.001 to 500 mg/kg of body weight/day of the compound of the compound of Formulas I through VI, as well as any of the various compounds in the patents and patent applications cited above for the compounds of formulas I through VI, as well as the compounds disclosed in copending patent application Ser. Nos. 11/542,920, 11/542,833, and 11/543,182 filed of even date herewith. An especially preferred dosage is about 0.01 to 25 mg/kg of body weight/day of the compound, or a pharmaceutically acceptable salt, solvate or ester of the compound.

The compounds of this invention may also be useful in combination (administered together or sequentially in any desired order) with one or more of anti-cancer treatments such as radiation therapy, and/or one or more anti-cancer agents different from the compounds of Formulas I through VI, as well as the various compounds in the patents and patent applications cited above for the compounds of formulas I through VI, as well as the compounds disclosed in copending patent application Ser. Nos. 11/542,920, 11/542,833, and 11/543,182 filed of even date herewith. The compounds of the present invention can be present in the same dosage unit as the anti-cancer agent or in separate dosage units.

Non-limiting examples of the compounds of Formula I useful in the practice of the present methods include those that are shown on pages 5-56 and 117-1058 of the afore-mentioned US 2006/0128725, some of which are listed below:

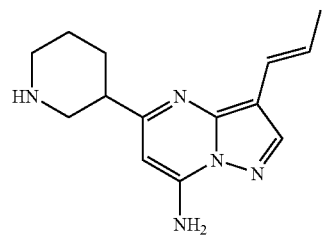

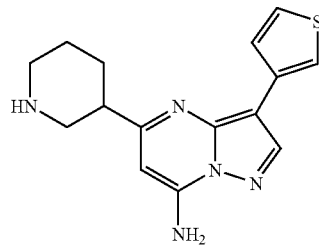

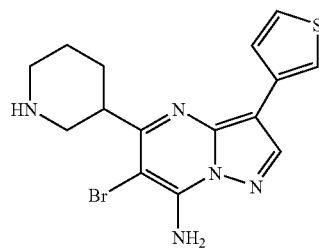

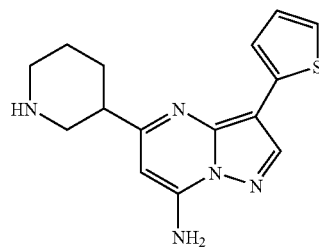

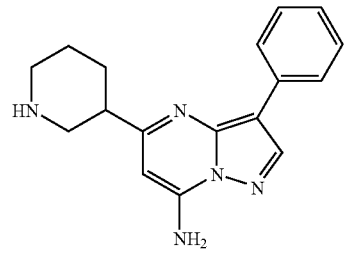

-continued
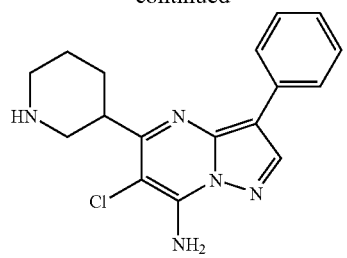
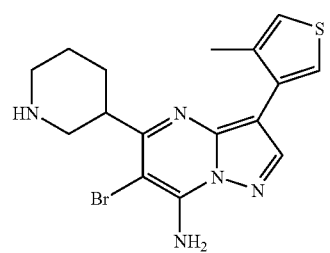
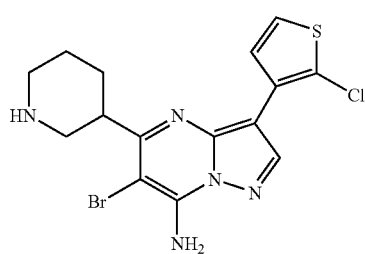
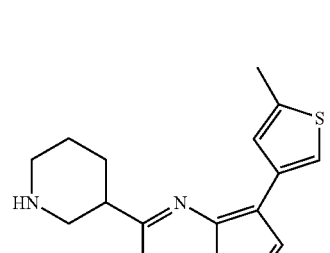
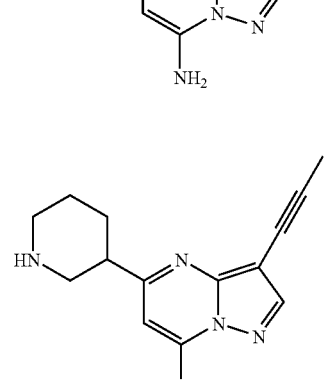
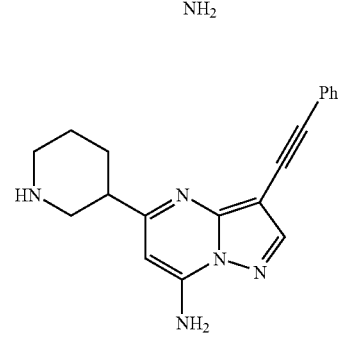
-continued
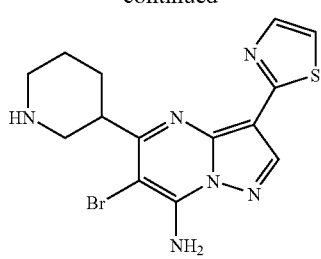
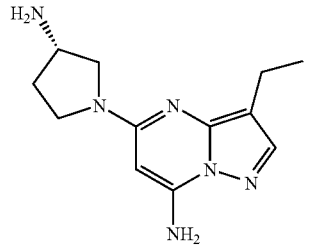
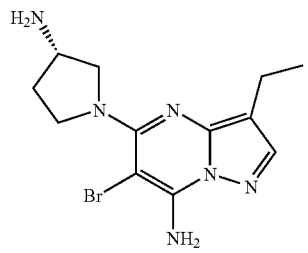
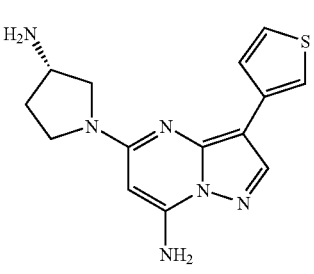
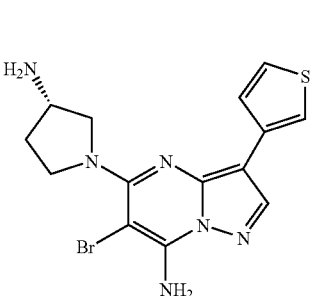
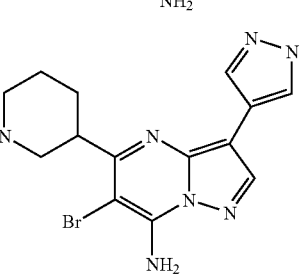

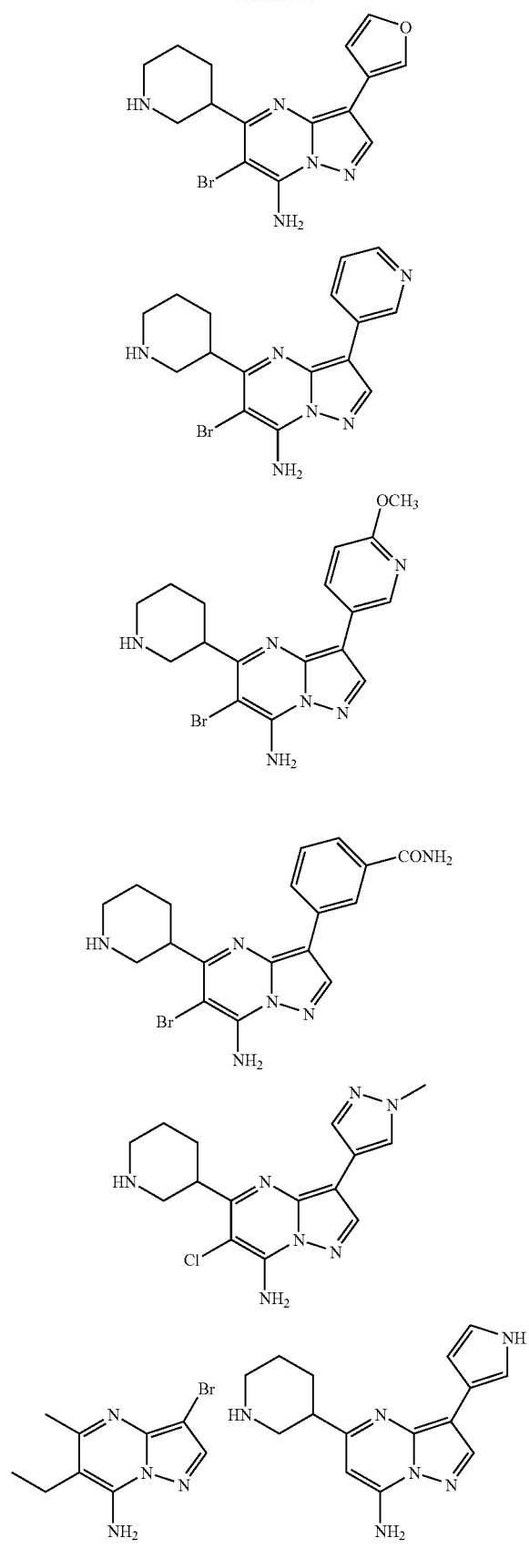
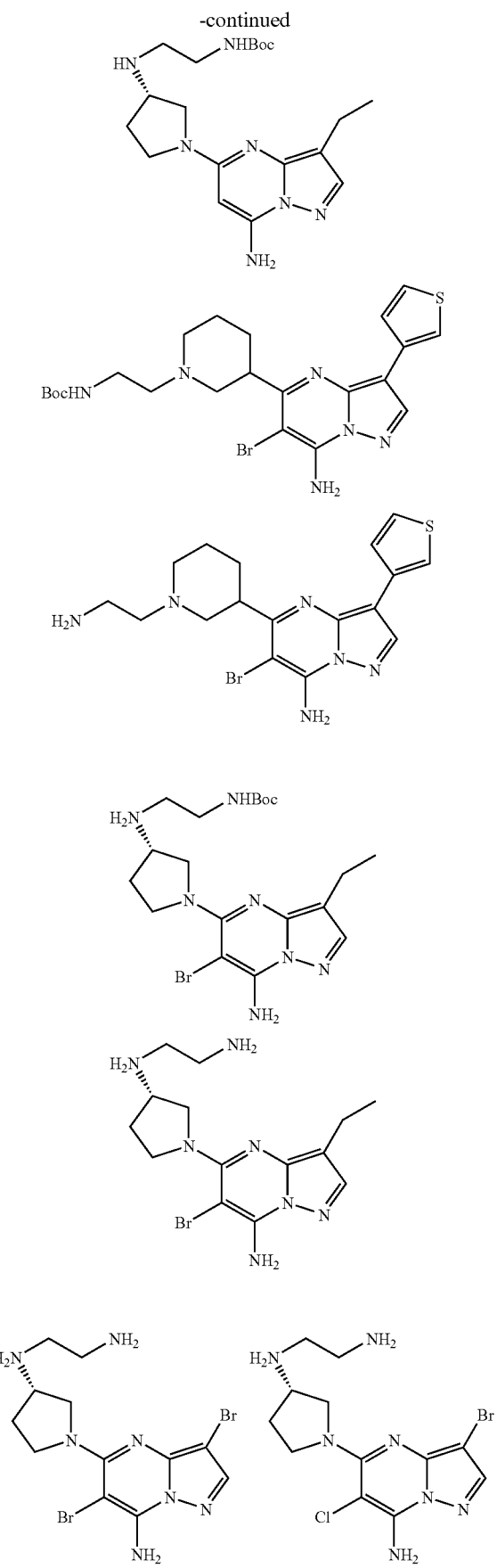

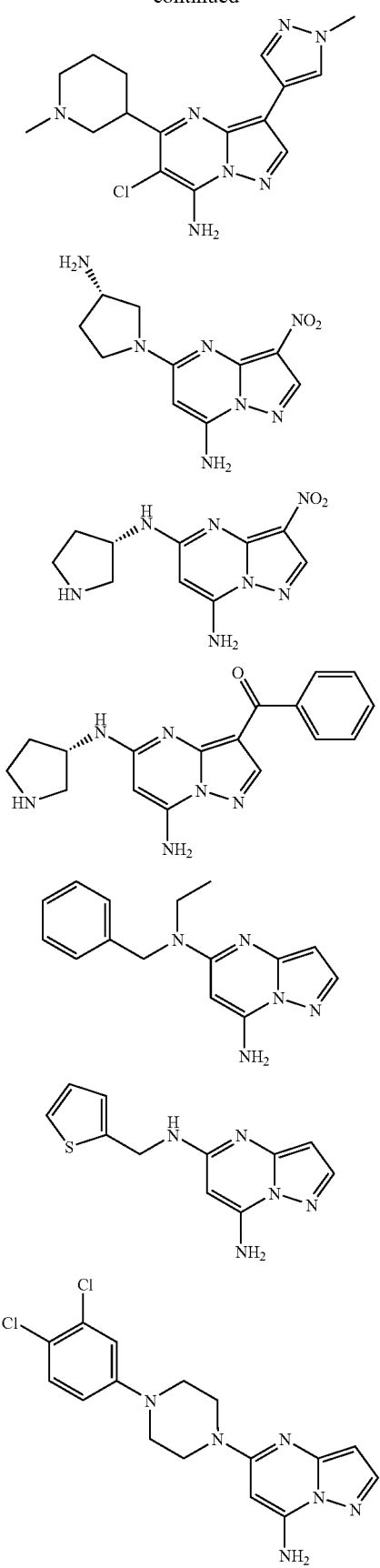
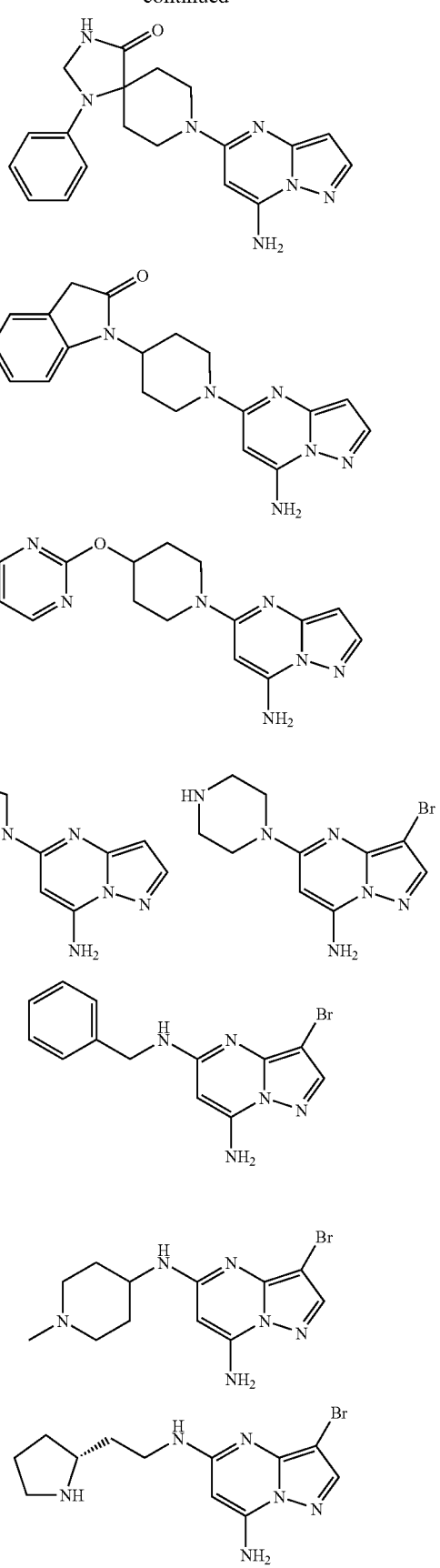

31
-continued
32
-continued
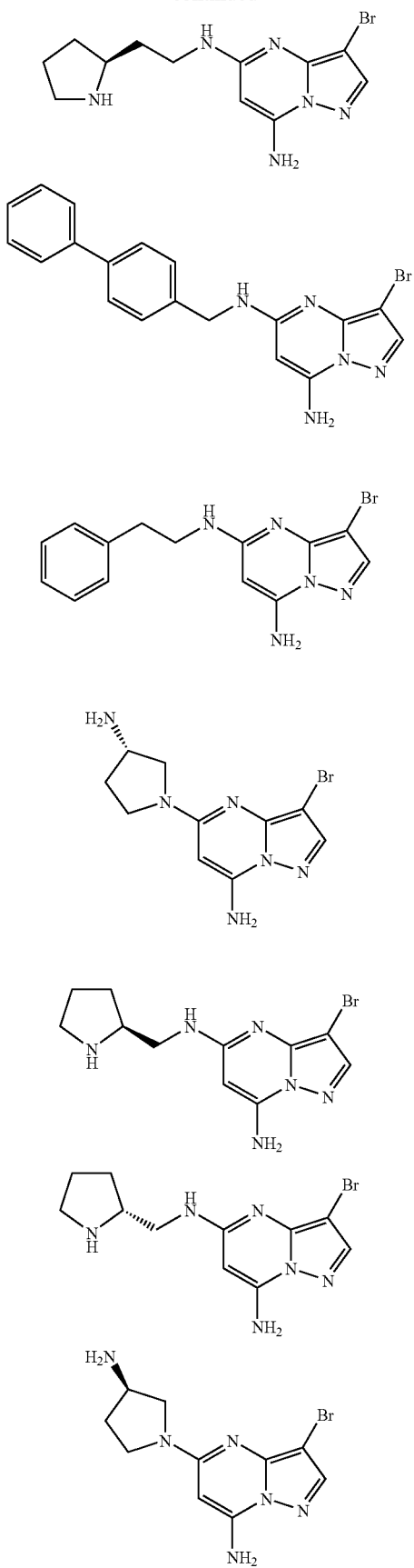
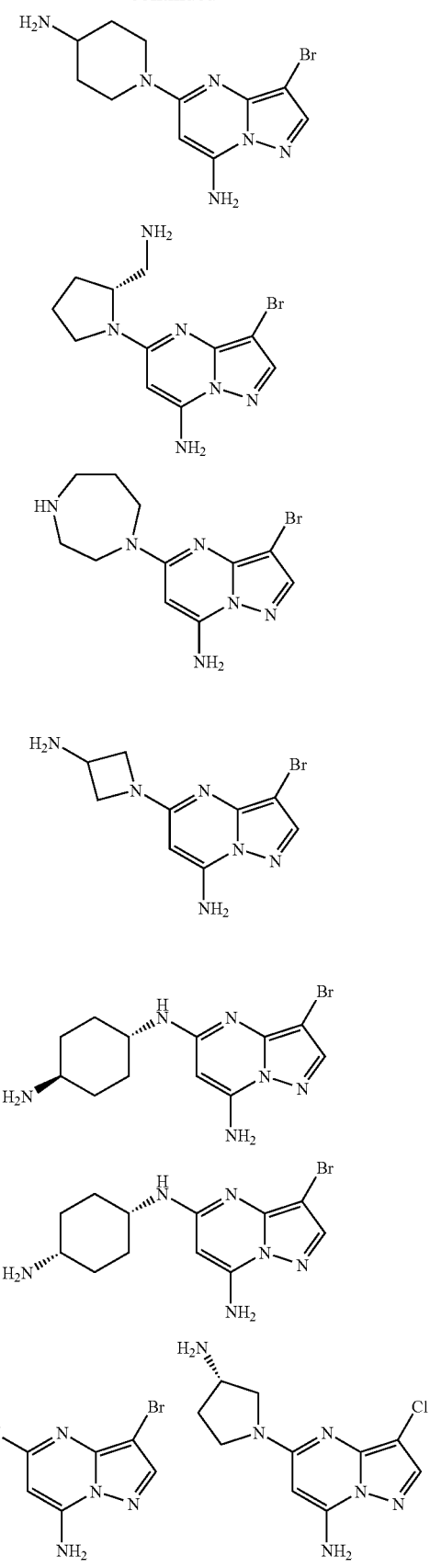

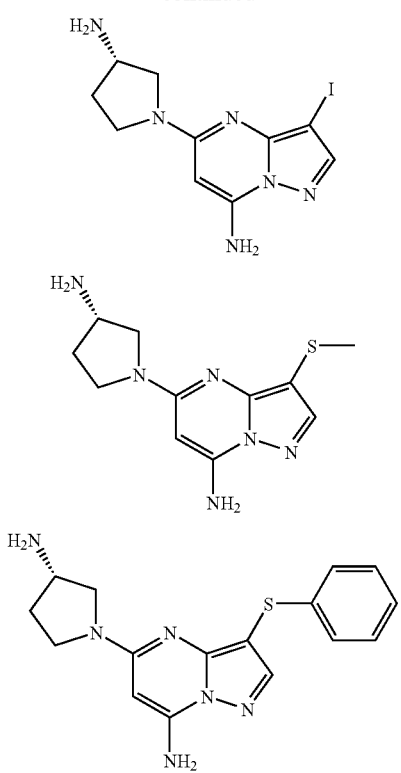
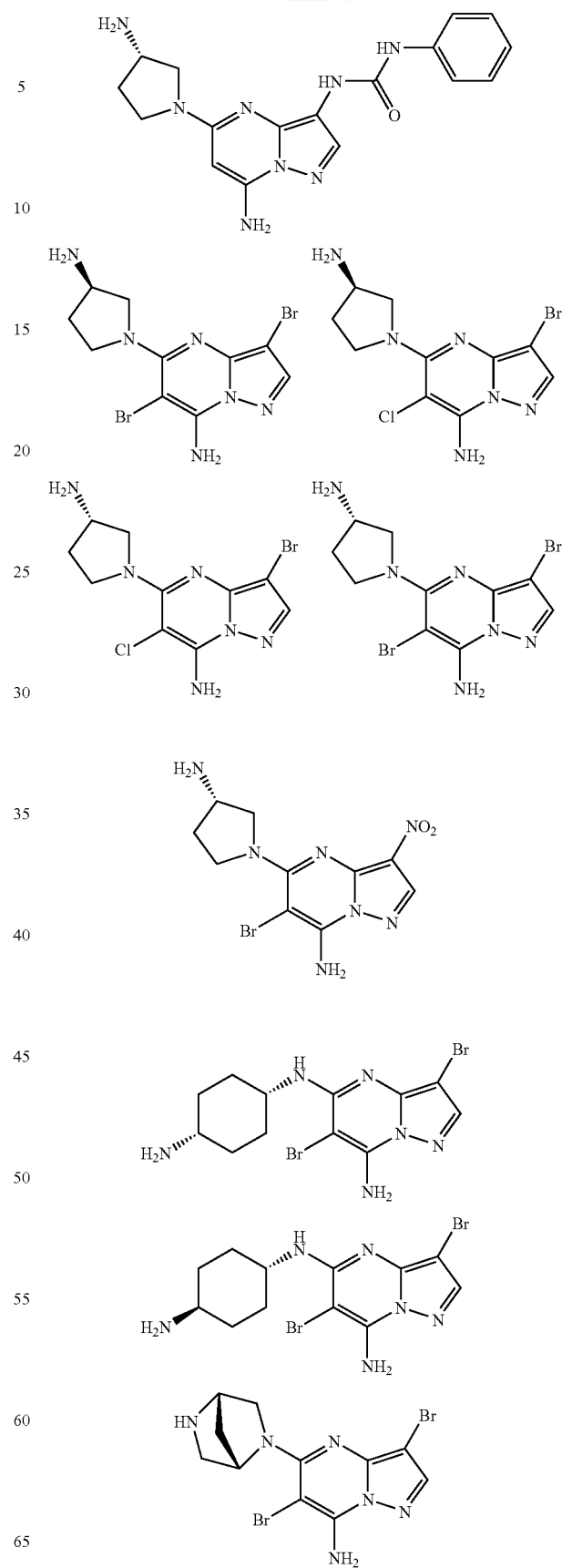

-continued
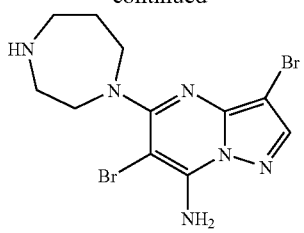
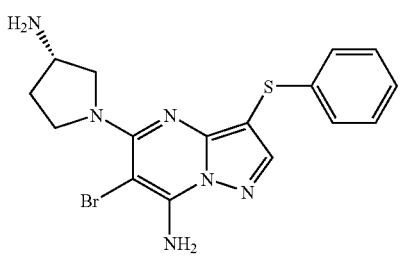
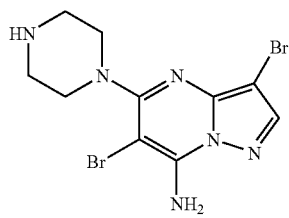
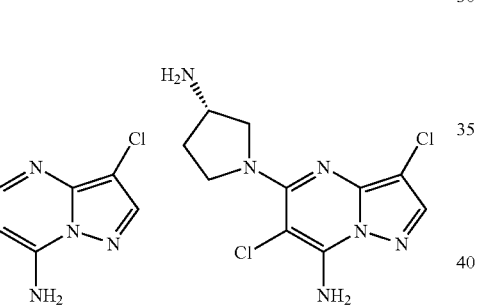
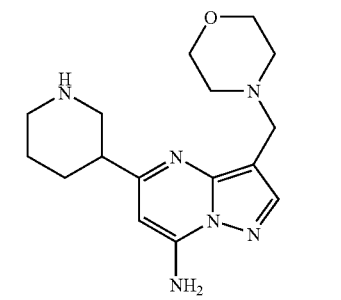
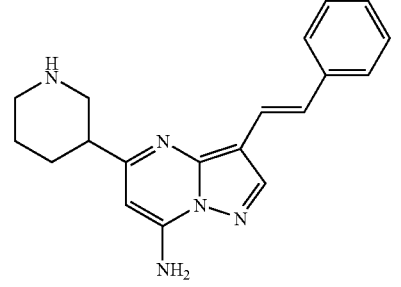
-continued
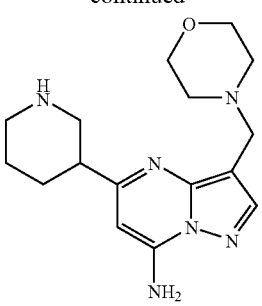
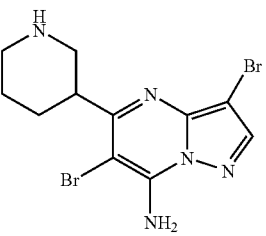
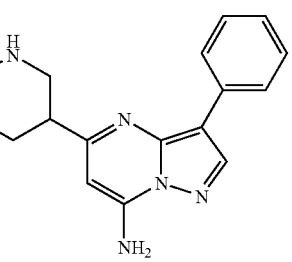
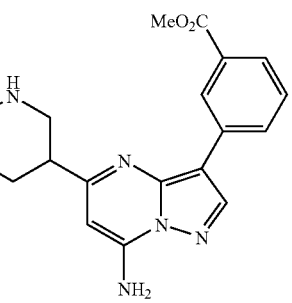
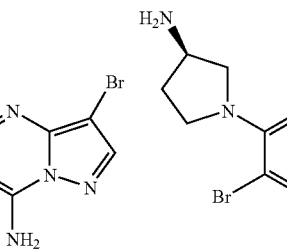
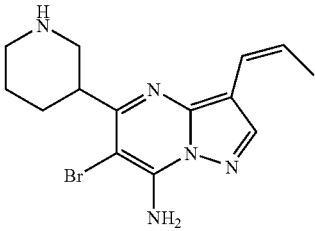

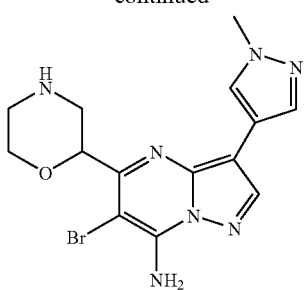
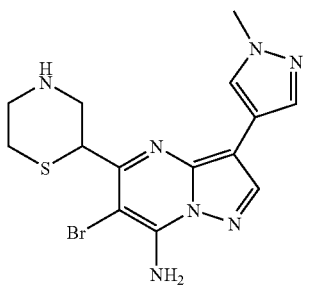
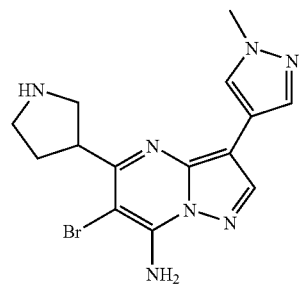
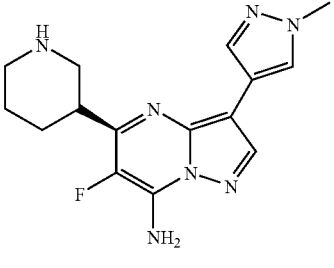
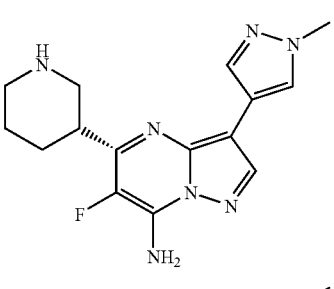
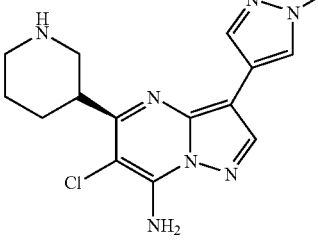
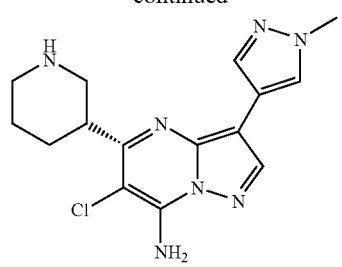
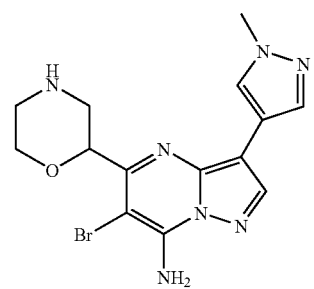
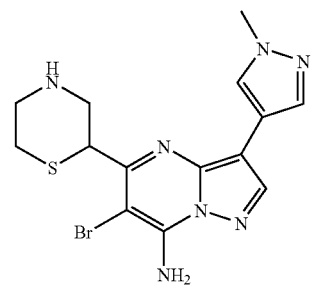
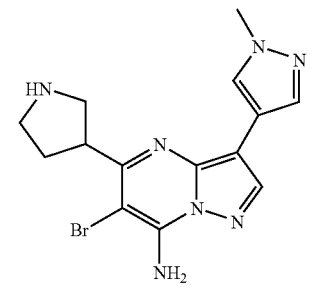
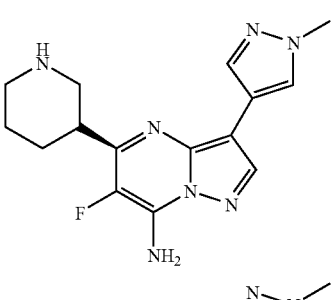
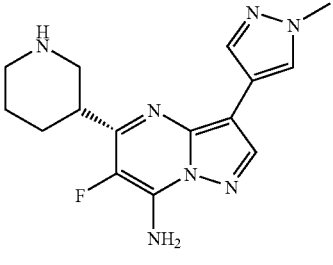

-continued
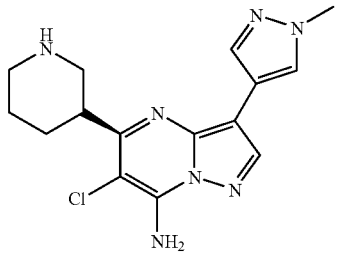
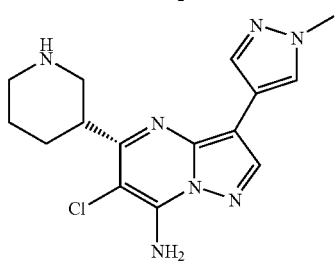
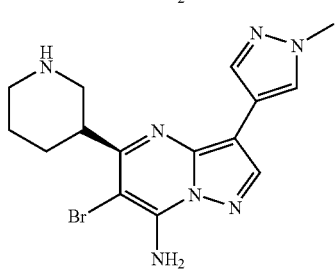
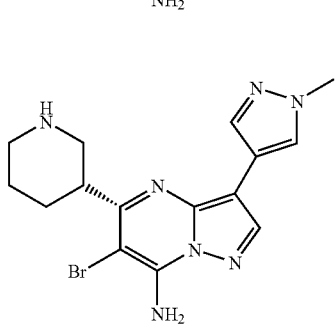
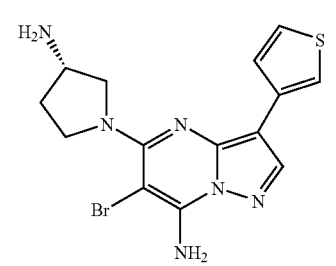
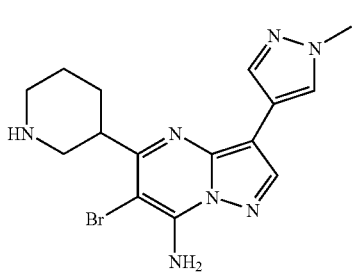
-continued
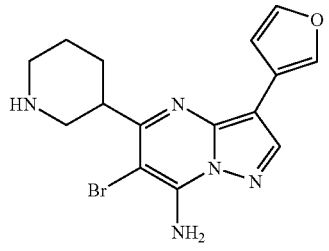
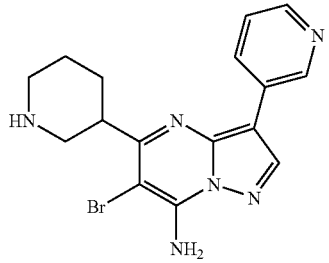
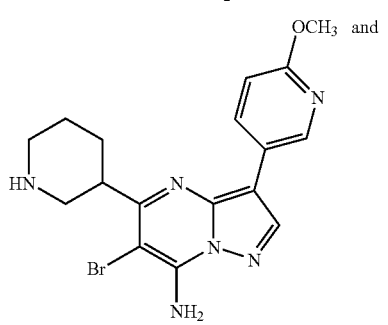
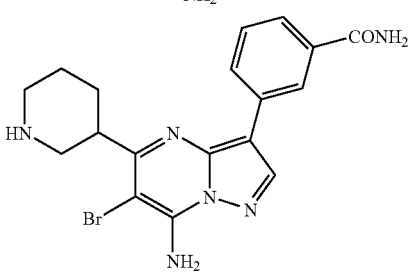
or a pharmaceutically acceptable salt, solvate, ester, isomer or prodrug thereof.
Non-limiting examples of additional compounds of Formula I useful in the practice of the present methods include those that are shown on pages 4-52 and 60-983 of the aforementioned US 2004/0209878, some of which are listed below:
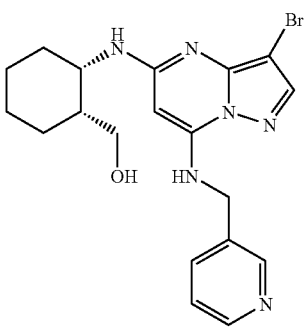

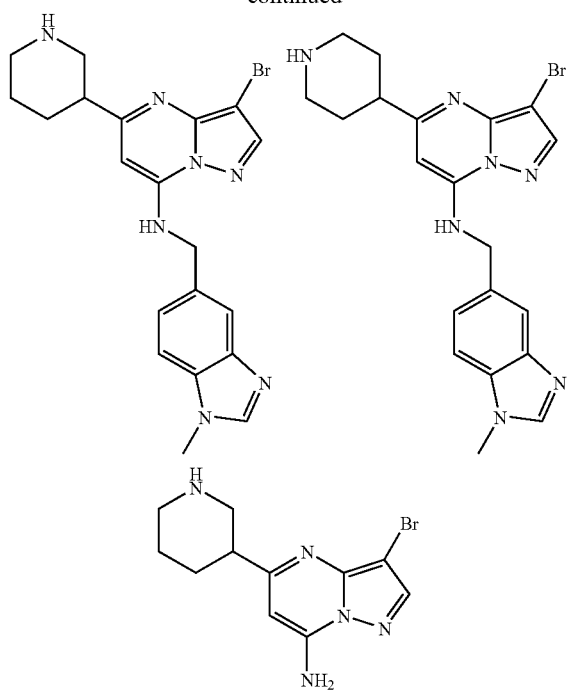
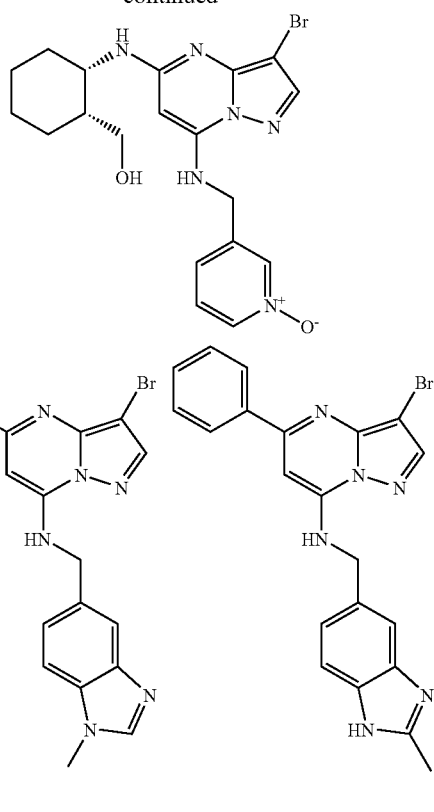
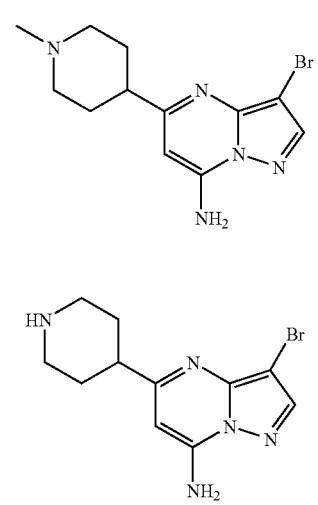
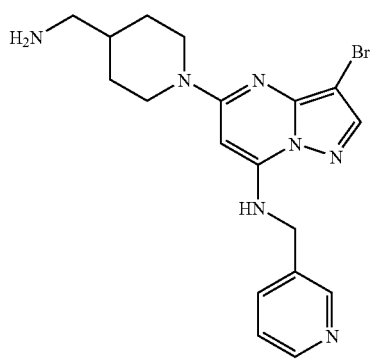

43
-continued
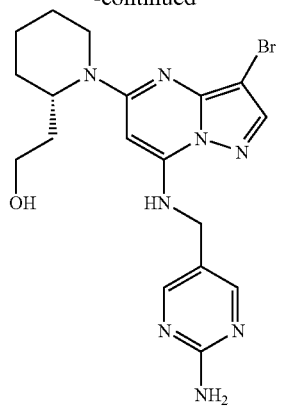
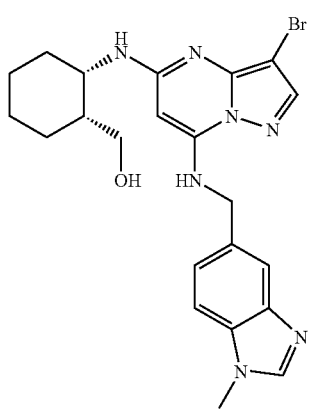
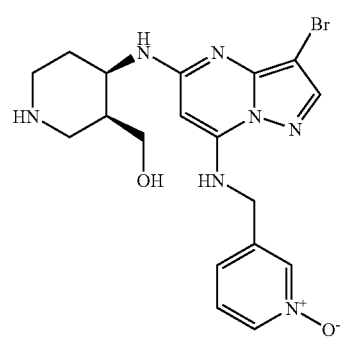
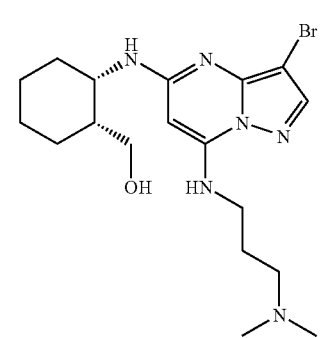
44
-continued
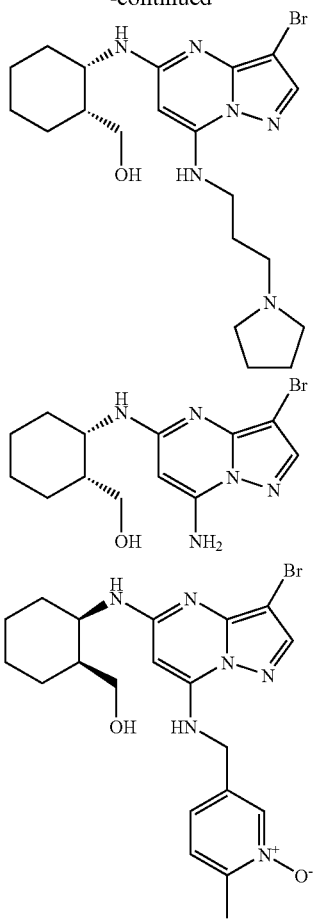
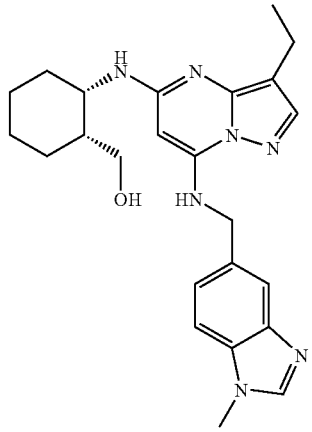
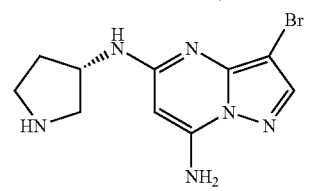
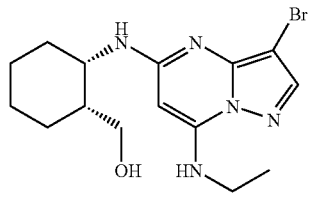

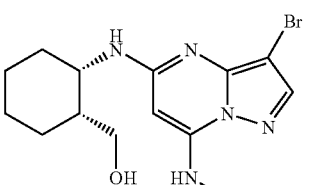
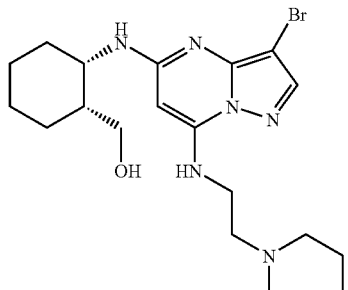
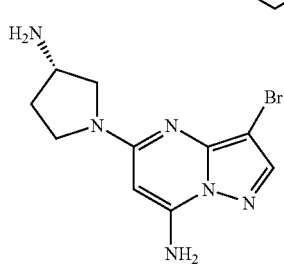
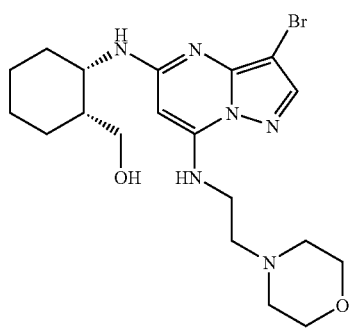
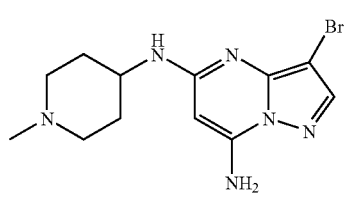
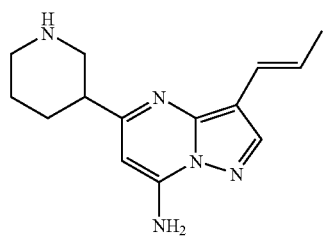
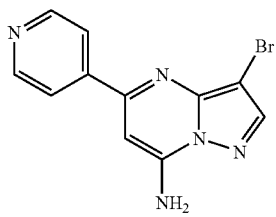
or a pharmaceutically acceptable salt, solvate, ester or prodrug thereof.
Non-limiting examples of compounds from copending patent application Ser. No. 11/542,920 filed of even date herewith suitable in the methods of the present invention include:
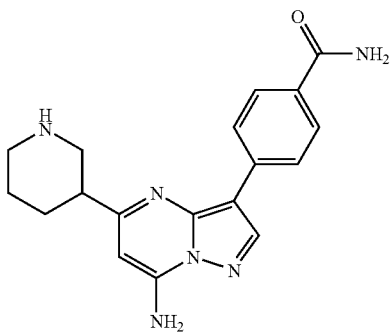
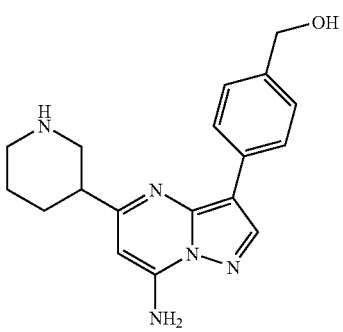
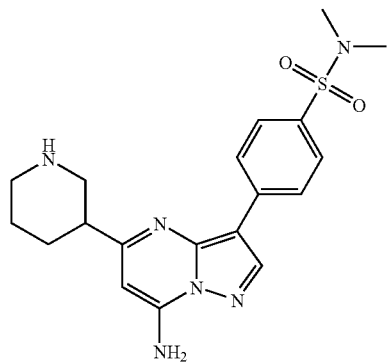

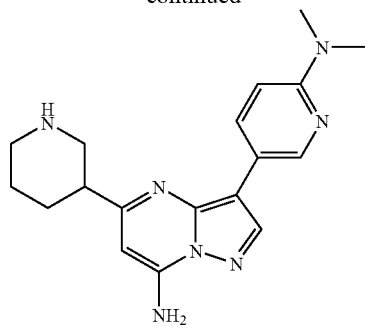
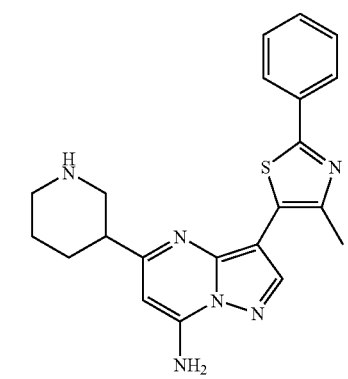
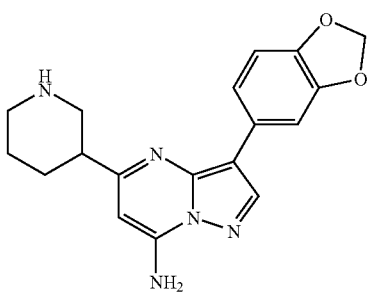
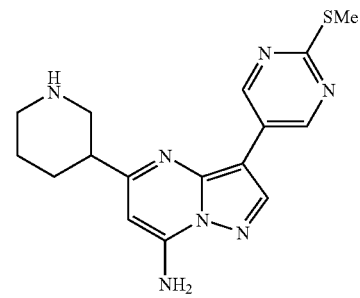
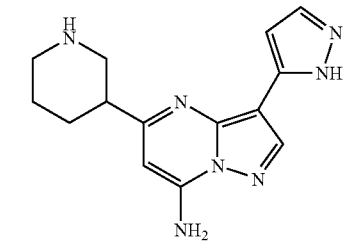
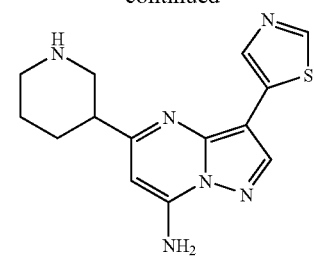
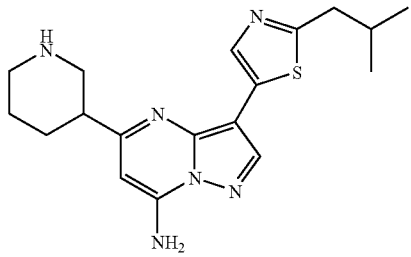
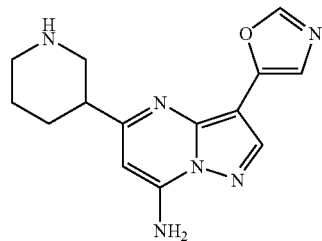
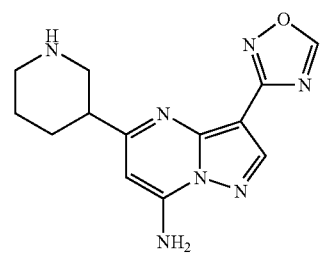
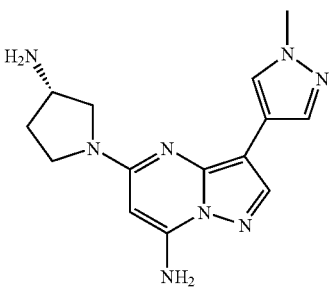
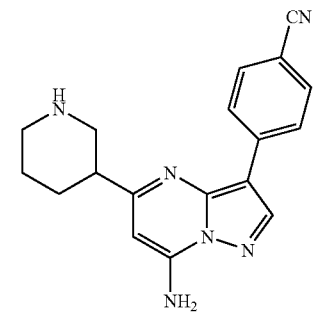

-continued
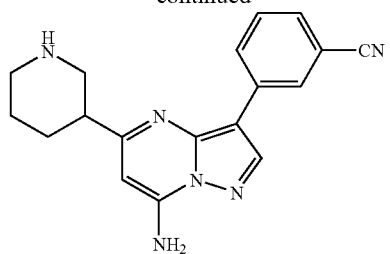
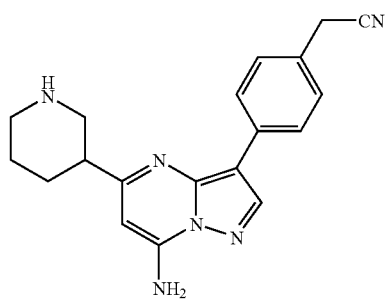
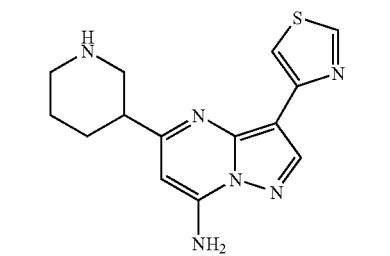
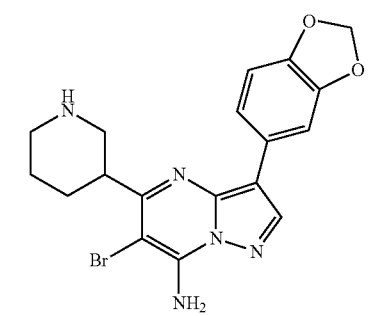
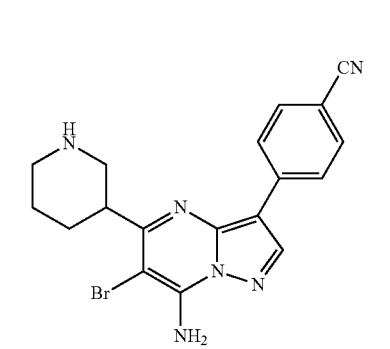
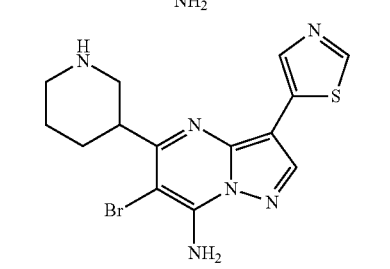
-continued
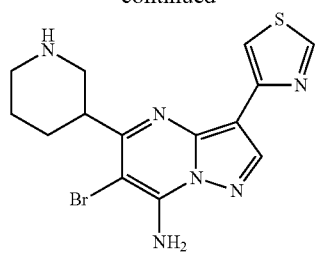
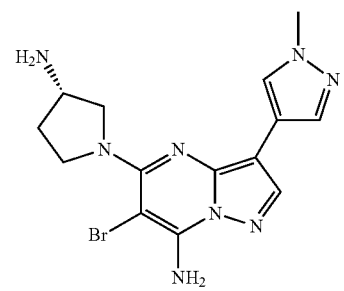
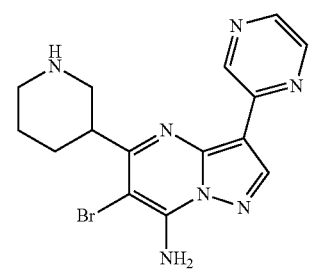
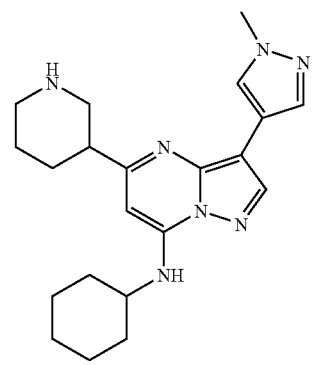
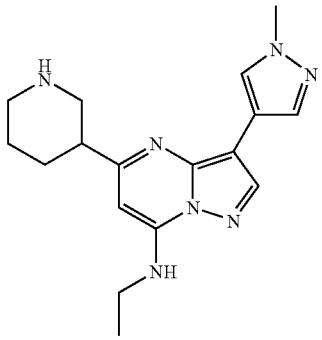

51
-continued
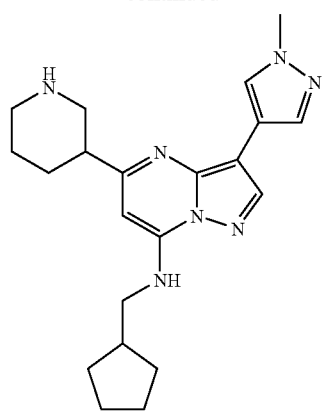
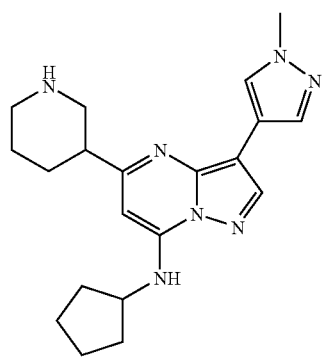
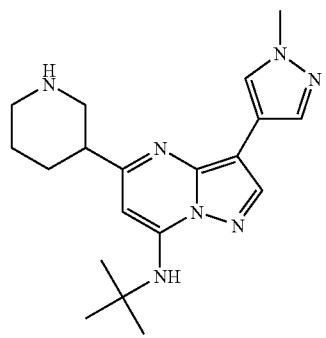
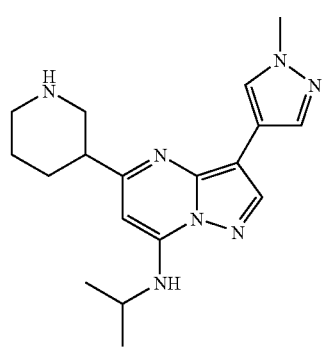
52
-continued
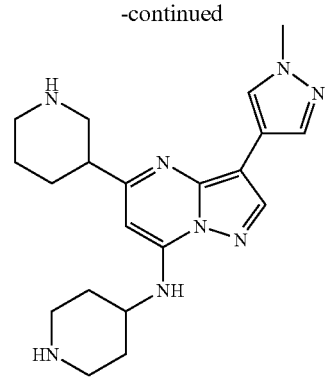
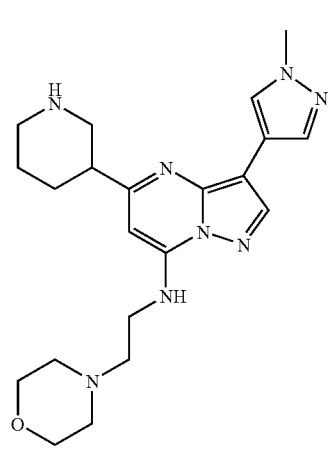
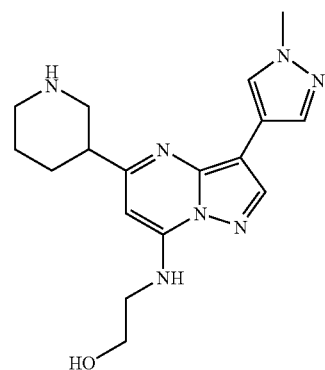
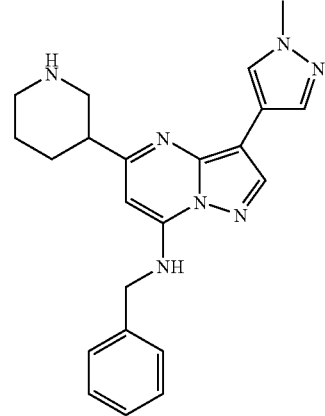

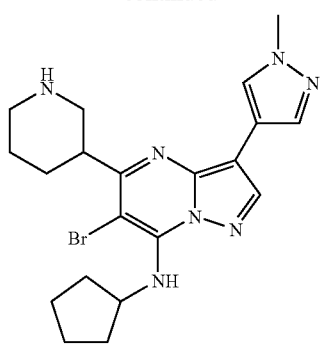
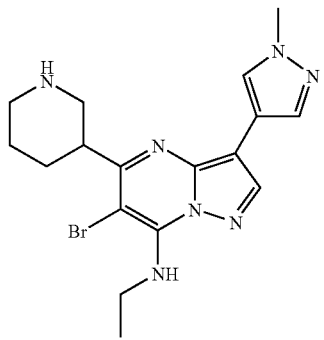
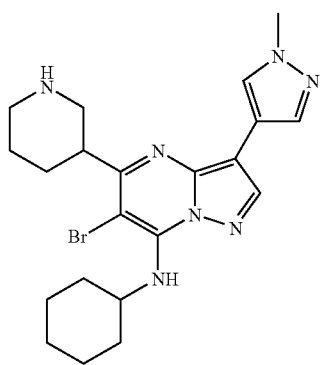
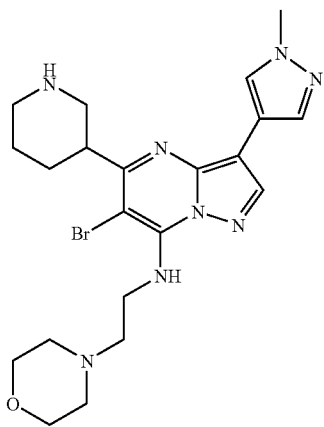
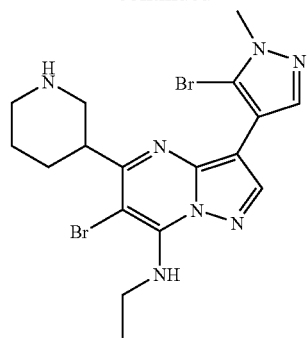
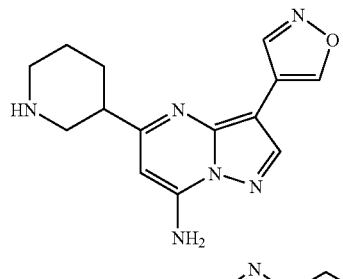
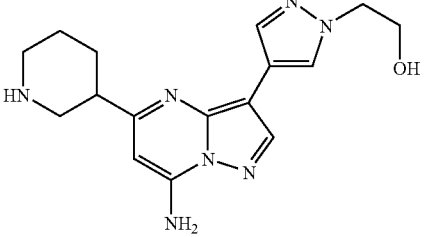
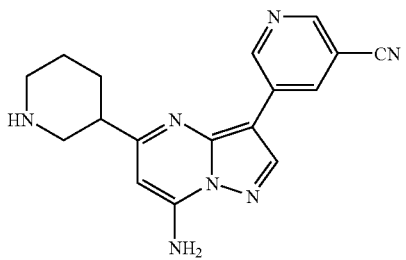
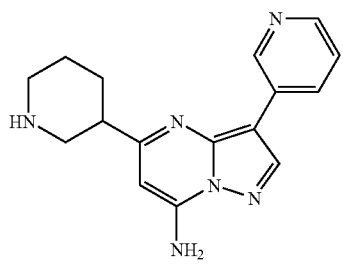
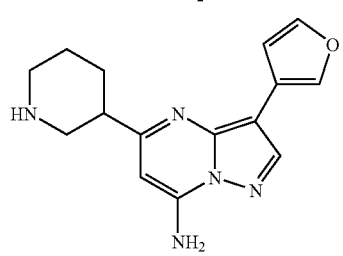

55
-continued
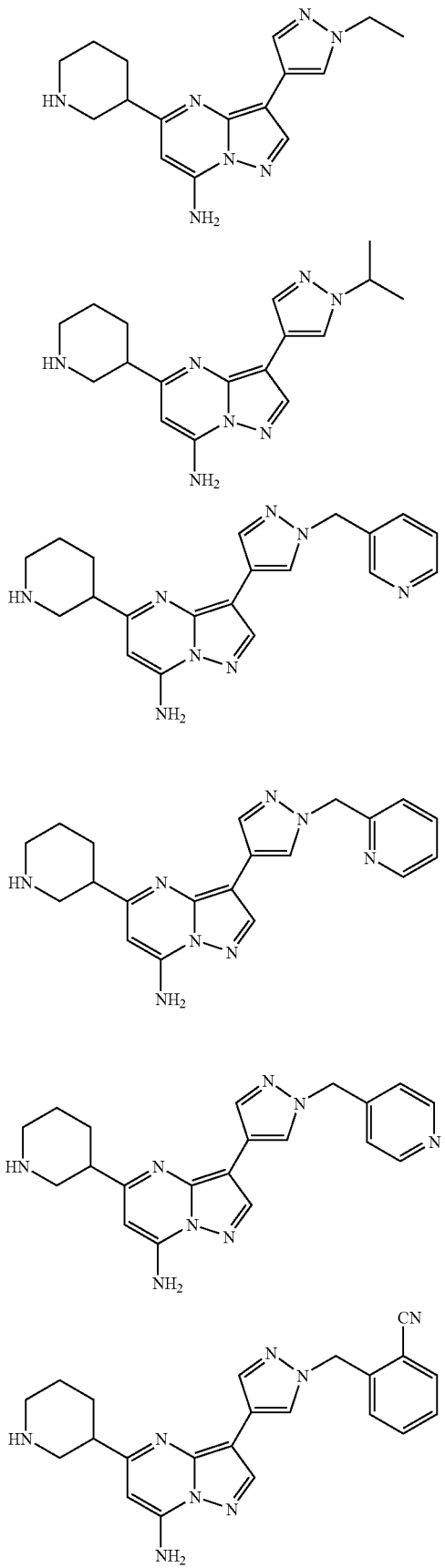
56
-continued
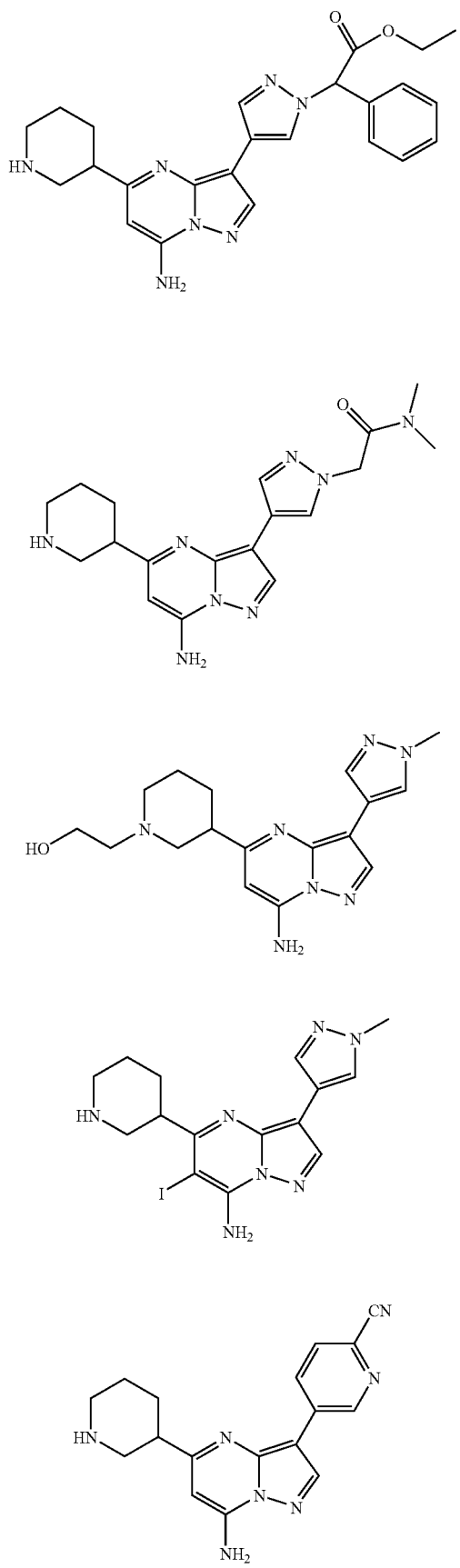

57
-continued
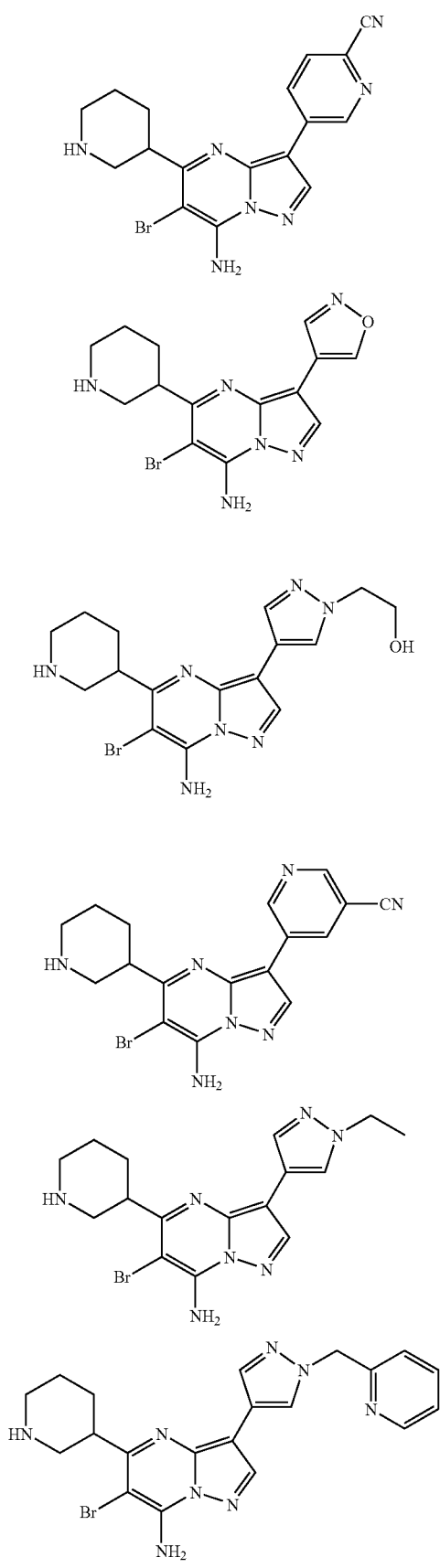
58
-continued
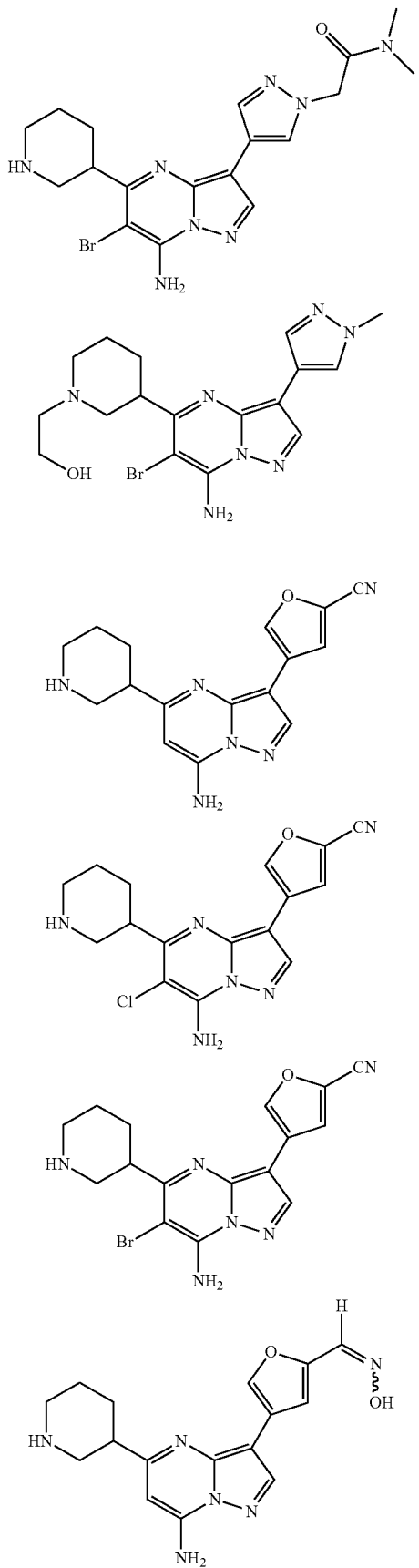

59
-continued
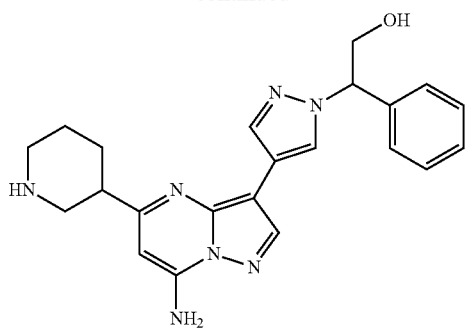
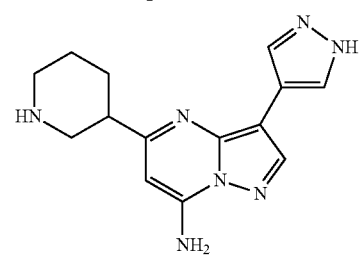
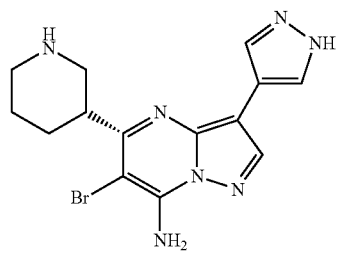
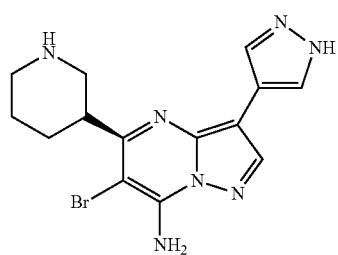
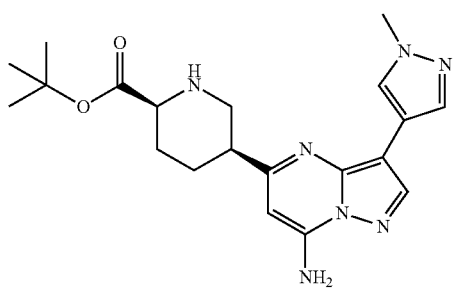
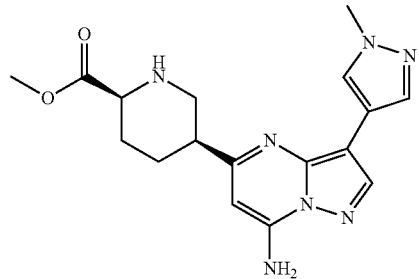
60
-continued
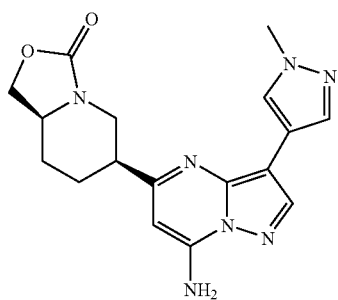
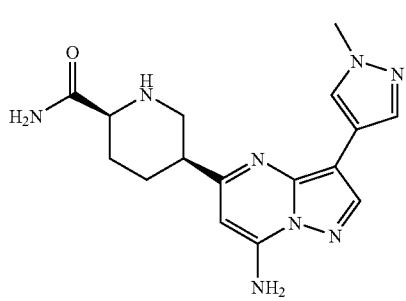
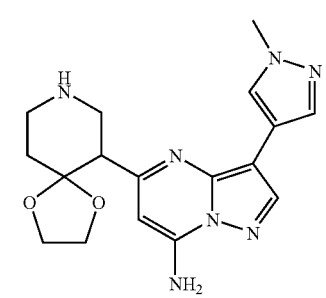
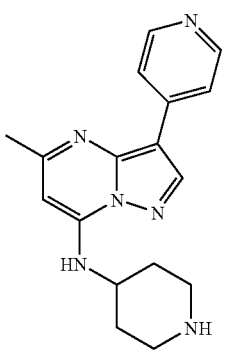
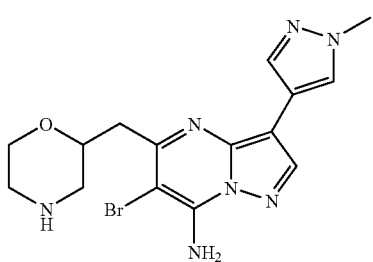

-continued
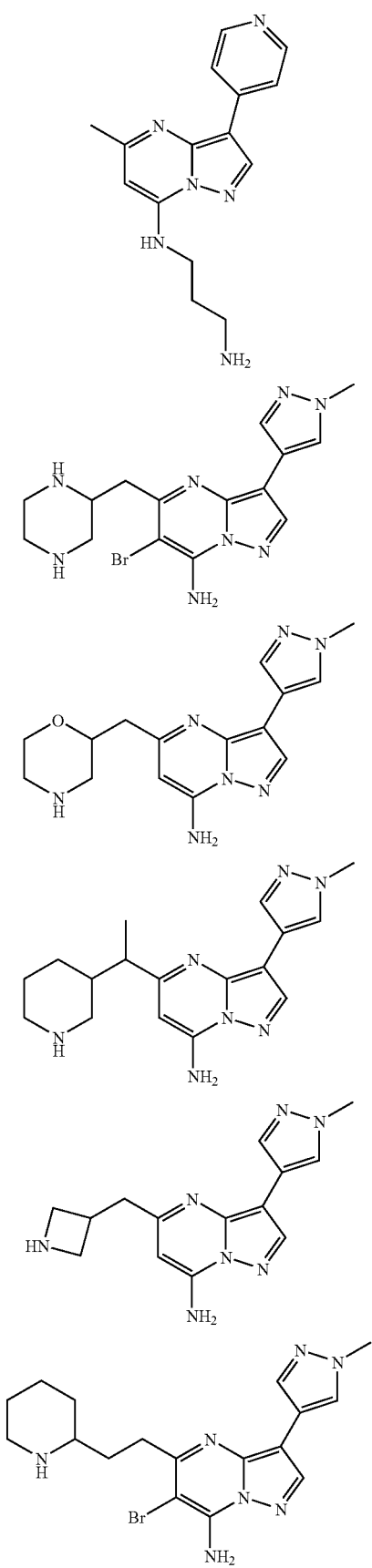
-continued
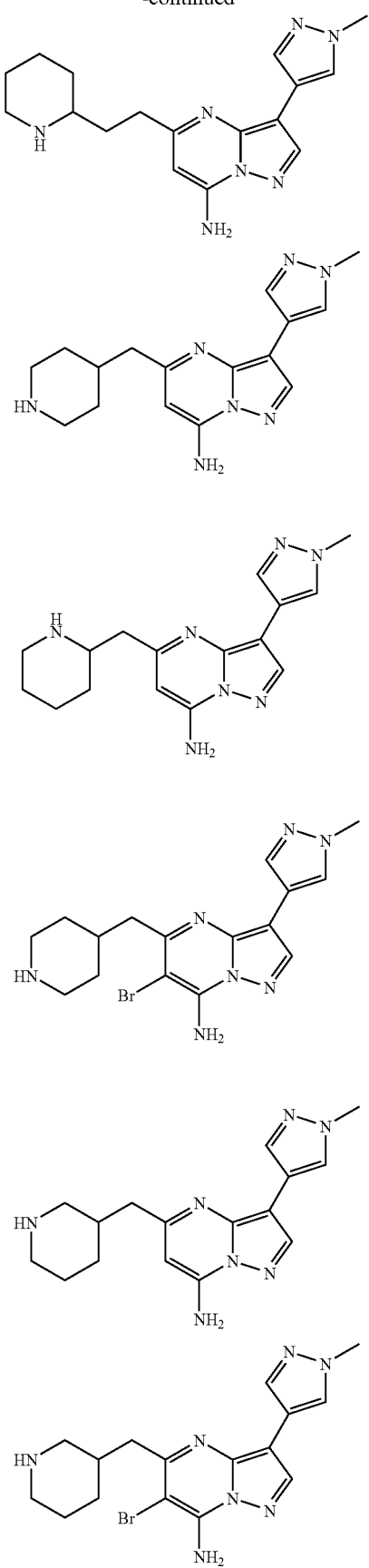

-continued
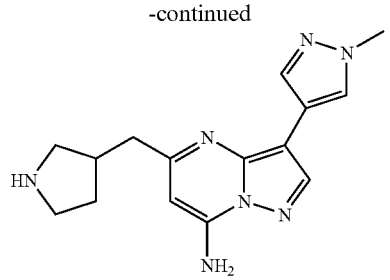
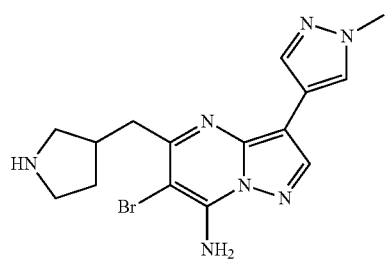
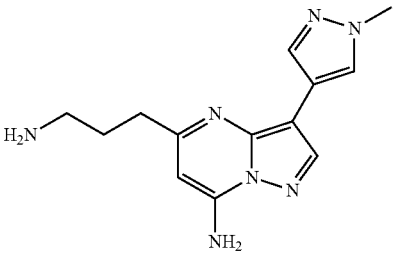
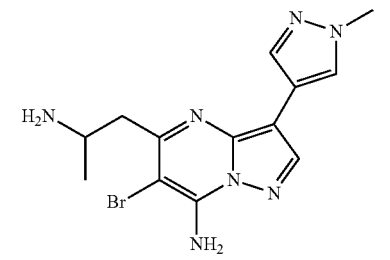
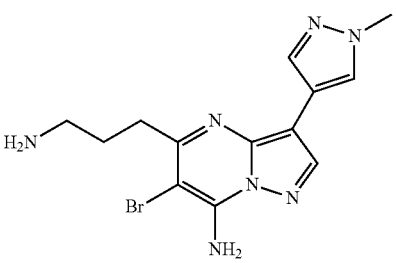
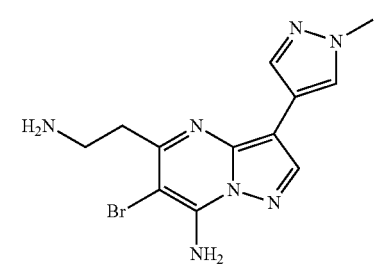
-continued
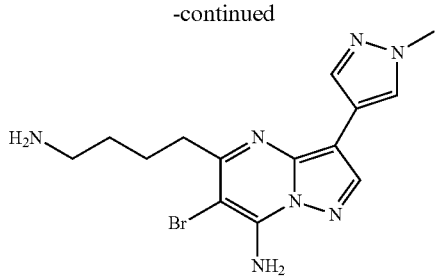
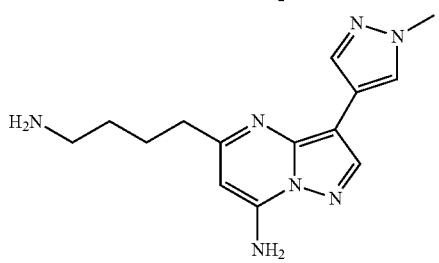
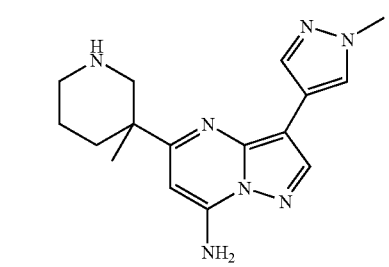
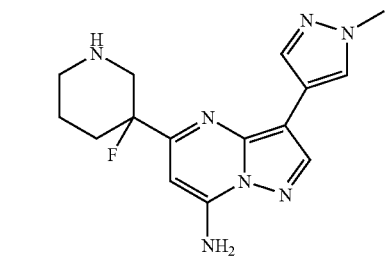
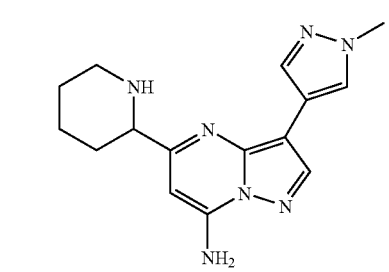
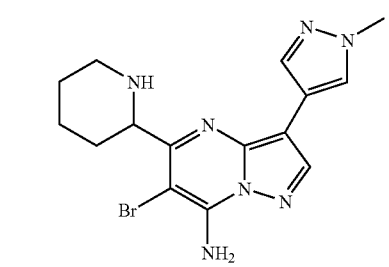

65
-continued
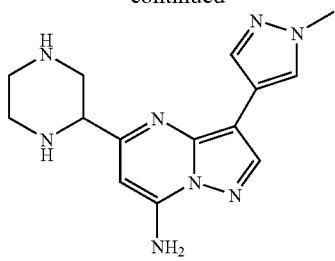
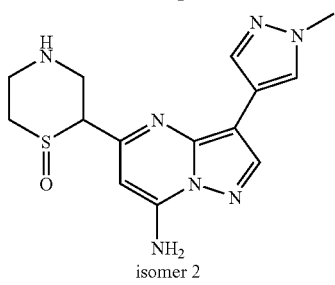
isomer 2
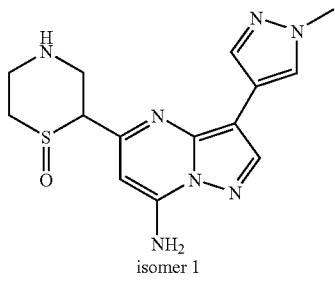
isomer 1
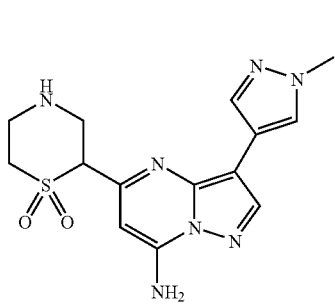
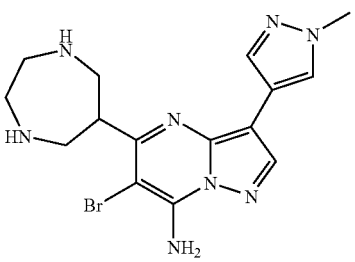
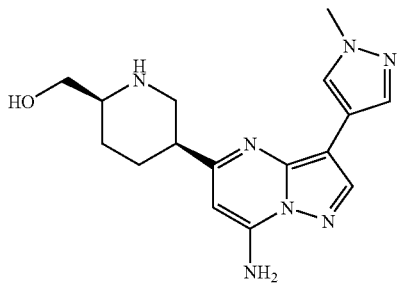
66
-continued
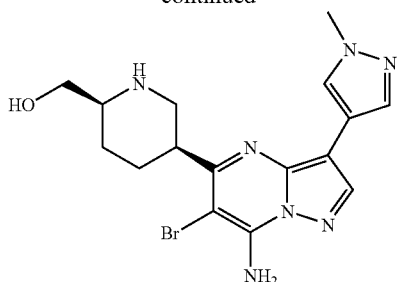
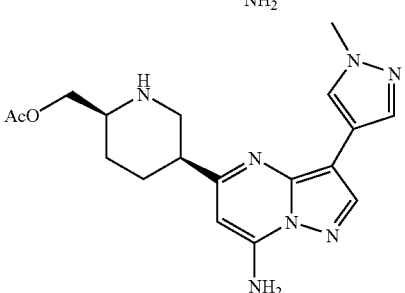
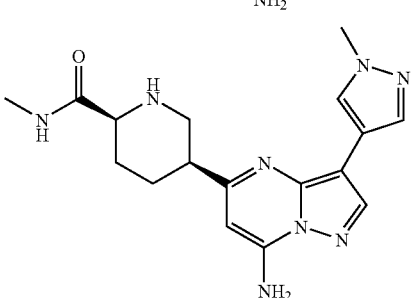
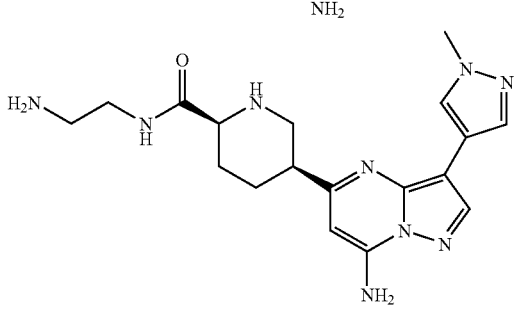
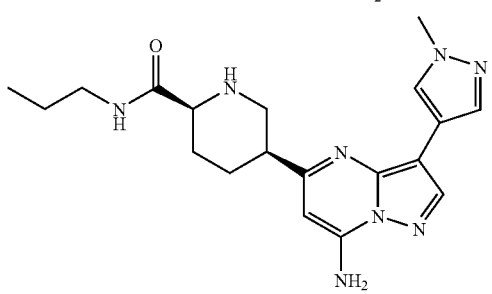
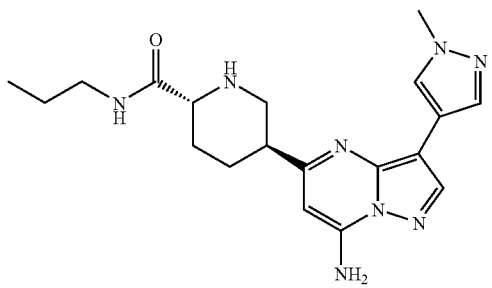

67
-continued
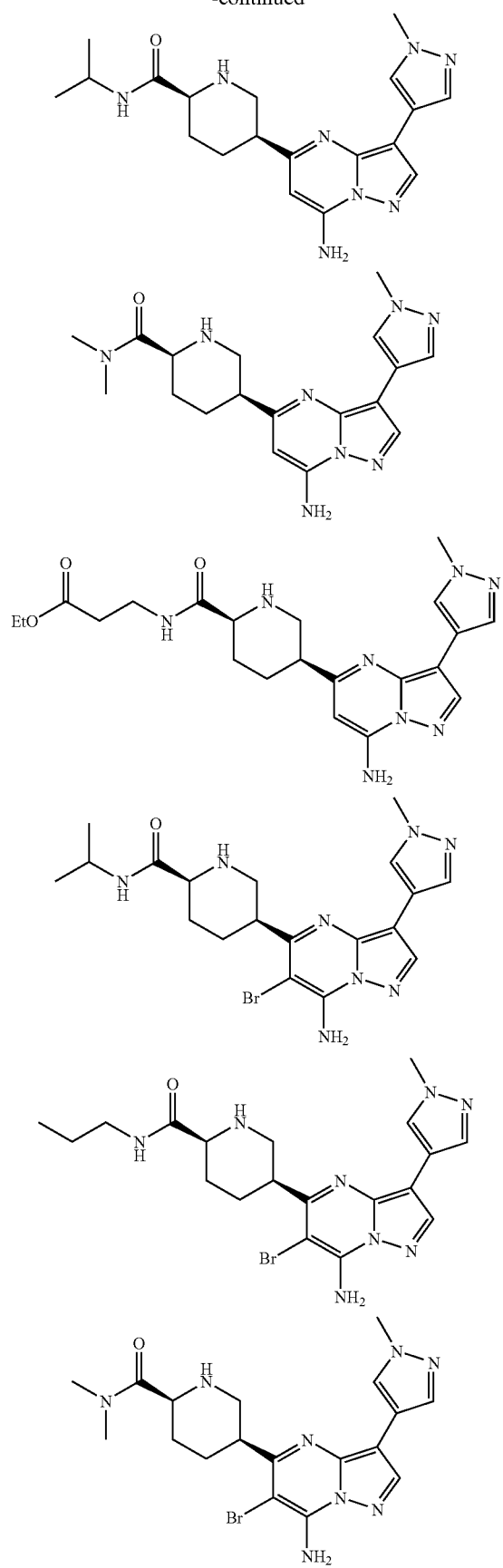
68
-continued
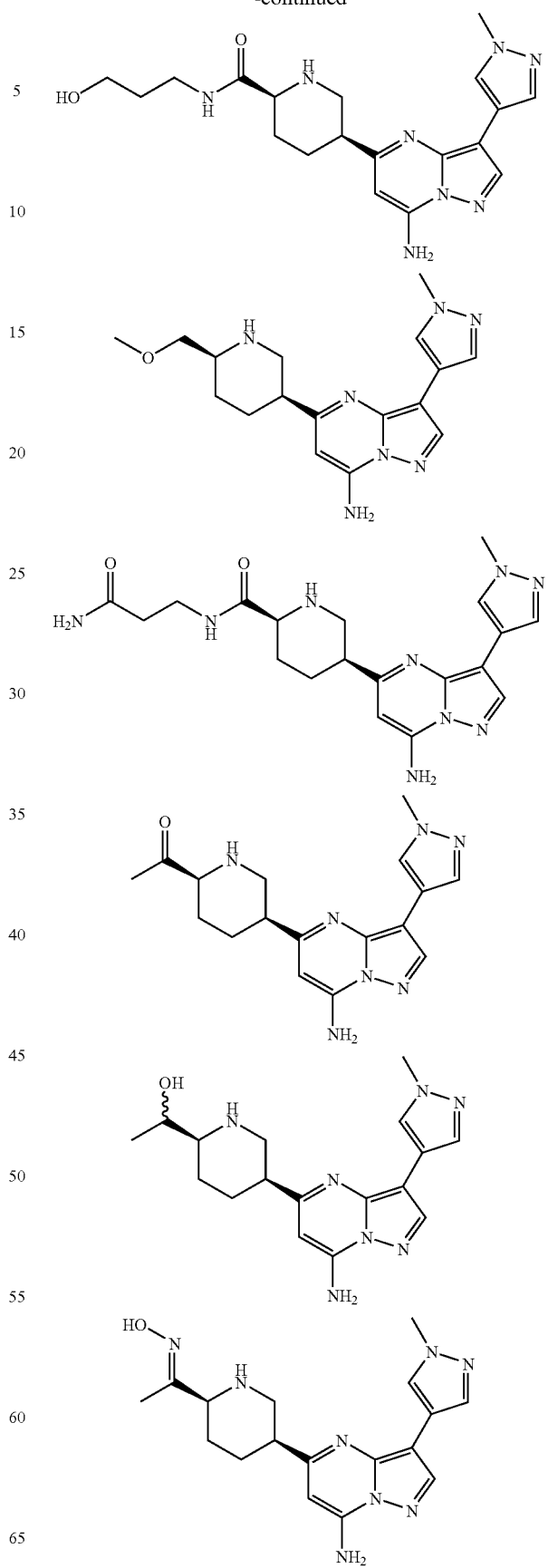

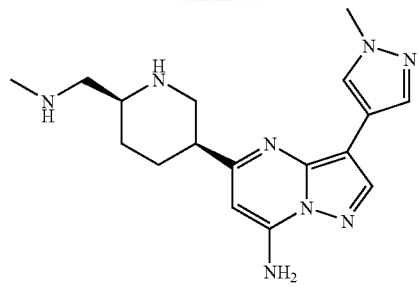
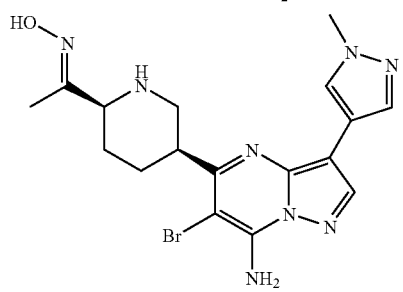
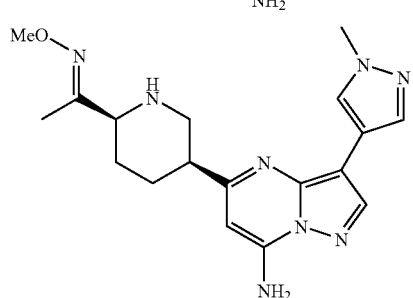
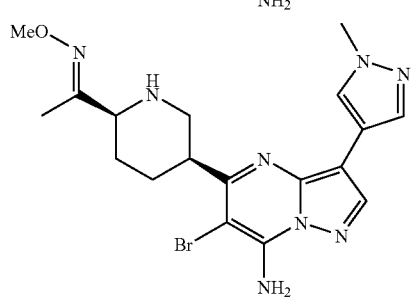
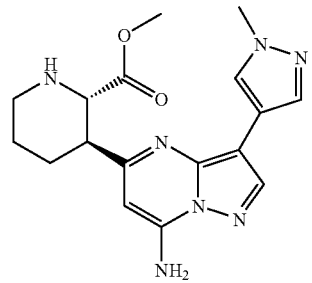
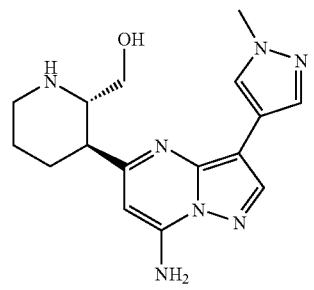
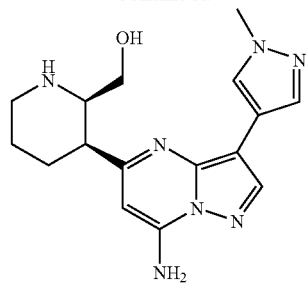
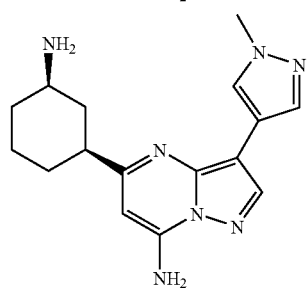
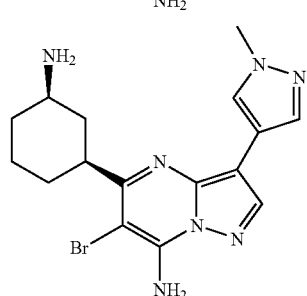
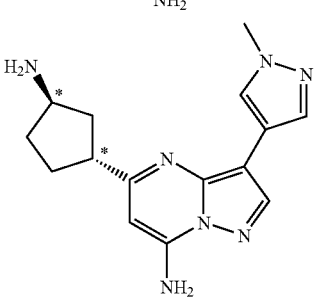
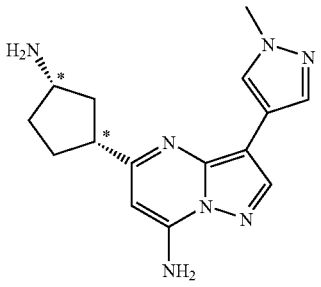
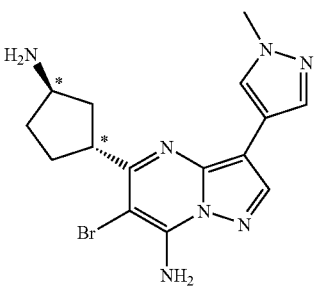

71
-continued
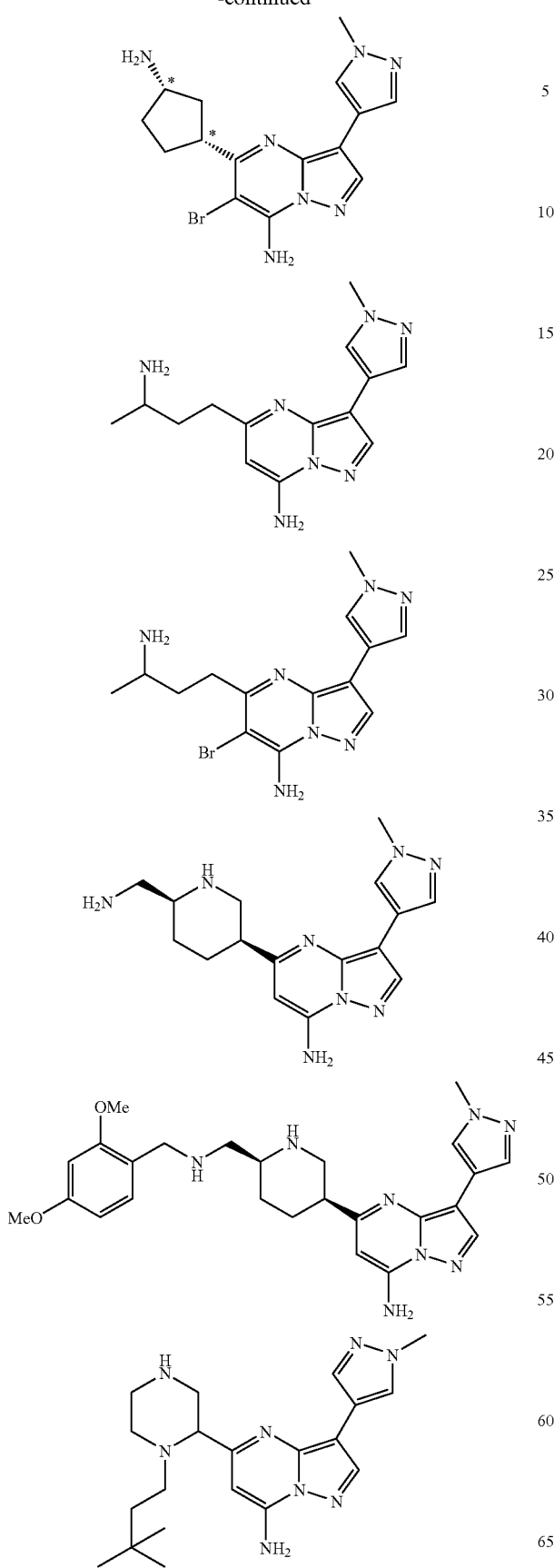
72
-continued
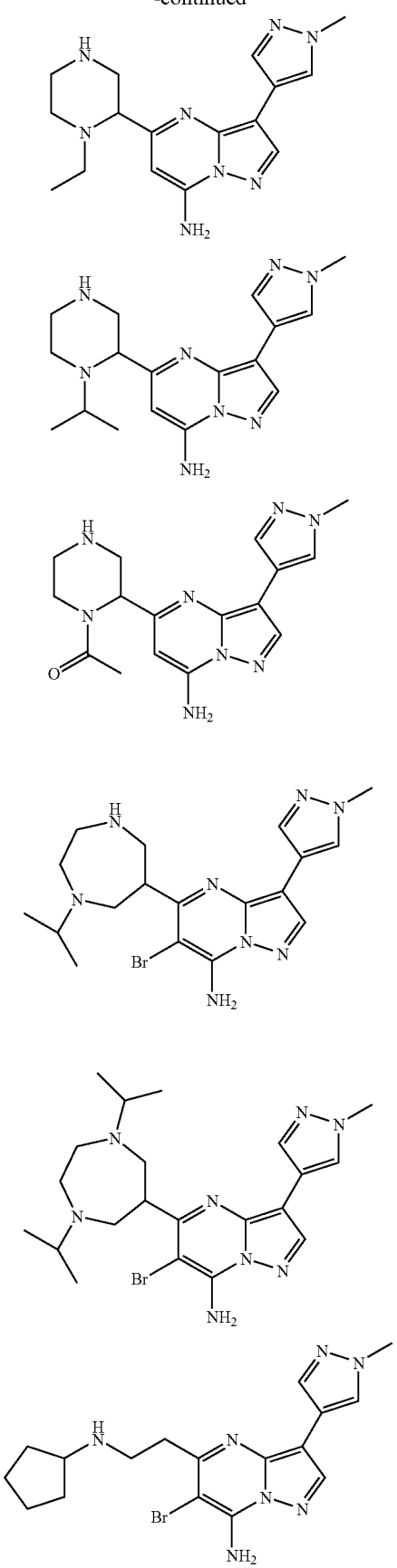

73
-continued
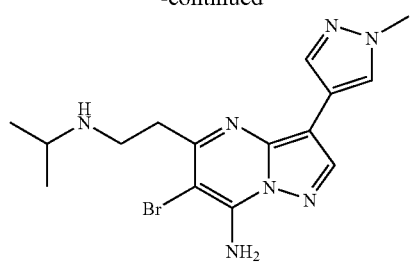
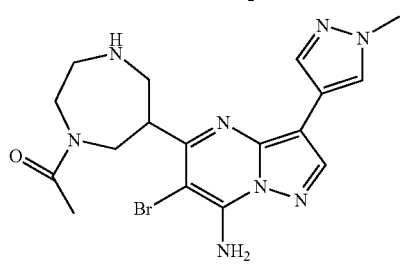
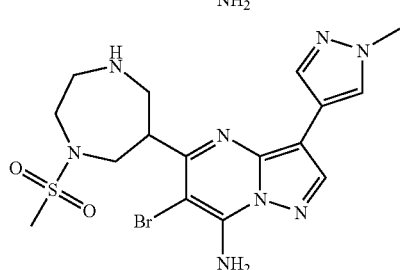
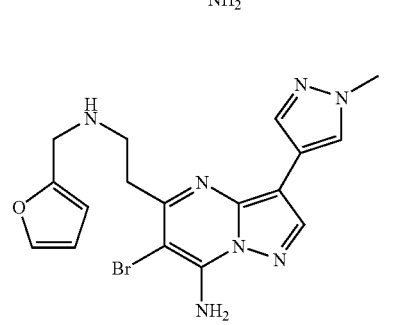
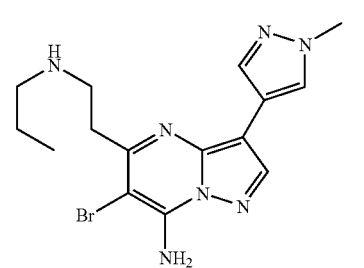
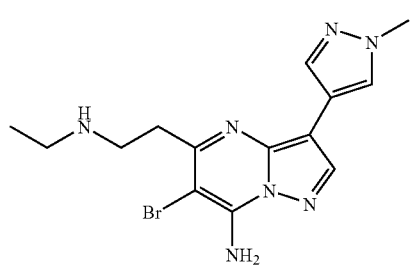
74
-continued
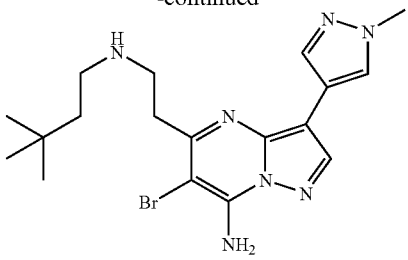
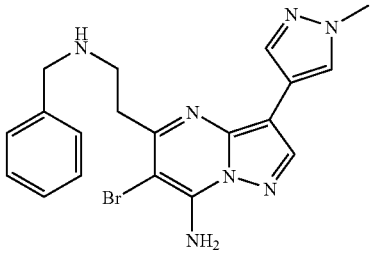
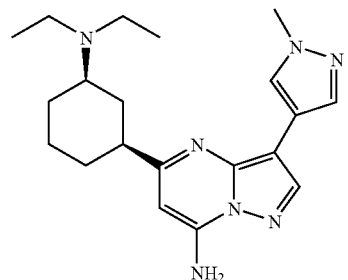
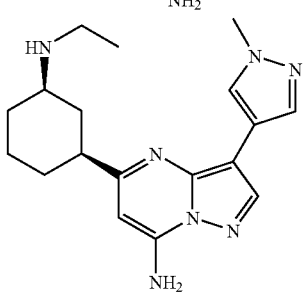
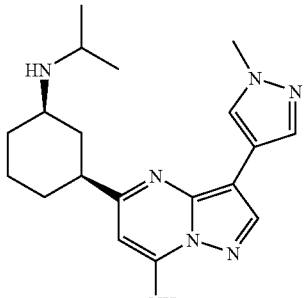
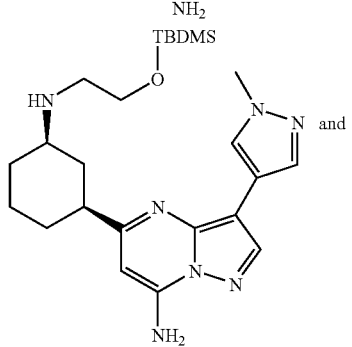
and

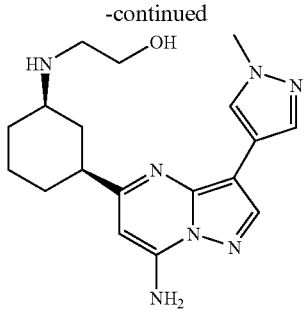
or a pharmaceutically acceptable salt, solvate, ester, isomer or prodrug thereof.
Non-limiting examples of compounds belonging to Formula II suitable in the methods of the present invention include those shown on pages 4-14 and 42-79 of the aforementioned US 2006/0041131 some of which are listed below:
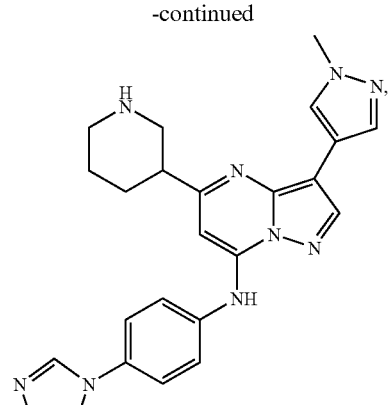
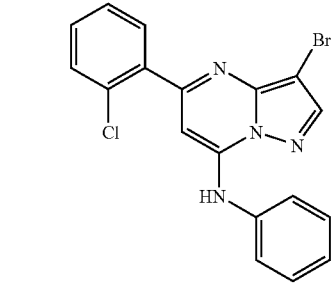
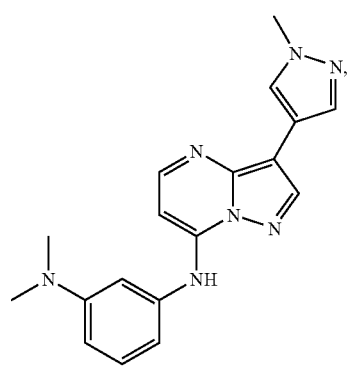
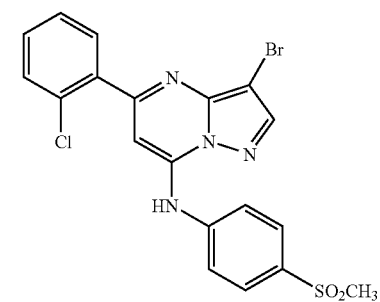
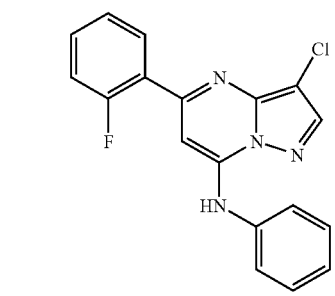
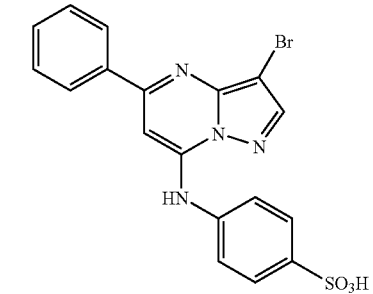

77
-continued
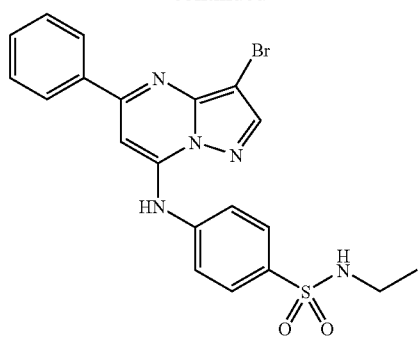
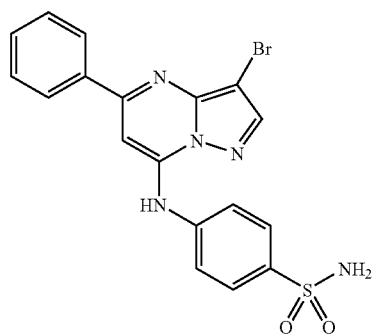
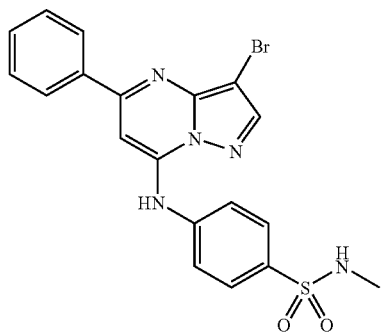
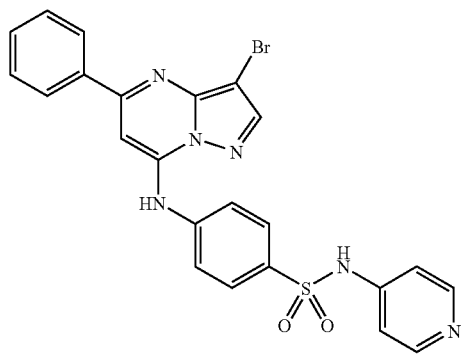
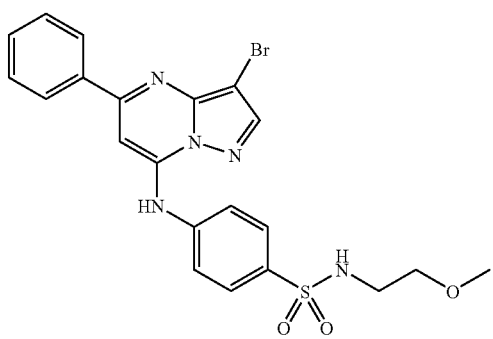
78
-continued
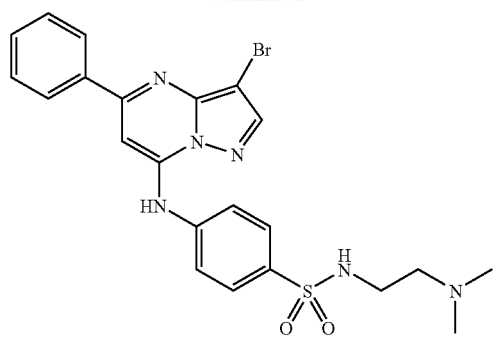
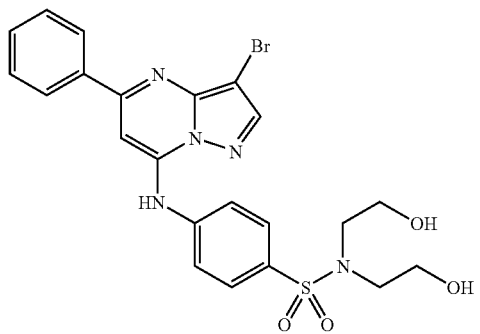
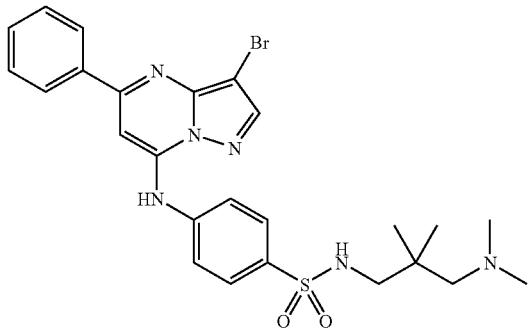
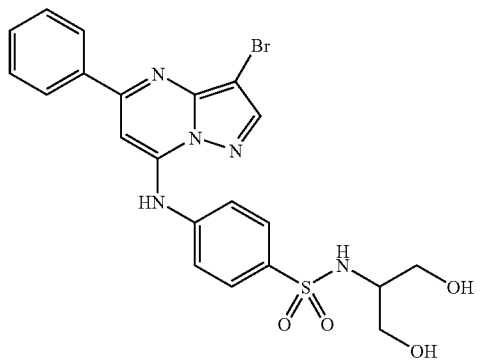
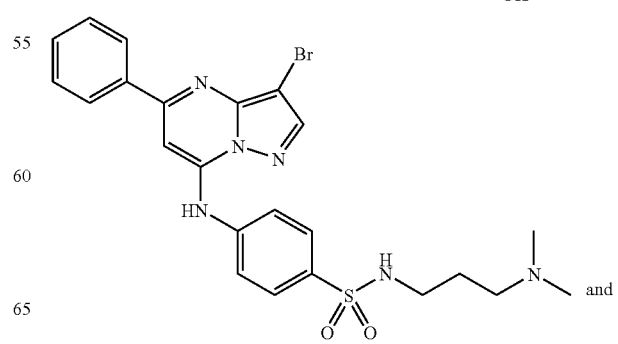
and

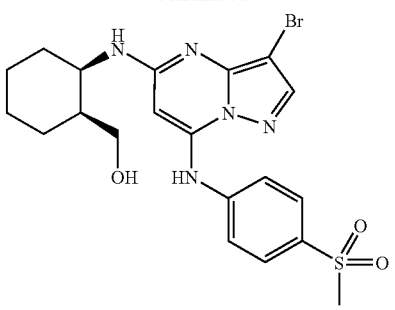
or a pharmaceutically acceptable salt, solvate, ester, isomer or prodrug thereof.
Non-limiting examples of compounds of Formula II from copending patent application Ser. No. 11/542,833 filed of even date herewith suitable in the methods of the present invention include:
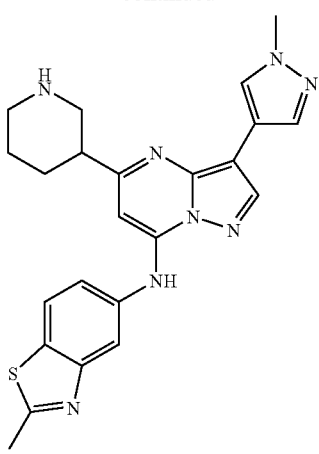
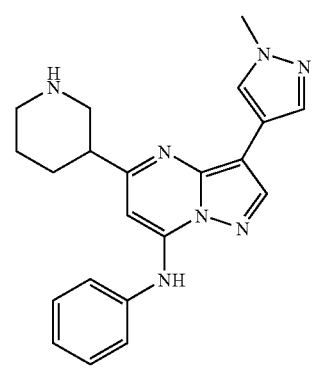
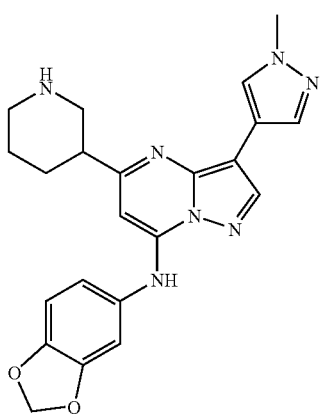
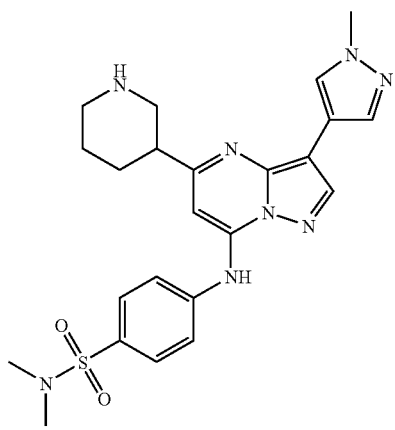
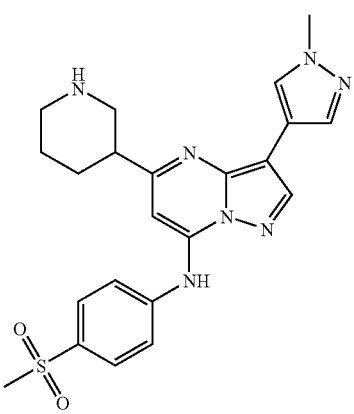
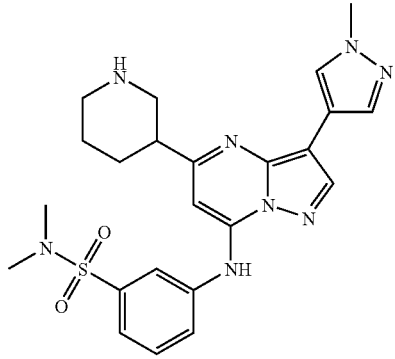

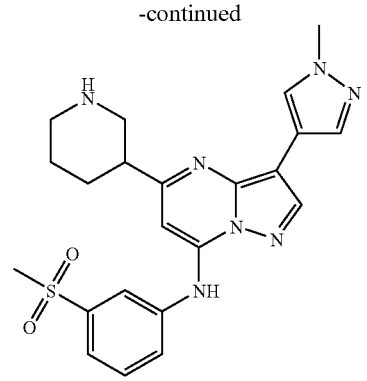

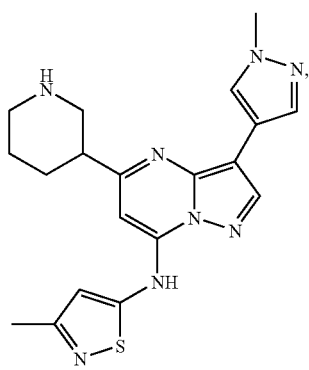

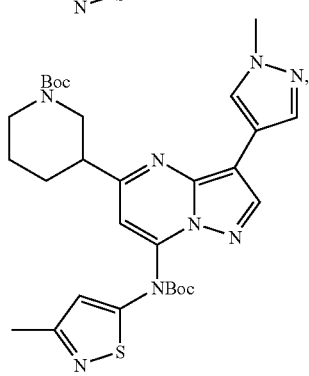

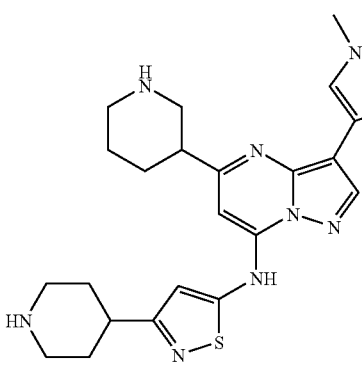

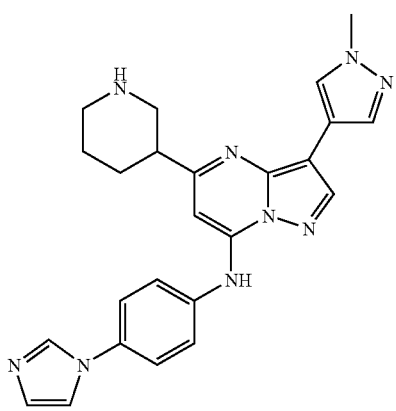

or a pharmaceutically acceptable salt, solvate, ester, isomer or prodrug thereof.

Non-limiting examples of the compounds of Formula III suitable in the practice of the methods of the present invention include those shown on pages 4-12 and 42-60 of the aforementioned US 2006/0040958 some of which are listed below:

or a pharmaceutically acceptable salt, solvate, ester, isomer or prodrug thereof.

Non-limiting examples of compounds of Formula III from copending patent application Ser. No. 11/543,182 filed of even date herewith suitable in the methods of the present invention include:

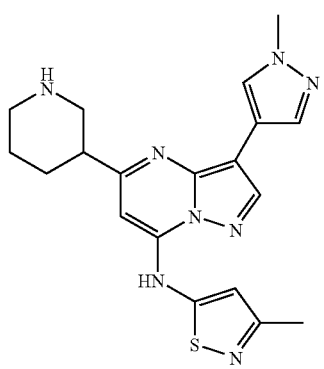
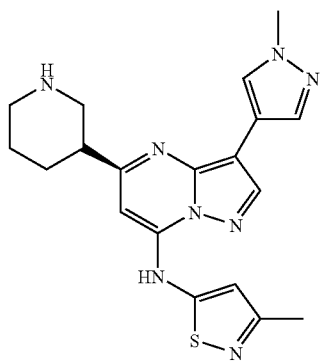
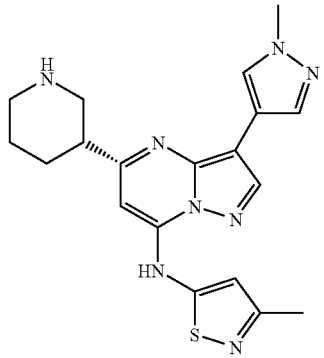
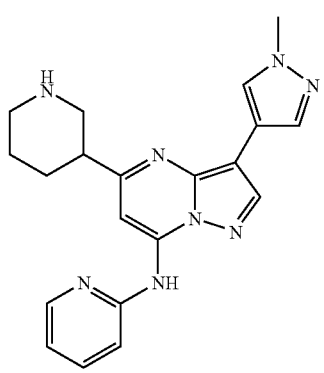
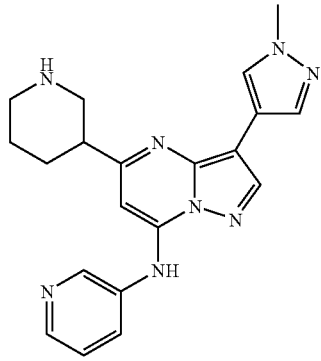
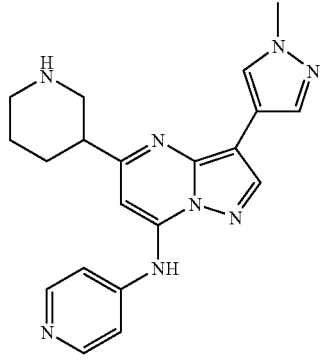
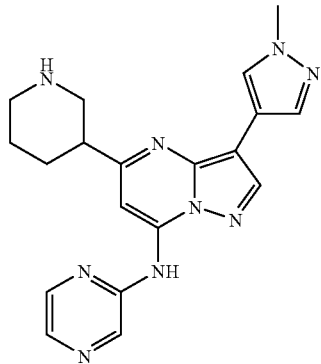
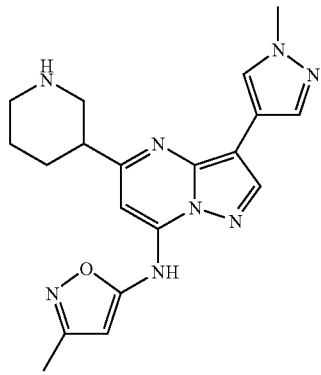

85
-continued
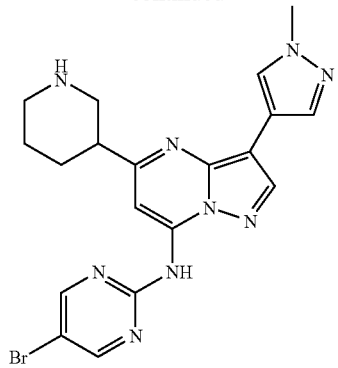
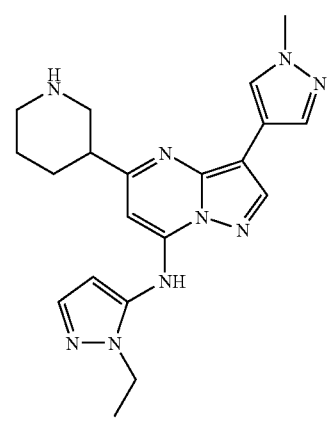
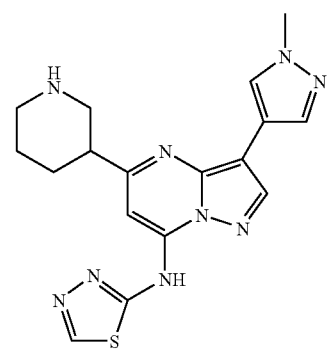
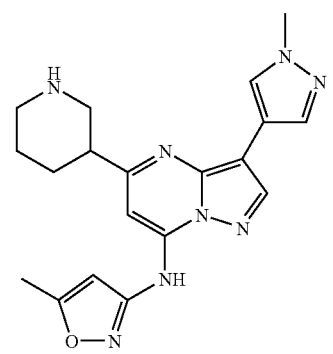
86
-continued
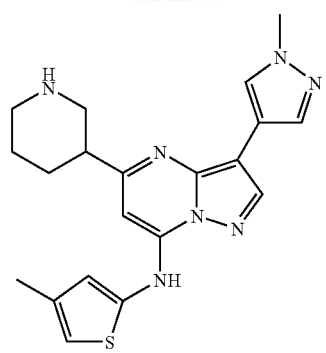
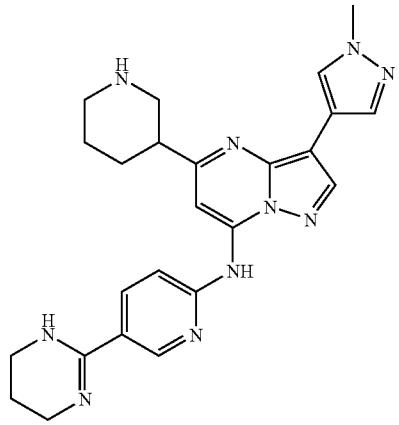
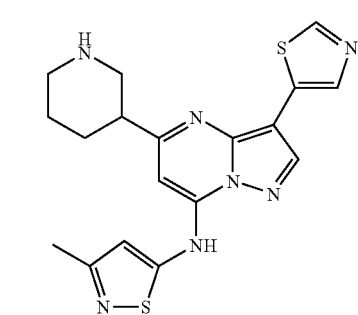
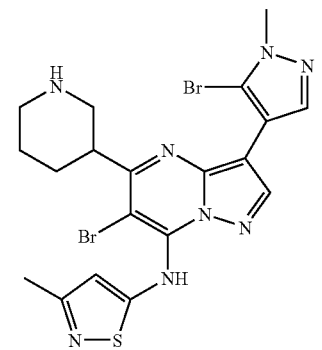

87
-continued
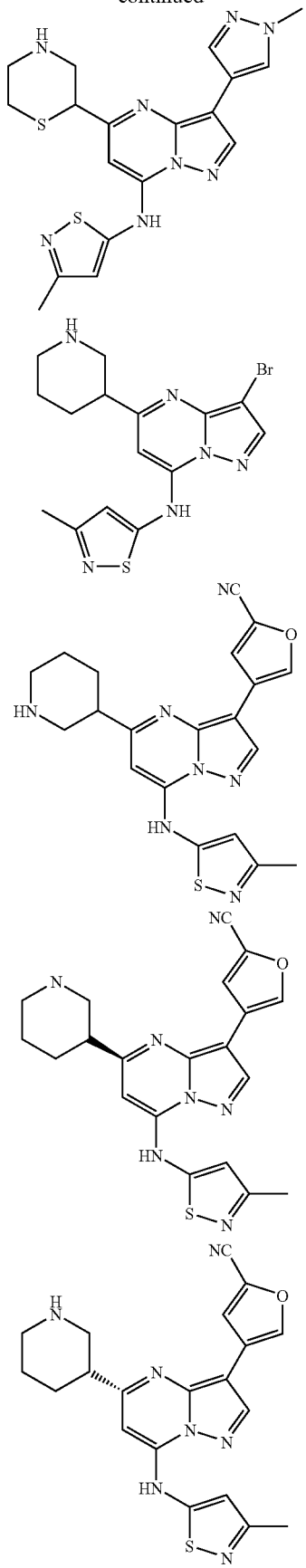
88
-continued
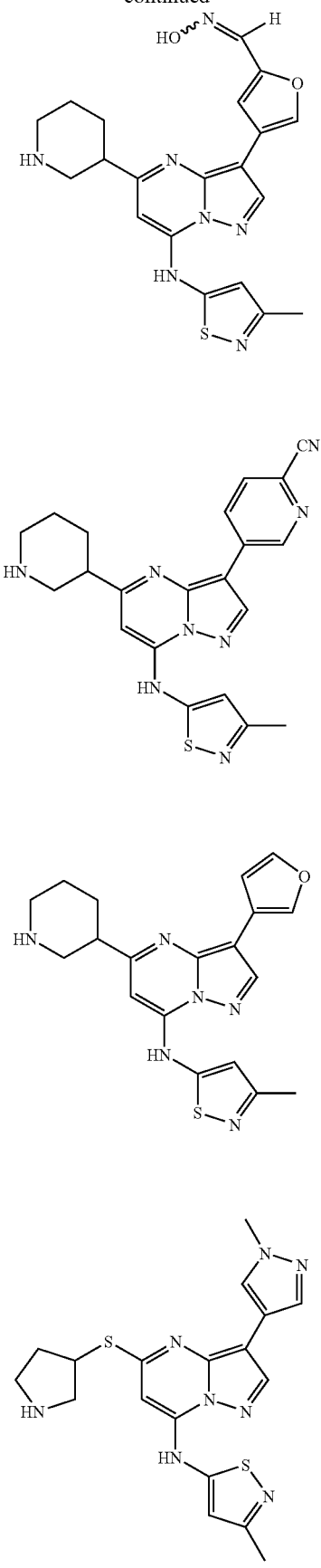

89
-continued
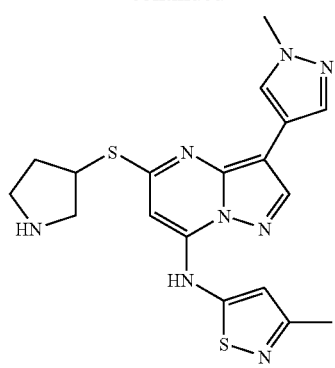
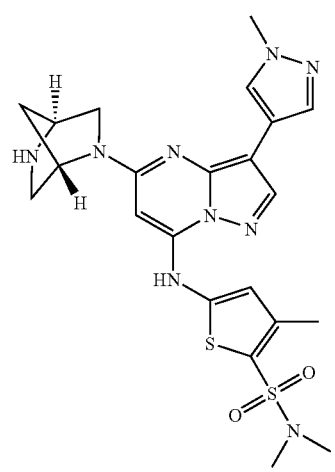
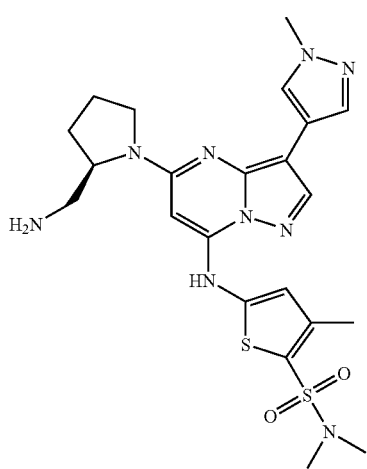
90
-continued
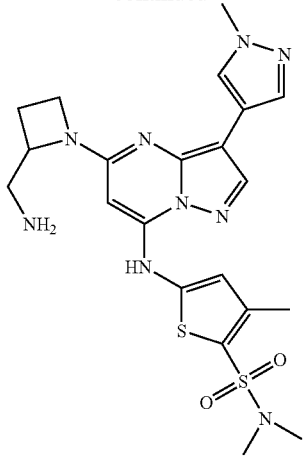
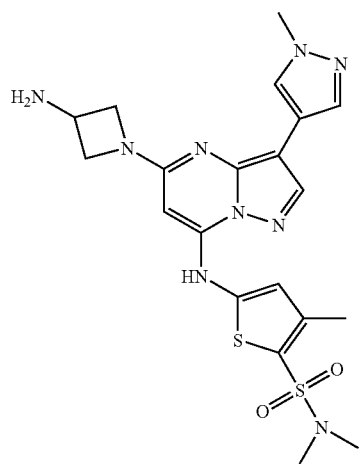
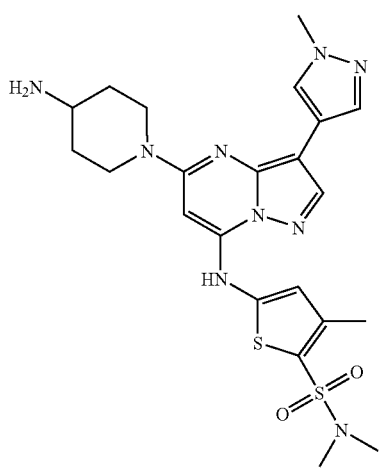

91
-continued
92
-continued
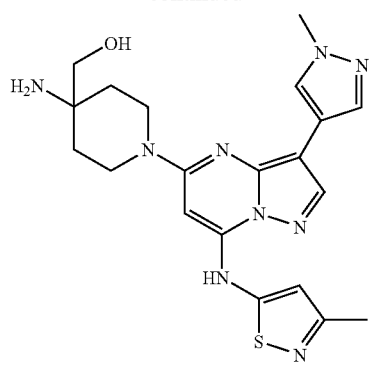
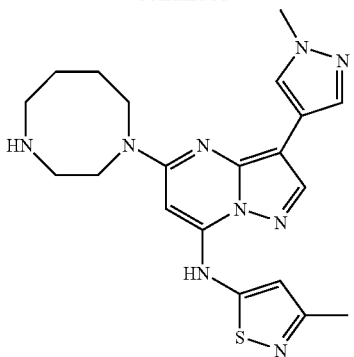
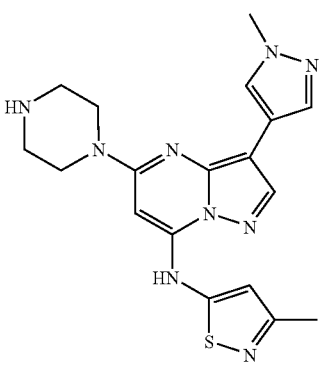
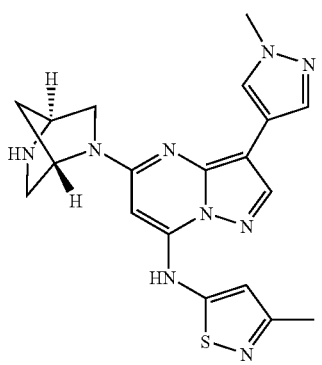
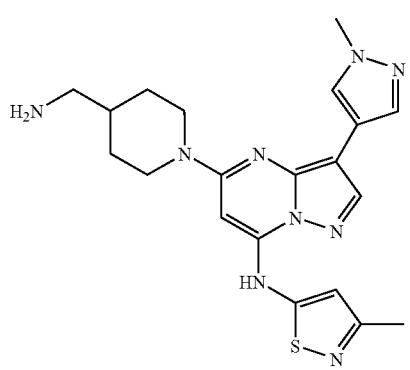

93
-continued
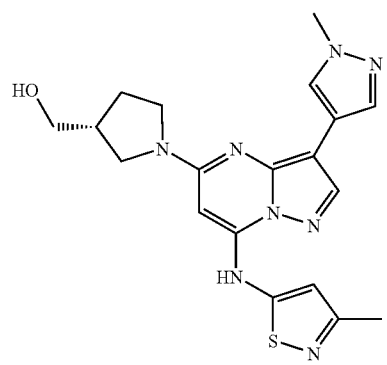
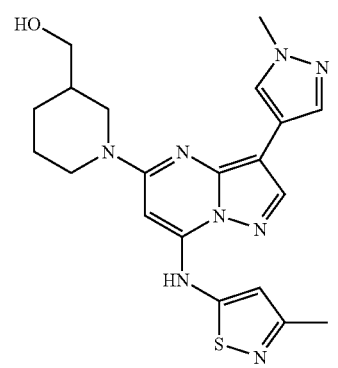
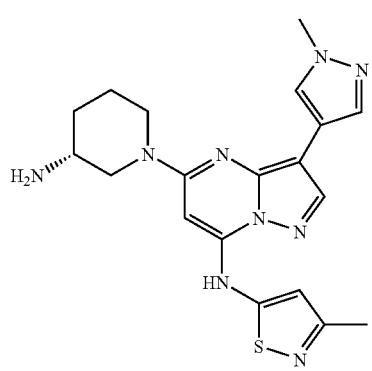
94
-continued
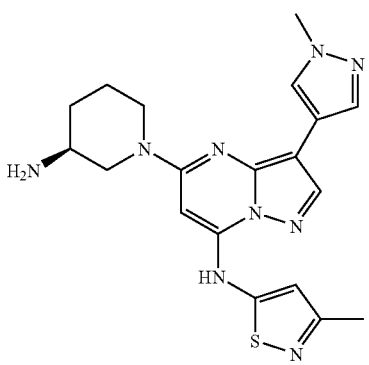
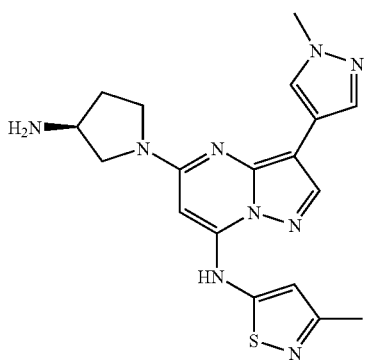
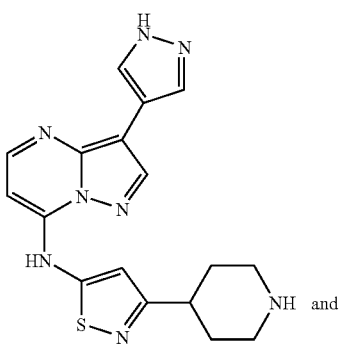
and

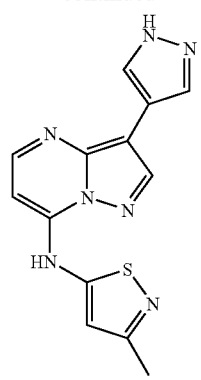
or a pharmaceutically acceptable salt, solvate, ester, isomer or prodrug thereof. Non-limiting examples of the compounds of Formula IV suitable in the practice of the methods of the present invention include those that are shown in col. 5-10 and col. 61-72 of the afore-mentioned U.S. Pat. No. 7,084,271 some of which are shown below:
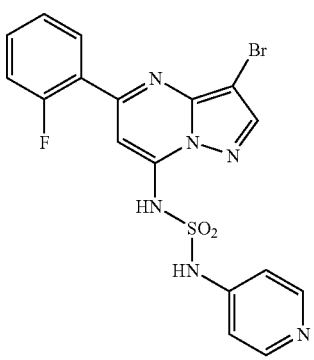
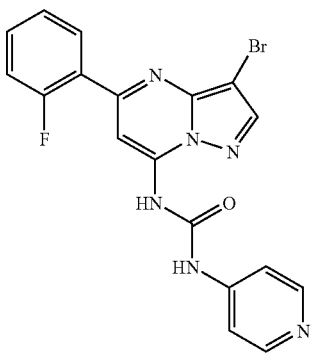
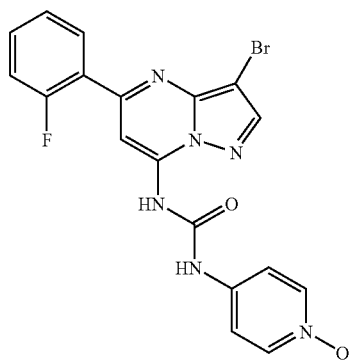
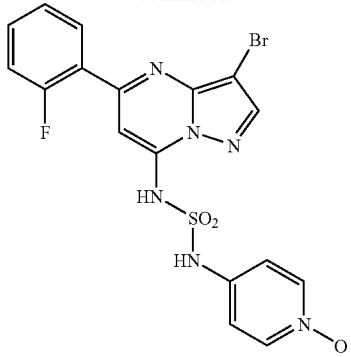
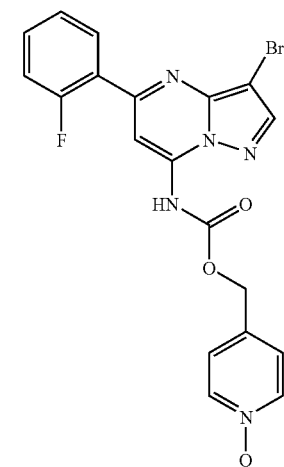
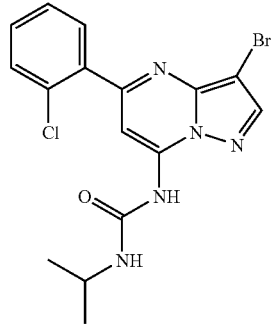
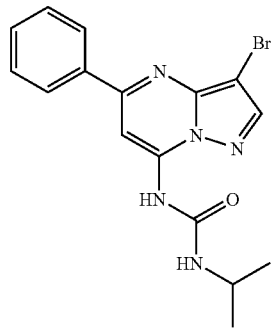

97
-continued
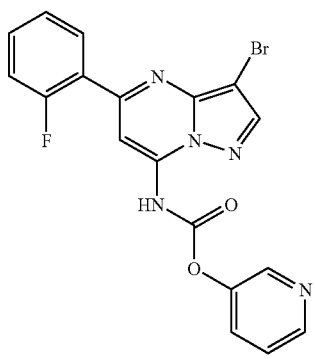
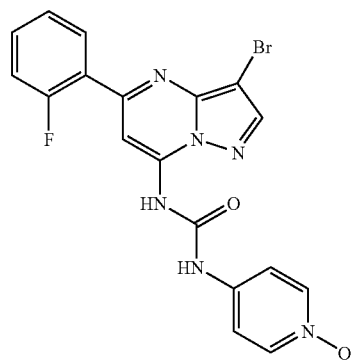
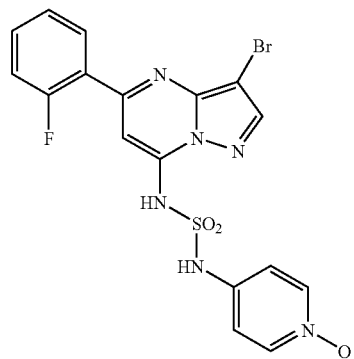
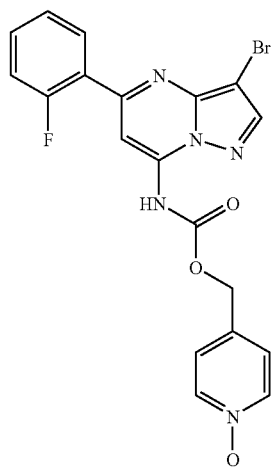
98
-continued
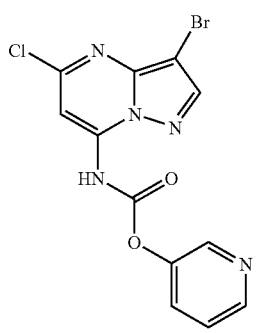
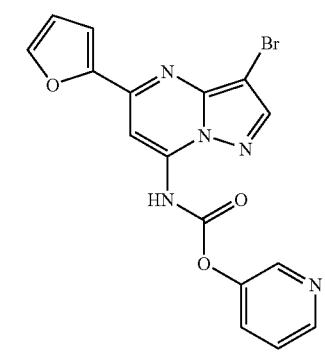
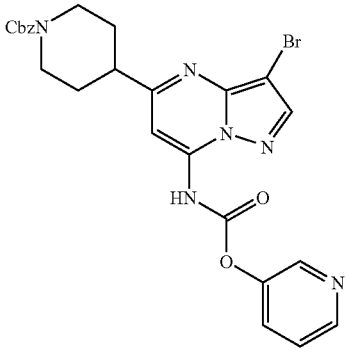
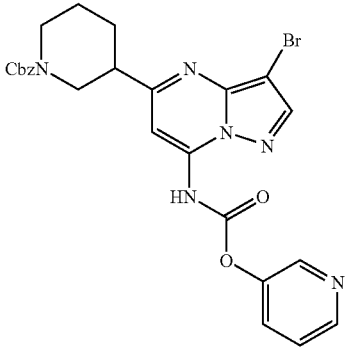

99
-continued
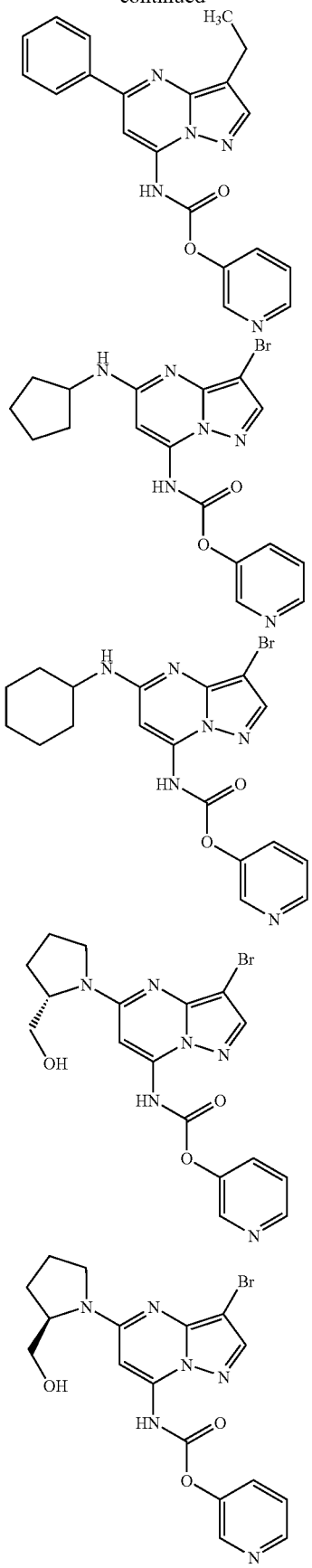
100
-continued
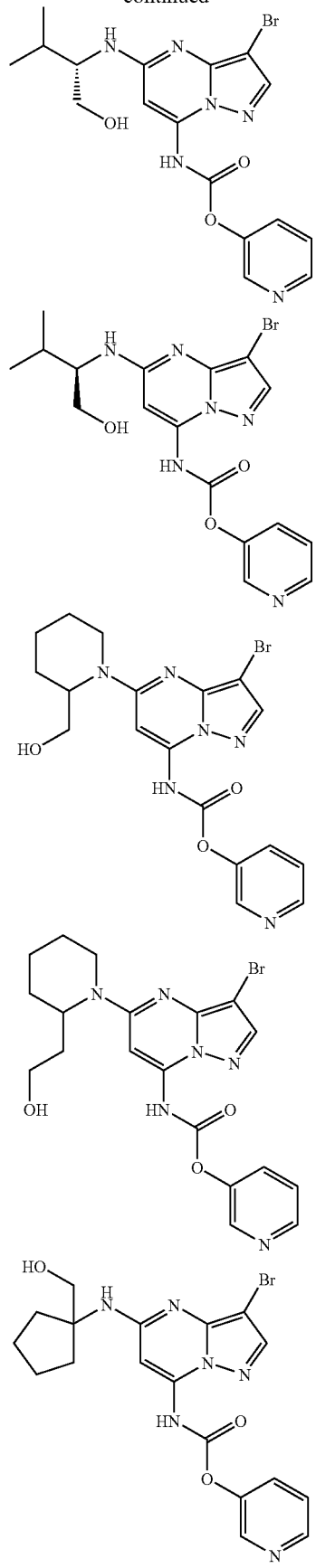

-continued
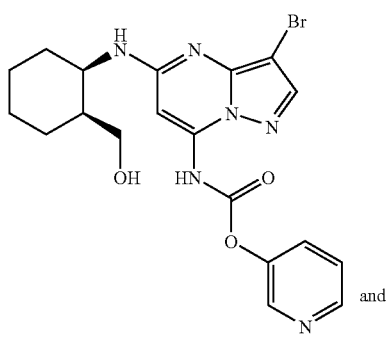
and
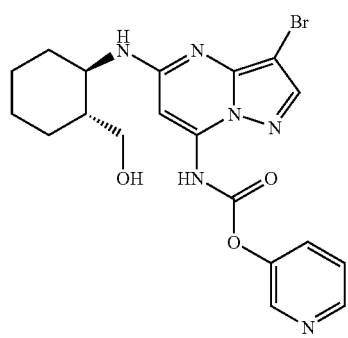
or a pharmaceutically acceptable salt, solvate, ester, isomer or prodrug thereof. Non-limiting examples of the compounds of Formula V suitable in the practice of the methods of the present invention include those on col. 6-col. 15 and col. 69-col. 87 of the afore-mentioned U.S. Pat. No. 7,074,924 some of which are shown below:
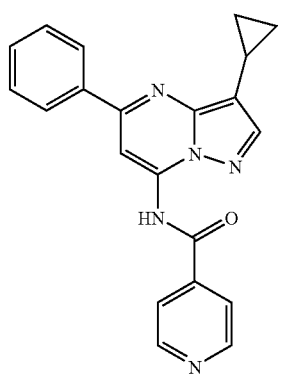
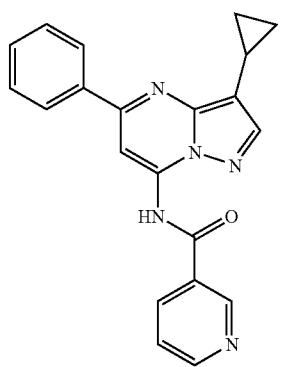
-continued
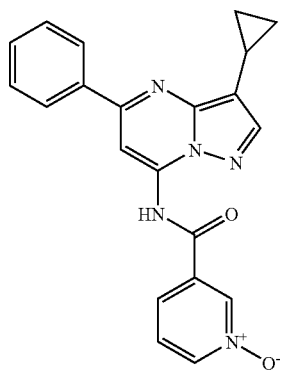
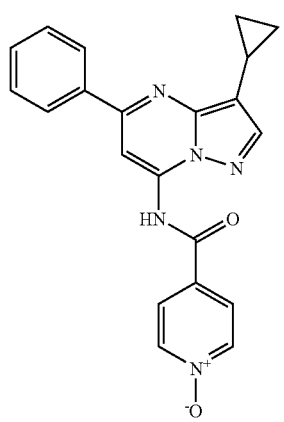
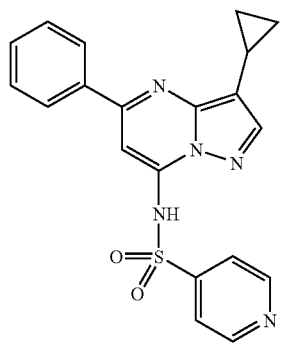
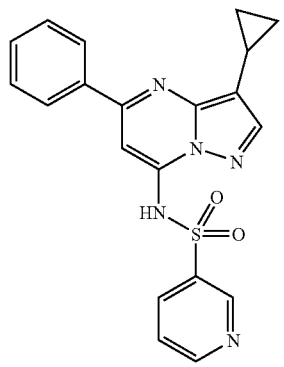

103
-continued
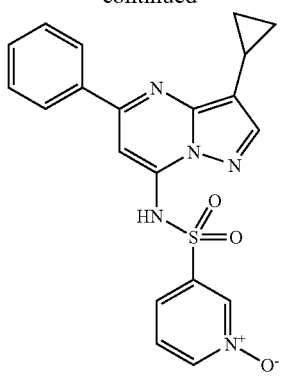
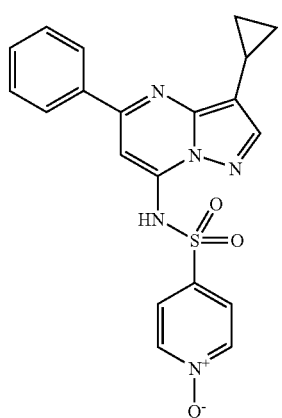
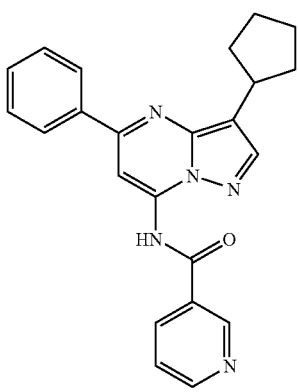
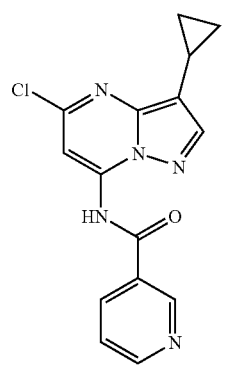
104
-continued
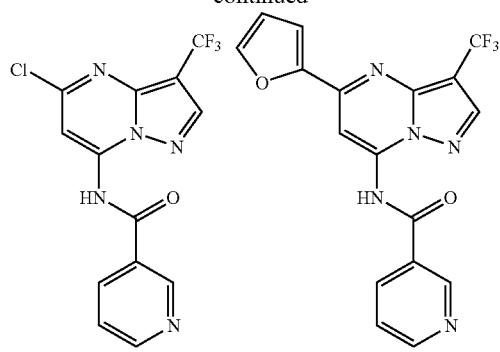
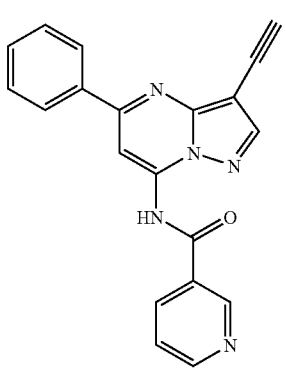
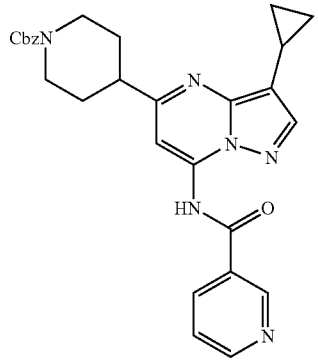
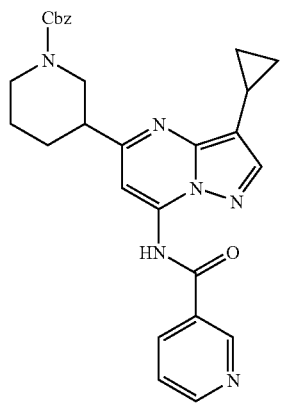

105
-continued
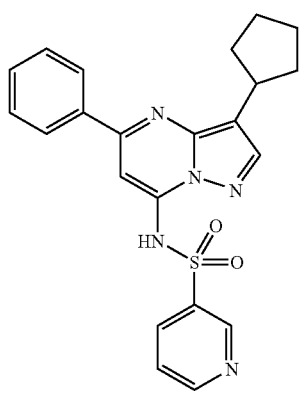
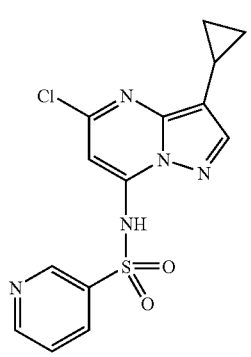
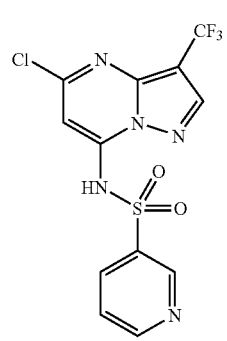
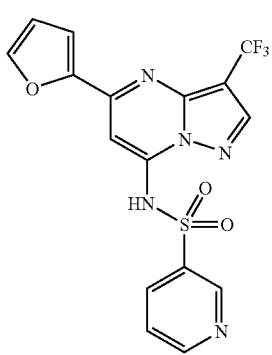
106
-continued
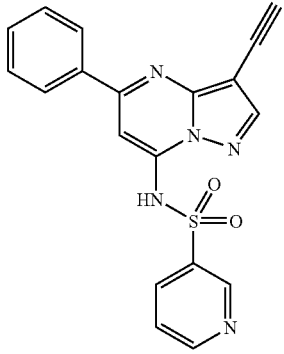
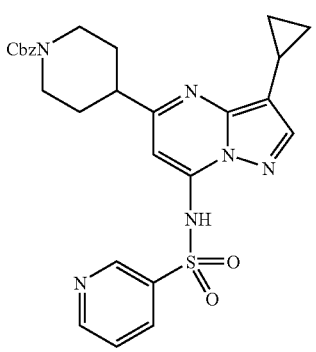
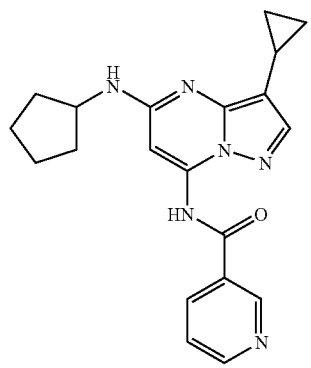

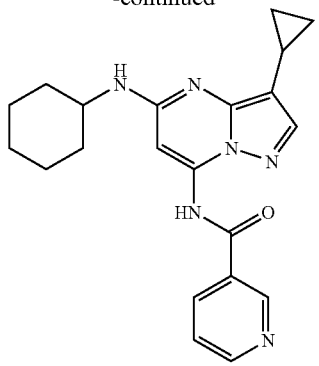
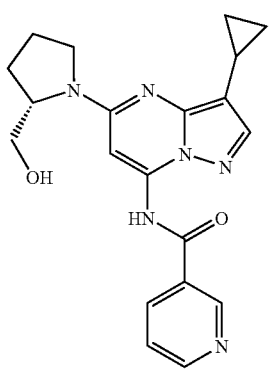
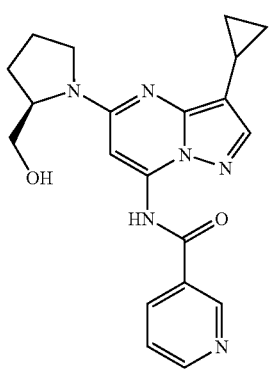
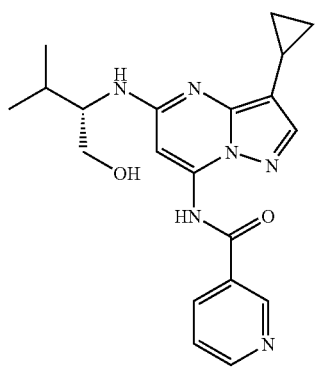
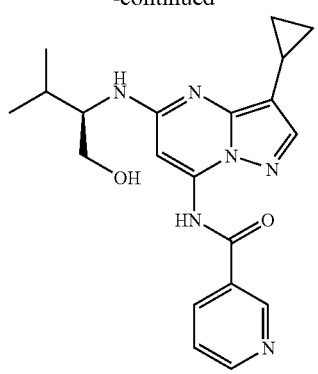
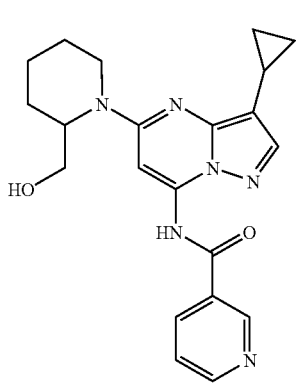
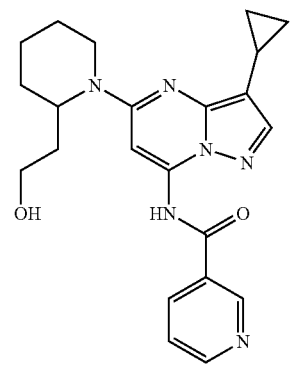
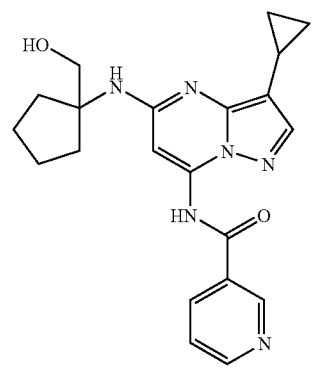

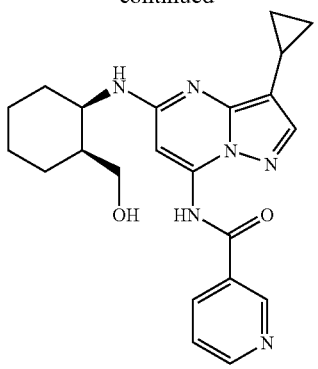
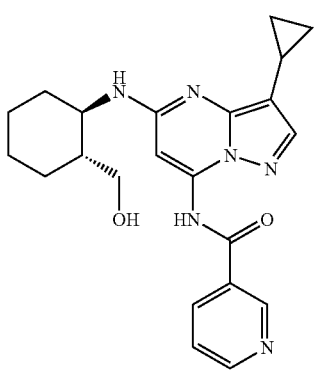
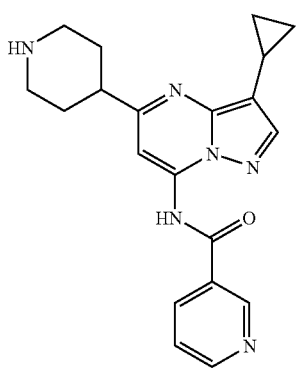
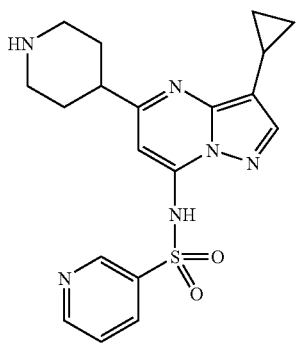
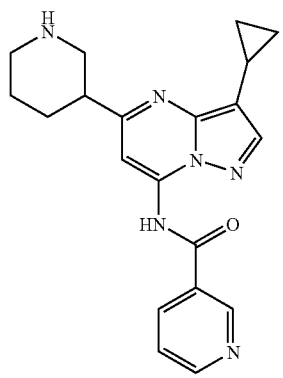
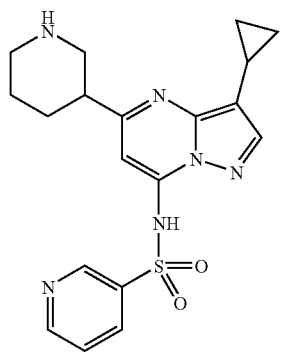
or a pharmaceutically acceptable salt, solvate, ester, isomer or prodrug thereof.
Non-limiting examples of compounds of Formula VI from copending patent application Ser. No. 11/542,921 filed of even date herewith, suitable in the methods of the present invention include:
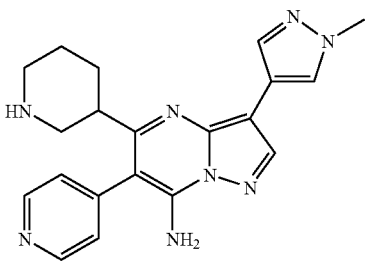
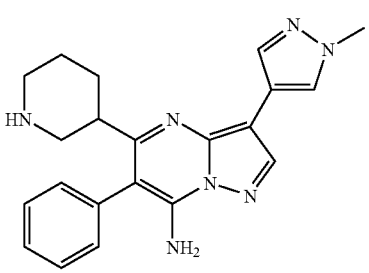

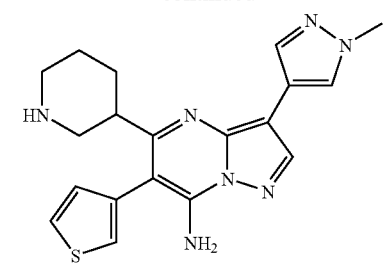
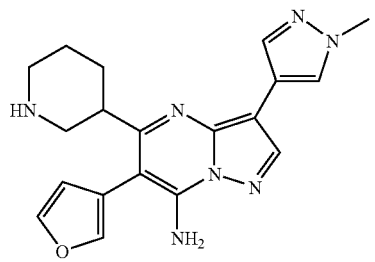
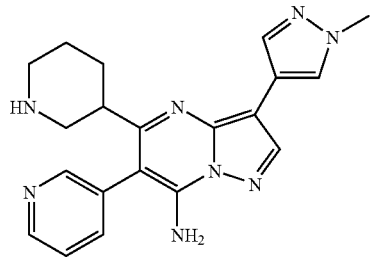
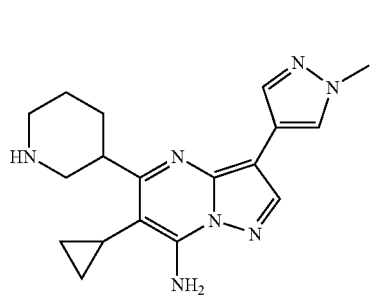
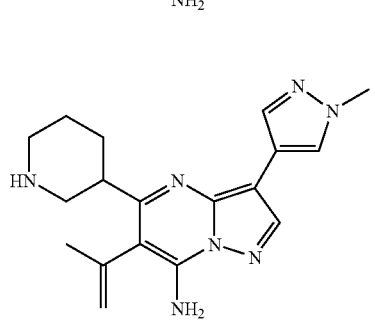
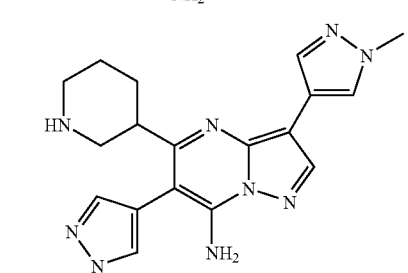
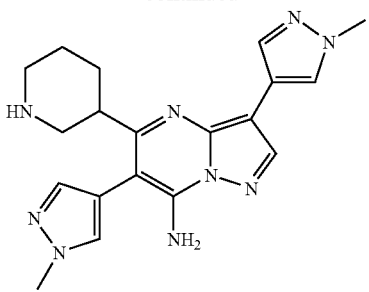
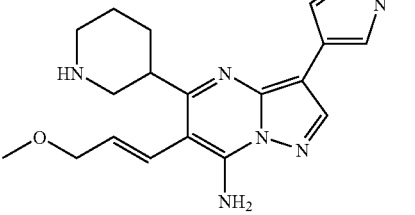
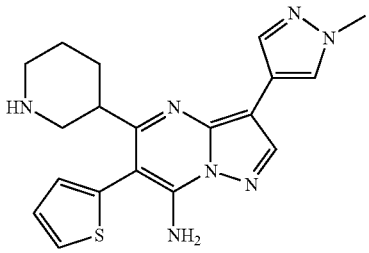
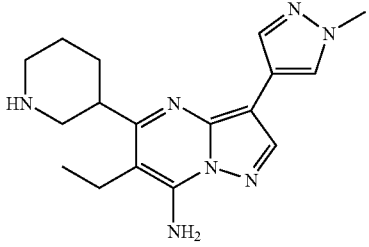
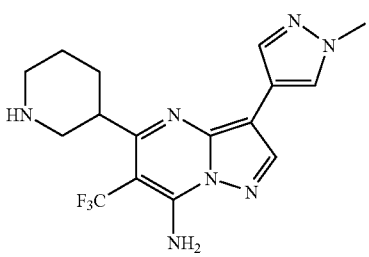
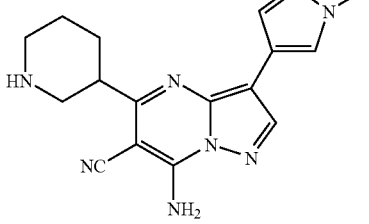

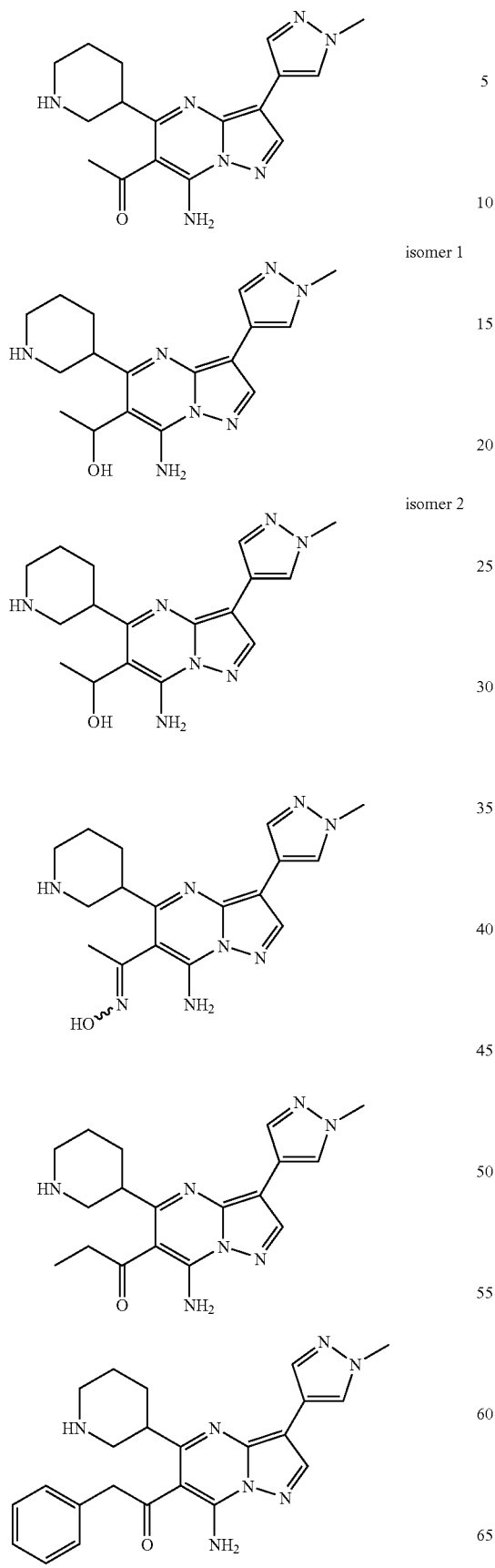
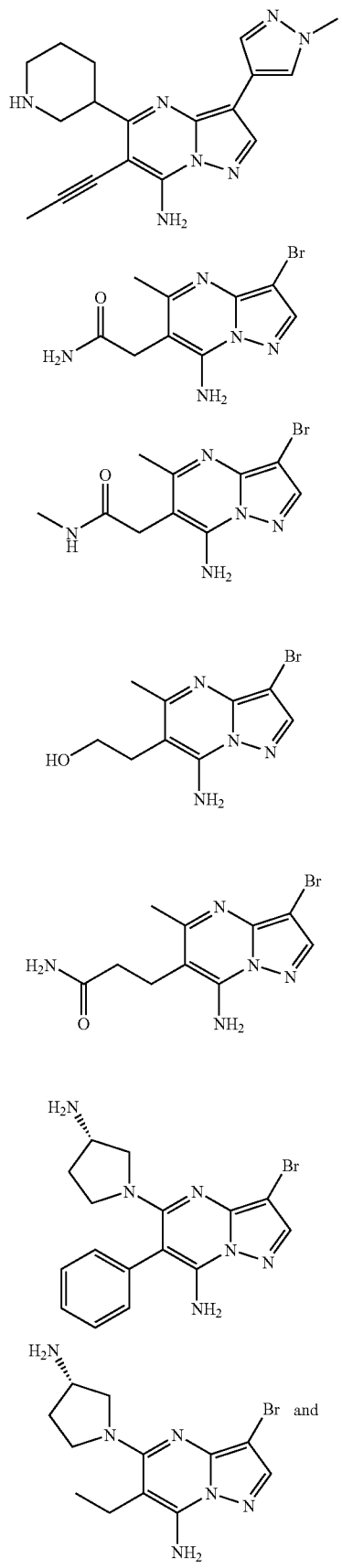

-continued

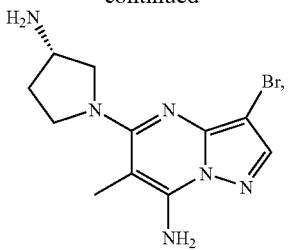

or a pharmaceutically acceptable salt, solvate, ester, isomer or prodrug thereof.

As noted above, the compounds of Formula VI are disclosed in copending patent application Ser. No. 11/542,921 filed of even date herewith.

In some embodiments of the compound of Formula VI, $R^2$ is selected from the group consisting of —$CF_3$; —CN; —$NO_2$; —$NR^5R^{6a}$; —$C(O)R^6$; —$S(O_2)R^7$; —$S(O_2)NR^5R^{10}$; —$N(R^5)S(O_2)R^7$; —$N(R^5)C(O)NR^5R^{10}$; alkyl; alkenyl; alkynyl; heterocyclyl; heterocyclylalkyl; halo; haloalkyl; cycloalkyl; aryl; arylalkyl; arylalkenyl; arylalkynyl; heteroarylalkyl; alkynylalkyl; aryl fused with an aryl or heteroaryl group; heteroaryl; heteroaryl fused with an aryl or heteroaryl group;

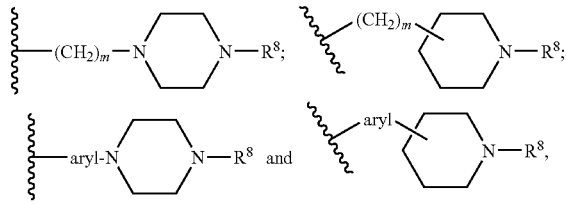

wherein each of the alkyl, alkenyl, alkynyl, heterocyclyl, heterocyclylalkyl, haloalkyl, cycloalkyl, aryl, arylalkyl, arylalkenyl, arylalkynyl, heteroarylalkyl, and alkynylalkyl groups of $R^2$ can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$,—$NR^5R^6$,—$(CR^5R^{11})_pNR^5R^6$,—$C(O_2)R^5$,—$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$, —$C(=N-OH)$, and —$N(R^5)C(O)NR^5R^6$, with the proviso that no carbon adjacent to a nitrogen atom on a heterocyclyl ring carries a —$OR^5$ moiety.

In other embodiments of the compound of Formula VI, $R^2$ is selected from the group consisting of —$CF_3$; —CN; —$NO_2$; —$NR^5R^{6a}$; —$C(O)R^6$; —$S(O_2)R^7$; —$S(O_2)NR^5R^{10}$; —$N(R^5)S(O_2)R^7$; —$N(R^5)C(O)NR^5R^{10}$; alkenyl; alkynyl; heterocyclyl; heterocyclylalkyl; halo; haloalkyl; cycloalkyl; aryl; arylalkyl; arylalkenyl; arylalkynyl; heteroarylalkyl; alkynylalkyl; aryl fused with an aryl or heteroaryl group; heteroaryl; heteroaryl fused with an aryl or heteroaryl group; substituted alkyl;

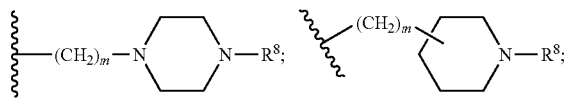

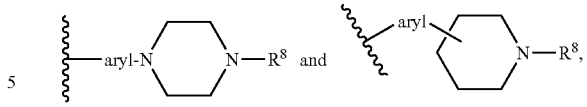

wherein each of the alkenyl, alkynyl, heterocyclyl, heterocyclylalkyl, haloalkyl, cycloalkyl, aryl, arylalkyl, arylalkenyl, arylalkynyl, heteroarylalkyl, and alkynylalkyl groups of $R^2$ can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$, —$NR^5R^6$, —$C(=N-OH)$, —$(CR^5R^{11})_pNR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$, with the proviso that no carbon adjacent to a nitrogen atom on a heterocyclyl ring carries a —$OR^5$ moiety and the substituted alkyl is independently substituted with one or more of the above moieties.

In other embodiments of the compound of Formula VI, $R^2$ is selected from the group consisting of halo; —$NO_2$; —$NR^5R^{6a}$; —$C(O)R^6$; —$SR^6$; —$N(R^5)C(O)NR^5R^{10}$; alkyl; alkenyl; alkynyl; aryl; arylalkynyl; heteroaryl; wherein each of the alkyl, alkenyl, alkynyl, aryl, arylalkynyl, and heteroaryl groups of $R^2$ can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$,—$NR^5R^6$,—$(CR^5R^{11})_pNR^5R^6$,—$C(O_2)R^5$,—$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$, —$C(=N-OH)$, and —$N(R^5)C(O)NR^5R^6$, with the proviso that no carbon adjacent to a nitrogen atom on a heterocyclyl ring carries a —$OR^5$ moiety.

In other embodiments of the compound of Formula VI, $R^2$ is phenyl, napthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl or tetralinyl, then $R^3$ is selected from the group consisting of —$NR^5R^{6a}$ with the proviso that $R^5$ and $R^{6a}$ are not $C_1$-$C_4$ alkyl or $C_3$-$C_6$ cycloalkyl; —$C(O)N(R^5R^6)$; aryl; arylalkyl; heterocyclyl; heterocyclylalkyl; heteroaryl; heteroarylalkyl; substituted alkyl;

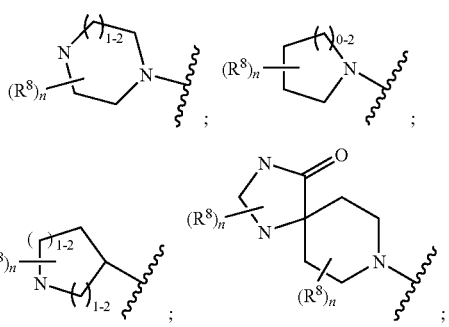

-continued

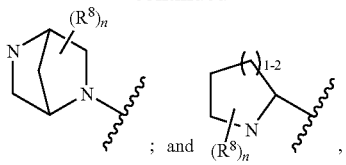
; and , wherein each of the aryl, arylalkyl, heterocyclyl, heterocyclylalkyl, heteroaryl, heteroarylalkyl, substituted alkyl and the heterocyclic moieties whose structures are shown immediately above for $R^3$ can be unsubstituted or optionally independently substituted with one or more moieties which can be the same or different, each moiety being independently selected from the group consisting of halo, alkyl, aryl, cycloalkyl, $CF_3$, CN, $-OCF_3$, $-(CR^{11}R^{11})_gOR^5$, $-OR^5$, $-NR^5R^6$, $-(CR^5R^{11})_pNR^5R^6$, $-C(O_2)R^5$, $-C(O)R^5$, $-C(O)NR^5R^6$, $-SR^6$, $-S(O_2)R^6$, $-C(=N-OH)$, $-S(O_2)NR^5R^6$, $-N(R^5)S(O_2)R^7$, $-N(R^5)C(O)R^7$ and $-N(R^5)C(O)NR^5R^6$, with the proviso that no carbon adjacent to a nitrogen atom on a heterocyclyl ring carries a $-OR^5$ moiety.

In other embodiments of the compound of Formula VI, $R^2$ is aryl substituted with 1-3 aryl or heteroaryl groups which can be the same or different and are each independently selected from the group consisting of phenyl, pyridyl, thiophenyl, furanyl and thiazolo groups.

In other embodiments of the compound of Formula VI, $R^2$ is heteroaryl substituted with 1-3 aryl or heteroaryl groups which can be the same or different and are each independently selected from the group consisting of phenyl, pyridyl, thiophenyl, furanyl and thiazolo groups.

In other embodiments of the compound of Formula VI, $R^2$ is selected from the group consisting of heteroaryl, heteroarylalkyl, heterocyclyl and heterocyclylalkyl.

In other embodiments of the compound of Formula VI, $R^2$ is selected from the group consisting of

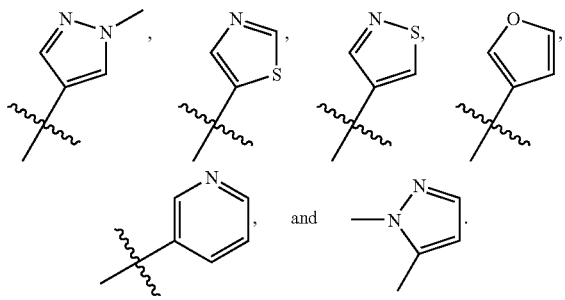

, and .

In some embodiments of the compound of Formula VI, $R^3$ is selected from the group consisting of H; $-NR^5R^{6a}$; $-OR^{6b}$; $-SR^6$; $-C(O)N(R^5R^6)$; alkynyl; cycloalkyl; aryl; arylalkyl; heterocyclyl; heterocyclylalkyl; heteroaryl; heteroarylalkyl;

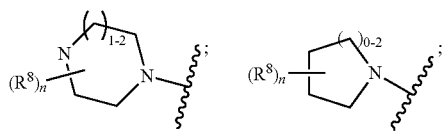

wherein each of the alkynyl; cycloalkyl, aryl, arylalkyl, heterocyclyl, heterocyclylalkyl, heteroaryl, heteroarylalkyl, and the heterocyclic moieties whose structures are shown immediately above for $R^3$ can be unsubstituted or optionally independently substituted with one or more moieties which can be the same or different, each moiety being independently selected from the group consisting of halo, alkyl, aryl, cycloalkyl, $-CF_3$, $-CN$, $-OCF_3$, $-(CR^{11}R^{11})_pOR^5$, $-OR^5$, $-NR^5R^6$, $-(CR^5R^{11})_pNR^5R^6$, $-C(O_2)R^5$, $-C(O)R^5$, $-C(O)NR^5R^6$, $-SR^6$, $-C(=N-OH)$, $-S(O_2)R^6$, $-S(O_2)NR^5R^6$, $-N(R^5)S(O_2)R^7$, $-N(R^5)C(O)R^7$ and $-N(R^5)C(O)NR^5R^6$, with the proviso that no carbon adjacent to a nitrogen atom on a heterocyclyl ring carries a $-OR^5$ moiety.

In other embodiments of the compound of Formula VI, $R^3$ is selected from the group consisting of H; $-NR^5R^{6a}$; $-OR^{6b}$; $-SR^6$; $-C(O)N(R^5R^6)$; alkynyl; cycloalkyl; aryl; arylalkyl; heterocyclyl; heterocyclylalkyl; heteroaryl; heteroarylalkyl; substituted alkyl;

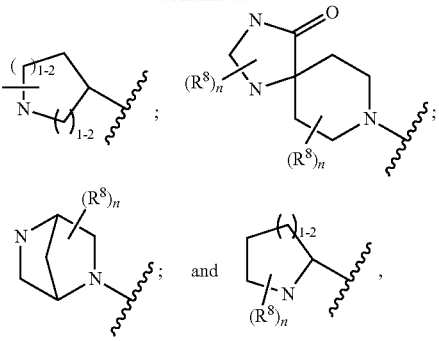

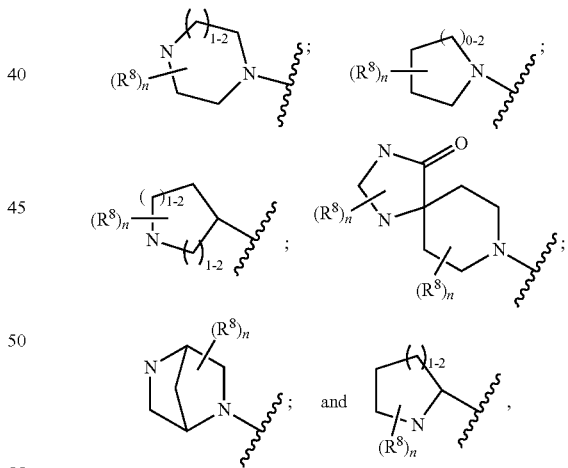

; and , wherein each of the alkynyl; cycloalkyl, aryl, arylalkyl, heterocyclyl, heterocyclylalkyl, heteroaryl, heteroarylalkyl, and the heterocyclic moieties whose structures are shown immediately above for $R^3$ can be unsubstituted or optionally independently substituted with one or more moieties which can be the same or different, each moiety being independently selected from the group consisting of halo, alkyl, aryl, cycloalkyl, $-CF_3$, $-CN$, $-OCF_3$, $-(CR^{11}R^{11})_pOR^5$, $-OR^5$, $-NR^5R^6$, $-(CR^5R^{11})_pNR^5R^6$, $-C(O_2)R^5$, $-C(O)R^5$, $-C(O)NR^5R^6$, $-SR^6$, $-C(=N-OH)$, $-S(O_2)R^6$, $-S(O_2)NR^5R^6$, $-N(R^5)S(O_2)R^7$, $-N(R^5)C(O)R^7$ and —N(R$^5$)C(O)NR$^5$R$^6$, with the proviso that no carbon adjacent to a nitrogen atom on a heterocyclyl ring carries a —OR$^5$ moiety, and wherein the substituted alkyl is substituted with one or more of the above moieties.

In other embodiments of the compound of Formula VI, R$^3$ is selected from the group consisting of —NR$^5$R$^{6a}$; —OR$^{6b}$; —SR$^6$; —C(O)N(R$^5$R$^6$); alkyl; aryl; arylalkyl; heterocyclyl; heterocyclylalkyl; heteroaryl; heteroarylalkyl;

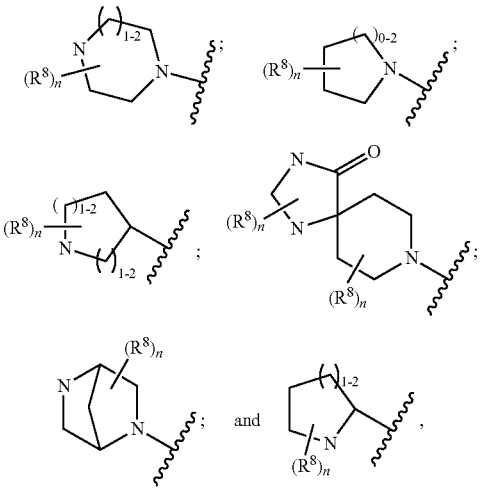

wherein each of the alkyl, aryl, arylalkyl, heterocyclyl, heterocyclylalkyl, heteroaryl, heteroarylalkyl, and the heterocyclic moieties whose structures are shown immediately above for R$^3$ can be unsubstituted or optionally independently substituted with one or more moieties which can be the same or different, each moiety being independently selected from the group consisting of halo, alkyl, aryl, cycloalkyl, —CF$_3$, —CN, —OCF$_3$, —(CR$^{11}$R$^{11}$)$_p$OR$^5$, —C(=N—OH), —OR$^5$, —NR$^5$R$^6$, —(CR$^5$R$^{11}$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$, with the proviso that no carbon adjacent to a nitrogen atom on a heterocyclyl ring carries a —OR$^5$ moiety.

In other embodiments of the compound of Formula VI, R$^3$ is selected from the group consisting of —NR$^5$R$^{6a}$; —C(O)N(R$^5$R$^6$); alkyl; alkynyl; cycloalkyl; aryl; arylalkyl; heterocyclyl; heterocyclylalkyl; heteroaryl; heteroarylalkyl; substituted alkyl;

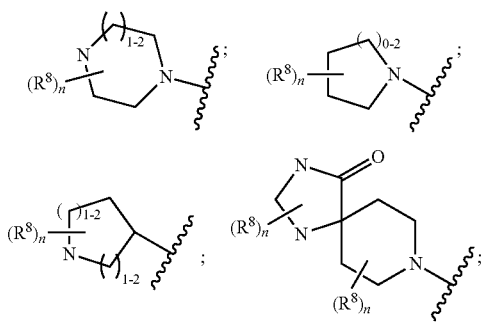

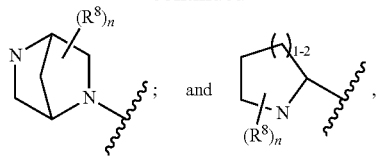

wherein each of the cycloalkyl, aryl, arylalkyl, heterocyclyl, heterocyclylalkyl, heteroaryl, heteroarylalkyl, substituted alkyl and the heterocyclic moieties whose structures are shown immediately above for R$^3$ is independently substituted with one or more moieties which can be the same or different, each moiety being independently selected from the group consisting of —CN, —NR$^5$R$^6$, —C(=N—OH), —(CR$^5$R$^{11}$)$_p$ NR$^5$R$^6$, —C(O)NR$^5$R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$.

In other embodiments of the compound of Formula VI, R$^3$ is selected from the group consisting of —NR$^5$R$^{6a}$; —C(O)N(R$^5$R$^6$);

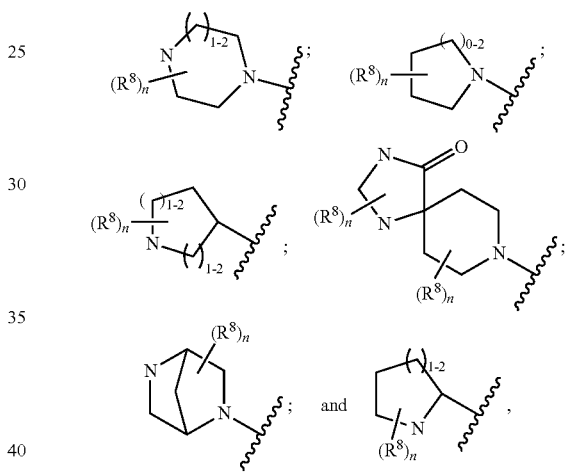

wherein each of the heterocyclic moieties whose structures are shown immediately above for R$^3$ can be unsubstituted or optionally independently substituted with one or more moieties which can be the same or different, each moiety being independently selected from the group consisting of halo, alkyl, aryl, cycloalkyl, CF$_3$, CN, —OCF$_3$, —(CR$^{11}$R$^{11}$)$_p$ OR$^5$, —OR$^5$, —NR$^5$R$^6$, —C(=N—OH), —(CR$^5$R$^{11}$)$_p$ NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$, with the proviso that no carbon adjacent to a nitrogen atom on a heterocyclyl ring carries a —OR$^5$ moiety.

In other embodiments of the compound of Formula VI, R$^3$ is NR$^5$R$^{6a}$, with the proviso that R$^5$ is aryl and R$^{6a}$ is selected from the group consisting of alkenyl, aryl, arylalkyl, arylalkenyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, CF$_3$, OCF$_3$, CN, —OR$^5$, —NR$^5$R$^{10}$, —C(R$^5$R$^{11}$)$_p$ —R$^9$, —N(R$^5$)Boc, —(CR$^5$R$^{11}$)$_p$OR$^5$, —C(O$_2$)R$^5$, —C(O)

$R^5$, —C(O)$NR^5R^{10}$, —$SO_3H$, —$SR^{10}$, —$S(O_2)R^7$, —$S(O_2)NR^5R^{10}$, —$N(R^5)S(O_2)R^7$, —C(=N—OH), —$N(R^5)C(O)R^7$ and —$N(R^5)C(O)NR^5R^{10}$.

In other embodiments of the compound of Formula VI, $R^3$ is selected from the group consisting of

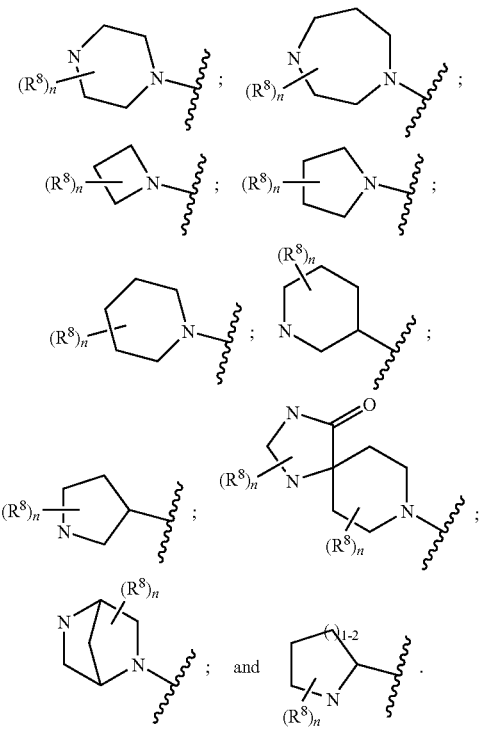

In other embodiments of the compound of Formula VI, $R^3$ is selected from the group consisting of

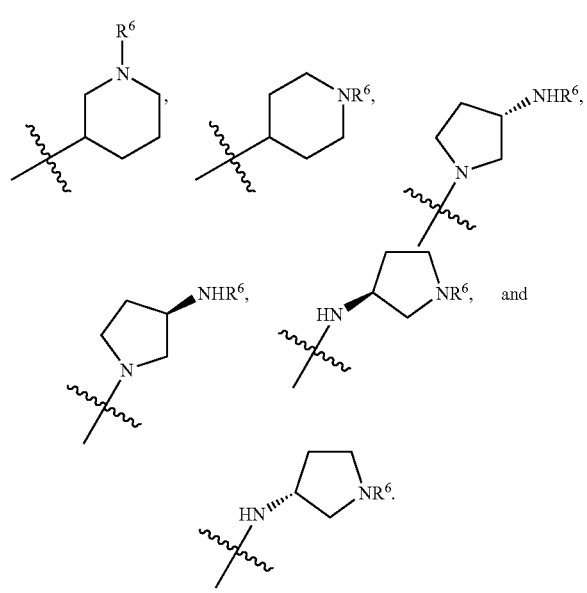

In other embodiments of the compound of Formula VI, $R^4$ is selected from the group consisting of —$CF_3$; —$NR^5R^{6a}$; —$(CR^5R^{11})_pC(O_2)R^6$; —C(O)—$N(R^5R^{10})$; —$OR^{6b}$; —$SR^6$; —$S(O_2)R^7$; —$S(O_2)NR^5R^{10}$; —$N(R^5)S(O_2)R^7$; —$N(R^5)C(O)R^7$; —$N(R^5)C(O)NR^5R^{10}$; heterocyclyl; heterocyclylalkyl; aryl; aryl fused with an aryl or heteroaryl group; heteroaryl; heteroaryl fused with an aryl or heteroaryl group; substituted alkyl;

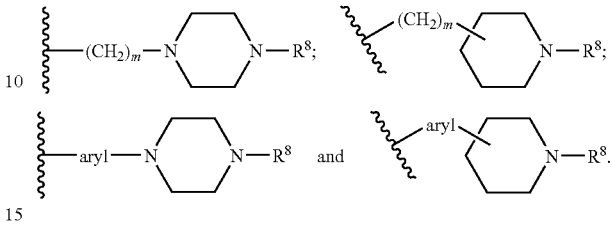

In other embodiments of the compound of Formula VI, $R^4$ is selected from the group consisting of —$CF_3$; —CN; —$NR^6R^{6a}$; —$OR^{6b}$; —$SR^6$; —$S(O_2)R^7$; —C(O)—N$(R^5R^{10})$; —$S(O_2)NR^5R^{10}$; —$N(R^5)S(O_2)R^7$; —$N(R^5)C(O)R^7$; —$N(R^5)C(O)NR^5R^{10}$; heterocyclyl; heterocyclylalkyl; aryl; fused aryl; heteroaryl; fused heteroaryl;

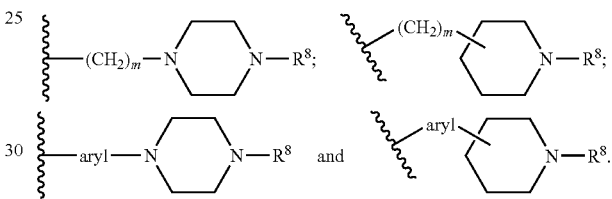

In other embodiments of the compound of Formula VI, $R^4$ is selected from the group consisting of: —$(CR^5R^{11})_pC(O_2)R^6$; —$(CR^5R^{11})_pC(O)NR^5R^{10}$; —C(O)—$N(R^5R^{10}$; hydroxyalkyl; aryl;

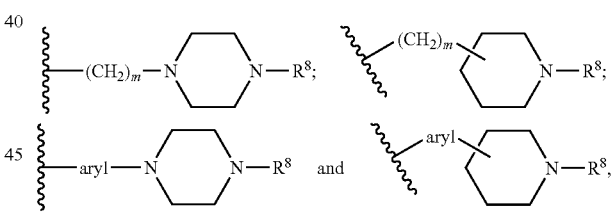

wherein one or more of the aryl and/or one or more of the heteroaryl groups of $R^4$ can be unsubstituted or optionally substituted with one or more moieties which can be the same or different, each moiety being independently selected from the group consisting of halo, —CN, —$OR^5$, —$SR^5$, —$S(O_2)R^6$, —$S(O_2)NR^5R^6$, —$NR^5R^6$, —C(O)$NR^5R^6$, $CF_3$, alkyl, aryl and $OCF_3$.

In other embodiments of the compound of Formula VI, $R^4$ is aryl substituted with 1-3 aryl or heteroaryl groups which can be the same or different and are each independently selected from the group consisting of phenyl, pyridyl, thiophenyl, furanyl and thiazolo groups.

In other embodiments of the compound of Formula VI, $R^4$ is heteroaryl substituted with 1-3 aryl or heteroaryl groups which can be the same or different and are each independently selected from the group consisting of phenyl, pyridyl, thiophenyl, furanyl and thiazolo groups.

In other embodiments of the compound of Formula VI, $R^4$ is selected from the group consisting of

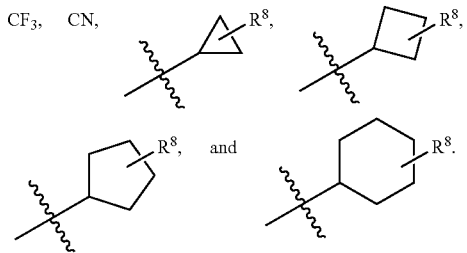

In other embodiments of the compound of Formula VI, $R^4$ is substituted alkyl which is independently substituted with one or more of the following moieties: halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$SR^6$, —$S(O_2)R^6$, —$C(=N—OH)$, —$S(O_2)NR^5R^6$, —$N(R^5)S(O_2)R^7$, —$N(R^5)C(O)R^7$ and —$N(R^5)C(O)NR^5R^6$, with the proviso that no carbon adjacent to a nitrogen atom on a heterocyclyl ring carries a —$OR^5$ moiety.

In another embodiment, the compound of Formula VI is a compound of the formula:

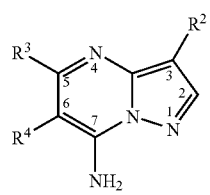

wherein $R^2$ is heteroaryl, $R^3$ is heterocyclyl and $R^4$ is heteroaryl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$SR^6$, —$S(O_2)R^6$, —$C(=N—OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of the formula:

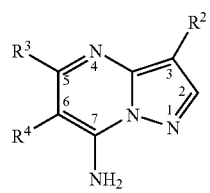

wherein $R^2$ is a pyrazolyl, $R^3$ is piperidinyl and $R^4$ is pyrazolyl, wherein each of said pyrazolyl and piperidinyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$SR^6$, —$S(O_2)R^6$, —$C(=N—OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of the formula:

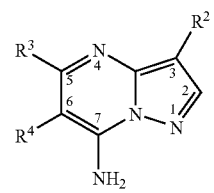

wherein $R^2$ is 1-methyl-pyrazol-4-yl, $R^3$ is piperidin-3-yl, and $R^4$ is pyridin-4-yl.

In another embodiment, this invention provides a compound of the formula:

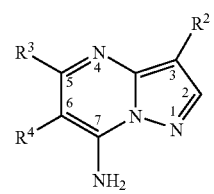

wherein $R^2$ is 1-methyl-pyrazol-4-yl, $R^3$ is piperidin-3-yl, and $R^4$ is thien-3-yl.

In another embodiment, the compound of Formula VI is a compound of the formula:

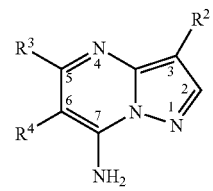

wherein R2 is heteroaryl, R3 is heterocyclyl and R4 is alkynyl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$SR^6$, —$S(O_2)R^6$, —$C(=N—OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of the formula:

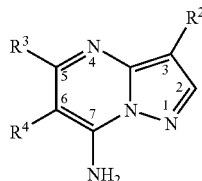

wherein R² is pyrazolyl, R³ is piperidinyl and R⁴ is propynyl.

In another embodiment, the compound of Formula VI is a compound of the formula:

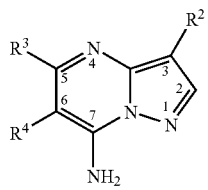

wherein R² is 1-methyl-pyrazol-4-yl, R³ is piperidin-3-yl and R⁴ is propynyl.

In another embodiment, the compound of Formula VI is a compound of the formula:

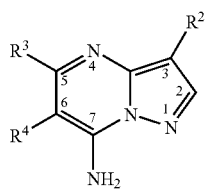

wherein R2 is heteroaryl, R3 is heterocyclyl and R4 is alkenyl (substituted with alkoxy), wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$NR⁵R⁶, —C(O₂)R⁵, —C(O)R⁵, —C(=N—OH), —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

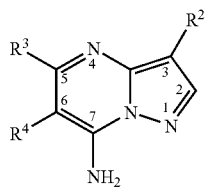

wherein R² is pyrazolyl, R³ is piperidinyl and R⁴ is alkenyl (substituted with alkoxy).

In another embodiment, the compound of Formula VI is a compound of the formula:

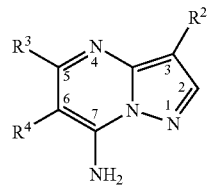

wherein R² is 1-methyl-pyrazol-4-yl, R³ is piperidin-3-yl and R⁴ is 3-(methoxy)propylene-1-yl.

In another embodiment, the compound of Formula VI is a compound of the formula:

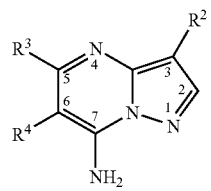

wherein R² is heteroaryl, R³ is heterocyclyl, and R⁴ is cycloalkyl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$NR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

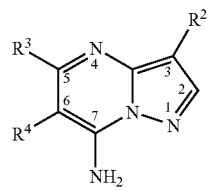

wherein R² is pyrazolyl. R³ is piperidinyl and R⁴ is cyclopropyl.

In another embodiment, the compound of Formula VI is a compound of the formula:

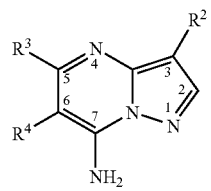

wherein R² is 1-methyl-pyrazol-4-yl, R³ is piperidin-3-yl and R⁴ is cyclopropyl.

In another embodiment, the compound of Formula VI is a compound of the formula:

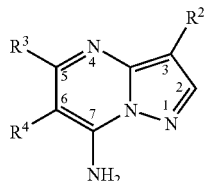

wherein $R^2$ is heteroaryl, $R^3$ is heterocyclyl and $R^4$ is cyano, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$ NR$^5$R$^6$, —C(O$_2$)R$^5$, —C(O)R$^5$, —C(O)NR$^5$R$^6$, —SR$^6$, —S(O$_2$)R$^6$, —C(=N—OH), —S(O$_2$)NR$^5$R$^6$, —N(R$^5$)S(O$_2$)R$^7$, —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of the formula:

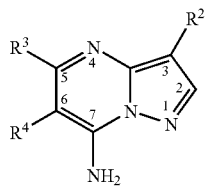

wherein $R^2$ is pyrazolyl, $R^3$ is piperidinyl and $R^4$ is cyano.

In another embodiment, the compound of Formula VI is a compound of the formula:

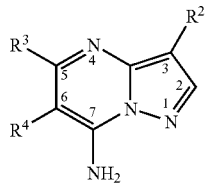

wherein $R^2$ is 1-methyl-pyrazol-4-yl, $R^3$ is piperidin-3-yl and $R^4$ is cyano.

In another embodiment, the compound of Formula VI is a compound of the formula:

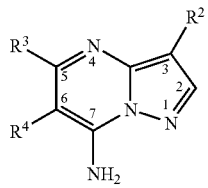

wherein $R^2$ is heteroaryl, $R^3$ is heterocyclyl and $R^4$ is hydroxyalkyl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$NR$^5$R$^6$, —C(O$_2$)R$^5$, —C(O)R$^5$, —C(O)NR$^5$R$^6$, —SR$^6$, —S(O$_2$)R$^6$, —C(=N—OH), —S(O$_2$)NR$^5$R$^6$, —N(R$^5$)S(O$_2$)R$^7$, —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of the formula:

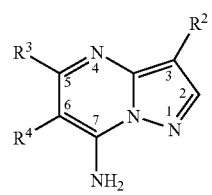

wherein $R^2$ is pyrazolyl, $R^3$ is piperidinyl and $R^4$ is 1-hydroxyethyl.

In another embodiment, the compound of Formula VI is a compound of the formula:

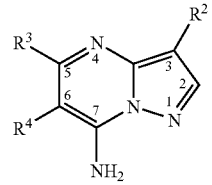

wherein $R^2$ is 1-methyl-pyrazol-4-yl, $R^3$ is piperidin-3-yl and $R^4$ is 1-hydroxyethyl.

In another embodiment, the compound of Formula VI is a compound of the formula:

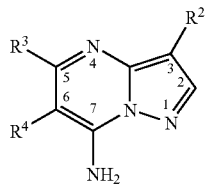

wherein $R^2$ is heteroaryl, $R^3$ is heterocyclyl and $R^4$ is —C(O)R$^6$, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$ NR$^5$R$^6$, —C(O$_2$)R$^5$, —C(O)R$^5$, —C(O)R$^5$, —C(O)NR$^5$R$^5$, —SR$^6$, —S(O$_2$)R$^6$, —C(=N—OH), —S(O$_2$)NR$^5$R$^6$, —N(R$^5$)S(O$_2$)R$^7$, —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of the formula:

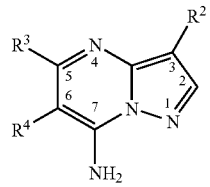

wherein R² is pyrazolyl, R³ is piperidinyl and R⁴ is methylcarbonyl.

In another embodiment, the compound of Formula VI is a compound of the formula:

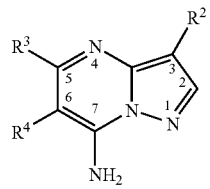

wherein R² is 1-methyl-pyrazol-4-yl, R³ is piperidin-3-yl and R⁴ is methylcarbonyl.

In another embodiment, the compound of Formula VI is a compound of the formula:

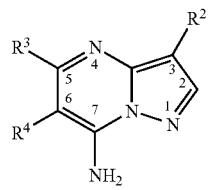

wherein R² is heteroaryl, R³ is heterocyclyl and R⁴ is aryl, wherein each of said aryl, heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$ NR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

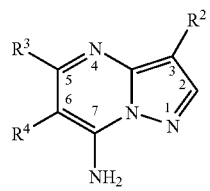

wherein R² is pyrazolyl, R³ is piperidinyl and R⁴ is phenyl.

In another embodiment, the compound of Formula VI is a compound of the formula:

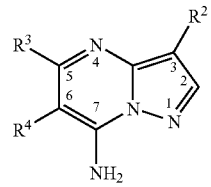

wherein R² is 1-methyl-pyrazol-4-yl, R³ is piperidin-3-yl and R⁴ is phenyl.

In another embodiment, the compound of Formula VI is a compound of the formula:

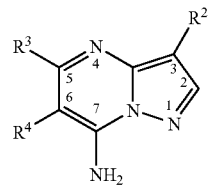

wherein R² is heteroaryl, R³ is heterocyclyl and R⁴ is heteroaryl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$ NR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

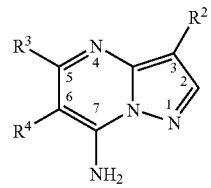

wherein R² is pyrazolyl, R³ is piperidinyl and R⁴ is furanyl.

In another embodiment, the compound of Formula VI is a compound of the formula:

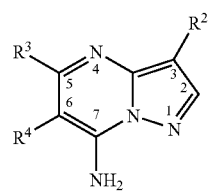

wherein R² is 1-methyl-pyrazol-4-yl, R³ is piperidin-3-yl and R⁴ is furan-3-yl.

In another embodiment, the compound of Formula VI is a compound of the formula:

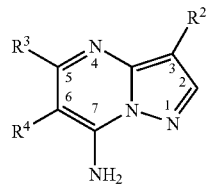

wherein R² is heteroaryl, R³ is heterocyclyl and R⁴ is heteroaryl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)ₚOR⁵, —OR⁵, —NR⁵R⁶, —(CR⁵R¹¹)ₚNR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

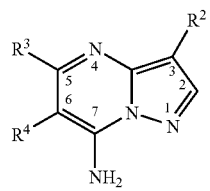

wherein R² is pyrazolyl, R³ is piperidinyl and R⁴ is pyridyl.

In another embodiment, the compound of Formula VI is a compound of the formula:

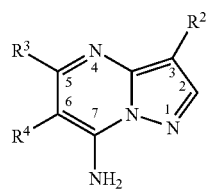

wherein R² is 1-methyl-pyrazol-4-yl, R³ is piperidin-3-yl and R⁴ is pyrid-3-yl.

In another embodiment, the compound of Formula VI is a compound of the formula:

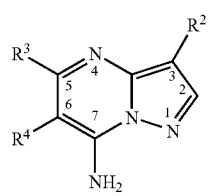

wherein R² is heteroaryl, R³ is heterocyclyl and R⁴ is alkenyl, wherein each of said alkenyl, heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)ₚOR⁵, —OR⁵, —NR⁵R⁶, —(CR⁵R¹¹)ₚNR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

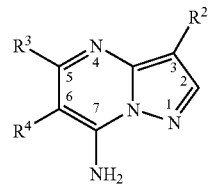

wherein R² is pyrazolyl, R³ is piperidinyl and R⁴ is alkenyl.

In another embodiment, the compound of Formula VI is a compound of the formula:

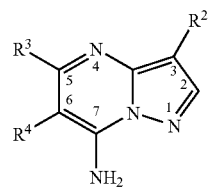

wherein R² is 1-methyl-pyrazol-4-yl, R³ is piperidin-3-yl and R⁴ is —C(=CH₂)—CH₃.

In another embodiment, the compound of Formula VI is a compound of the formula:

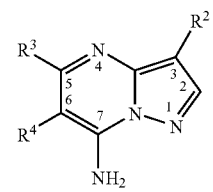

wherein R² is heteroaryl, R³ is heterocyclyl and R⁴ is heteroaryl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)ₚOR⁵, —OR⁵, —NR⁵R⁶, —(CR⁵R¹¹)ₚNR⁵R⁶, —C(O₂)R⁵, —C(O)R⁵, —C(O)NR⁵R⁶, —SR⁶, —S(O₂)R⁶, —C(=N—OH), —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R¹¹, and p are as defined earlier.

In another embodiment, the compound of Formula VI is a compound of the formula:

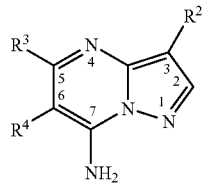

wherein R² is pyrazolyl, R³ is piperidinyl and R⁴ is pyrazolyl.

In another embodiment, the compound of Formula VI is a compound of the formula:

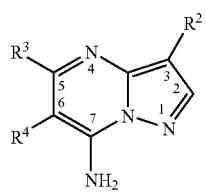

wherein R² is 1-methyl-pyrazol-4-yl, R³ is piperidin-3-yl and R⁴ is 1-hydroxyethyl-pyrazol-4-yl.

In another embodiment, the compound of Formula VI is a compound of the formula:

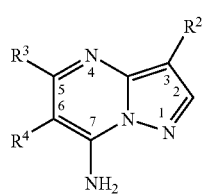

wherein R² is heteroaryl, R³ is heterocyclyl and R⁴ is heteroaryl, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$ NR⁵R⁶, —C(O₂)R⁵, —C(O)R⁵, —C(O) NR⁵R⁶, —SR⁶, —S(O₂)R⁶, —C(=N—OH), —S(O₂) NR⁵R⁶, —N(R⁵)S(O₂)R⁷, —N(R⁵)C(O)R⁷ and —N(R⁵)C (O)NR⁵R⁶, wherein R⁵, R⁶, R¹¹, and p are as defined earlier.

In another embodiment, the compound of Formula VI is a compound of the formula:

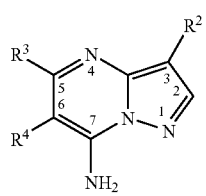

wherein R² is pyrazolyl, R³ is piperidinyl and R⁴ is thienyl.

In another embodiment, the compound of Formula VI is a compound of the formula:

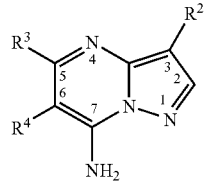

wherein R² is 1-methyl-pyrazol-4-yl, R³ is piperidin-3-yl and R⁴ is thien-2-yl.

In another embodiment, the compound of Formula VI is a compound of the formula:

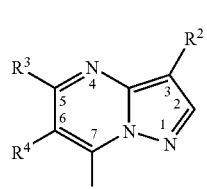

wherein R² is heteroaryl, R³ is heterocyclyl and R⁴ is alkyl, wherein each of said alkyl, heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR¹¹R¹¹)$_p$OR⁵, —OR⁵, —NR⁵R⁶, —(CR⁵R¹¹)$_p$ NR⁵R⁶, —C(O₂)R⁵, —C(O)R⁵, —C(O) NR⁵R⁶, —SR⁶, —S(O₂)R⁶, —C(=N—OH), —S(O₂) NR⁵R⁶, —N(R⁵)S(O₂)R⁷, —N(R⁵)C(O)R⁷ and —N(R⁵)C (O)NR⁵R⁶, wherein R⁵, R⁶, R¹¹, and p are as defined earlier.

In another embodiment, the compound of Formula VI is a compound of the formula:

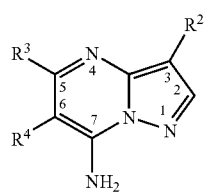

wherein R² is pyrazolyl, R³ is piperidinyl and R⁴ is ethyl.

In another embodiment, the compound of Formula VI is a compound of the formula:

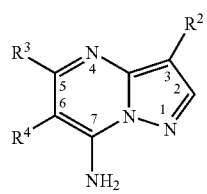

wherein R² is 1-methyl-pyrazol-4-yl, R³ is piperidin-3-yl and R⁴ is ethyl.

In another embodiment, the compound of Formula VI is a compound of the formula:

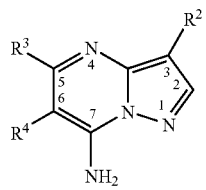

wherein $R^2$ is heteroaryl, $R^3$ is heterocyclyl and $R^4$ is an oxime, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$, —$NR^5R^6$, —$(CR^5R^{11})_p$ $NR^6$, —$C(O_2)R^5$, —$C(O)R^5$, —$C(O)NR^5R^6$, —$SR^6$, —$S(O_2)R^6$, —$C(=N-OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of the formula:

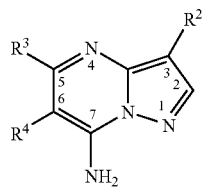

wherein $R^2$ is pyrazolyl, $R^3$ is piperidinyl and $R^4$ is an oxime.

In another embodiment, the compound of Formula VI is a compound of the formula:

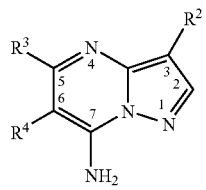

wherein $R^2$ is 1-methyl-pyrazol-4-yl, $R^3$ is piperidin-3-yl and $R^4$ is —$C(=N-OH)-CH_3$.

In another embodiment, the compound of Formula VI is a compound of the formula:

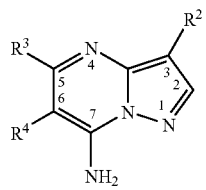

wherein $R^2$ is heteroaryl, $R^3$ is heterocyclyl and $R^3$ is a ketone, wherein each of said heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$, —$NR^5R^6$, —$(CR^5R^{11})_p$ $NR^5R^6$, —$C(O_2)R^5$, —$C(O)R^5$, —$C(O)NR^5R^6$, —$SR^6$, —$S(O_2)R^6$, —$C(=N-OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of the formula:

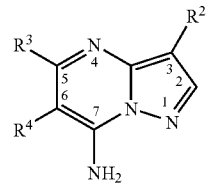

wherein $R^2$ is pyrazolyl, $R^3$ is piperidinyl and $R^4$ is a ketone.

In another embodiment, the compound of Formula VI is a compound of the formula:

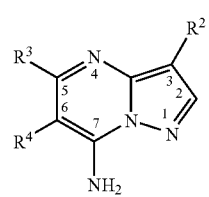

wherein $R^2$ is 1-methyl-pyrazol-4-yl, $R^3$ is piperidin-3-yl and $R^4$ is —$C(O)-CH_2-CH_3$.

In another embodiment, the compound of Formula VI is a compound of the formula:

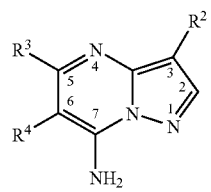

wherein $R^2$ is heteroaryl. $R^3$ is heterocyclyl and $R^4$ is a ketone, wherein each of said aryl, heteroaryl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_pOR^5$, —$OR^5$, —$NR^5R^6$, —$(CR^5R^{11})$ $NR^5R^6$, —$C(O_2)R^5$, —$C(O)R^5$, —$C(O)NR^5R^6$, —$SR^6$, —$S(O_2)R^6$, —$C(=N-OH)$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and pane as defined earlier.

In another embodiment, the compound of Formula VI is a compound of the formula:

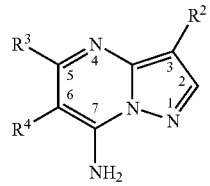

wherein R² is pyrazolyl, R³ is piperidinyl and R⁴ is a ketone.

In another embodiment, the compound of Formula VI is a compound of the formula:

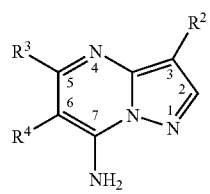

wherein R² is 1-methyl-pyrazol-4-yl, R³ is piperidin-3-yl and R⁴ is benzylcarbonyl.

In another embodiment, the compound of Formula VI is a compound of the formula:

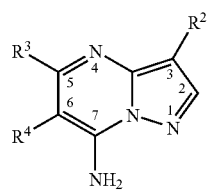

wherein R² is halo, R³ is alkyl and R⁴ is an amide, wherein said alkyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR$^{11}$R$^{11}$)$_p$OR⁵, —OR⁵, —NR⁵R⁶, —(CR⁵R$^{11}$)$_p$NR⁵R⁶, —C(O₂)R⁵, —C(O)R⁵, —C(=N—OH), —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R$^{11}$, and p are as defined earlier.

In another embodiment, the compound of Formula VI is a compound of the formula:

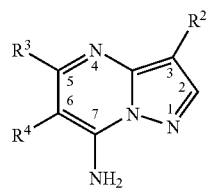

wherein R² is bromo, R³ is alkyl and R⁴ is an amide.

In another embodiment, the compound of Formula VI is a compound of the formula:

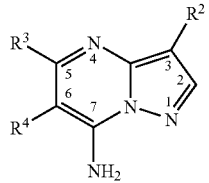

wherein R² is bromo, R³ is methyl and R⁴ is —CH₂—C(O)—NH₂.

In another embodiment, the compound of Formula VI is a compound of the formula:

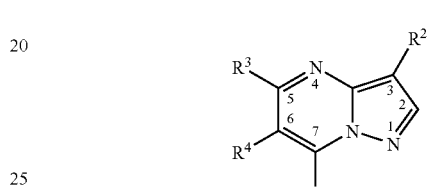

wherein R² is halo, R³ is alkyl and R⁴ is an amide, wherein said alkyl can be unsubstituted or optionally independently substituted with one or more moieties which can be the same or different, each moiety being independently selected from the group consisting of halo, alkyl, aryl, heteroaryl, cycloalkyl, —CF₃, —CN, —OCF₃, —(CR$^{11}$R$^{11}$)$_p$OR⁵, —OR⁵, —NR⁵R⁶, —(CR⁵R$^{11}$)$_p$NR⁵R⁶, —C(O₂)R⁵, —C(O)R⁵, —C(=N—OH), —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶, wherein R⁵, R⁶, R$^{11}$, and p are as defined earlier.

In another embodiment, the compound of Formula VI is a compound of the formula:

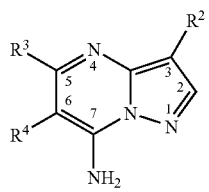

wherein R² is bromo, R³ is alkyl and R⁴ is an amide.

In another embodiment, the compound of Formula VI is a compound of the formula:

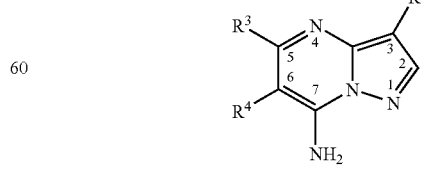

wherein R² is bromo, R³ is methyl and R⁴ is —CH₂—C(O)—NHCH₃.

In another embodiment, the compound of Formula VI is a compound of the formula:

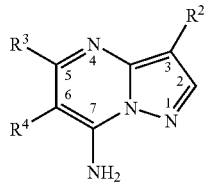

wherein $R^2$ is halo, $R^3$ is alkyl and $R^4$ is a hydroxyalkyl, wherein said alkyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —C(=N—OH), —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of the formula:

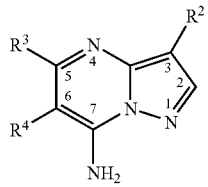

wherein $R^2$ is bromo, $R^3$ is alkyl and $R^4$ is a hydroxyalkyl.

In another embodiment, the compound of Formula VI is a compound of the formula:

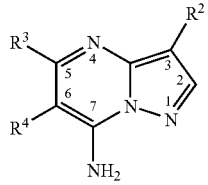

wherein $R^2$ is bromo, $R^3$ is methyl and $R^4$ is 2-hydroxyethyl.

In another embodiment, the compound of Formula VI is a compound of the formula:

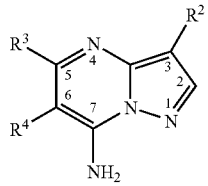

wherein $R^2$ is halo, $R^3$ is alkyl and $R^4$ is an amide, wherein said alkyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$NR$^5$R$^6$, —C(O$_2$)R$^5$, —C(O)R$^5$, —C(=N—OH), —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of the formula:

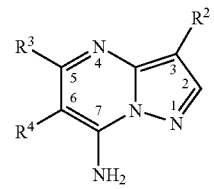

wherein $R^2$ is bromo, $R^3$ is alkyl and $R^4$ is an amide.

In another embodiment, the compound of Formula VI is a compound of the formula:

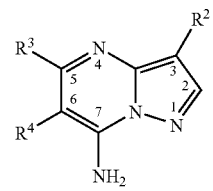

wherein $R^2$ is bromo, $R^3$ is methyl and $R^4$ is —CH$_2$—CH$_2$—C(O)—NHCH$_3$.

In another embodiment, the compound of Formula VI is a compound of the formula:

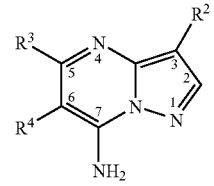

wherein $R^2$ is halo, $R^3$ is heterocyclyl and $R^4$ is aryl, wherein each of said aryl and heterocyclyl can be unsubstituted or optionally independently substituted with one or more moieties which can be the same or different, each moiety being independently selected from the group consisting of halo, alkyl, aryl, heteroaryl, cycloalkyl, —CF$_3$, —CN, —OCF$_3$, —(CR$^{11}$R$^{11}$)$_p$OR$^5$, —OR$^5$, —NR$^5$R$^6$, —(CR$^5$R$^{11}$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —C(=N—OH), —N(R$^5$)C(O)R$^7$ and —N(R$^5$)C(O)NR$^5$R$^6$, wherein R$^5$, R$^6$, R$^{11}$, and p are as defined earlier.

In another embodiment, the compound of Formula VI is a compound of formula:

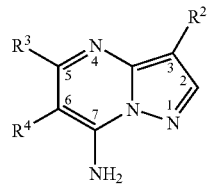

wherein $R^2$ is bromo. $R^3$ is pyrrolidinyl and $R^4$ is an aryl.

In another embodiment, the compound of Formula VI is a compound of formula:

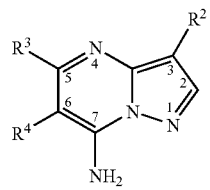

wherein $R^2$ is bromo, $R^3$ is 3-amino-pyrrolidin-1-yl and $R^4$ is phenyl.

In another embodiment, the compound of Formula VI is a compound of formula:

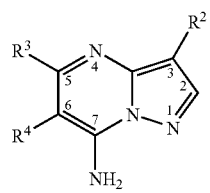

wherein $R^2$ is halo, $R^3$ is heterocyclyl and $R^4$ is alkyl, wherein each of said alkyl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$C(=N-OH)$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of formula:

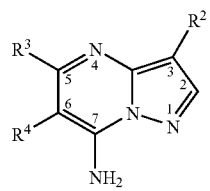

wherein $R^2$ is bromo, $R^3$ is pyrrolidinyl and $R^4$ is an alkyl.

In another embodiment, the compound of Formula VI is a compound of formula:

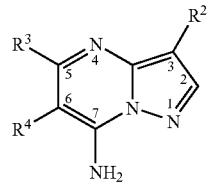

wherein $R^2$ is bromo, $R^3$ is 3-amino-pyrrolidin-1-yl and $R^4$ is ethyl.

In another embodiment, the compound of Formula VI is a compound of formula:

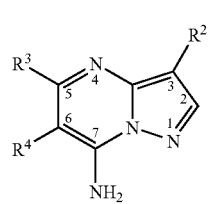

wherein $R^2$ is halo, $R^3$ is heterocyclyl and $R^4$ is alkyl, wherein each of said alkyl and heterocyclyl can be unsubstituted or optionally independently substituted with one or more moieties which can be the same or different, each moiety being independently selected from the group consisting of halo, alkyl, aryl, heteroaryl, cycloalkyl, —$CF_3$, —CN, —$OCF_3$, —$(CR^{11}R^{11})_p OR^5$, —$OR^5$, —$NR^5R^6$, —$(CR^5R^{11})_p NR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$C(=N-OH)$, —$N(R^5)C(O)R^7$ and —$N(R^5)C(O)NR^5R^6$, wherein $R^5$, $R^6$, $R^{11}$, and p are as defined earlier.

In another embodiment, the compound of Formula VI is a compound of formula:

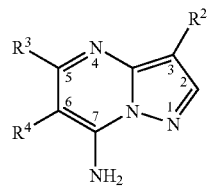

wherein $R^2$ is bromo, $R^3$ is pyrrolidinyl and $R^4$ is an alkyl.

In another embodiment, the compound of Formula VI is a compound of formula:

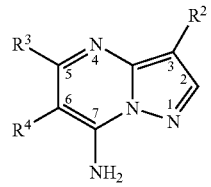

wherein $R^2$ is bromo, $R^3$ is 3-amino-pyrrolidin-1-yl and $R^4$ is methyl.

As used above, and throughout this disclosure, the following terms, unless otherwise indicated, shall be understood to have the following meanings:

"Patient" or "Subject" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core, Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, —C(CH$_3$)$_2$— and the like which form moieties such as, for example:

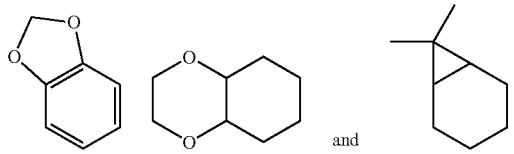

and

"Heteroarylalkyl" means a heteroaryl moiety as defined above linked via an alkyl moiety (defined above) to a parent core. Non-limiting examples of suitable heteroarylalkyls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

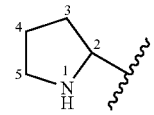

there is no —OH attached directly to carbons marked 2 and 5.

It should also be noted that tautomeric forms such as, for example, the moieties:

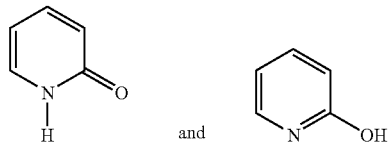

are considered equivalent in certain embodiments of this invention.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form", "isolated", or "in isolated and purified form" for a compound refers to the physical state of said compound after being isolated from a synthetic process or natural source or combination thereof. Thus, the term "purified", "in purified form", "isolated", or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The compounds of Formulas I-VI may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$. One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formulas I-VI can form salts which are also within the scope of this invention. Reference to a compound of Formulas I-VI herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulas I-VI contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula Formulas I-VI may be formed, for example, by reacting a compound of Formulas I-VI with an amount of acid or base, such as an equivalent amount, in a medium such as one in which the salt precipitates or in an aqueous medium followed by lyophilization.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, oxime (e.g. =N—OH)), and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, oxime (e.g., —C(=N—OH)), aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

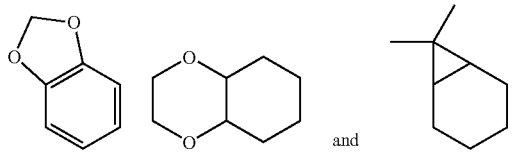

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

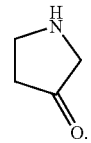

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

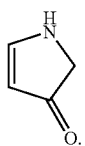

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

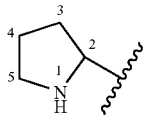

there is no —OH attached directly to carbons marked 2 and 5.

It should also be noted that tautomeric forms such as, for example, the moieties:

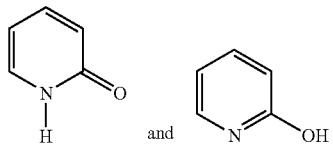

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems s*(1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound shown above as being useful in the methods of this invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound shown above as being useful in the methods of this invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (3-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound shown above as being useful in the methods of this invention contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$ alkanyl, arylacyl and α-aminoacyl, or α-aminoacyl-α-aminoacyl, where each α-aminoacyl group is independently selected from the naturally occurring L-amino acids, P(O) $(OH)_2$, —$P(O)(O(C_1-C_6)alkyl)_2$ or glycosyl (the radical resulting from the removal of a hydroxyl group of the hemiacetal form of a carbohydrate), and the like.

If a compound shown above as being useful in the methods of this invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N or di-N,N—$(C_1-C_6)$alkylaminoalkyl, —$C(Y^4)Y^5$ wherein $Y^4$ is H or methyl and $Y^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds shown above as being useful in the methods of this invention of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds shown above as being useful in the methods of this invention can form salts which are also within the scope of this invention. Reference to a compound shown above as being useful in the methods of this invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound shown above as being useful in the methods of this invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds shown above as being useful in the methods of this invention may be formed, for example, by reacting a compound shown above as being useful in the methods of this invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of formulas I through VI, as well as the compounds disclosed in copending patent application Ser. No. 11/542,920, 11/542,833, and 11/543,182 filed of even date herewith, and salts, solvates, esters and prodrugs thereof, may exist in their tautomeric form (for example, as an amide or imino ether). All such tautomeric forms are contemplated herein as part of the present invention.

The compounds of formulas I through VI, as well as the compounds disclosed in copending patent application Ser. No. 11/542,920, 11/542,833, and 11/543,182 filed of even date herewith may contain asymmetric or chiral centers, and, therefore, exist in different stereoisomeric forms. It is intended that all stereoisomeric forms of the compounds of formulas I through VI, as well as the compounds disclosed in copending patent application Ser. No. 11/542,920, 11/542, 833, and 11/543,182 filed of even date herewith, as well as mixtures thereof, including racemic mixtures, form part of the present invention. In addition, the present invention embraces all geometric and positional isomers. For example, if a compound of formulas I through VI, as well as the compounds disclosed in copending patent application Ser. No. 11/542,920, 11/542,833, and 11/543,182 filed of even date herewith incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds shown above as being useful in the methods of this invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound shown above as being useful in the methods of this invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of compounds of formulas I through VI, as well as the compounds disclosed in copending patent application Ser. No. 11/542,920, 11/542,833, and 11/543,182 filed of even date herewith (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds shown above as being useful in the methods of this invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds shown above as being useful in the methods of this invention, and of the salts, solvates, esters and prodrugs of the compounds shown above as being useful in the methods of this invention, are intended to be included in the present invention.

The compounds according to the invention can have pharmacological properties; in particular, the compounds of formulas I through VI, as well as the compounds disclosed in copending patent application Ser. No. 11/542,920, 11/542,833, and 11/543,182 filed of even date herewith can be inhibitors, regulators or modulators of protein kinases. Non-limiting examples of protein kinases that can be inhibited, regulated or modulated include CHK kinases, such as CHK1 and CHK2, Akt kinases, Pim kinases, tyrosine kinases, such as the HER subfamily (including, for example, EGFR (HER1), HER2, HER5 and HER0), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)), non-receptor protein tyrosine kinases, for example LCK, Src, Frk, Btk, Csk, Abl, Zap70, Fes/Fps, Fak, Jak, Ack, and LIMK, growth factor receptor tyrosine kinases such as VEGF-R2, FGF-R, TEK, and the like.

The compounds of formulas I through VI, as well as the compounds disclosed in copending patent application Ser. No. 11/542,920, 11/542,833, and 11/543,182 filed of even date herewith can be inhibitors of protein kinases such as, for example, the inhibitors of the checkpoint kinases such as CHK1, CHK2 and the like. Preferred compounds can exhibit $IC_{50}$ values of less than about 5 µm, preferably about 0.001 to about 1.0 µm, and more preferably about 0.001 to about 0.1 µm. For example, the compounds shown in Table 1 exhibited CHK1 inhibitory activity ($IC_{50}$) of the values shown therein. The assay methods are described in the Examples set forth later below.

TABLE 1

| CMPD | $IC_{50}$ (µM) |
|---|---|
| 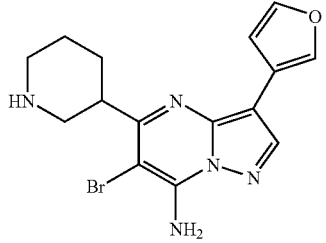 | 0.025 |
| 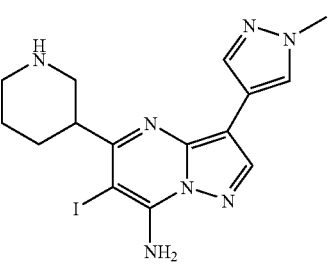 | 0.003 |
| 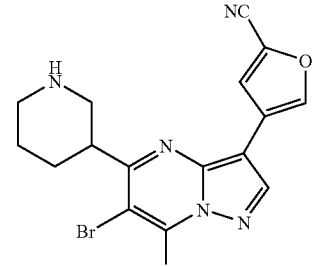 | 0.004 |
| 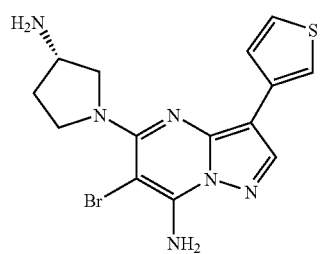 | 0.43 |
| 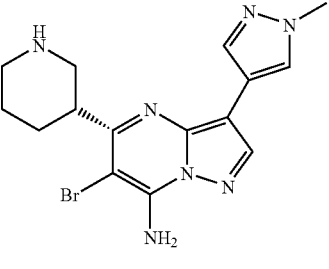 | 0.002 |

TABLE 1-continued

| CMPD | IC$_{50}$ (μM) |
|---|---|
| (structure) | 0.05 |
| (structure) | 0.006 |
| (structure) | 0.005 |
| (structure) | 0.2 |
| (structure) | 0.011 |
| (structure) | 0.009 |
| (structure) | 0.4 |
| (structure) | 0.12 |
| (structure) | 0.017 |
| (structure) | 0.09 |

TABLE 1-continued
| CMPD | IC$_{50}$ (μM) |
|---|---|
| 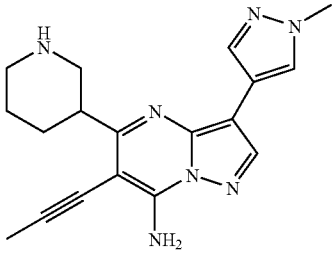 | 0.045 |
| 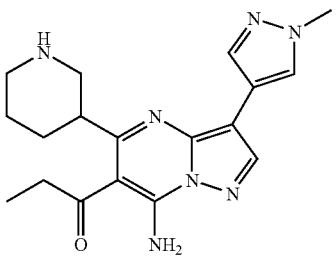 | 0.012 |
| 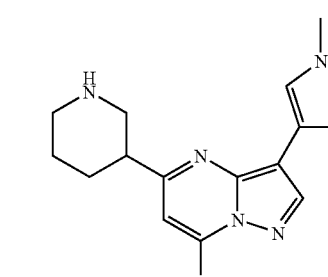 | 0.06 |
| 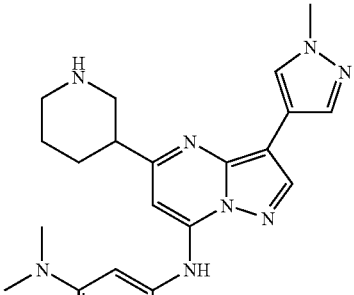 | 0.25 |
TABLE 1-continued
| CMPD | IC$_{50}$ (μM) |
|---|---|
| 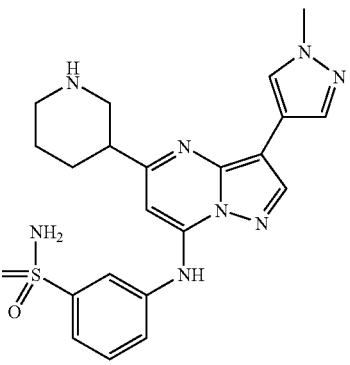 | 0.39 |
| 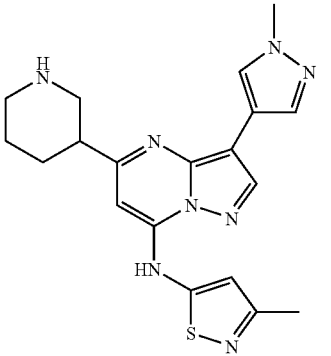 | 0.007 |
| 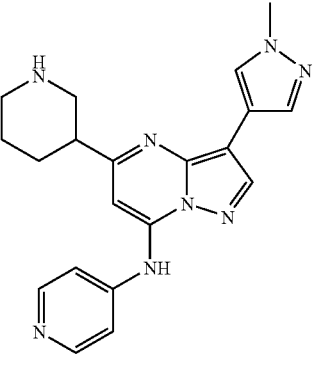 | 0.1 |
| 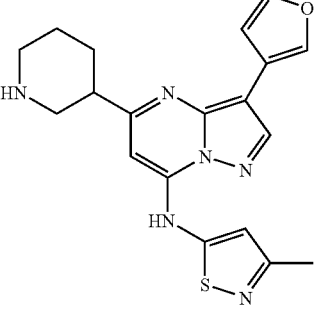 | 0.007 |

TABLE 1-continued

| CMPD | IC$_{50}$ (μM) |
|---|---|
| (structure) | 0.05 |

In any of the above methods, the compounds of formulas I through VI, as well as the compounds disclosed in copending patent application Ser. No. 11/542,920, 11/542,833, and 11/543,182 filed of even date herewith can be coadministered with one or more anti-cancer agents that are chemically different from the compounds of formulas I through VI, as well as the compounds disclosed in copending patent application Ser. No. 11/542,920, 11/542,833, and 11/543,182 filed of even date herewith, i.e, they contain different atoms, arrangement of atoms, etc.

Non-limiting examples of suitable anti-cancer agents include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (J. Cell Sci, (1995) 108, 2897. Compounds of Formulas I through VI may also be administered sequentially with known anticancer or cytotoxic agents when a combination formulation is inappropriate. The invention is not limited to any particular sequence of administration; compounds of formulas I through VI, as well as the compounds disclosed in copending patent application Ser. No. 11/542,920, 11/542, 833, and 11/543,182 filed of even date herewith may be administered either prior to, during, or after the administration of the known anticancer or cytotoxic agent or agents listed above. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians and are to be considered as part of this invention.

Accordingly, in an aspect, the methods of this invention include combinations comprising an amount of at least one compound of any of formulas I through VI, as well as the compounds disclosed in copending patent application Ser. No. 11/542,920, 11/542,833, and 11/543,182 filed of even date herewith, or a pharmaceutically acceptable salt or solvate thereof, and an amount of one or more anti-cancer treatments and/or anti-cancer agents listed above wherein the amounts of the compounds/treatments result in desired therapeutic effect.

Another aspect of the present invention is a method of inhibiting one or more Checkpoint kinases in a patient in need thereof, comprising administering to the patient a therapeutically effective amount of at least one compound of any of formulas I through VI, as well as the compounds disclosed in copending patent application Ser. No. 11/542,920, 11/542,833, and 11/543,182 filed of even date herewith or a pharmaceutically acceptable salt, solvate, ester or prodrug thereof.

Another aspect of the present invention is a method of treating, or slowing the progression of, a disease associated with one or more Checkpoint kinases in a patient in need thereof, comprising administering a therapeutically effective amount of at least one compound of any of formulas I through VI, as well as the compounds disclosed in copending patent application Ser. No. 11/542,920, 11/542,833, and 11/543,182 filed of even date herewith or a pharmaceutically acceptable salt, solvate, ester or prodrug thereof.

Yet another aspect of the present invention is a method of treating one or more diseases associated with Checkpoint kinase, comprising administering to a mammal in need of such treatment an amount of a first compound, which is a compound of any of formulas I through VI, as well as the compounds disclosed in copending patent application Ser. No. 11/542,920, 11/542,833, and 11/543,182 filed of even date herewith, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one compound of any of formulas I through VI, as well as the compounds disclosed in copending patent application Ser. No. 11/542,920, 11/542,833, and 11/543,182 filed of even date herewith, or a pharmaceutically acceptable salt, solvate, ester or prodrug or thereof.

In the above methods, the checkpoint kinase to be inhibited can be CHK1 and/or CHK2.

In the tyrosine kinase treatment methods discussed above, the tyrosine kinase can be VEGFR2, EGFR, HER2, SRC, JAK and/or TEK.

The pharmacological properties of the compounds of this invention may be confirmed by a number of pharmacological assays. The exemplified pharmacological assays which are described herein below have been carried out with compounds according to the invention and their salts, solvates, esters or prodrugs.

This invention is also directed to methods using pharmaceutical compositions which comprise at least one compound of any of formulas I through VI, as well as the compounds disclosed in copending patent application Ser. No. 11/542,920, 11/542,833, and 11/543,182 filed of even date herewith, or a pharmaceutically acceptable salt, solvate, ester or prodrug of the compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences, 18th Edition*, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

The methods of the present invention can use a kit comprising a therapeutically effective amount of at least one compound of Formulas I-VI, or a pharmaceutically acceptable salt, solvate, ester or prodrug of the compound and a pharmaceutically acceptable carrier, vehicle or diluent.

The methods of the present invention can use a kit comprising an amount of at least one compound of any of formulas I through VI, as well as the compounds disclosed in copending patent application Ser. No. 11/542,920, 11/542,833, and 11/543,182 date herewith, or a pharmaceutically acceptable salt, solvate, ester or prodrug of the compound and an amount of at least one anticancer therapy and/or anticancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, ¹H spectra were obtained on either a Varian VXR-200 (200 MHz, ¹H), Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min-stop. The retention time and observed parent ion are given.

The following solvents and reagents may be referred to by their abbreviations in parenthesis:
Thin layer chromatography: TLC
dichloromethane: $CH_2Cl_2$
ethyl acetate: AcOEt or EtOAc
methanol: MeOH
trifluoroacetate: TFA
triethylamine: $Et_3N$ or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.
dimethoxyethane: DME The preparation of the compounds of Formula VI (in copending application Ser. No. 11/542,921 filed of even date herewith) is illustrated below:

Preparative Example 1

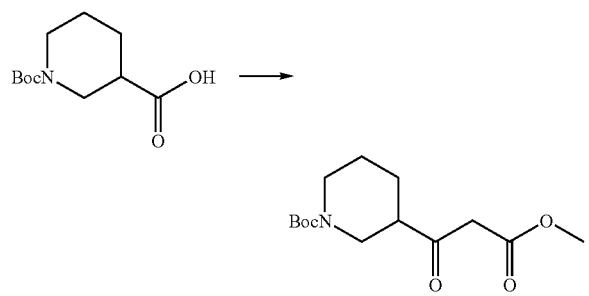

$SOCl_2$ (18.5 mL) was added slowly under $N_2$ to a stirred mixture of the acid (50.0 g, 218 mmol) and pyridine (44.0 mL) in anhydrous $CH_2Cl_2$ (300 mL). The mixture was stirred at 25° C. for 20 min, then Meldrum's acid (35.0 g, 243 mmol) and DMAP (66.6 g, 546 mmol) were added and the mixture was stirred under $N_2$ for 1 hr. Then $Et_2O$ (2 L) was added, the mixture was washed with 1 M HCl (3×500 mL), brine (500 mL), and the organic layer was dried over $Na_2SO_4$, filtered, and the solvent was evaporated. The residue was dissolved in MeOH (580 mL), and the mixture was refluxed for 4 hr. The solvent was evaporated and the residue was purified by column chromatography on silica gel with 10:1 $CH_2Cl_2$/EtOAc as eluent. Pale yellow oil (26.5 g, 43%) was obtained.

Preparative Example 2

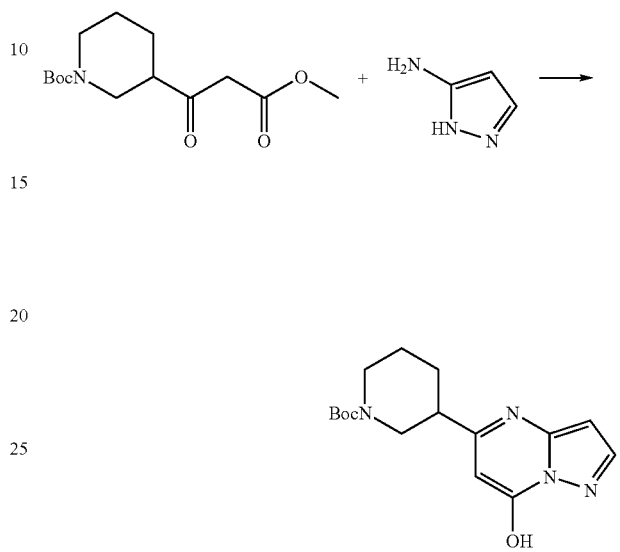

A mixture of the beta-ketoester from Preparative Example 1 (20.0 g, 70.1 mmol) and 3-aminopyrazole (5.40 g, 65.0 mmol) in anhydrous toluene (60 mL) was stirred and refluxed under $N_2$ for 24 hr. The solvent was evaporated and the residue was purified by column chromatography on silica gel with 20:1 $CH_2Cl_2$/MeOH as eluent. White solid (15.0 g, 73%) was obtained. LC-MS: 319 [M+H].

Preparative Example 3-4

By essentially same procedure set forth in Preparative Example 2, combining 3-aminopyrazole with the corresponding beta-ketoesters, compounds given in Column 1 of Table 1A were prepared.

TABLE 1A

| Ex. | Column 1 | Data |
|---|---|---|
| 3 | (structure) | LCMS: MH⁺ = 236 |
| 4 | (structure) | |

Preparative Example 5

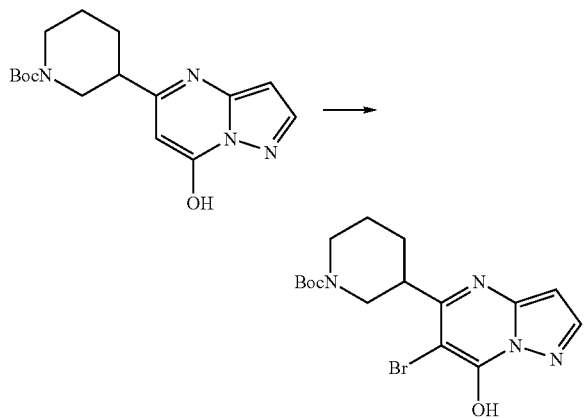

A solution of Br$_2$ (1.06 g, 6.67 mmol) in CH$_2$Cl$_2$ (5 mL) was added under N$_2$ to a stirred solution of the product from Preparative Example 2 (2.12 g, 6.67 mmol) in t-BuNH$_2$ (20 mL). The mixture was stirred for 18 hr, the solvents were evaporated, and the residue was purified by column chromatography on silica gel with 20:1 CH$_2$Cl$_2$/MeOH as eluent. Slightly gray solid (1.98 g, 75%) was obtained. LC-MS: 399 [M+H].

Preparative Example 6

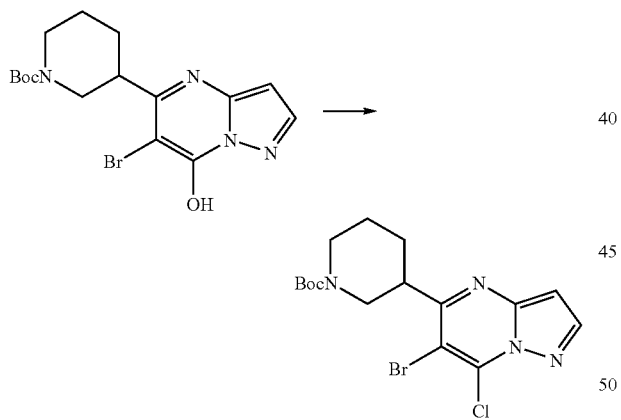

A mixture of the product from Preparative Example 5 (1.40 g, 3.53 mmol), N,N-dimethylaniline (853 mg, 7.06 mmol), and POCl$_3$ (6 mL) was stirred at 50° C. for 3 days. Excess of POCl$_3$ was evaporated and the residue was purified by column chromatography on silica gel with 20:1 CH$_2$Cl$_2$/EtOAc as eluent. Colorless solid foam (830 mg, 57%) was obtained. LC-MS: 417 [M+H].

Preparative Example 7-8

By essentially same procedure set forth in Preparative Example 6, compounds given in Column 1 of Table 2 were prepared.

TABLE 2

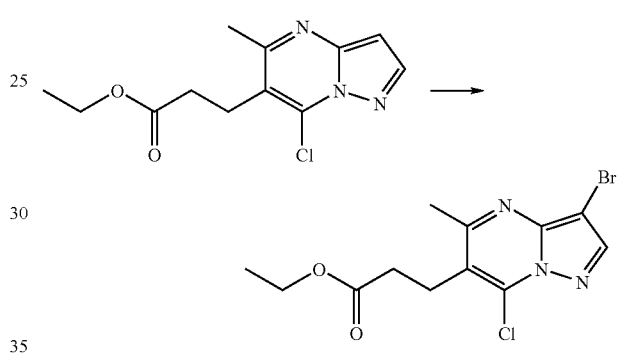

| Ex. | Column 1 | Data |
|---|---|---|
| 7 | (structure) | LCMS: MH$^+$ = 254 |
| 8 | (structure) | |

Preparative Example 9

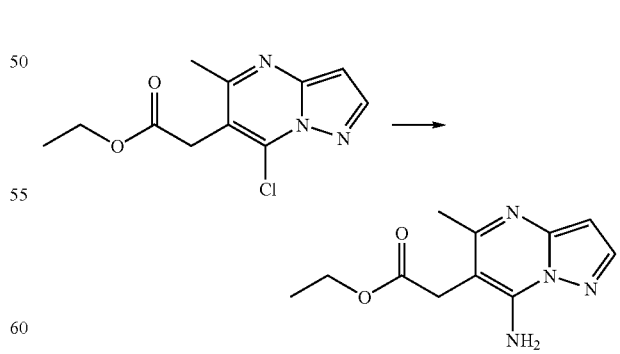

A solution of NBS (2.66 g, 14.9 mmol) in anhydrous CH$_3$CN (20 mL) was added under N$_2$ to a stirred solution of the product from Preparative Example 8 (4.00 g, 14.9 mmol) in anhydrous CH$_3$CN (60 mL). The mixture was stirred for 18 hr, the solvents were evaporated, and the residue was purified by column chromatography on silica gel with 30:1 CH$_2$Cl$_2$/EtOAc as eluent. Pale yellow solid foam (4.90 g, 94%) was obtained. LC-MS: 348 [M+H].

Preparative Example 10

A mixture of the product from Preparative Example 7 (1.00 g, 3.95 mmol), 2.0 M NH$_3$ in 2-propanol (20.0 mL), and conc. aqueous NH$_4$OH (5.0 mL) was stirred in a closed pressure vessel at 90° C. for 20 hr. The solvents were evaporated and the residue was purified by column chromatography on silica gel with 7:1 CH$_2$Cl$_2$/7N NH$_3$ in MeOH as eluent. Pale yellow solid (225 mg, 28%) was obtained. LC-MS: 235 [M–H]. Mp=181-182° C.

Preparative Example 11

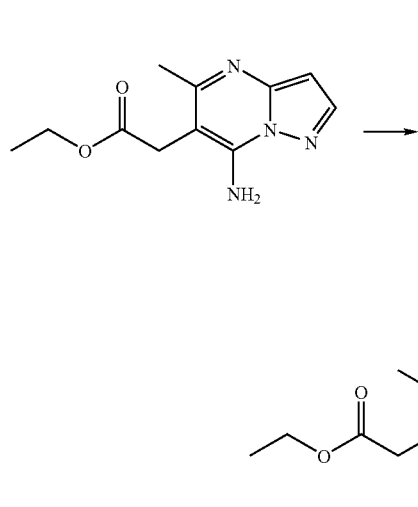

A solution of NBS (356 mg, 2.00 mmol) in anhydrous CH$_3$CN (20 mL) was added under N$_2$ to a stirred solution of the product from Preparative Example 10 (468 mg, 2.00 mmol) in anhydrous CH$_3$CN (10 mL) and CH$_2$Cl$_2$ (10 mL). The mixture was stirred for 4 hr, the solvents were evaporated, and the residue was purified by column chromatography on silica gel with 2:1 CH$_2$Cl$_2$/EtOAc as eluent. White solid (530 mg, 85%) was obtained. LC-MS: 313 [M]. Mp=150-152° C.

Preparative Example 12

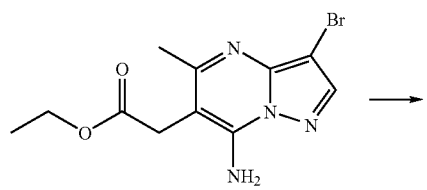

A mixture of the product from Preparative Example 11 (100 mg, 0.32 mmol), 2.0 M NH$_3$ in 2-propanol (2.0 mL), and conc. aqueous NH$_4$OH (0.5 mL) was stirred in a closed pressure vessel at 80° C. for 24 hr. The solvents were evaporated and the residue was purified by column chromatography on silica gel with 10:1 CH$_2$Cl$_2$/MeOH as eluent. White solid (13 mg, 14%) was obtained. LC-MS: 284 [M+]. Mp=209-211° C.

Preparative Example 13

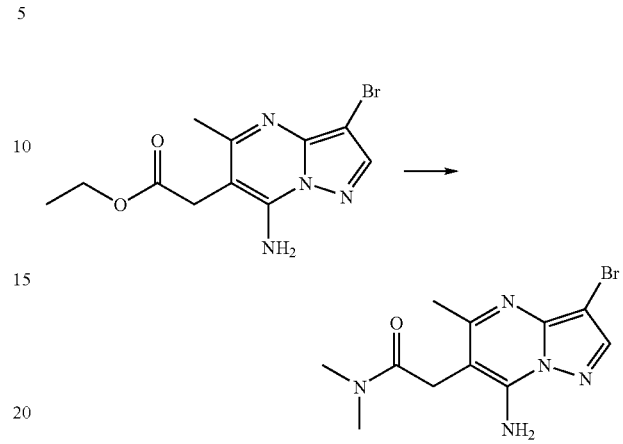

A mixture of the product from Preparative Example 11 (100 mg, 0.32 mmol) and 2.0 M Me$_2$NH in THF (5.0 mL) was stirred in a closed pressure vessel at 60° C. for 72 hr. The solvents were evaporated and the residue was purified by column chromatography on silica gel with 10:1 CH$_2$Cl$_2$/MeOH as eluent. White solid (5 mg, 5%) was obtained. LC-MS: 313 [M+H]. Mp=215-217° C.

Preparative Example 14

By essentially same procedure set forth in Preparative Example 13, only using MeNH$_2$ solution in THF, compound given below was prepared.

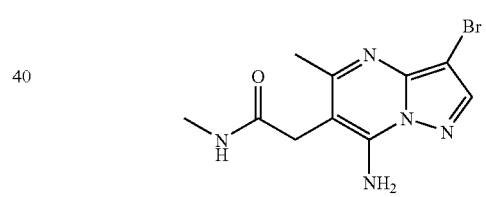

White solid. LC-MS: 298 [M+]. Mp=222-224° C.

Preparative Example 15

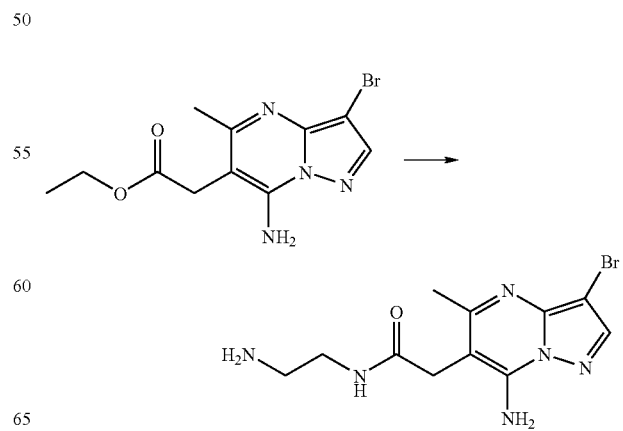

A mixture of the product from Preparative Example 11 (200 mg, 0.64 mmol) and ethylenediamine (0.10 mL) in dioxane (2.0 mL) was stirred under $N_2$ at 90° C. for 24 hr. The solvents were evaporated and the residue was purified by column chromatography on silica gel with 4:1 $CH_2Cl_2$/7N $NH_3$ in MeOH as eluent. White solid (101 mg, 48%) was obtained. LC-MS: 329 [M+2H]. Mp=215-217° C.

Preparative Example 16

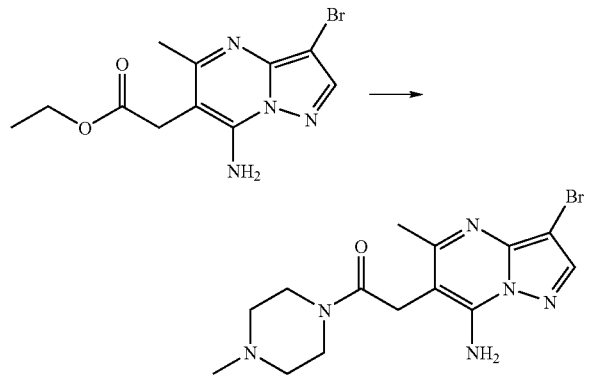

A mixture of the product from Preparative Example 11 (200 mg, 0.64 mmol) and 1-methylpiperazine (0.40 mL) was stirred under $N_2$ at 100° C. for 72 hr. The excess of 1-methylpiperazine was evaporated and the residue was purified by column chromatography on silica gel with 20:1 $CH_2Cl_2$/7N $NH_3$ in MeOH as eluent. White solid (155 mg, 66%) was obtained. LC-MS: 367 [M+]. Mp=122-125° C.

Preparative Example 17

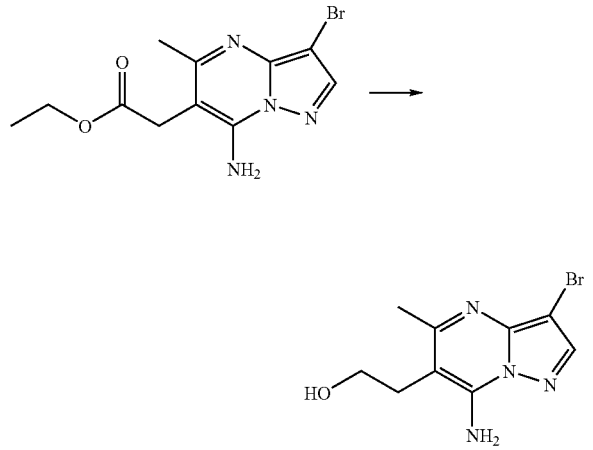

1.0 M $LiAlH_4$ in THF (0.22 mL) was added at 0° C. to a stirred solution of the product from Preparative Example 11 (150 mg, 0.48 mmol) in THF (8.0 mL). The mixture was stirred for 30 min at 0° C., then more 1.0 M $LiAlH_4$ in THF (0.80 mL) was added. The mixture was stirred at 0° C. for 20 min, then quenched with MeOH (4 mL). The solvents were evaporated and the residue was purified by column chromatography on silica gel with 20:1 $CH_2Cl_2$/MeOH as eluent. White solid (59 mg, 45%) was obtained. LC-MS: 271 [M+]. Mp=234-236° C.

Preparative Example 18

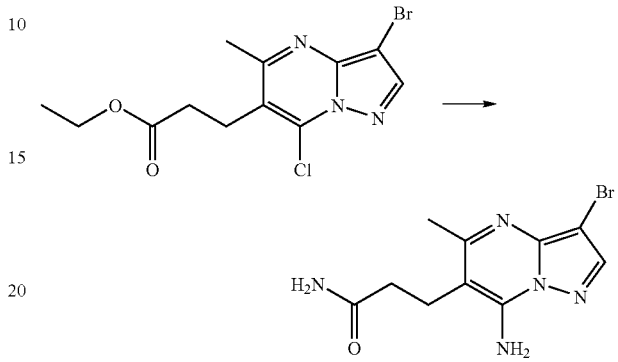

A mixture of the product from Preparative Example 9 (500 mg, 1.45 mmol), 2.0 M $NH_3$ in 2-propanol (10.0 mL), and conc. aqueous $NH_4OH$ (2.5 mL) was stirred in a closed pressure vessel at 70° C. for 24 hr. The solvents were evaporated and the residue was purified by column chromatography on silica gel with 8:1 $CH_2Cl_2$/MeOH as eluent. White solid (151 mg, 35%) was obtained. LC-MS: 299 [M+H]. Mp=211-213° C.

Preparative Example 19

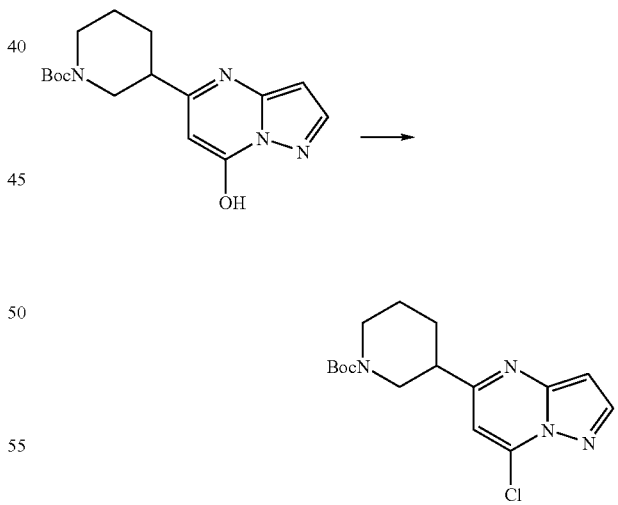

A mixture of the product from Preparative Example 2 (12.50 g, 39.3 mmol), N,N-dimethylaniline (15.5 mL), and $POCl_3$ (125 mL) was stirred at 25° C. for 4 days. Excess of $POCl_3$ was evaporated and the residue was poured into saturated aqueous $NaHCO_3$ (600 mL). The mixture was extracted with $CH_2Cl_2$ (3×200 mL), the combined extracts were dried over $Na_2SO_4$, filtered, and the solvent was evaporated. The residue was purified by column chromatography on silica gel with 8:1 CH$_2$Cl$_2$/EtOAc as eluent. Pale yellow wax (9.41 g, 71%) was obtained. LC-MS: 337 [M+].

Preparative Example 20

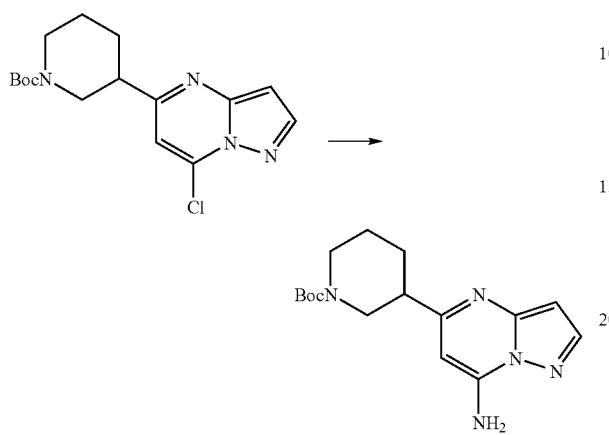

A mixture of the product from Preparative Example 19 (8.00 g, 23.8 mmol), 2.0 M NH$_3$ in 2-propanol (50 mL), and conc. aqueous NH$_4$OH (5 mL) was stirred in a closed pressure vessel at 70° C. for 28 hr. The solvents were evaporated and the residue was purified by column chromatography on silica gel with 10:1 CH$_2$Cl$_2$/MeOH as eluent. White solid (7.40 g, 98%) was obtained. LC-MS: 318 [M+H].

Preparative Example 21

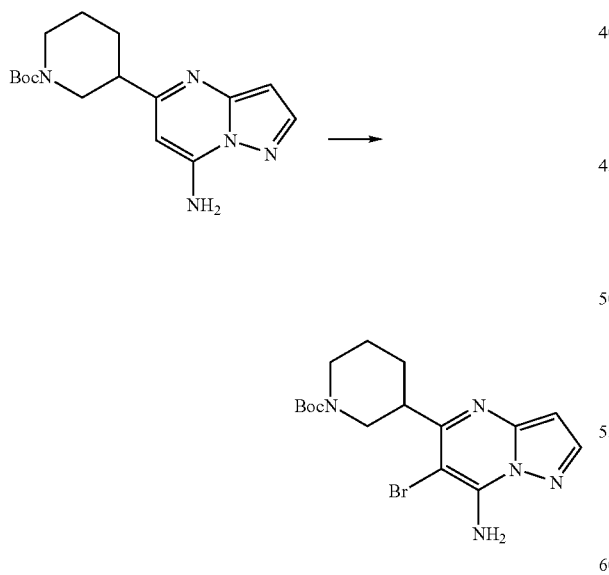

A solution of Br$_2$ (15.2 g, 95.2 mmol) in dry CH$_2$Cl$_2$ (100 mL) was added dropwise to a stirred solution of the amine from Preparative Example 20 (30.2 g, 95.2 mmol) in tert-BuNH$_2$ (300 mL) and CH$_2$Cl$_2$ (100 mL). The mixture was stirred at 25° C. for 20 hrs, the solvents were evaporated and the residue was purified by column chromatography on silica gel with 40:1 CH$_2$Cl$_2$/MeOH as eluent. White solid (29.8 g, 79%) was obtained. LC-MS: 396 [M+].

Preparative Example 22

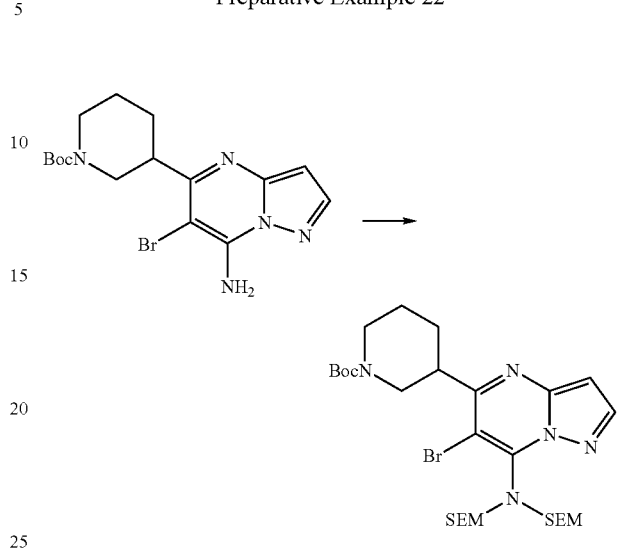

A mixture of the product from Preparative Example 21 (2.50 g, 6.31 mmol), SEMCl (3.69 g, 22.1 mmol), and diisopropylethylamine (5.70 g, 44.2 mmol) in dry 1,2-dichloroethane (20 mL) was stirred and refluxed under N$_2$ for 6 hr. The mixture was then poured into saturated aqueous NaHCO$_3$ solution (250 mL), extracted with CH$_2$Cl$_2$ (3×50 mL), dried over Na$_2$SO$_4$, and filtered. The solvents were evaporated and the residue was purified by column chromatography on silica gel with 80:1 CH$_2$Cl$_2$/EtOAc as eluent. Slightly yellow oil (1.60 g, 39%) was obtained.

Preparative Example 23

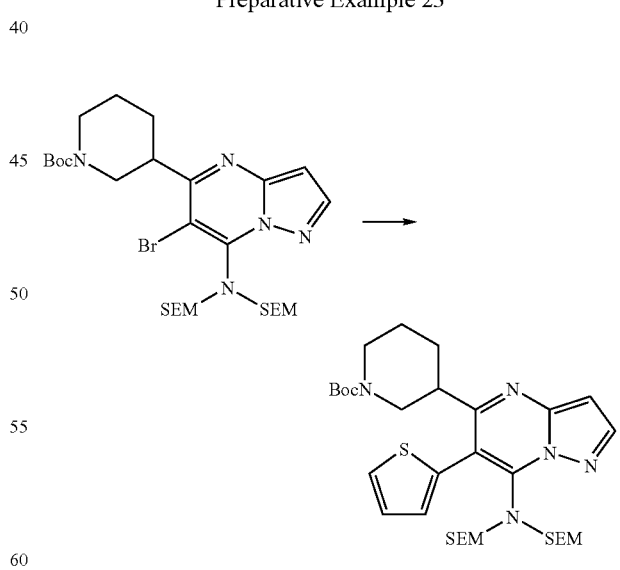

A mixture of the product from Preparative Example 22 (200 mg, 0.31 mmol), 2-thienylboronic acid (59 mg, 0.46 mmol), Pd[PPh$_3$]$_4$ (35 mg, 0.03 mmol), and Na$_2$CO$_3$ (99 mg, 0.93 mmol) in 1,2-dimethoxyethane (3 mL) and H$_2$O (0.6 mL) was stirred and refluxed under N$_2$ for 72 hr. The solvents were evaporated and the residue was purified by column chromatography on silica gel with 10:1 hexane/EtOAc as eluent. Slightly yellow wax (54 mg, 27%) was obtained.

Preparative Example 24

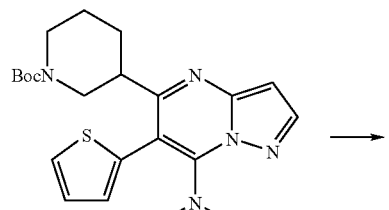

A solution of NBS (13 mg, 0.075 mmol) in anhydrous CH$_3$CN (1 mL) was added under N$_2$ to a stirred solution of the product from Preparative Example 23 (53 mg, 0.080 mmol) in anhydrous CH$_3$CN (1 mL). The mixture was stirred for 1 hr, the solvents were evaporated, and the residue was purified by column chromatography on silica gel with 10:1 hexane/EtOAc as eluent. Slightly yellow wax (36 mg, 66%) was obtained.

Preparative Example 25

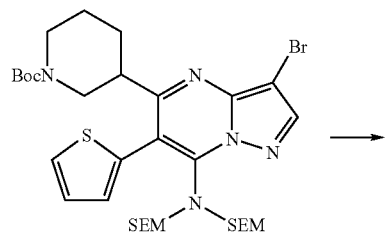

A mixture of the product from Preparative Example 24 (35 mg, 0.048 mmol), 1-methyl-4-(4,4,5,5-tetramethyl-1,3,2-dioxaborolan-2-yl)-1H-pyrazole (15 mg, 0.071 mmol), Pd[PPh$_3$]$_4$ (6 mg, 0.005 mmol), and Na$_2$CO$_3$ (20 mg, 0.071 mmol) in 1,2-dimethoxyethane (1.5 mL) and H$_2$O (0.3 mL) was stirred and refluxed under N$_2$ for 20 hr. The solvents were evaporated and the residue was purified by column chromatography on silica gel with 2:1 hexane/EtOAc as eluent. Yellow wax (10 mg, 29%) was obtained.

Preparative Example 26

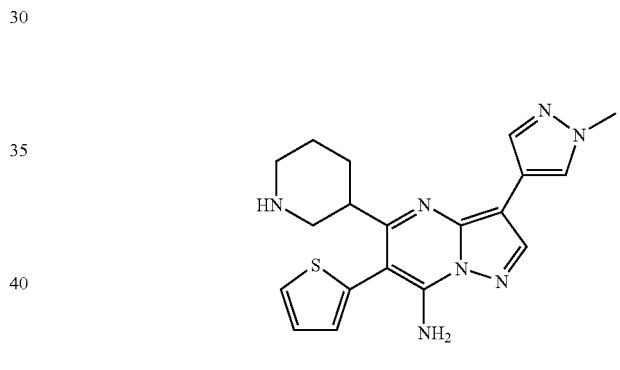

A mixture of the product from Preparative Example 25 (10 mg) and 3N aqueous HCl (0.5 mL) in EtOH (0.5 mL) was stirred at 60° C. for 1.5 hr. The solvents were evaporated, Na$_2$CO$_3$ (100 mg) and 6:1 mixture of CH$_2$Cl$_2$/MeOH (0.5 mL) were added to the residue and the mixture was stirred under N$_2$ for 15 min. Then it was loaded onto a column and it was purified by column chromatography on silica gel with 10:1 CH$_2$Cl$_2$/7N NH$_3$ in MeOH as eluent. White solid (4 mg, 80%) was obtained. LC-MS: 380 [M+H]. Mp=241-243° C.

Preparative Example 27-36

By essentially same sequence of procedures set forth in Preparative Examples 23-26 only using different boron reagents given in Column 1 for the Suzuki couplings with the intermediate from preparative Example 22, compounds given in Column 2 of Table 3 were prepared.

TABLE 3
| Ex. | Column 1 | Column 2 | Data |
|---|---|---|---|
| 27 | 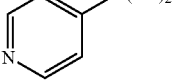 | 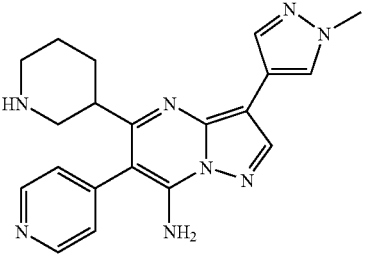 | LCMS:<br>MH+ = 375<br>Mp >250° C. |
| 28 | 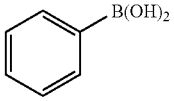 | 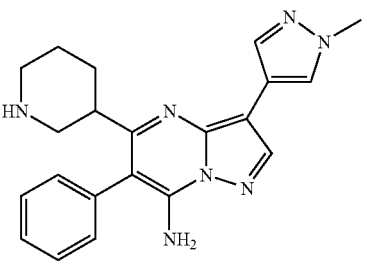 | LCMS:<br>MH+ = 374<br>Mp = 229-232° C. |
| 29 | 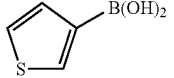 | 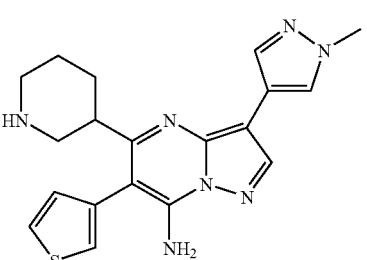 | LCMS:<br>MH+ = 380<br>Mp = 250-253° C. |
| 30 | 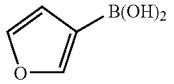 | 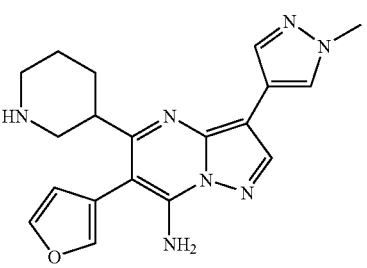 | LCMS:<br>MH+ = 364<br>Mp = 290-294° C. |
| 31 | 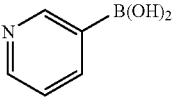 | 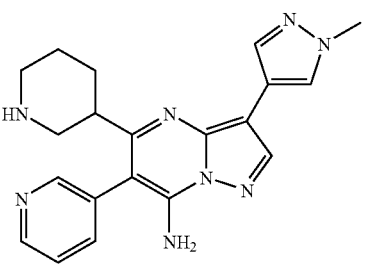 | LCMS:<br>MH+ = 375 |
| 32 | 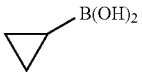 | 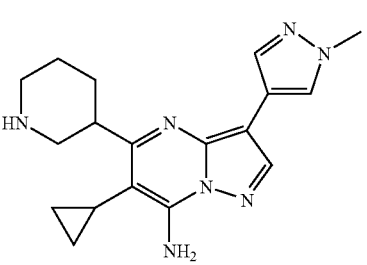 | LCMS:<br>MH+ = 338<br>Mp = 183-186° C. |

TABLE 3-continued
| Ex. | Column 1 | Column 2 | Data |
|---|---|---|---|
| 33 | 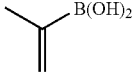 | 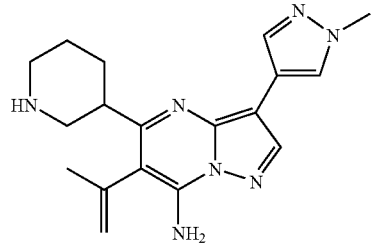 | LCMS:<br>MH⁺ = 338<br>Mp = 227-230° C. |
| 34 | 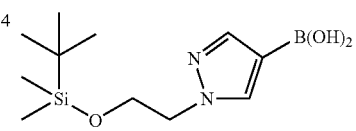 | 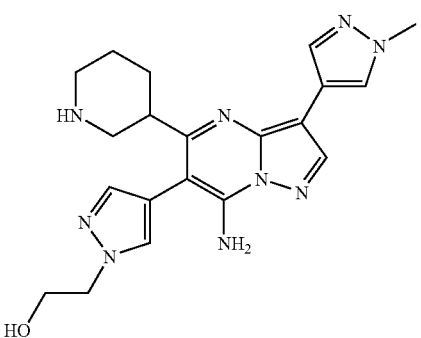 | LCMS:<br>MH⁺ = 408<br>Mp = 219-222° C. |
| 35 | 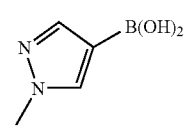 | 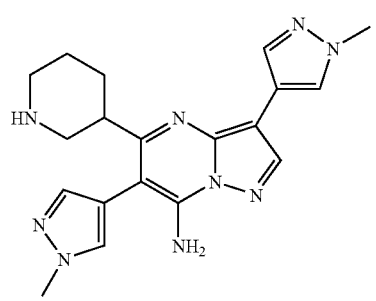 | LCMS:<br>MH⁺ = 378<br>Mp = 272-275° C. |
| 36 | 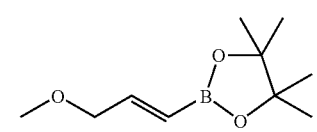 | 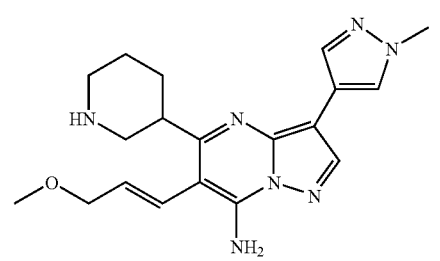 | LCMS:<br>MH⁺ = 368 |

Preparative Example 37

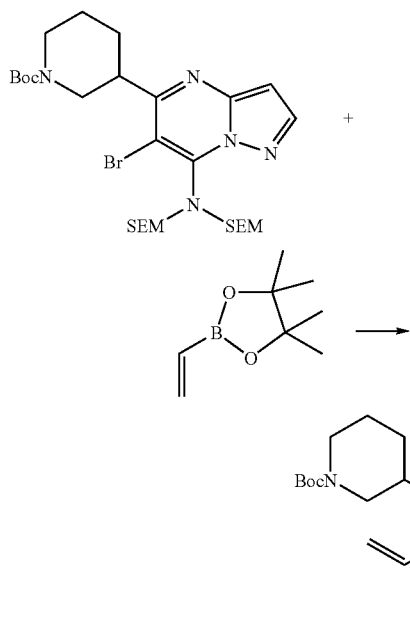

A mixture of the product from Preparative Example 22 (400 mg, 0.62 mmol), the vinylboronate (143 mg, 0.93 mmol), Pd[PPh$_3$]$_4$ (68 mg, 0.06 mmol), and Na$_2$CO$_3$ (262 mg, 2.48 mmol) in 1,2-dim (6 mL) and H$_2$O (1.2 mL) was stirred and refluxed under N$_2$ for 48 hr. The solvents were evaporated and the residue was purified by column chromatography on silica gel with 6:1 hexane/EtOAc as eluent. Slightly yellow wax (312 mg, 85%) was obtained.

Preparative Example 38

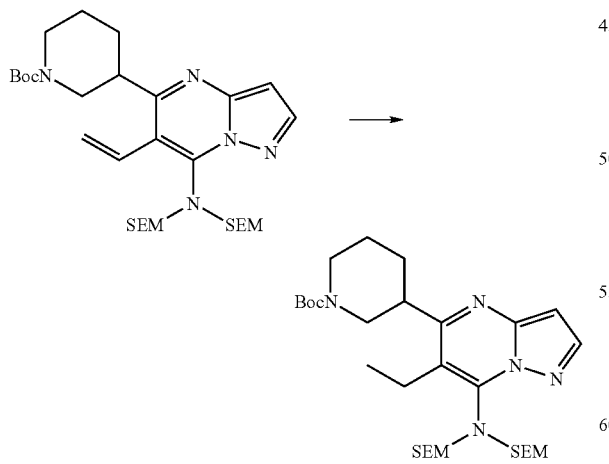

A mixture of the product from Preparative Example 37 (150 mg) and 10% Pd/C (70 mg) in EtOAc (5 mL) was stirred under H$_2$ atmosphere for 72 hr. The solvents were evaporated and the residue was purified by column chromatography on silica gel with 5:1 hexane/EtOAc as eluent. Slightly yellow wax (118 mg, 79%) was obtained.

Preparative Example 39

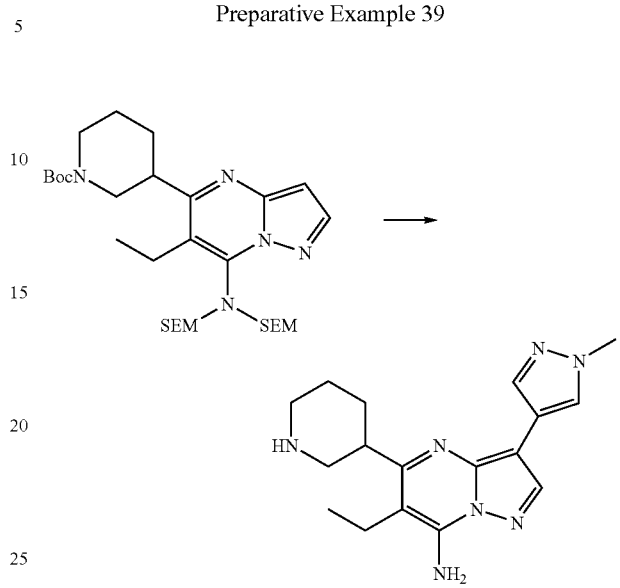

By essentially same sequence of procedures set forth in Preparative Examples 24-26 starting from the compound from preparative Example 38, the title compound was prepared. LC-MS: 326 [M+H]. Mp=76-78° C.

Preparative Example 40

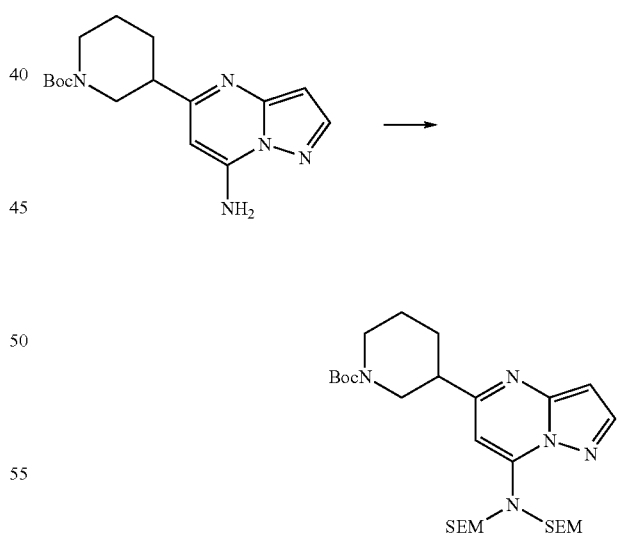

A mixture of the product from Preparative Example 20 (2.00 g, 6.30 mmol), SEMCl (3.69 g, 22.10 mmol), and diisopropylethylamine (5.70 g, 44.20 mmol) in dry 1,2-dichloroethane (20 mL) and was stirred and refluxed under N$_2$ for 2 hr. The mixture was then poured into saturated aqueous NaHCO$_3$ solution (100 mL), extracted with CH$_2$Cl$_2$ (3×30 mL), dried over Na$_2$SO$_4$, and filtered. The solvents were evaporated and the residue was purified by column chroma-

Preparative Example 41

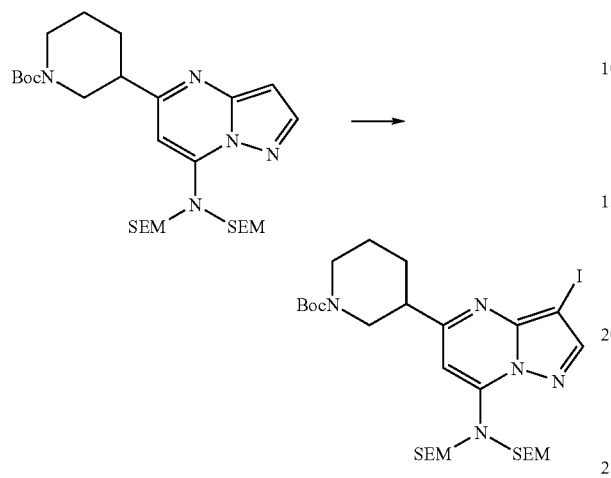

A solution of N-iodosuccinimide (0.90 g, 4.00 mmol) in anhydrous CH$_3$CN (10 mL) was added under N$_2$ to a stirred solution of the product from Preparative Example 40 (2.50 g, 4.33 mmol) in anhydrous CH$_3$CN (10 mL). The mixture was stirred for 1 hr, the solvents were evaporated, and the residue was purified by column chromatography on silica gel with 40:1 CH$_2$Cl$_2$/EtOAc as eluent. Slightly yellow wax (2.57 g, 92%) was obtained.

Preparative Example 42

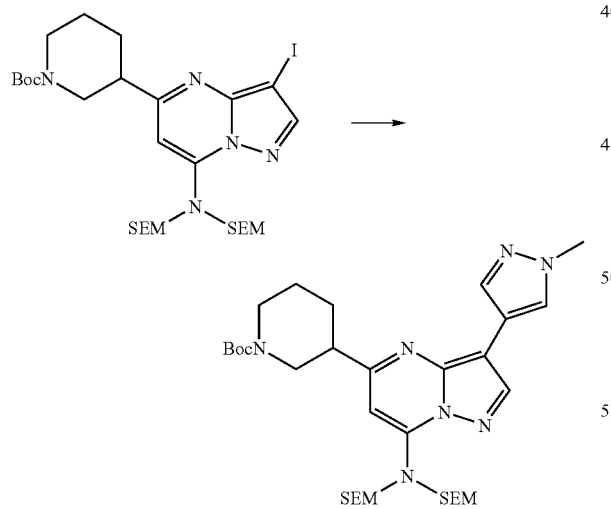

A mixture of the product from Preparative Example 41 (1.50 g, 2.13 mmol), 1-methyl-4-(4,4,5,5-tetramethyl-1,3,2-dioxaborolan-2-yl)-1H-pyrazole (0.89 g, 4.26 mmol), PdCl$_2$dppf.CH$_2$Cl$_2$ (171 mg, 0.21 mmol), and K$_3$PO$_4$ (1.81 g, 8.52 mmol) in 1,2-dimethoxyethane (30 mL) and H$_2$O (6 mL) was stirred and refluxed under N$_2$ for 3 hr. The solvents were evaporated and the residue was purified by column chromatography on silica gel with 15:1 CH$_2$Cl$_2$/EtOAc as eluent. Slightly yellow oil (2.76 g, 76%) was obtained.

Preparative Example 43

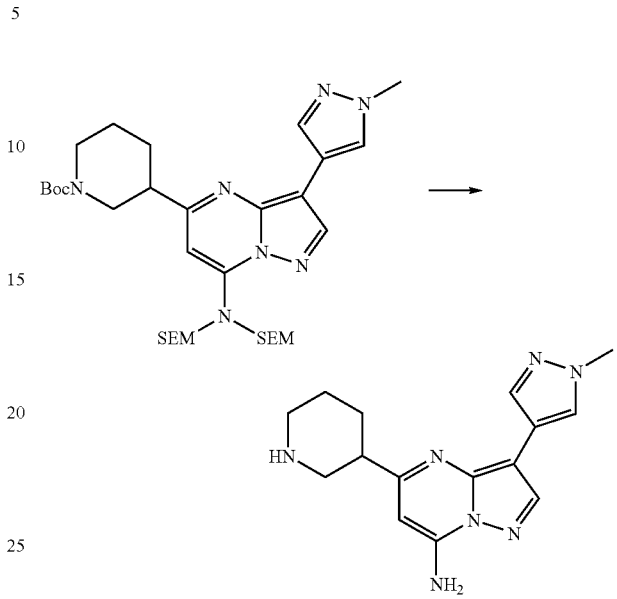

A mixture of the product from Preparative Example 42 (1.00 g) and 3N aqueous HCl (20 mL) in EtOH (20 mL) was stirred at 60° C. for 1.5 hr. The solvents were evaporated, Na$_2$CO$_3$ (2.0 g) and 6:1 mixture of CH$_2$Cl$_2$/MeOH (20 mL) were added to the residue and the mixture was stirred under N$_2$ for 15 min. Then it was loaded onto a column and it was purified by column chromatography on silica gel with 6:1 CH$_2$Cl$_2$/7N NH$_3$ in MeOH as eluent. White solid (405 mg, 90%) was obtained. LC-MS: 298 [M+H].

Preparative Example 44

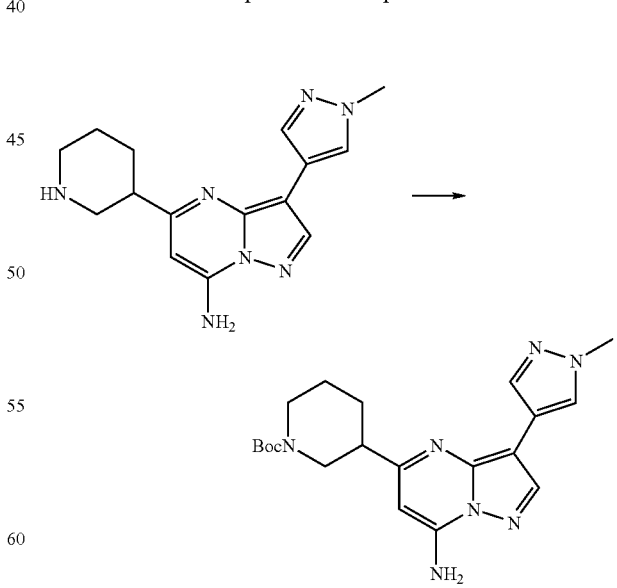

Boc$_2$O (441 mg, 2.02 mmol) was added to a stirred solution of the product from Preparative Example 43 (500 mg, 1.68 mmol) and triethylamine (2.0 mL) in anhydrous CH$_2$Cl$_2$ (10 mL). The mixture was stirred at 25° C. for 18 hr, then it was poured into saturated aqueous NaHCO₃ solution (60 mL), extracted with CH₂Cl₂ (3×10 mL), dried over Na₂SO₄, and filtered. The solvents were evaporated and the residue was purified by column chromatography on silica gel with 20:1 CH₂Cl₂/MeOH as eluent. Pale yellow solid (670 mg, 100%) was obtained. LC-MS: 398 [M+H].

Preparative Example 45

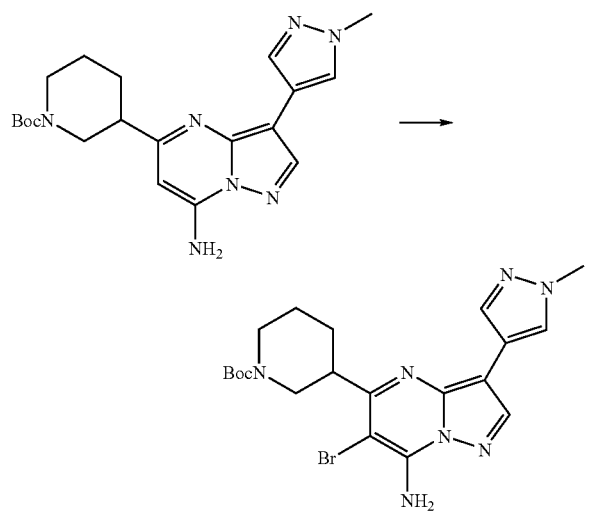

A solution of Br₂ (191 mg, 1.19 mmol) in dry CH₂Cl₂ (4 mL) was added dropwise to a stirred solution of the product from Preparative Example 44 (500 mg, 1.26 mmol) in tert-BuNH₂ (10 mL) and CH₂Cl₂ (5 mL). The mixture was stirred at 25° C. for 20 hrs, the solvents were evaporated and the residue was purified by column chromatography on silica gel with 1:1 CH₂Cl₂/EtOAc as eluent. White solid (415 mg, 73%) was obtained. LC-MS: 476 [M+].

Preparative Example 46

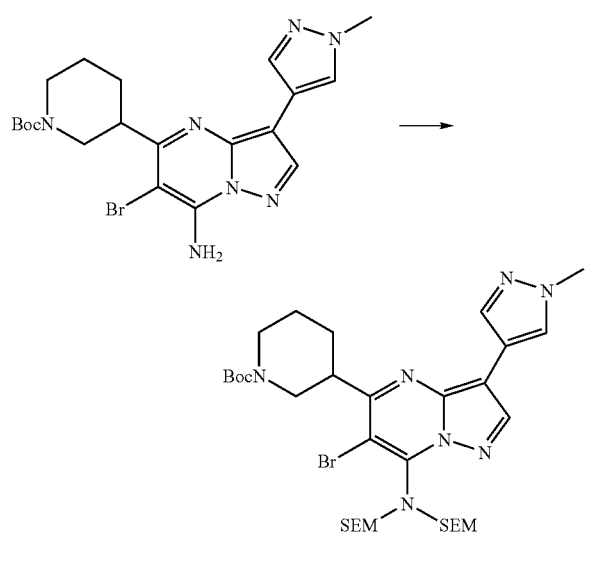

A mixture of the product from Preparative Example 45 (410 mg, 0.86 mmol), SEMCl (503 mg, 3.01 mmol), and diisopropylethylamine (777 mg, 6.02 mmol) in dry 1,2-dichloroethane (4 mL) and was stirred and refluxed under N₂ for 20 hr. The mixture was then poured into saturated aqueous NaHCO₃ solution (60 mL), extracted with CH₂Cl₂ (3×10 mL), dried over Na₂SO₄, and filtered. The solvents were evaporated and the residue was purified by column chromatography on silica gel with 7:1 CH₂Cl₂/EtOAc as eluent. Slightly yellow wax (214 mg, 34%) was obtained.

Preparative Example 47

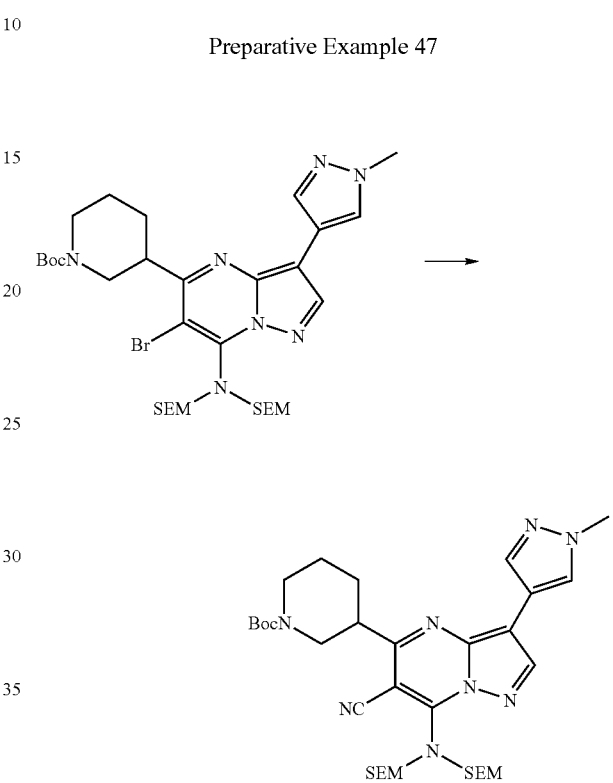

A mixture of the product from Preparative Example 46 (100 mg, 0.14 mmol), tributyltin cyanide (63 mg, 0.20 mmol), and Pd[PPh₃]₄ (16 mg, 0.014 mmol) in anhydrous dioxane (2 mL) was stirred at 100° C. under N₂ for 20 hr. Bis(tri-t-butylphospine)palladium (40 mg, 0.078 mmol) was then added to the mixture and the mixture was stirred at 100° C. under N₂ for additional 24 hr. The solvent was evaporated and the residue was purified by column chromatography on silica gel with 6:1 hexane/EtOAc as eluent. Slightly yellow wax (48 mg, 51%) was obtained. LC-MS: 683 [M+H].

Preparative Example 48

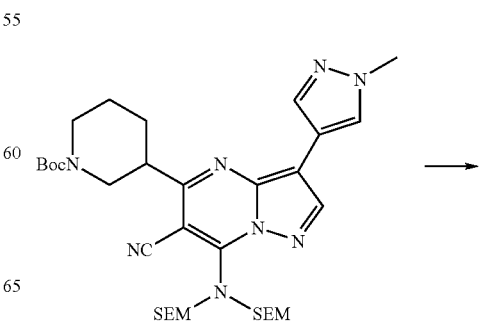

-continued

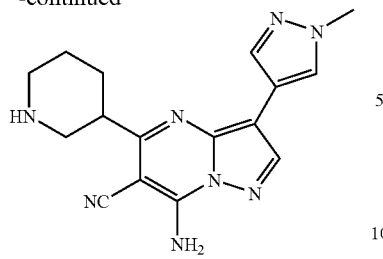

A mixture of the product from Preparative Example 47 (48 mg) and 3N aqueous HCl (1.0 mL) in EtOH (1.0 mL) was stirred at 60° C. for 1 hr. The solvents were evaporated, Na$_2$CO$_3$ (200 mg) and 6:1 mixture of CH$_2$Cl$_2$/MeOH (1.0 mL) were added to the residue and the mixture was stirred under N$_2$ for 15 min. Then it was loaded onto a column and it was purified by column chromatography on silica gel with 8:1 CH$_2$Cl$_2$/7N NH$_3$ in MeOH as eluent. White solid (13 mg, 57%) was obtained. LC-MS: 323 [M+H]. Mp=101-105° C.

Preparative Example 49

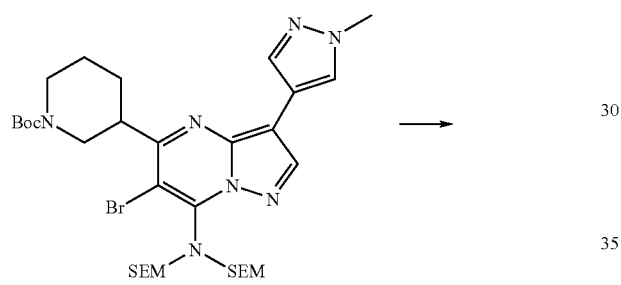

-continued

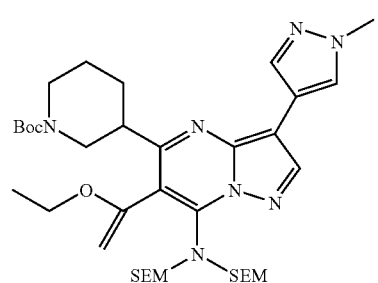

A mixture of the product from Preparative Example 46 (400 mg, 0.54 mmol), tributyl (1-ethoxyvinyl)tin (294 mg, 0.81 mmol), and Pd[PPh$_3$]$_4$ (62 mg, 0.054 mmol) in anhydrous dioxane (8 mL) was stirred at 100° C. under N$_2$ for 72 hr. The solvent was evaporated and the residue was purified by column chromatography on silica gel with 6:1 CH$_2$Cl$_2$/EtOAc as eluent. Slightly yellow wax (326 mg, 83%) was obtained.

Preparative Example 50-51

By essentially same procedures set forth in Preparative Example 49 only using different tin reagents given in Column 1 for the Stille couplings with the intermediate from preparative Example 46, compounds given in Column 2 of Table 4 were prepared.

TABLE 4

| Ex. | Column 1 | Column 2 |
|---|---|---|
| 50 | ![phenylacetylene-SnBu3] | ![product 50] |
| 51 | ![propyne-SnBu3] | ![product 51] |

Preparative Example 52

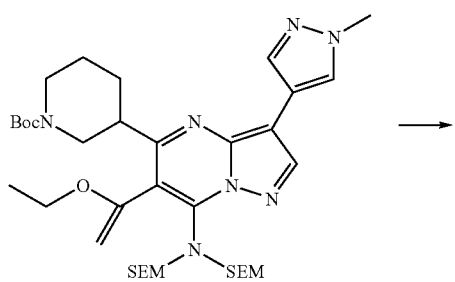

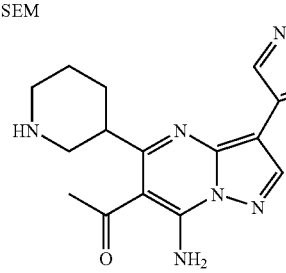

A mixture of the product from Preparative Example 49 (320 mg) and 3N aqueous HCl (3 mL) in EtOH (3 mL) was stirred at 60° C. for 1.5 hr. The solvents were evaporated, NaHCO$_3$ (2.0 g) and 6:1 mixture of CH$_2$Cl$_2$/MeOH (7 mL) were added to the residue and the mixture was stirred under N$_2$ for 15 min. Then it was loaded onto a column and it was purified by column chromatography on silica gel with 12:1 CH$_2$Cl$_2$/7N NH$_3$ in MeOH as eluent. White solid (120 mg, 81%) was obtained. LC-MS: 340 [M+H]. Mp=93-97° C.

Preparative Example 53a (Isomer 1) and 53b (Isomer 2)

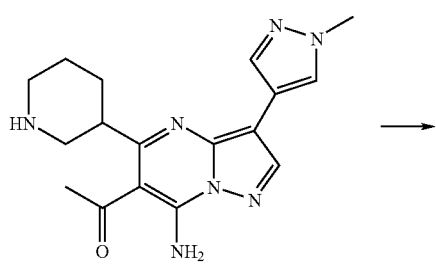

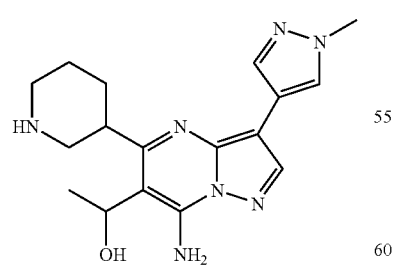

Compound 53 (isomer 53a and isomer 53b)

NaBH$_4$ (16 mg, 0.44 mmol) was added to a stirred solution of the product from Preparative Example 52 (30 mg, 0.088 mmol) in anhydrous MeOH (3 mL). The mixture was stirred under N$_2$ for 60 min, then the solvent was evaporated and the residue was purified by preparative TLC chromatography on silica gel with 5:1 CH$_2$Cl$_2$/7N NH$_3$ in MeOH as eluent. Two isomers were obtained. Isomer 1(less polar): white solid (5 mg); Mp=130-133° C.; LC-MS: 342 [M+H]. Isomer 2(more polar): white solid (6 mg); Mp=199-202° C.; LC-MS: 342 [M+H].

Preparative Example 54

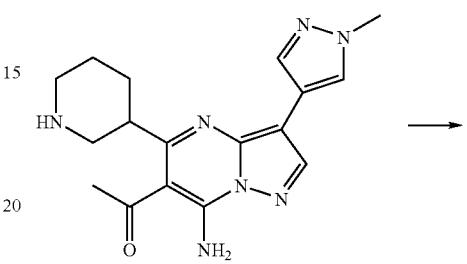

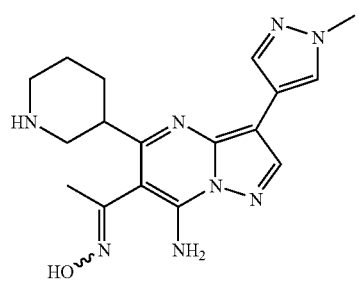

A mixture of the product from Preparative Example 52 (40 mg, 0.12 mmol), NH$_2$OH.HCl (10 mg, 0.14 mmol), and triethylamine (0.20 mL) in 1,2-dichloroethane (1 mL) and MeOH (1 mL) was stirred in a closed flask at 25° C. for 20 hr. The solvent was evaporated and the residue was purified by preparative TLC chromatography on silica gel with 5:1 CH$_2$Cl$_2$/7N NH$_3$ in MeOH as eluent. Slightly yellow solid (10 mg, 24%) was obtained. LC-MS: 355 [M+H]. Mp=228-230° C.

Preparative Example 55

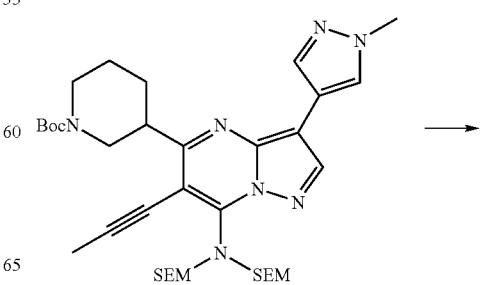

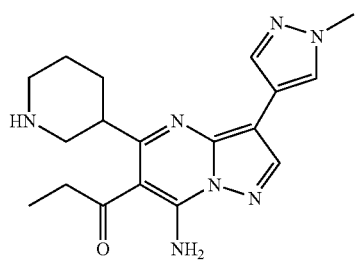

A mixture of the product from Preparative Example 51 (55 mg) and 3N aqueous HCl (2.8 mL) in EtOH (2.8 mL) was stirred at 60° C. for 1.5 hr. The solvents were evaporated, $Na_2CO_3$ (0.3 g) and 6:1 mixture of $CH_2Cl_2$/MeOH (4 mL) were added to the residue and the mixture was stirred under $N_2$ for 15 min. Then it was loaded onto a preparative TLC plate and it was purified by preparative TLC on silica gel with 10:1 $CH_2Cl_2$/7N $NH_3$ in MeOH as eluent. Yellow wax (12 mg, 48%) was obtained. LC-MS: 354 [M+H].

Preparative Example 56

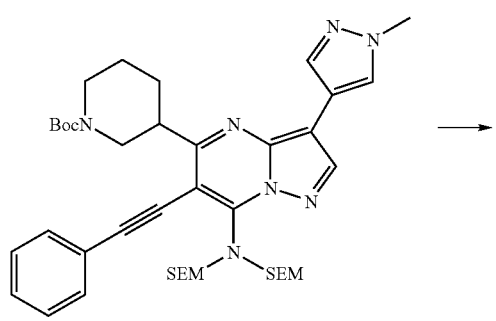

The compound was prepared by essentially the same procedure as given in Preparative Example 55, starting from the product from Preparative Example 50. Yellow wax. LC-MS: 416 [M+H].

Preparative Example 57

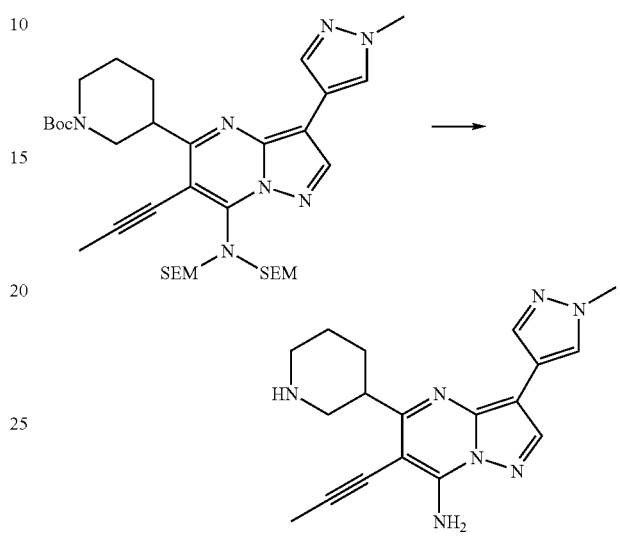

A mixture of the product from Preparative Example 51 (64 mg) in TFA (0.5 mL) and $H_2O$ (0.5 mL) was stirred at 25° C. for 1 hr. Toluene (5 mL) was added to the mixture and the solvents were evaporated. $NaHCO_3$ (0.3 g) and 6:1 mixture of $CH_2Cl_2$/MeOH (4 mL) were added to the residue and the mixture was stirred under $N_2$ for 15 min. Then it was loaded onto a preparative TLC plate and it was purified by preparative TLC on silica gel with 10:1 $CH_2Cl_2$/7N $NH_3$ in MeOH as eluent. White semi-solid (13 mg, 42%) was obtained. LC-MS: 336 [M+11].

Preparative Example 58

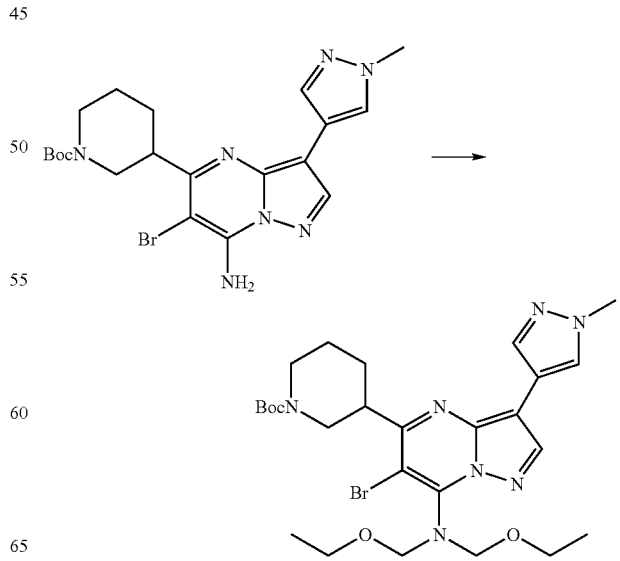

A mixture of the product from Preparative Example 45 (1.0 eq.), chloromethyl ethyl ether (4.0 eq.), and diisopropylethylamine (8.0 eq.) in dry 1,2-dichloroethane is stirred and refluxed under N₂ for 20 hr. The mixture is then poured into saturated aqueous NaHCO₃ solution, extracted with CH₂Cl₂, dried over Na₂SO₄, and filtered. The solvents are evaporated and the residue is purified by column chromatography on silica gel with 7:1 CH₂Cl₂/EtOAc as eluent.

Preparative Example 59

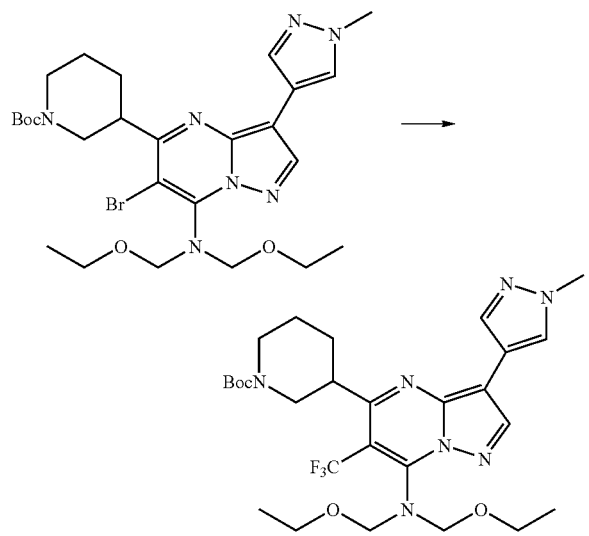

A mixture of the product from Preparative Example 58 (1.0 eq.), CF₃SiEt₃ (3.6 eq.), KF (3.6 eq.), and CuI (4.5 eq.) in DMF is stirred in a closed pressure vessel at 80° C. for 3 d. CH₂Cl₂ is added, the mixture is filtered through Celite, the solvent is evaporated, and the residue is chromatographed to yield the product.

Preparative Example 60

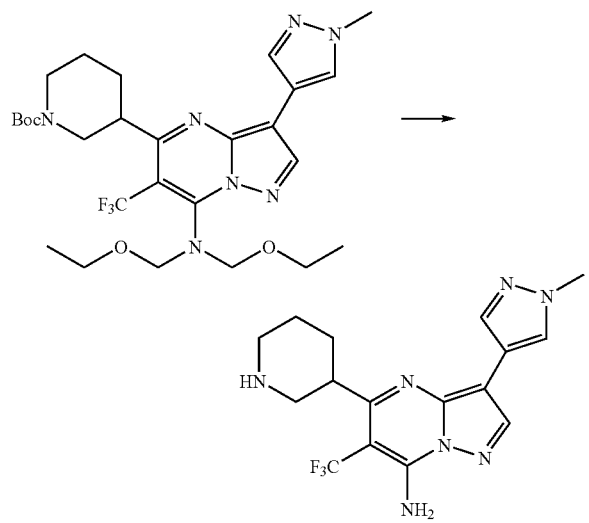

A mixture of the product from Preparative Example 59 and 3N aqueous HCl and EtOH is stirred at 60° C. for 1.5 hr. The solvents are evaporated, NaHCO₃ and 6:1 mixture of CH₂Cl₂/MeOH are added to the residue and the mixture is stirred under N₂ for 15 min. Then it is loaded onto a preparative TLC plate and it is purified by preparative TLC on silica gel with 10:1 CH₂Cl₂/7N NH₃ in MeOH as eluent.

Preparative Example 61

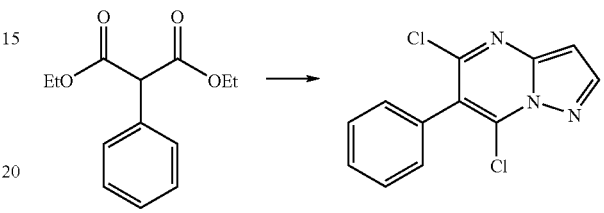

Diethyl phenyl malonate (2.0 g, 8.5 mmol), 3-aminopyrazole (0.7 g, 1.0 eq.) and tri-N-butyl amine (2.2 mL, 1.1 eq.) was heated to 180° C. for 4 hours. The reaction mixture was cooled to room temperature and slurried in EtOAc overnight. The mixture was filtered and dried in vacuo to give a white solid (2.98 g). This solid was dissolved in POCl₃ (20 mL) and dimethyl aniline (4 mL) was added and the reaction mixture heated to reflux overnight. The resulting solution was cooled to room temperature and poured into ice (400 g). The resulting mixture was extracted with EtOAc (3×100 mL). The combined organics were washed with H₂O (5×150 mL) and brine, dried over Na₂SO₄, filtered and concentrated in vacuo. The crude product was purified by flash chromatography using an 8% EtOAc in hexanes solution as eluent to give a tan solid (0.35 g, 16% yield).

Preparative Examples 62-63

Following the procedure set forth in Preparative Example 1 but utilizing the commercially available substituted diethyl malonates (as indicated) in Table 4.1 with 3-aminopyrazole, the substituted pyrazolo[1,5-a]pyrimidine adducts were prepared (Products).

TABLE 4.1

| Prep. Ex. | malonate | Product | Yield (%) |
|---|---|---|---|
| 62 | ![structure] | ![structure] | 11 |
| 63 | ![structure] | ![structure] | 26 |

Preparative Example 64

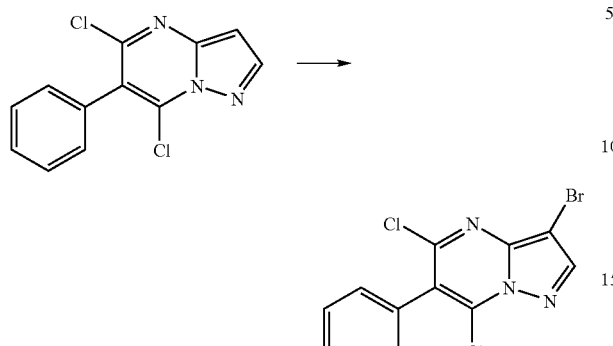

To a solution of 5,7-dichloro adduct (0.35 g, 1.33 mmol) from Preparative Example 61 in CH₃CN at 0° C. was added NBS (0.26 g, 1.46 mmol) in a single portion. The mixture was stirred for 3 hours at 0° C. and was concentrated under reduced pressure. The crude product was partitioned between Et₂O (7 mL) and H₂O (2 mL) and the layers were separated. The organic layer was washed sequentially with H₂O (1×2 mL) and brine (2×2 mL). The organic layer was dried (MgSO₄), filtered and concentrated under reduced pressure to afford an off-white solid (0.42 g, 90% yield) that was used without further purification. LC-MS [M+H]=344.0; 95% purity.

Preparative Examples 65-66

Following the procedure set forth in Preparative Example 64 but utilizing the 5,7-dichloro adducts (as indicated) from Table 4.1, the substituted pyrazolo[1,5-a]pyrimidine adducts were prepared (Products).

TABLE 4.2

| Prep. Ex. | Preparative Example of 5,7-dichloro adduct | Product | 1. Yield (%) 2. LC-MS |
|---|---|---|---|
| 65 | 62 | (structure) | 1. 96  2. 296.0 |
| 66 | 63 | (structure) | 1. 95  2. 294.1 |

Preparative Example 67

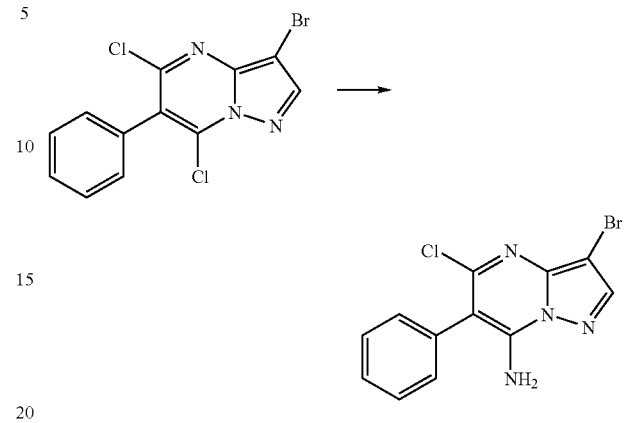

To a pressure tube charged with the 5,7-dichloro adduct (0.40 g, 1.16 mmol) from Preparative Example 64 and a stirbar was added 2M NH₃ in IPA (5 mL) and conc. NH₄OH (2 mL). The tube was sealed and heated to 80° C. The mixture was stirred for 12 h, cooled to rt, and concentrated under reduced pressure. The crude product was purified by preparative thin-layer chromatography (6×1000 μM plates) using a 30:1 mixture of CH₂Cl₂/MeOH (7M NH₃) as eluent to afford (0.15 g, 41% yield) as a white solid. mp>210° C. LC-MS: 325.1 [M+H]

Examples 68-69

Following the procedure set forth in Example 67 but utilizing the 5,7-dichloro adducts (as indicated) from Table 4.2, the substituted pyrazolo[1,5-a]pyrimidine adducts were prepared (Products) in Table 4.3.

TABLE 4.3

| Ex. | Preparative Example of 5,7-dichloro adduct | Product | 1. Yield (%) 2. LC-MS 3. mp (° C.) |
|---|---|---|---|
| 68 | 65 | (structure) | 1. 52  2. 277.0  3. 135-138 |
| 69 | 66 | (structure) | 1. 42  2. 263.1  3. 178-182 |

Preparative Example 70

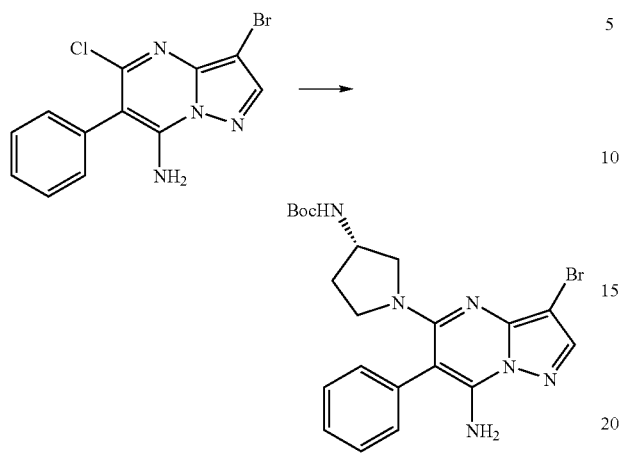

To a mixture of 7-amino adduct (0.10 g, 0.31 mmol) from Example 67 in NMP (1.5 mL) at rt was added NaHCO$_3$ (78 mg, 0.93 mmol) followed by (S)-(−)-3-(Boc-amino)pyrrolidine (86 mg, 0.46 mmol). The mixture was affixed with a reflux condenser and was heated to 140° C. The mixture was stirred for 14 h, cooled to rt, and concentrated under reduced pressure. The crude product was purified by preparative thin-layer chromatography (6×1000 μM plates) using a 35:1 mixture of CH$_2$Cl$_2$/MeOH as eluent to afford (68 mg, 46% yield) as a yellow/brown solid. LC-MS [M+H]=475.1; 92% purity.

Preparative Examples 71-72

Following the procedure set forth in Preparative Example 70 but utilizing the 5,7-dichloro adducts (as indicated) from Table 4.3, the substituted pyrazolo[1,5-a]pyrimidine adducts were prepared (Products) in Table 4.4.

TABLE 4.4

| Prep. Ex. | Example of 7-amino adduct | Product | 1. Yield (%) 2. LC-MS |
|---|---|---|---|
| 71 | 68 | BocHN-pyrrolidine-pyrazolopyrimidine-Br (ethyl, NH$_2$) | 1. 76 2. 427.1 |
| 72 | 69 | BocHN-pyrrolidine-pyrazolopyrimidine-Br (methyl, NH$_2$) | 1. 47 2. 413.1 |

Example 73

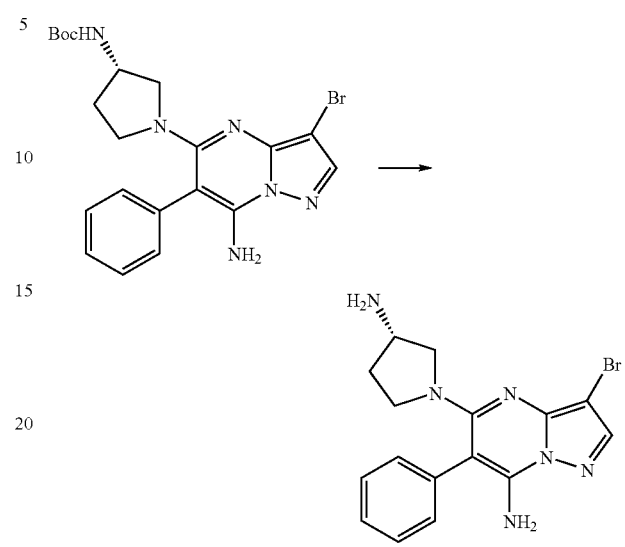

To a mixture of 7-amino adduct (68 mg, 0.14 mmol) from Preparative Example 70 in CH$_2$Cl$_2$ (2 mL) at 0° C. was added TFA (0.5 mL) dropwise. The resulting mixture was stirred for 12 h at rt and was concentrated under reduced pressure. The crude material was partitioned between EtOAc (5 mL) and sat. aq. Na$_2$CO$_3$ (2 mL) and the layers were separated. The aqueous layer was extracted with EtOAc (2×5 mL) and the organic layers were combined. The organic layer was washed with brine (1×3 mL), dried (Na$_2$SO$_4$), filtered, and concentrated under reduced pressure. The crude product was purified by preparative thin-layer chromatography (4×1000 μM plates) using a 15:1 mixture of CH$_2$Cl$_2$/MeOH (7M NH$_3$) as eluent to afford (40 mg, 46% yield) as a light tan solid. mp 167-170° C.; LC-MS: 375 [M+H]

Examples 74-75

Following the procedure set forth in Example 73 but utilizing the Boc adducts (as indicated) from Table 4.4, the substituted pyrazolo[1,5-a]pyrimidine adducts were prepared (Products) in Table 4.5.

TABLE 4.5

| Ex. | Ex. of Boc adduct | Product | 1. Yield (%) 2. LC-MS 3. mp (° C.) |
|---|---|---|---|
| 74 | 71 | H$_2$N-pyrrolidine-pyrazolopyrimidine-Br (ethyl, NH$_2$) | 1. 68 2. 325.2 3. 135-138 |

TABLE 4.5-continued

| Ex. | Ex. of Boc adduct | Product | 1. Yield (%) 2. LC-MS 3. mp (° C.) |
|---|---|---|---|
| 75 | 72 | 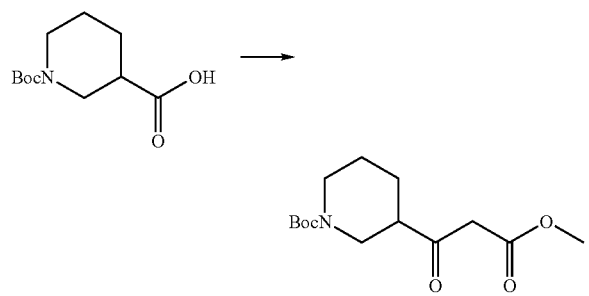 | 1. 80 2. 313.2 3. 143-144 |

The preparation of the compounds of copending application Ser. No. 11/542,920 is illustrated below:

Preparative Example X-10-C

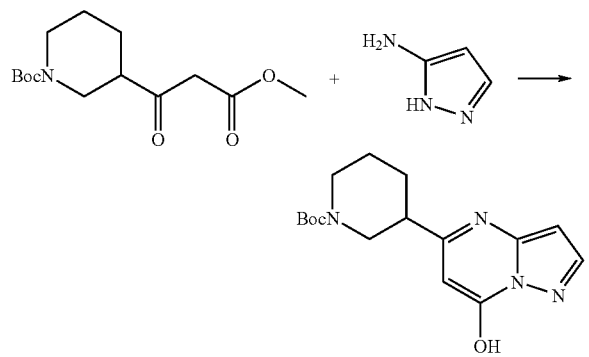

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (300 mL). The mixture was stirred at 25° C. for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, filtered, and the solvent was evaporated. The residue was dissolved in MeOH (580 mL), and the mixture was refluxed for 4 hr. The solvent was evaporated and the residue was purified by column chromatography on silica gel with 10:1 CH$_2$Cl$_2$/EtOAc as eluent. Pale yellow oil (26.5 g, 43%) was obtained.

Preparative Example X-20-C

A mixture of the beta-ketoester from Preparative Example X-10-C (20.0 g, 70.1 mmol) and 3-aminopyrazole (5.40 g, 65.0 mmol) in anhydrous toluene (60 mL) was stirred and refluxed under N$_2$ for 24 hr. The solvent was evaporated and the residue was purified by column chromatography on silica gel with 20:1 CH$_2$Cl$_2$/MeOH as eluent. White solid (15.0 g, 73%) was obtained. LC-MS: 319 [M+H].

Preparative Example X-30-C

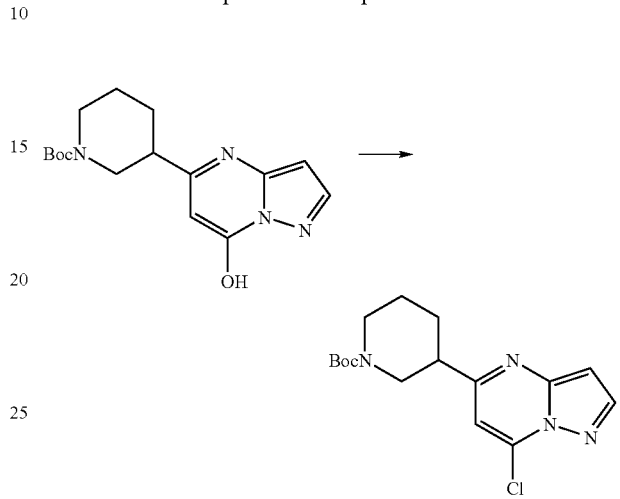

A mixture of the product from Preparative Example X-20-C (12.50 g, 39.3 mmol), N,N-dimethylaniline (15.5 mL), and POCl$_3$ (125 mL) was stirred at 25° C. for 4 days. Excess of POCl$_3$ was evaporated and the residue was poured into saturated aqueous NaHCO$_3$ (600 mL). The mixture was extracted with CH$_2$Cl$_2$ (3×200 mL), the combined extracts were dried over Na$_2$SO$_4$, filtered, and the solvent was evaporated. The residue was purified by column chromatography on silica gel with 8:1 CH$_2$Cl$_2$/EtOAc as eluent. Pale yellow wax (9.41 g, 71%) was obtained. LC-MS: 337 [M+].

Preparative Example X-40-C

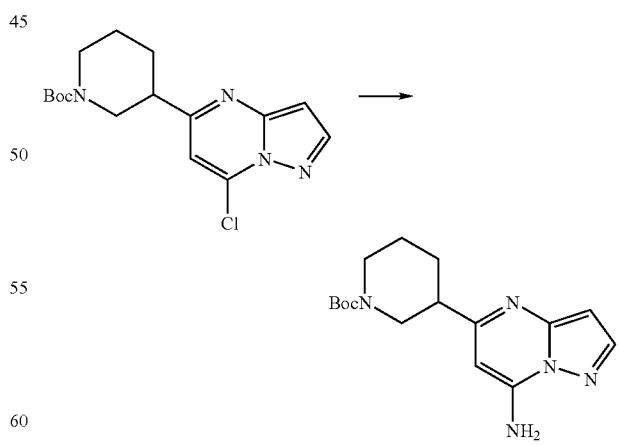

A mixture of the product from Preparative Example X-30-C (8.00 g, 23.8 mmol), 2.0 M NH$_3$ in 2-propanol (50 mL), and conc. aqueous NH$_4$OH (5 mL) was stirred in a closed pressure vessel at 70° C. for 28 hr. The solvents were evaporated and the residue was purified by column chromatography on silica gel with 10:1 CH₂Cl₂/MeOH as eluent. White solid (7.40 g, 98%) was obtained. LC-MS: 318 [M+H].

Preparative Example X-50-C

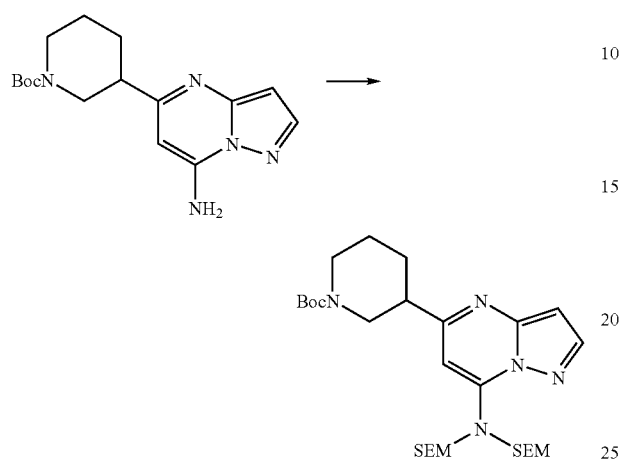

A mixture of the product from Preparative Example X-40-C (2.00 g, 6.30 mmol), SEMCI (3.69 g, 22.10 mmol), and diisopropylethylamine (5.70 g, 44.20 mmol) in dry 1,2-dichloroethane (20 mL) and was stirred and refluxed under N₂ for 2 hr. The mixture was then poured into saturated aqueous NaHCO₃ solution (100 mL), extracted with CH₂Cl₂ (3×30 mL), dried over Na₂SO₄, and filtered. The solvents were evaporated and the residue was purified by column chromatography on silica gel with 15:1 CH₂Cl₂/EtOAc as eluent. Slightly yellow oil (2.76 g, 76%) was obtained.

Preparative Example X-60-C

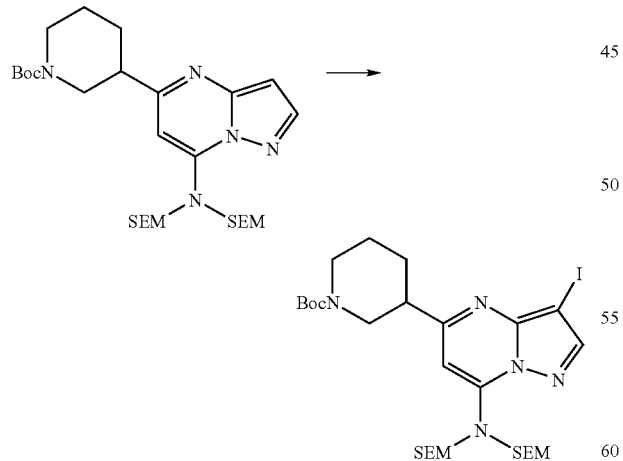

A solution of N-iodosuccinimide (0.90 g, 4.00 mmol) in anhydrous CH₃CN (10 mL) was added under N₂ to a stirred solution of the product from Preparative Example 50-C (2.50 g, 4.33 mmol) in anhydrous CH₃CN (10 mL). The mixture was stirred for 1 hr, the solvents were evaporated, and the residue was purified by column chromatography on silica gel with 40:1 CH₂Cl₂/EtOAc as eluent. Slightly yellow wax (2.57 g, 92%) was obtained.

Preparative Example X-61-C

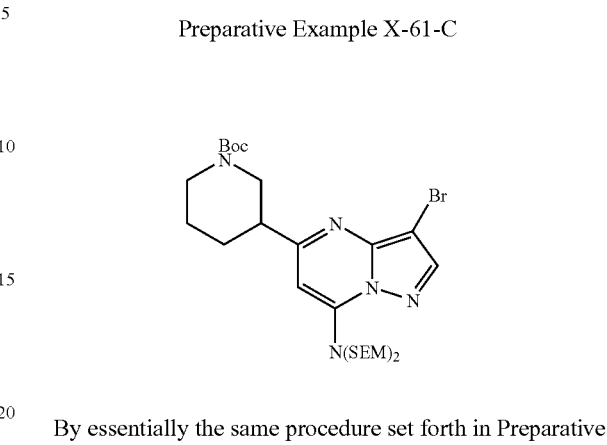

By essentially the same procedure set forth in Preparative Example X-60-C only substituting NBS for NIS, the above compound was prepared.

Preparative Example X-70-C

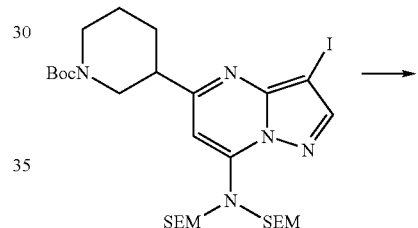

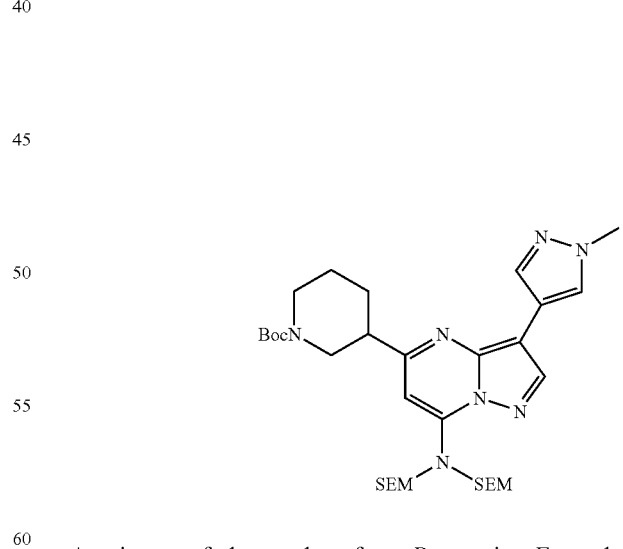

A mixture of the product from Preparative Example X-60-C (1.50 g, 2.13 mmol), 1-methyl-4-(4,4,5,5-tetramethyl-1,3,2-dioxaborolan-2-yl)-1H-pyrazole (0.89 g, 4.26 mmol), PdCl₂dppf.CH₂Cl₂ (171 mg, 0.21 mmol), and K₃PO₄ (1.81 g, 8.52 mmol) in 1,2-dimethoxyethane (30 mL) and H₂O (6 mL) was stirred and refluxed under N₂ for 3 hr. The solvents were evaporated and the residue was purified by column chromatography on silica gel with 5:1 CH₂Cl₂/EtOAc as eluent. Yellow wax (1.13 g, 81%) was obtained.

Preparative Example X-80-C

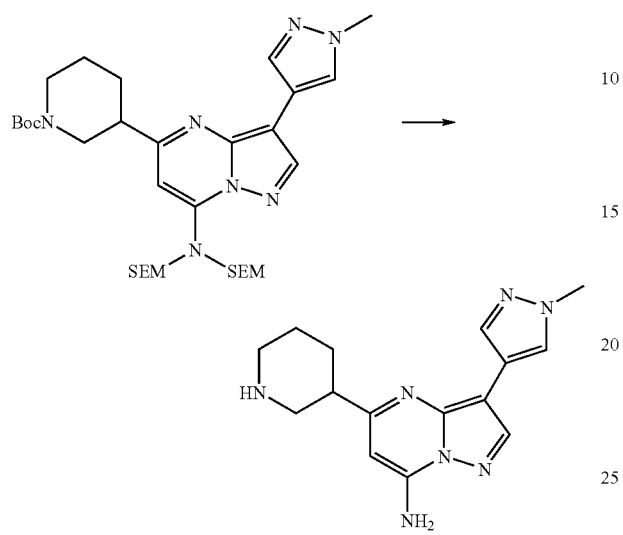

A mixture of the product from Preparative Example X-70-C (1.00 g) and 3N aqueous HCl (20 mL) in EtOH (20 mL) was stirred at 60° C. for 1.5 hr. The solvents were evaporated, Na₂CO₃ (2.0 g) and 6:1 mixture of CH₂Cl₂/MeOH (20 mL) were added to the residue and the mixture was stirred under N₂ for 15 min. Then it was loaded onto a column and it was purified by column chromatography on silica gel with 6:1 CH₂Cl₂/7N NH₃ in MeOH as eluent. White solid (405 mg, 90%) was obtained. LC-MS: 298 [M+H].

Preparative Example X-90-C

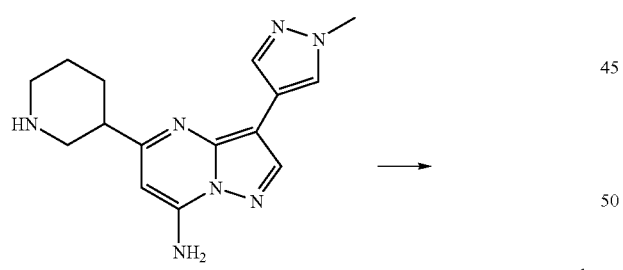

Boc₂O (441 mg, 2.02 mmol) was added to a stirred solution of the product from Preparative Example X-80-C (500 mg, 1.68 mmol) and triethylamine (2.0 mL) in anhydrous CH₂Cl₂ (10 mL). The mixture was stirred at 25° C. for 18 hr, then it was poured into saturated aqueous NaHCO₃ solution (60 mL), extracted with CH₂Cl₂ (3×10 mL), dried over Na₂SO₄, and filtered. The solvents were evaporated and the residue was purified by column chromatography on silica gel with 20:1 CH₂Cl₂/MeOH as eluent. Pale yellow solid (670 mg, 100%) was obtained. LC-MS: 398 [M+H].

Preparative Example X-100-C

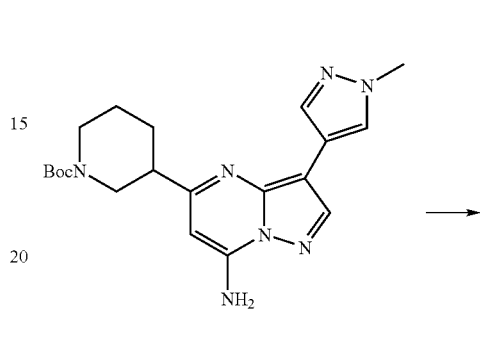

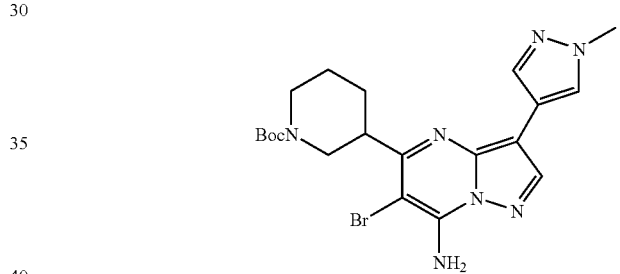

A solution of Br₂ (191 mg, 1.19 mmol) in dry CH₂Cl₂ (4 mL) was added dropwise to a stirred solution of the product from Preparative Example X-90-C (500 mg, 1.26 mmol) in tert-BuNH₂ (10 mL) and CH₂Cl₂ (5 mL). The mixture was stirred at 25° C. for 20 hrs, the solvents were evaporated and the residue was purified by column chromatography on silica gel with 1:1 CH₂Cl₂/EtOAc as eluent. White solid (415 mg, 73%) was obtained. LC-MS: 476 [M+].

Preparative Example X-110-C

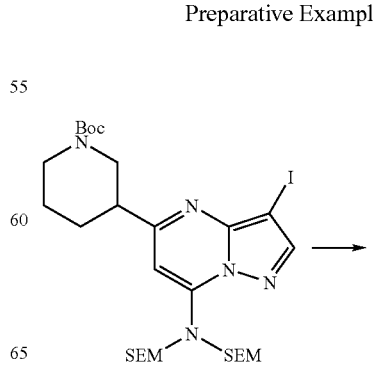

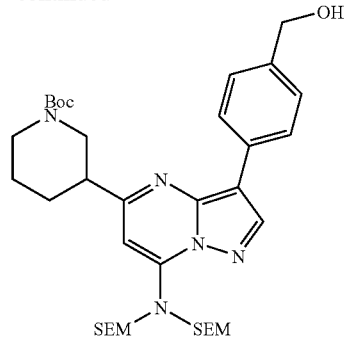

To a solution 3-iodo adduct (0.40 g, 0.57 mmol) from Preparative Example X-60-C in a mixture of DME/H$_2$O (15 mL/3 mL) at rt was added 4-hydroxymethylphenyl boronic acid (0.17 g, 1.14 mmol), Na$_2$CO$_3$ (0.18 g, 1.70 mmol), and PdCl$_2$(dppf) (46 mg, 0.057 mmol). The mixture was degassed under house vacuum 6× and filled with N$_2$ and was heated to 95° C. The mixture was stirred for 5 h, cooled to rt, and concentrated under reduced pressure. The crude residue was partitioned between CH$_2$Cl$_2$ (10 mL) and water (3 mL) and the layers were separated. The aqueous layer was extracted with CH$_2$Cl$_2$ (2×10 mL) and the organic layers were combined. The organic layer was dried (Na$_2$SO$_4$), filtered and concentrated under reduced pressure. The crude product was purified by preparative thin-layer chromatography (6×1000 μM plates) using a 3:1 mixture of hexanes/EtOAc as eluent to afford (0.38 g, 96% yield) as a yellow semisolid. LC-MS:= 684.4 [M+H] 98% purity.

Preparative Examples X-120-C to X-210-C

Following the procedure set forth in Preparative Example X-110-C but utilizing the boronic acid/boronates (as indicated) in Table X-10-C and commercially available amines, the substituted pyrazolo[1,5-a]pyrimidine adducts were prepared (Products).

TABLE X-10-C

| Prep. Ex. X- | Boronic Acid/Boronate | Product | 1. Yield (%) 2. LC-MS |
|---|---|---|---|
| 120-C | | | 1. 88 2. 697.5 |
| 130-C | | | 1. 88 2. 761.5 |
| 140-C | | | 1. 60 2. 698.5 |

TABLE X-10-C-continued
| Prep. Ex. X- | Boronic Acid/Boronate | Product | 1. Yield (%) 2. LC-MS |
|---|---|---|---|
| 150-C | 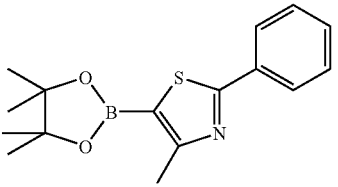 | 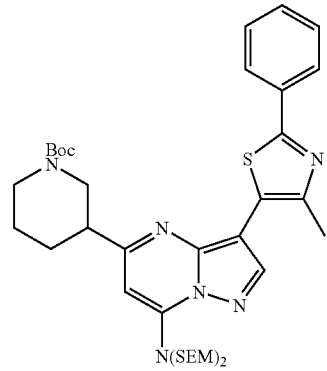 | 1. 71 2. 751.2 |
| 160-C | 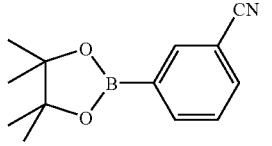 | 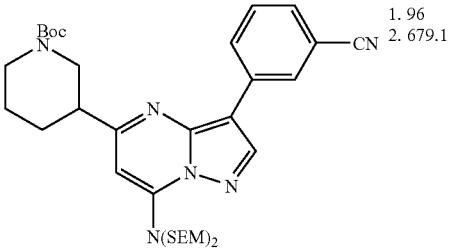 | 1. 96 2. 679.1 |
| 170-C | 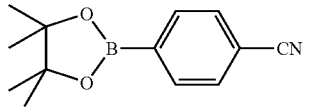 | 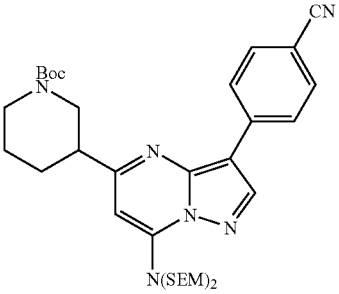 | 1. 97 2. 679.1 |
| 180-C | 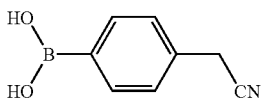 | 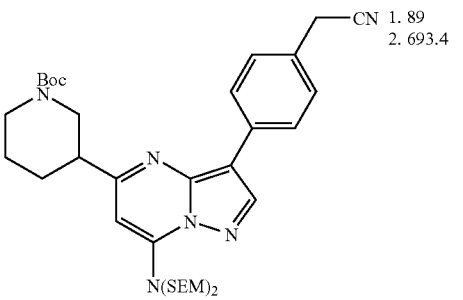 | 1. 89 2. 693.4 |
| 190-C | 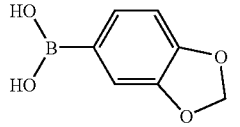 | 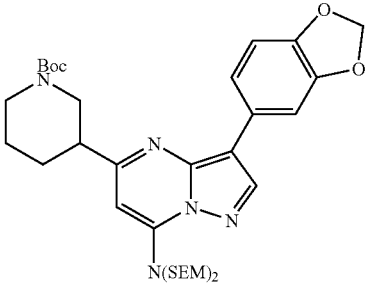 | 1. 90 2. 698.4 |

TABLE X-10-C-continued

| Prep. Ex. X- | Boronic Acid/Boronate | Product | 1. Yield (%) 2. LC-MS |
|---|---|---|---|
| 200-C | HO-B(OH)-pyrimidine-SMe | Boc-piperidine-pyrazolo[1,5-a]pyrimidine with pyrimidine-SMe and N(SEM)$_2$ | 1. 67 2. 702.5 |
| 210-C | HO-B(OH)-pyrazole | Boc-piperidine-pyrazolo[1,5-a]pyrimidine with pyrazole and N(SEM)$_2$ | 1. 41 2. 644.5 |

Preparative Example X-220-C

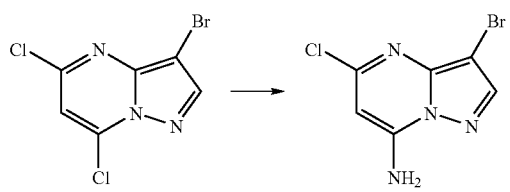

To a pressure tube charged with 3-bromo-5,7-dichloropyrazolo[1,5-a]pyrimidine (3 g, 0.11 mol) from and a stir bar was added conc. NH$_4$OH (~90 mL) at rt. The tube was capped, heated to 85° C., and stirred for 12 h. The mixture was cooled to rt and concentrated under reduced pressure. The crude product was taken up in water (70 mL) and was filtered. The ppt was washed sequentially with water (1×50 mL) and Et$_2$O (1×50 mL). The crude product was placed under high vacuum to afford 2.4 g (88% yield) of a yellow solid. LC-MS: 249.1 [M+H]; 97% purity.

Preparative Example X-230-C

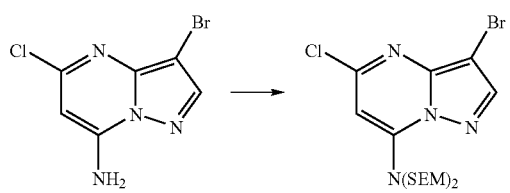

To a mixture of 7-amino adduct (1.0 g, 4.0 mmol) from Preparative Example X-220-C in DCE (8 mL) at rt was added DIPEA (4.9 mL, 28.2 mmol) followed by SEMCl (2.2 mL, 12.1 mmol). The resulting mixture was heated to 90° C. and was stirred for 12 h. The mixture was cooled to rt and sat. aq. NaHCO$_3$ (35 mL) was added followed by dilution with CH$_2$Cl$_2$ (50 mL). The layers were separated and the aqueous layer was extracted with CH$_2$Cl$_2$ (3×50 mL). The organic layers were combined, dried (Na$_2$SO$_4$), filtered, and concentrated under reduced pressure. The crude product was purified by flash chromatography using a 7:1 mixture of hexanes/EtOAc to afford 2.0 g (97% yield) of a yellow oil.

Preparative Example X-240-C

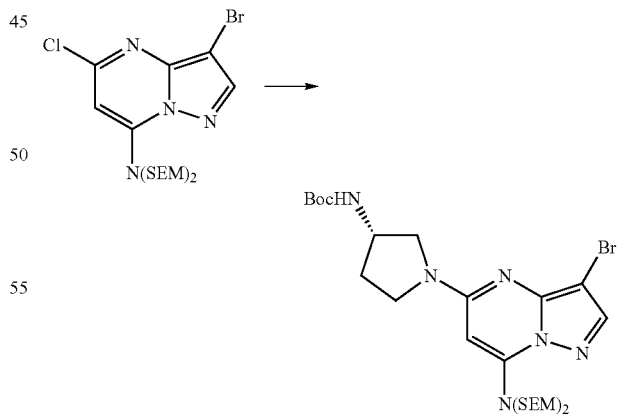

To a mixture of 5-chloro adduct (0.50 g, 0.98 mmol) from Preparative Example X-230-C in NMP (3 mL) at rt was added (S)-3-(Boc-amino)pyrrolidine (0.28 g, 1.5 mmol) followed by NaHCO$_3$ (0.19 g, 2.2 mmol). 12.1 mmol). The resulting mixture was heated to 130° C. and was stirred for 12 h. The mixture was concentrated under reduced pressure purified by preparative TLC using 8×1000 µM plates with a 40:1 mixture of CH₂Cl₂/MeOH as eluent to afford 0.51 g (79% yield) of a light yellow solid. LC-MS: 659.4 [M+H]; 94% purity.

Preparative Example X-250-C

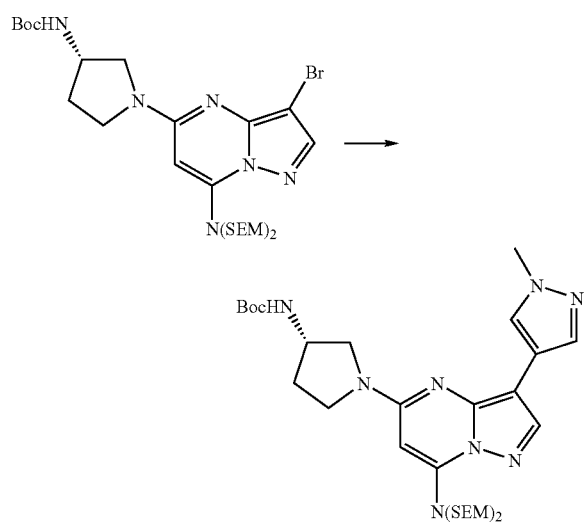

By the same method used in Preparative Example X-110-C, the 3-bromo derivative (0.42 g, 0.64 mmol) from Preparative Example 240-C was treated with 1-methyl-4-(4,4,5,5-tetramethyl-1,3,2-dioxaborolan-2-yl)-1H-pyrazole (0.27 g, 1.28 mmol) to afford 0.10 g (24% yield) of a white semisolid. LC-MS: 659.0 [M+H]; 95% purity.

Preparative Example X-260-C

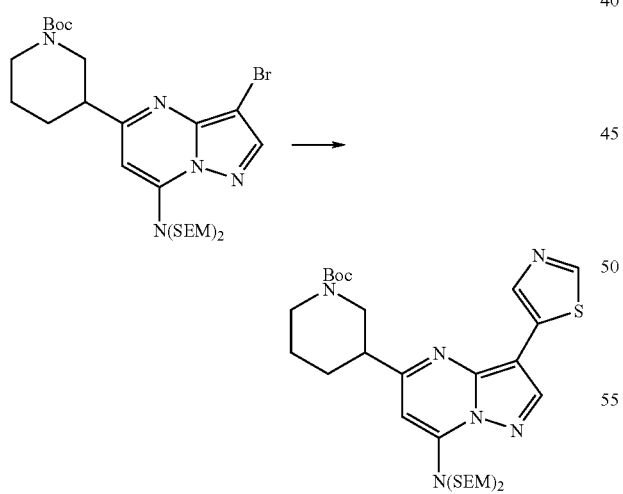

To a solution of 3-Br adduct (0.45 g, 0.69 mmol) from Preparative Example X-61-C in CH₃CN (4 mL) at rt was 4-tributylstannylthiazole (0.51 g, 1.37 mmol) followed by PdCl₂(PPh₃)₂ (48 mg, 0.069 mmol). The resulting mixture was degassed under aspirator vacuum and filled with N₂ six times. The mixture was fitted with a condenser and was heated to 80° C. The mixture was stirred for 12 h, cooled to rt, and diluted with EtOAc (10 mL). The mixture was filtered thru a Celite pad which was washed with CH₂Cl₂ (1×5 mL) and MeOH (1×5 mL). The resulting filtrate was concentrated under reduced pressure and was placed under high vacuum. The crude product was purified by preparative thin-layer chromatography (6×1000 µM plates) using a 40:1 mixture of CH₂Cl₂/MeOH as eluent to afford 0.28 g (61% yield) as an orange oil. LC-MS: =661.4 [M+H] 71% purity.

Preparative Example X-270-C

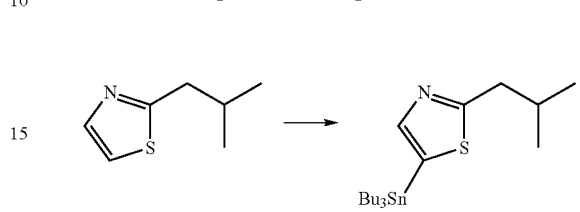

To a solution of 2-isobutylthiazole (5.0 mL, 35.4 mmol) in THF (100 mL) at −78° C. was added a 2 M solution of LDA (21.0 mL, 42.2 mmol) dropwise over 10 min. After 1 h at this temperature, Bu₃SnCl (11.5 mL, 42.4 mmol) was added dropwise. The mixture was allowed to gradually warm to rt over about 3 h whereupon the mixture was quenched with sat.aq. NH₄Cl (15 mL) and diluted with Et₂O (70 mL). The layers were separated and the aqueous layer was extracted with Et₂O (2×70 mL). The organic layers were combined, dried (MgSO₄), filtered and concentrated under reduced pressure to afford the desired compound as an orange/brown oil. MS:=430.4 The material was taken on crude to the next transformation without purification.

Preparative Example X-280-C

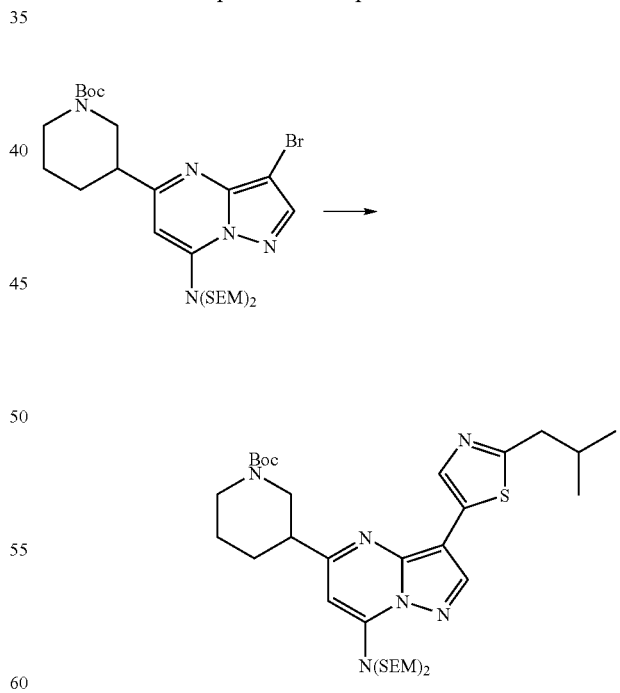

Utilizing the procedure in Preparative Example X-260-C, the 3-Br adduct (0.40 g, 0.61 mmol) from Preparative Example X-61-C was treated with the tributylstannylthiazole (0.52 g, 1.22 mmol) from Preparative Example X-17 to afford 0.34 g (77% yield) of a orange/brown oil. LC-MS:=717.4 [M+H] 62% purity.

Example X-10-C

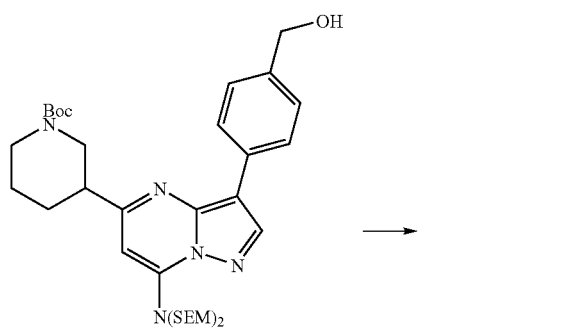

To a solution of adduct (0.25 g, 0.37 mmol) from Preparative Example X-110-C in EtOH (3 mL) at rt was added 3M HCl (3 mL). The resulting solution was heated to 60° C. and was stirred for 5 h (until complete by TLC). The mixture was cooled to rt and concentrated under reduced pressure. The crude material was taken up in 7M $NH_3$ in MeOH (3 mL) and stirred for 3 h. The mixture was concentrated under reduced pressure and was purified by preparative thin-layer chromatography (4×1000 μM plates) using a 10:1 mixture of $CH_2Cl_2$/MeOH (7M $NH_3$) as eluent to afford (20 mg, 17% yield) as an off-white solid. LC-MS:=324.2 [M+H] 99% purity.

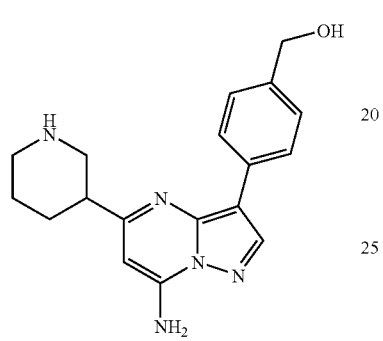

Examples X20-C-X130-C

Following the procedure set forth in Example X-10-C, the indicated Preparative Examples in Column 2 of Table X-20-C were converted to the substituted pyrazolo[1,5-a]pyrimidine adducts shown in Column 3 of Table X-20-C were prepared.

TABLE X-20-C

| Ex. X- | Column 2 | Column 3 | 1. Yield (%) 2. LC-MS 3. mp (° C.) |
|---|---|---|---|
| 20-C | [structure with benzamide, SEM groups] | [structure with benzamide, NH2] | 1. 12 2. 337.2 3. 134-137 |
| 30-C | [structure with sulfonamide, SEM groups] | [structure with sulfonamide, NH2] | 1. 11 2. 401.2 3. 167-169 |

TABLE X-20-C-continued
| Ex. X- | Column 2 | Column 3 | 1. Yield (%) 2. LC-MS 3. mp (° C.) |
|---|---|---|---|
| 40-C | 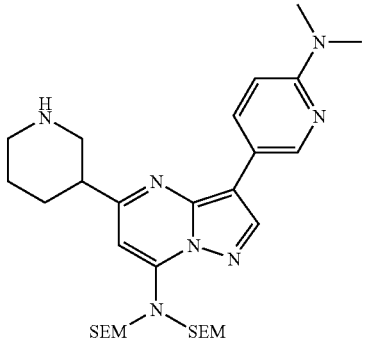 | 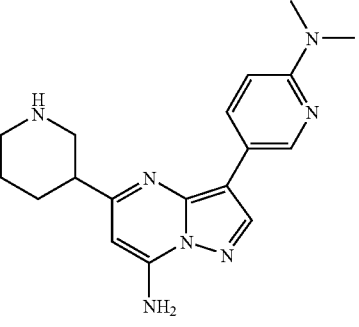 | 1. 25 2. 338.2 3. 123-125 |
| 50-C | 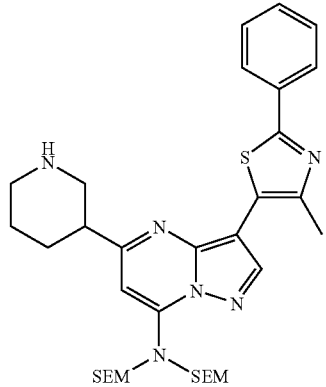 | 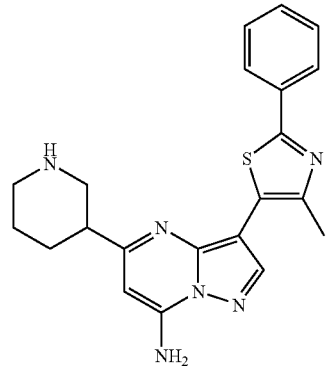 | 1. 57 2. 391.2 3. 165-167 |
| 60-C | 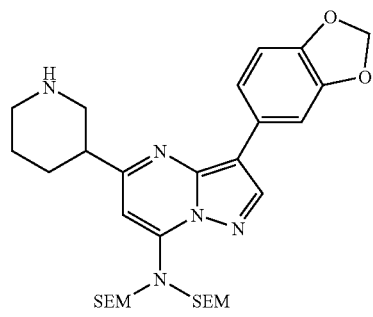 | 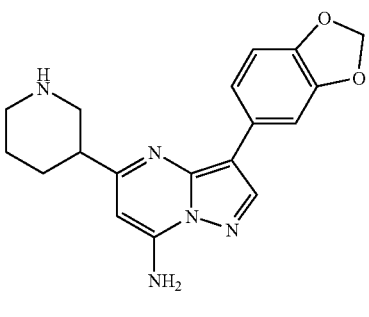 | 1. 42 2. 338.2 3. 156-160 |
| 70-C | 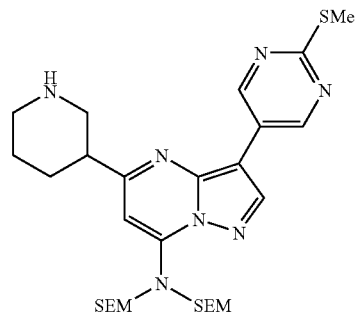 | 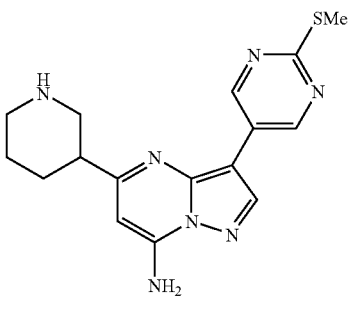 | 1. 25 2. 342.2 3. 156-159 |

TABLE X-20-C-continued

| Ex. X- | Column 2 | Column 3 | 1. Yield (%)<br>2. LC-MS<br>3. mp (° C.) |
|---|---|---|---|
| 80-C | | | 1. 48<br>2. 284.2<br>3. 145-147 |
| 90-C | | | 1. 70<br>2. 301.2<br>3. 148-150 |
| 100-C | | | 1. 27<br>2. 357.2<br>3. 130-132 |
| 110-C | | | 1. 45<br>2. 285.2.2<br>3. 167-169 |
| 120-C | | | 1. 85<br>2. 286.2<br>3. 145-148 |

TABLE X-20-C-continued

| Ex. X- | Column 2 | Column 3 | 1. Yield (%) 2. LC-MS 3. mp (° C.) |
|---|---|---|---|
| 130-C | 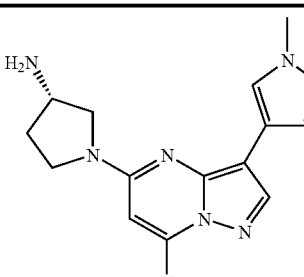 | 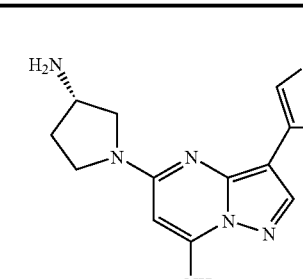 | 1. 25 2. 299.2 3. 185-187 |

Example X-140-C

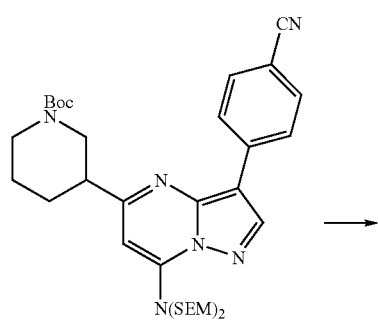

⟶

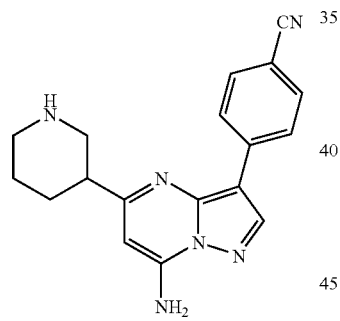

To a solution of adduct (0.28 g, 0.41 mmol) from Preparative Example X-170-C in water (4 mL) at rt was added TEA (4 mL). The resulting solution was stirred at rt for 4 h (until complete by TLC) and was concentrated under reduced pressure. The crude material was taken up in 7M $NH_3$ in MeOH (3 mL) and stirred for 3 h. The mixture was concentrated under reduced pressure and was purified by preparative thin-layer chromatography (4×1000 μM plates) using a 10:1 mixture of $CH_2Cl_2$/MeOH (7M $NH_3$) as eluent to afford (60 mg, 46% yield) as a yellow solid. mp 167-169° C.; LC-MS:=319.2 [M+H] 99% purity.

Examples X150-C-X160-C

Following the procedure set forth in Example X-140-C, the compounds in Column 2 of Table 30-C were converted to the substituted pyrazolo[1,5-a]pyrimidine adducts (Column 3) found in Table X-30-C.

TABLE X-30-C

| Ex. X- | Column 2 | Column 3 | 1. Yield (%) 2. LC-MS 3. mp (° C.) |
|---|---|---|---|
| 150-C | 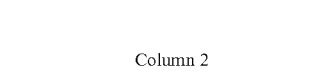 |  | 1. 29 2. 319.4 3. 176-178 |

TABLE X-30-C-continued

| Ex. X- | Column 2 | Column 3 | 1. Yield (%)<br>2. LC-MS<br>3. mp (° C.) |
|---|---|---|---|
| 160-C | | | 1. 29<br>2. 333.2<br>3. 145-147 |

Preparative Example X-290-C

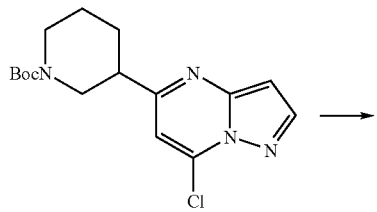

A solution of NBS (4.03 g, 22.7 mmol) in anhydrous CH₃CN (40 mL) was added under N₂ to a stirred solution of the product from Preparative Example X-30-C (7.63 g, 22.7 mmol) in anhydrous CH₃CN (60 mL) and CH₂Cl₂ (20 mL). The mixture was stirred for 2 hr, the solvents were evaporated, and the residue was purified by column chromatography on silica gel with 20:1 CH₂Cl₂/EtOAc as eluent. Pale yellow solid foam (9.20 g, 97%) was obtained.

Preparative Example X-300-C

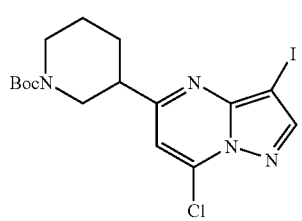

By essentially same procedure set forth in Preparative Example X-290-C, reaction of 7-Cl adduct from Preparative Example X-30-C with N-iodosuccinimide afforded the title compound.

Preparative Example X-310-C

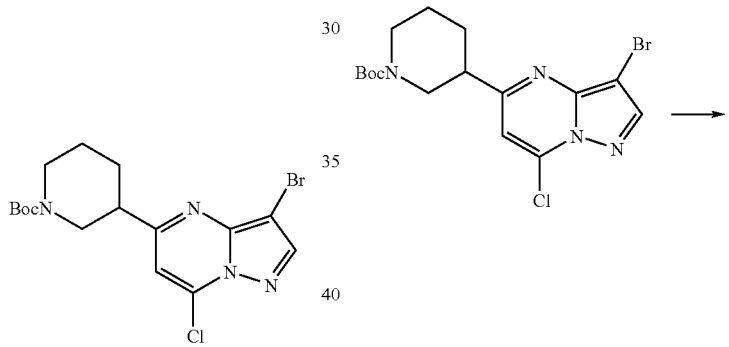

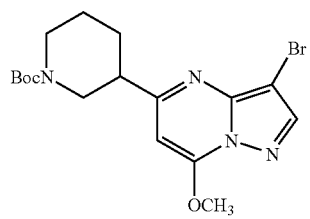

A mixture of the product from Preparative Example X-290-C (8.00 g, 19.3 mmol) and MeONa (2.16 g, 40.0 mmol) in anhydrous MeOH (100 mL) was stirred for 20 hr. CH₂Cl₂ (200 mL) was then added, the mixture was filtered through Celite, the solvent was evaporated, and the residue was purified by column chromatography on silica gel with 2:1 CH₂Cl₂/EtOAc as eluent. White solid (7.75 g, 98%) was obtained.

Preparative Example X-320-C

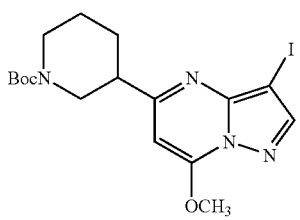

By essentially same procedure set forth in Preparative Example X-310-C, starting from the compound from Preparative Example X-300-C, the title compound was prepared.

Preparative Example X-330-C

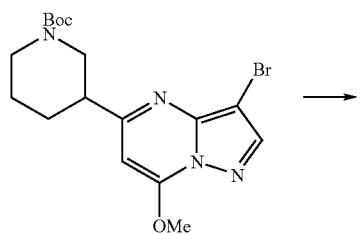

To a solution of 3-Br adduct (0.25 g, 0.61 mmol) from Preparative Example X-310-C in CH₃CN (3 mL) at rt was 5-tributylstannylthiazole (0.46 g, 1.22 mmol) followed by PdCl₂(PPh₃)₂ (43 mg, 0.069 mmol). The resulting mixture was degassed under aspirator vacuum and filled with N₂ six times. The mixture was fitted with a condenser and was heated to 80° C. The mixture was stirred for 12 h, cooled to rt, and diluted with EtOAc (10 mL). The mixture was filtered thru a Celite pad which was washed with EtOAc (3×5 mL), CH₂Cl₂ (1×5 mL) and MeOH (1×5 mL). The resulting filtrate was concentrated under reduced pressure and was placed under high vacuum. The crude product was purified by preparative thin-layer chromatography (6×1000 µM plates) using a 20:1 mixture of CH₂Cl₂/MeOH as eluent to afford 0.19 g (75% yield) as a yellow semisolid. LC-MS:=416.2 [M+H] 66% purity.

Preparative Example X-340-C

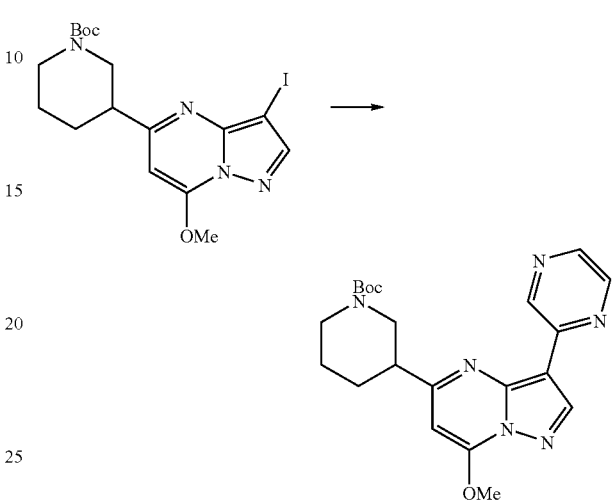

To a solution of 3-I adduct (0.40 g, 0.87 mmol) from Preparative Example X-320-C in dioxane (3 mL) at rt was 2-tributylstannylthiazole (0.40 g, 1.09 mmol) followed by Pd(PPh₃)₄ (63 mg, 0.055 mmol). The mixture was fitted with a condenser and was heated to 90° C. and was stirred at this temperature for 12 h. The mixture was cooled to it and concentrated under reduced pressure. The crude product was purified by preparative thin-layer chromatography (6×1000 1.1M plates) using a 20:1 mixture of CH₂Cl₂/MeOH as eluent to afford 0.16 g (45% yield) as a yellow semisolid. LC-MS:= 411.2 [M+H] 84% purity.

Preparative Example X-350-C

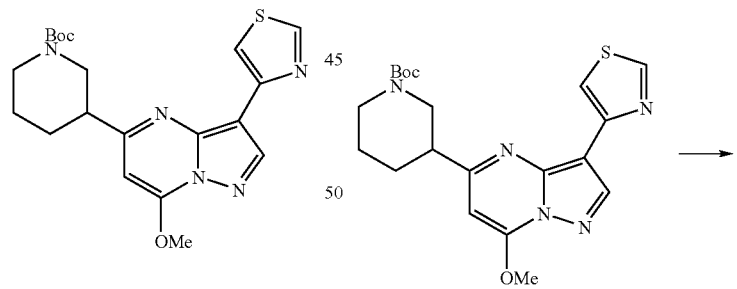

To a pressure tube charged with 7-methoxy adduct (0.18 g, 0.45 mmol) from Preparative Example X-330-C and a stir bar was added 7M NH₃ in MeOH (5 mL). The tube was capped, heated to 80° C., and stirred for 72 h. The mixture was cooled to rt, concentrated under reduced pressure, and placed under high vacuum. The crude material was purified by preparative thin-layer chromatography (4×1000 µM plates) using a 20:1 mixture of CH$_2$Cl$_2$/MeOH (7M NH$_3$) as eluent to afford 120 mg (66% yield) of a yellow semisolid off-white solid. MS=401.2 [M+H].

Preparative Example X-360-C

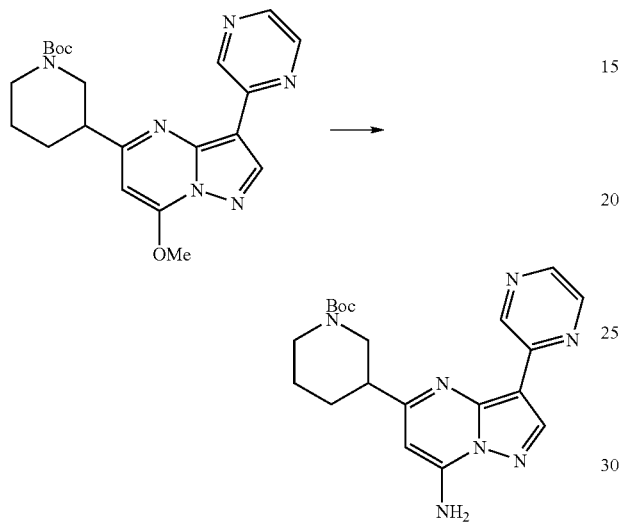

In an analogous fashion as described in Preparative Example X-350-C, the 7-methoxy adduct (0.16 g, 0.39 mmol) from Preparative Example X-340-C was converted to 52 mg (34% yield) of the title compound. LC-MS:=396.2 [M+H] 74% purity.

Example X-170-C

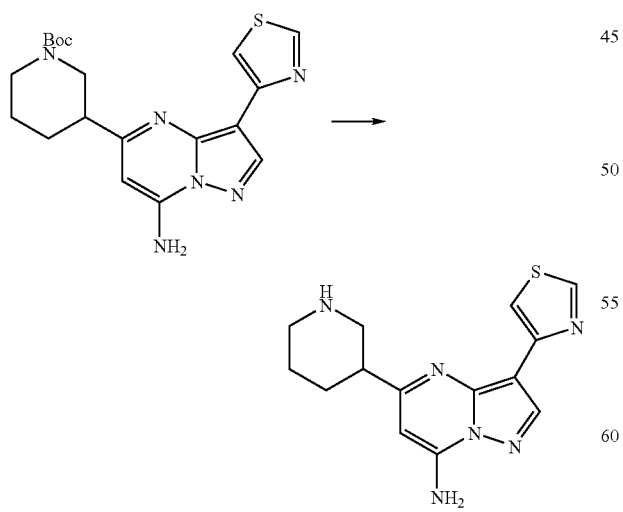

To a mixture of Boc adduct (0.12 g, 0.30 mmol) from Preparative Example X-350-C in CH$_2$Cl$_2$ (2 mL) at rt was added TFA (0.4 mL) dropwise. The resulting mixture was stirred for 12 h, concentrated under reduced pressure, and placed under high vacuum to remove trace volatiles. The resulting semisolid was dissolved in 7M NH$_3$ in MeOH (5 mL), stirred for 4 h, and concentrated under reduced pressure. The crude material was purified by preparative thin-layer chromatography (4×1000 µM plates) using a 6:1 mixture of CH$_2$Cl$_2$/MeOH (7M NH$_3$) as eluent to afford 67 mg (75% yield) of a white solid. mp 162-165° C.; MS=301.2 [M+H].

Example X-180-C

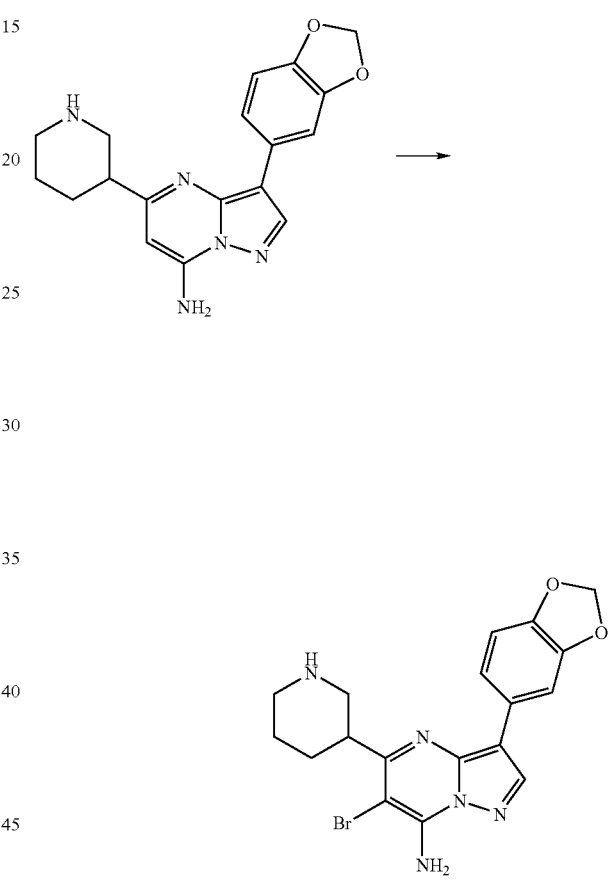

To a mixture of piperidine adduct (41 mg, 0.12 mmol) from Example X-170-C in CH$_3$CN (2 mL) at rt was added NBS (22 mg, 0.12 mmol) in one portion. The resulting mixture was stirred for at 0° C. for 2 h and rt for 1 h. The mixture was concentrated under reduced pressure and placed under high vacuum to remove trace volatiles. The crude material was purified by preparative thin-layer chromatography (4×1000 µM plates) using a 12:1 mixture of CH$_2$Cl$_2$/MeOH (7M NH$_3$) as eluent to afford 27 mg (54% yield) of a light tan solid. mp 109-112° C.; MS=418.2 [M+H]; 85% purity.

Examples X190-C-X220-C

Following the procedure set forth in Example X-180-C utilizing the compounds in Column 2 of Table X-40-C the substituted 6-Br pyrazolo[1,5-a]pyrimidine adducts in Column 3 of Table X-40-C were prepared.

TABLE X-40-C
| Ex. X- | Column 2 | Column 3 | 1. Yield (%) 2. LC-MS 3. mp (° C.) |
|---|---|---|---|
| 190-C | | | 1. 46 2. 397.2 3. 167-169 |
| 200-C | | | 1. 28 2. 381.2 3. 178-180 |
| 210-C | | | 1. 50 2. 381.2 3. 178-182 |
| 220-C | | | 1. 42 2. 379.2 3. 75-77 |
Preparative Example X-360-C
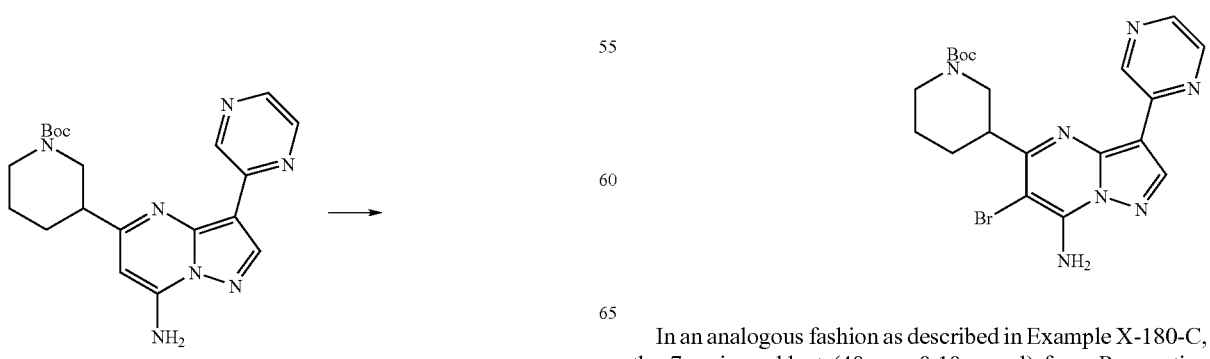
In an analogous fashion as described in Example X-180-C, the 7-amino adduct (40 mg, 0.10 mmol) from Preparative Example X-360-C was converted to 40 mg (83% yield) of the above compound. LC-MS:=476.3 [M-41] 98% purity.

Example X-230-C

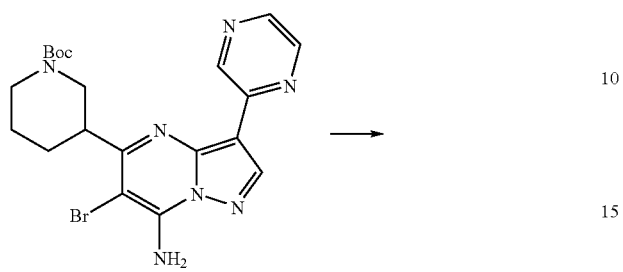

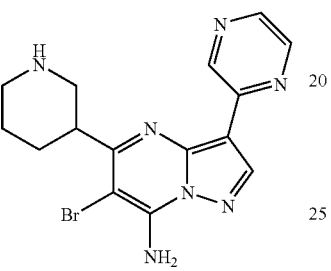

In an analogous fashion as described in Example X-17β-C, the 7-amino adduct (20 mg, 0.10 mmol) from Preparative Example X-360-C was converted to 15 mg (94% yield) of a pale yellow solid. mp 144-146° C.; LC-MS:=374.1 [M+H] 90% purity.

Preparative Example X-370-C

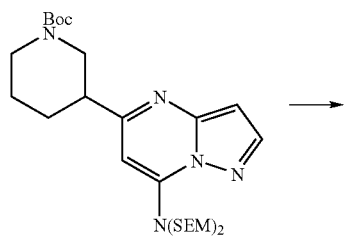

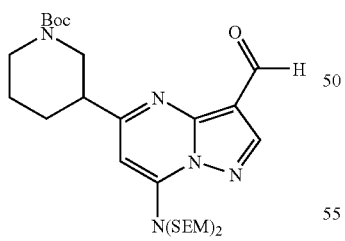

To a solution of 3-H adduct (0.50 g, 0.87 mmol) from Preparative Example X-50-C in DMF (5.4 mL) at 0° C. was added POCl$_3$ (0.13 mL, 1.39 mmol) dropwise. The resulting solution was stirred at rt for 12 h and then was recooled to 0° C. 1N NaOH (5 mL) and CH$_2$Cl$_2$ (10 mL) were carefully added the layers were separated. The aqueous layer was extracted with CH$_2$Cl$_2$ (2×10 mL) and the organic layers were combined. The organic layer was dried (Na$_2$SO$_4$), filtered, and concentrated under reduced pressure. The crude material was purified by preparative thin-layer chromatography (6×1000 μM plates) using a 2:1 mixture of hexanes/EtOAc to afford 90 mg (17% yield) of a light yellow semisolid. MS=606.3 [M+H].

Preparative Example X-380-C

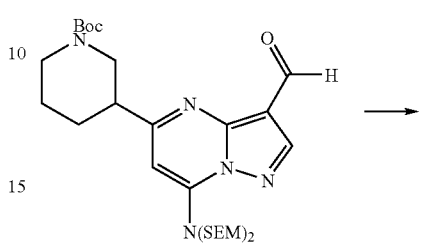

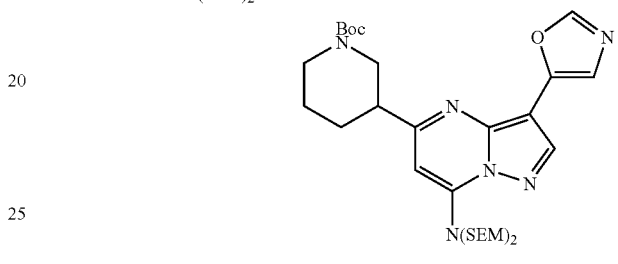

To a solution of 3-formyl adduct (90 mg, 0.15 mmol) from Preparative Example X-370-C in MeOH (1.5 mL) at rt was added Tos-Mic (29 mg, 0.15 mmol) and K$_2$CO$_3$ (21 mg, 0.15 mmol). The mixture was affixed with a condenser and was heated to reflux. After 4 h, the mixture was cooled to rt and concentrated under reduced pressure. The resultant semisolid was partitioned between CH$_2$Cl$_2$ (3 mL) and water (1 mL). The layers were separated and the aqueous layer was extracted with CH$_2$Cl$_2$ (2×10 mL). The organic layers were combined and washed with brine (1×5 mL). The organic layer was dried (Na$_2$SO$_4$), filtered, and concentrated under reduced pressure. The crude material was purified by preparative thin-layer chromatography (4×1000 μM plates) using a 40:1 mixture of CH$_2$Cl$_2$/MeOH (7M NH$_3$) to afford 67 mg (69% yield) of an orange/brown solid. LC-MS=606.3 [M+H] 93% purity.

Preparative Example X-390-C

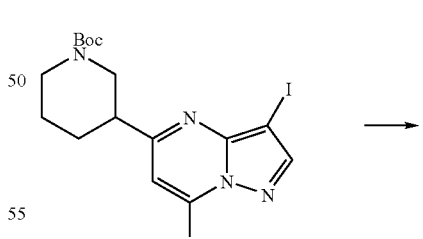

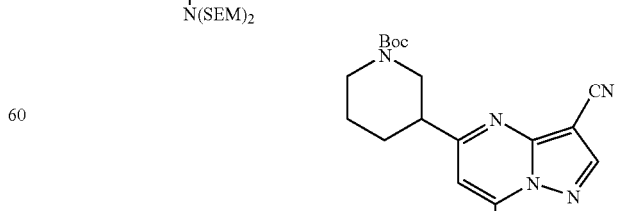

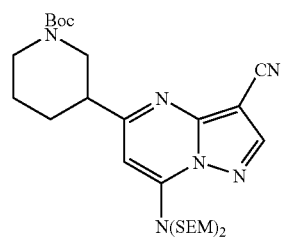

To a round bottom flask charged with 3-I adduct (0.25 g, 0.35 mmol) from Preparative Example X-60-C, KCN (26 mg, 0.40 mmol), CuI (20 mg, 0.035 mmol), Pd(PPh₃)₄ (8 mg, 0.035 mmol) and stir bar was added degassed THF (9 mL). The mixture was heated to reflux and was stirred for 5 h (until complete by TLC). The mixture was cooled to rt and diluted with EtOAc (5 mL). The mixture was filtered thru a pad of Celite which was subsequently washed with EtOAc (2×5 mL). The resulting filtrate was washed sequentially with water (2×2 mL) and brine (2×2 mL). The organic layer was dried (Na₂SO₄), filtered, and concentrated under reduced pressure. The crude material was purified by preparative thin-layer chromatography (4×1000 μM plates) using a 50:1 mixture of CH₂Cl₂/MeOH to afford 169 mg (80% yield) of a light yellow semisolid. LC-MS=606.3 [M+H]; 94% purity.

Preparative Example X-400-C

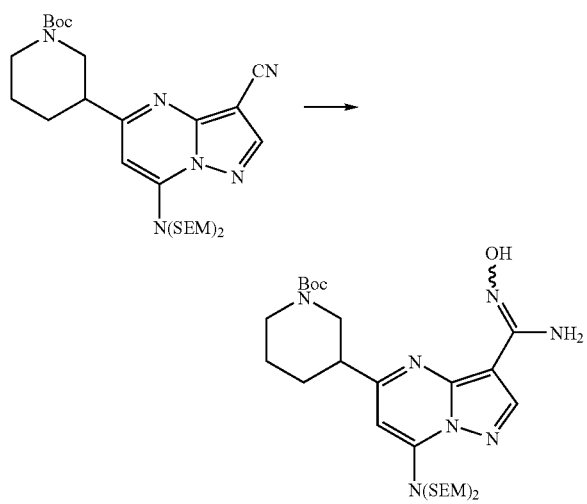

To a solution of 3-CN adduct (0.15 g, 0.25 mmol) from Preparative Example X-390-C was added NaHCO₃ (84 mg, 1.0 mmol) and hydroxylamine hydrochloride (35 mg, 0.50 mmol). The mixture was affixed with a condenser and was heated to reflux and stirred for 12 h at this temperature. The mixture was cooled to rt and filtered thru a medium sintered-glass funnel. The resulting ppt was washed with MeOH (2×5 mL) and the resultant filtrate was concentrated under reduced pressure to afford 155 mg (97% yield) of a yellow solid. LC-MS=636.3 [M+H]; 80% purity. This material was carried on without further purification.

Preparative Example X-410-C

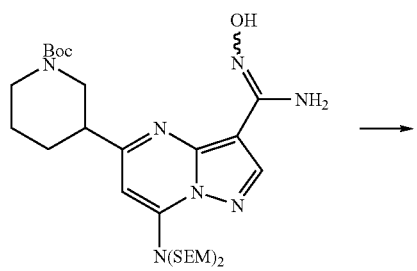

-continued

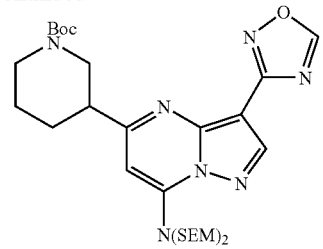

A solution of amidooxime adduct (0.17 g, 0.25 mmol) from Preparative Example X-400-C in triethylorthoformate (3 mL) was heated at 80° C. for 12 h. The mixture was cooled to rt whereupon PPTS (94 mg, 0.38 mmol) was added and the mixture was reheated to 80° C. and stirred for 4 h. The mixture was cooled to rt and was concentrated under reduced pressure. The crude material was purified by preparative thin-layer chromatography (6×1000 μM plates) using a 50:1 mixture of CH₂Cl₂/MeOH to afford 110 mg (68% yield) of alight yellow semisolid. LC-MS=646.4 [M+H]; 65% purity.

Preparative Example X-420-C

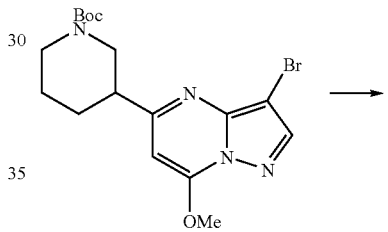

To a mixture of Boc derivative (3.0 g, 7.3 mmol) from Preparative Example X-310-C in DME/H₂O (16 mL/4 mL) was added 1-methyl-4-(4,4,5,5-tetramethyl-1,3,2-dioxaborolan-2-yl)-1H-pyrazole (2.8 g, 13.5 mmol) and Na₂CO₃ (3.9 g, 36.4 mmol). N₂ was bubbled thru the solution for 20 min with stirring whereupon PdCl₂(PPh₃)₂ (0.39 g, 0.47 mmol) was added. The mixture was heated to 110° C. and was stirred for 12 h. The mixture was cooled to rt, concentrated under reduced pressure and placed under high vacuum. The crude product was purified by flash chromatography using a 30:1 mixture of CH$_2$Cl$_2$/MeOH as eluent to afford 1.57 g (52% yield) as an orange/brown solid. LC-MS:=413.2 [M+H] 97% purity.

Preparative Example 420-C

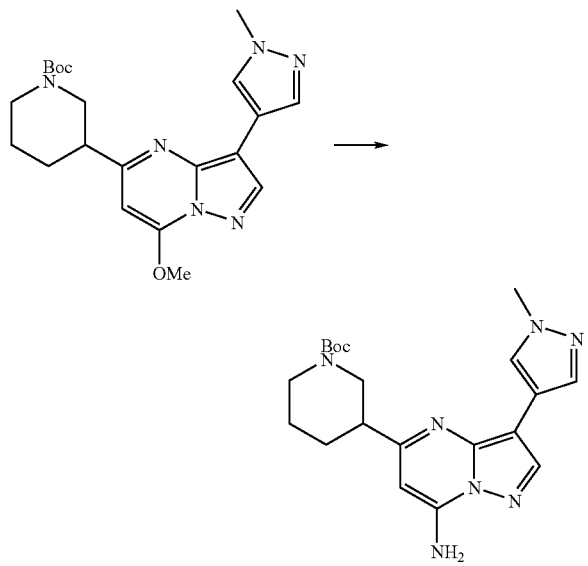

In an analogous fashion as described in Preparative Example X-350-C, the 7-methoxy adduct (2.0 g, 4.8 mmol) from Preparative Example X-420-C was converted to 600 mg (32% yield) of the title compound. LC-MS:=398.2 [M+H]; 93% purity.

Preparative Example X-430-C

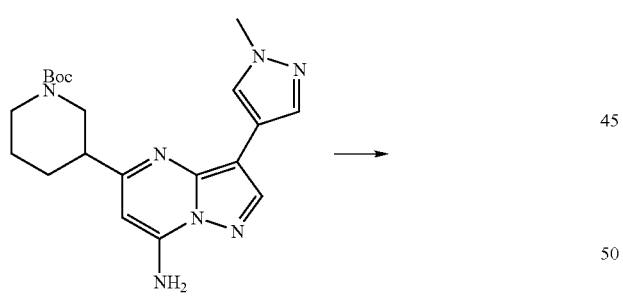

To a solution of Boc adduct (0.60 g, 1.51 mmol) from Preparative Example X-420-C in CH$_2$Cl$_2$ (10 mL) at rt was added DMAP (0.21 g, 1.7 mmol) followed by Boc$_2$O (0.36 g, 1.7 mmol). The mixture was allowed to warm to rt and stir for 12 h. The mixture was washed with water (2×3 mL) and brine (2×3 mL). The organic layer was dried (Na$_2$SO$_4$), filtered, and concentrated under reduced pressure. The crude material was purified by preparative TLC using 6×1000 mM plates with 20:1 CH$_2$Cl$_2$/MeOH (7N NH$_3$) as eluent to afford 0.35 g (47% yield) as an off-white solid. LC-MS:=498.3 [M+H]; 99% purity.

Preparative Example X-440-C

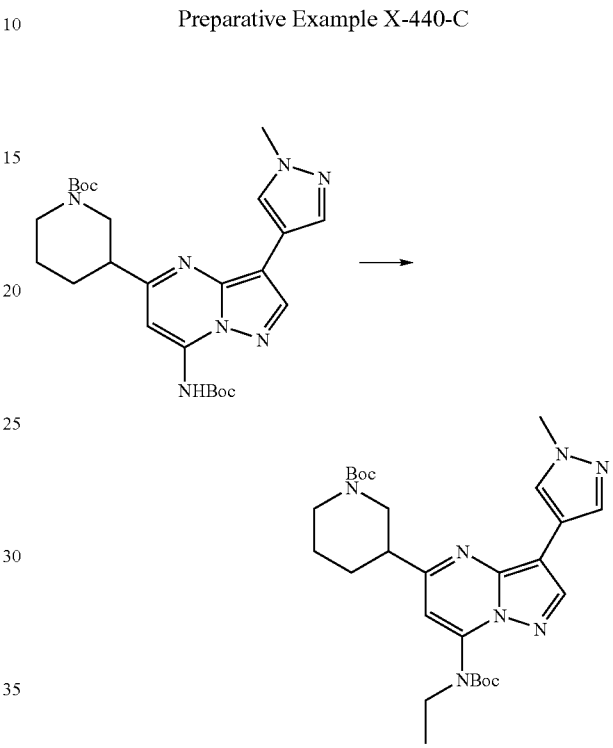

To a solution of Boc adduct (0.10 g, 0.20 mmol) from Preparative Example X-430-C in CH$_3$CN (3 mL) at rt was added K$_2$CO$_3$ (55 mg, 0.40 mmol) followed by DI (24 µL, 0.31 mmol). The mixture stirred at rt for 12 h and was filtered thru a glass-sintered funnel. The ppt was washed with CH$_3$CN (10 mL) and the filtrate was concentrated under reduced pressure. The crude material was purified by preparative TLC using 2×1000 mM plates with 1:2 hexanes/EtOAc as eluent to afford 70 mg (67% yield) as an off-white solid. LC-MS:= 526.3 [M+H]; >85% purity.

Preparative Example X-450-C

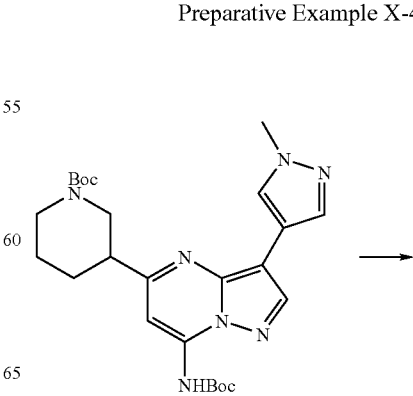

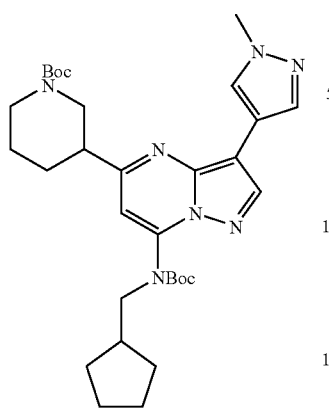

Utilizing the procedure in Preparative Example X-440-C, the Boc adduct (0.12 g, 0.24 mmol) from Preparative Example 430-C was treated with cyclopentylmethyl iodide (0.11 g, 0.48 mmol) to afford 50 mg (40% yield) of the title compound. LC-MS:=580.3 [M+H]; 89% purity.

Preparative Example X-460-C

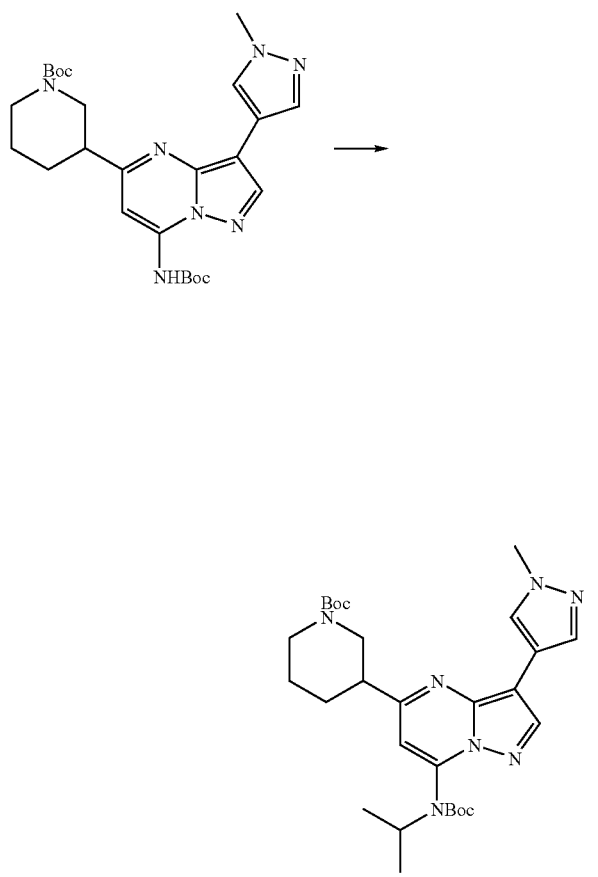

Utilizing the procedure in Preparative Example X-440-C, the Boc adduct (0.10 g, 0.20 mmol) from Preparative Example X-430-C was treated with 2-iodopropane (30 µL, 0.30 mmol) to afford 75 mg (32% yield) of the title compound. LC-MS:=540.3 [M+H]; 23% purity.

Preparative Example X-470-C

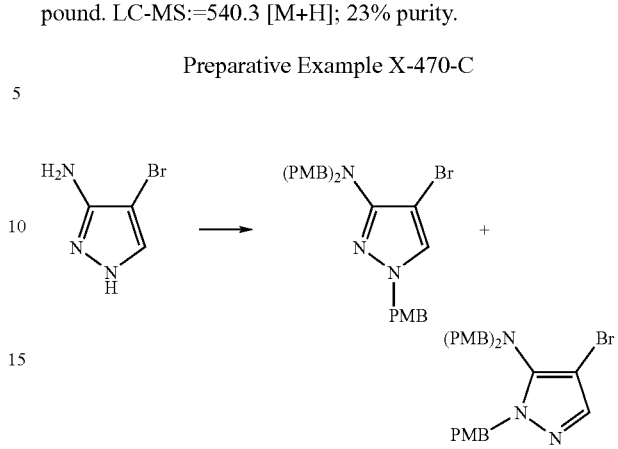

3-Amino-4-bromopyrazole (5 g, 30.9 mmol) and 4-methoxybenzyl chloride (21 g, 134 mmol, 4.3 equiv.) were combined in anhydrous DMF (25 mL) and added dropwise to a stirred suspension of sodium hydride (60% dispersion in mineral oil, 6.25 g, 156 mmol, 5 equiv.) in anhydrous DMF (50 mL). The resulting suspension was stirred 2 days at room temperature. Water (300 mL) was added slowly and the resulting mixture was extracted with ether (4×350 mL). The organic layers were combined, washed with brine, dried over anhydrous sodium sulfate and concentrated under reduced pressure. The crude product was dissolved in dichloromethane and purified by silica gel chromatography using a gradient from 10% to 20% ethyl acetate-hexanes. The product, a white solid, is obtained as a 60:40 mixture of the 1-benzylated-1H product and the 2-benzylated-2H product (14.96 g total, 93% yield).

Preparative Example X-480-C

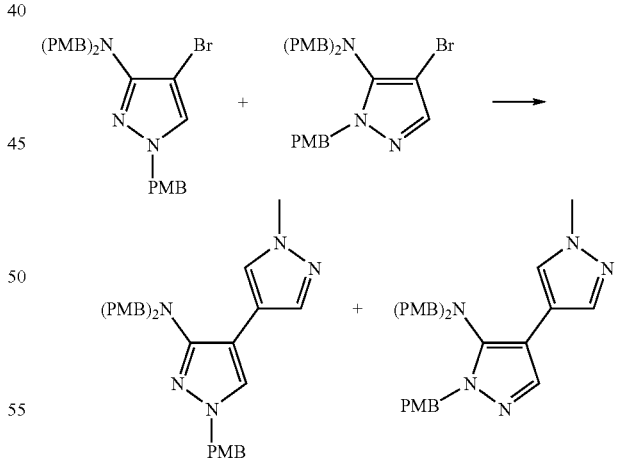

The compound from Preparative Example X-470-C (10 g, 19.15 mmol) and 1-methyl-4-(4,4,5,5-tetramethyl-1,3,2-dioxaborolan-2-yl)-1H-pyrazole (11.95 g, 57.42 mmol, 3.0 equiv.) were combined in 120 mL dimethoxyethane. 2M sodium carbonate solution (30 mL, 60 mmol, 3.1 equiv.) was added followed by tetrakis(triphenylphosphine) palladium(0) (2.36 g, 2.04 mmol, 0.11 equiv.). The mixture was stirred 16 hours at 90° C. After cooling to room temperature, water (200 mL) and brine (50 mL) were added and the mixture was extracted with ethyl acetate (2×200 mL). The extracts were combined, washed with brine, dried over anhydrous sodium sulfate and concentrated under reduced pressure. The crude product was dissolved in dichloromethane and purified by silica gel chromatography using a gradient from 33% to 66% ethyl acetate-hexanes. The 1-benzylated-1H product ($R_f$=0.27 in 66% ethyl acetate-hexanes) elutes first, followed by the 2-benzylated-2H-product ($R_f$=0.19 in 66% ethyl acetate-hexanes). The product is obtained as a yellow solid (5.60 g total, 56% yield) with an isomeric ratio of 62:38.

Preparative Example X-490-C

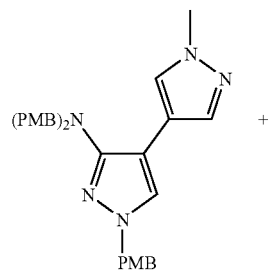

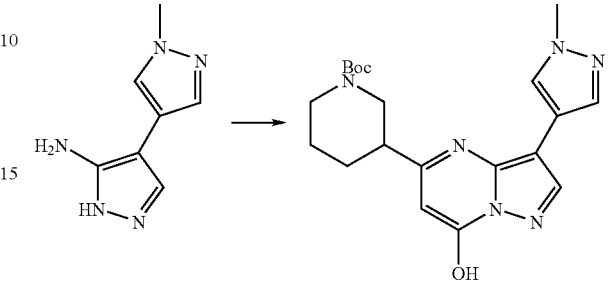

The compound from Preparative Example X-80-C (4.3 g, 8.22 mmol) was dissolved in trifluoroacetic acid (70 mL) and stirred 17 hours at reflux. After cooling, the trifluoroacetic acid was removed under reduced pressure. The resulting residue was dissolved in tetrahydrofuran (100 mL), methanol (50 mL) and 4N aqueous sodium hydroxide solution (25 mL, 100 mmol, 12 equiv.). The mixture was stirred 4 hours at 70° C. then cooled to room temperature. The mixture was concentrated and the residue was suspended in brine (100 mL) and water (40 mL). This mixture was extracted with 20% isopropanol in ethyl acetate (8×100 mL). The extracts were combined, dried over anhydrous sodium sulfate, filtered and concentrated under reduced pressure. The crude product was dissolved in 10% methanol in dichloromethane and purified by silica gel chromatography using 10% methanol-dichloromethane followed by 10% 7N ammonia in methanol-dichloromethane. The product is obtained as a tan to brown solid (1.03 g, 77% yield).

Preparative Example X-490-C

To a solution of aminopyrazole (0.74 g, 4.5 mmol) from Preparative Example X-490-C in toluene (40 mL) in a pressure tube at rt was added β-keto ester (1.5 g, 5.0 mmol) from Preparative Example X-10-C. The pressure tube was capped and heated to 110° C. and was stirred for 12 h. The mixture was cooled to rt and was concentrated under reduced pressure. The material was taken on crude to the next transformation. LC-MS:=399.2 [M+H]; 70% purity.

Preparative Example X-500-C

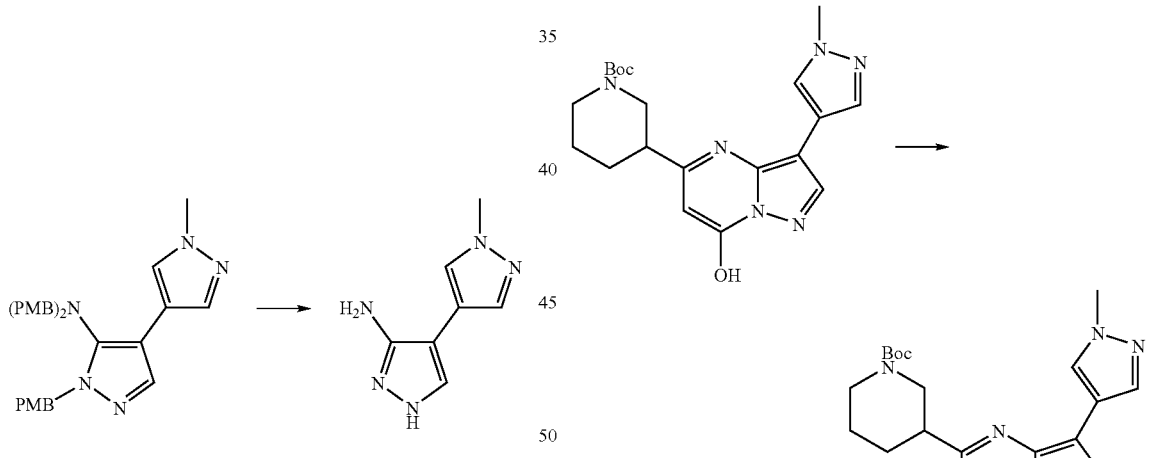

To a solution of 7-hydroxyl adduct (1.84 g, 4.5 mmol) from Preparative Example X-490-C in POCl₃ (13 mL, 0.14 mol) at rt was added N,N-dimethylaniline (2 mL, 15.8 mmol). The resulting solution was stirred at rt for 12 h (until complete by TLC) and was concentrated under reduced pressure. The crude material was cooled to 0° C. and was treated with CH₂Cl₂ (50 mL) and sat. aq. NaHCO₃ (10 mL). The layers were separated and the aqueous layer was extracted with CH₂Cl₂ (2×50 mL). The organic layers were combined, dried (Na₂SO₄), filtered, and concentrated under reduced pressure. The crude product was purified by flash chromatography using a 1:1 mixture of hexanes/CH$_2$Cl$_2$ as eluent to afford 1.4 g (96% yield) of a brown semisolid. LC-MS:=317.2 [M+H]; 95% purity.

Preparative Example X-510-C

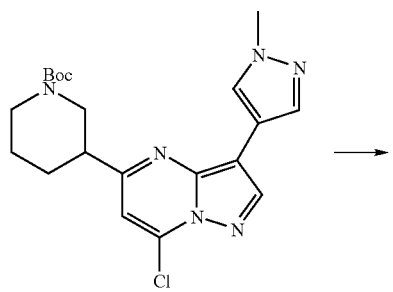

To a solution of 7-chloro adduct (30 mg, 0.072 mmol) from Preparative Example X-500-C in dioxane (1 mL) was added DIPEA (25 µL, 0.14 mmol) followed by cyclohexylamine (13 µL, 0.11 mmol). The mixture was heated to 90° C. and stirred for 3 h (until complete by TLC). The mixture was cooled to rt, concentrated under reduced pressure, and placed under high vacuum. The crude product was purified by flash chromatography using a 20:1 mixture of CH$_2$Cl$_2$/MeOH to afford 24 mg (69% yield) of an orange semisolid. MS=480.3 [M+H].

Preparative Examples X520-C-X560-C

Following the procedure set forth in Preparative Example X-510-C but utilizing the amines in Column 2 of Table X-50-C, the substituted pyrazolo[1,5-a]pyrimidine adducts in Column 3 of Table X-50-C were prepared

TABLE X-50-C

| Prep. Ex. X- | Column 2 | Column 3 | 1. Yield (%) 2. MS |
|---|---|---|---|
| 520-C | 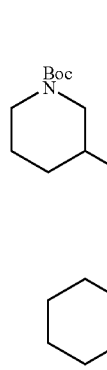 | | 1. 80 2. 454.4 |
| 530-C | | | 1. 72 2. 581.6 |
| 540-C | | | 1. 89 2. 466.4 |
| 550-C | | | 1. 79 2. 511.3 |
| 560-C | | | 1. 60 2. 425.5 |

Preparative Example X-570-C

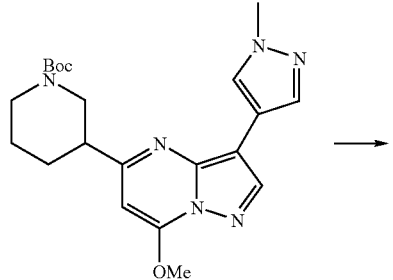

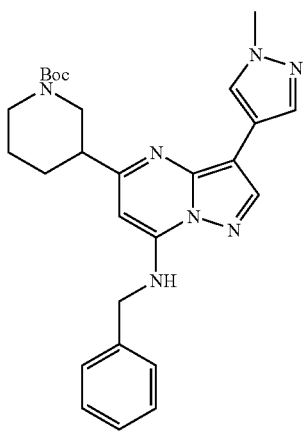

To a solution of 7-methoxy adduct (0.10 g, 0.24 mmol) from Preparative Example X-420-C in dioxane (1 mL) was added benzylamine (0.13 mL, 1.2 mmol). The mixture was heated to 90° C. and stirred for 72 h (until complete by TLC). The mixture was cooled to rt, concentrated under reduced pressure, and placed under high vacuum. The crude product was purified by flash chromatography using a 20:1 mixture of CH$_2$Cl$_2$/MeOH to afford 25 mg (21% yield) of an orange semisolid. LC-MS=488.3 [M+H]; 65% purity.

Preparative Example X-580-C

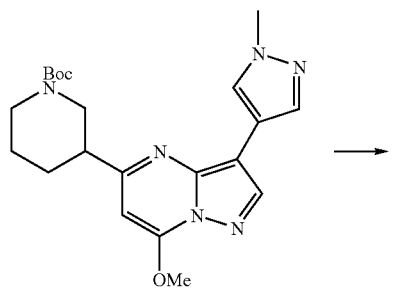

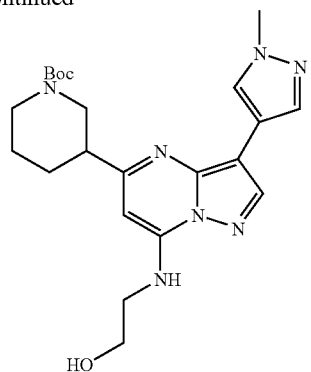

To a soln of ethanolamine (26 μL, 0.44 mmol) in dry DMSO (2 mL) at rt was added 60% NaH in oil (17 mg, 0.44 mmol) in one portion. The resulting mixture was stirred for 15 min at it where upon the 7-methoxy adduct (0.09 g, 0.22 mmol) from Preparative Example X-420-C was added in a single portion. The mixture was stirred for 72 h at it and quenched with sat. aq. NH$_4$Cl (1 mL). The mixture was extracted with a mixture of 10% IPA/CH$_2$Cl$_2$ (3×5 ml) and the organic layers were combined. The organic layer was washed with brine (1×3 mL), dried (Na$_2$SO$_4$), filtered and concentrated under reduced pressure. The crude product was purified by flash chromatography using a 20:1 mixture of CH$_2$Cl$_2$/MeOH (7M NH$_3$) to afford 120 mg (81% yield) of an orange semisolid. LC-MS=442.2 [M+H]; 85% purity.

Preparative Example X-590-C

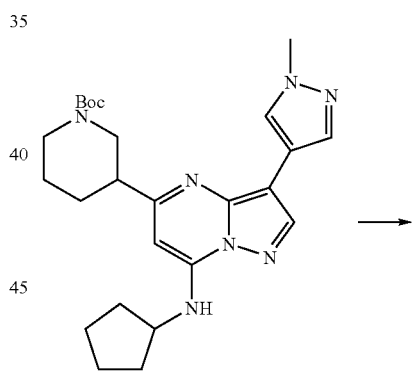

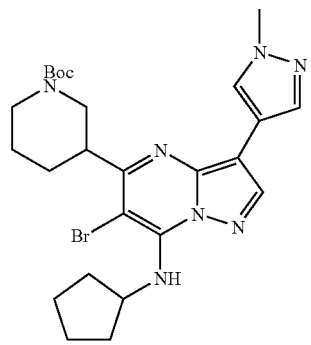

To a solution of Boc adduct (25 mg, 0.054 mmol) from Preparative Example X-540-C in CH$_2$Cl$_2$ (5 mL) at rt was added t-BuNH$_2$ (0.17 mL, 1.60 mmol). The mixture was stirred for 15 min whereupon Br$_2$ (2.5 mL, 0.048 mmol) was added dropwise and the reaction was stirred for 10 min (until complete by TLC). The mixture was concentrated to dryness and the crude product was purified by preparative thin-layer chromatography using 2×1000 mM plates with a 99:1 mixture of $CH_2Cl_2$/MeOH (7M $NH_3$) as eluent to afford 27 mg (92% yield) of an orange semisolid. LC-MS=545.3 [M+H]; 86% purity.

Preparative Examples X600-C-X620-C

Following the procedure set forth in Preparative Example 590-C but utilizing the corresponding Boc precursors in Column 2 of Table X-60-C, the substituted pyrazolo[1,5-a]pyrimidine adducts in Column 3 of Table X-60-C were prepared.

TABLE X-60-C

| Prep. Ex. X- | Column 2 | Column 3 | 1. Yield (%) 2. LC-MS |
|---|---|---|---|
| 600-C | | | 1. 84 2. 504.4 |
| 610-C | | | 1. 95 2. 558.3 |
| 620-C | | | 1. 87 2. 589.3 |

Example X-240-C

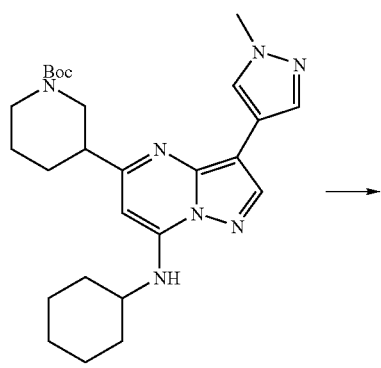

To a mixture of Boc adduct (23 mg, 0.048 mmol) from Preparative Example X-520-C in $CH_2Cl_2$ (1 mL) at rt was added TFA (0.25 mL) dropwise. The resulting mixture was stirred for 2 h, concentrated under reduced pressure, and placed under high vacuum to remove trace volatiles. The resulting semisolid was dissolved in 7M $NH_3$ in MeOH (5 mL), stirred for 4 h, and concentrated under reduced pressure. The crude material was purified by preparative thin-layer chromatography (4×1000 μM plates) using a 6:1 mixture of $CH_2Cl_2$/MeOH (7M $NH_3$) as eluent to afford 14 mg (77% yield) of a pale yellow solid. mp 131-133° C.; MS=380.2 [M+H].

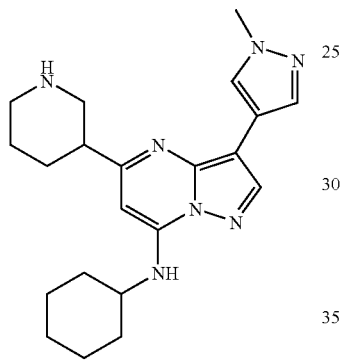

Examples X250-C-X370-C

Following the procedure set forth in Example X-240-C utilizing the indicated Boc precursors in Column 2 of Table X-70-C, the substituted pyrazolo[1,5-a]pyrimidine adducts in Column 3 of Table X-70-C were prepared.

TABLE X-70-C

| Ex. X- | Column 2 | Column 3 | 1. Yield (%) 2. LC-MS 3. mp (° C.) |
|---|---|---|---|
| 250-C | | | 1. 99 2. 326.2 3. 121-124 |

TABLE X-70-C-continued

| Ex. X- | Column 2 | Column 3 | 1. Yield (%)<br>2. LC-MS<br>3. mp (° C.) |
|---|---|---|---|
| 260-C | | | 1. 86<br>2. 380.3<br>3. 118-121 |
| 270-C | | | 1. 94<br>2. 366.2<br>3. 128-131 |
| 280-C | | | 1. 65<br>2. 354.2<br>3. 116-118 |
| 290-C | | | 1. 34<br>2. 340.2<br>3. 165-167 |

TABLE X-70-C-continued

| Ex. X- | Column 2 | Column 3 | 1. Yield (%) 2. LC-MS 3. mp (° C.) |
|---|---|---|---|
| 300-C | | | 1. 12 2. 381.3 3. 166-168 |
| 310-C | | | 1. 99 2. 411.3 3. 148-151 |
| 320-C | | | 1. 42 2. 342.2 3. 114-116 |

TABLE X-70-C-continued

| Ex. X- | Column 2 | Column 3 | 1. Yield (%) 2. LC-MS 3. mp (° C.) |
|---|---|---|---|
| 330-C | | | 1. 36 2. 388.3 3. 146-148 |
| 340-C | | | 1. 38 2. 444.4 3. 128-131 |
| 350-C | | | 1. 38 2. 404.2 3. 136-138 |
| 360-C | | | 1. 43 2. 458.2 3. 145-148 |

TABLE X-70-C-continued

| Ex. X- | Column 2 | Column 3 | 1. Yield (%)<br>2. LC-MS<br>3. mp (° C.) |
|---|---|---|---|
| 370-C | 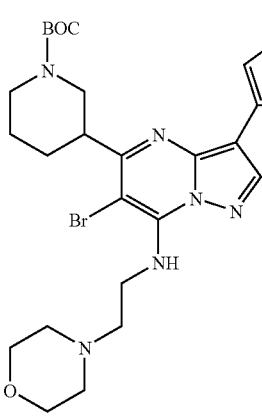 | 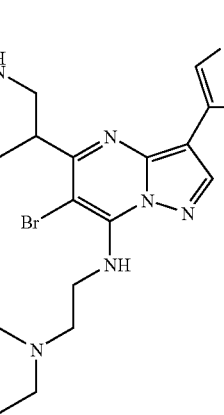 | 1. 97<br>2. 489.2<br>3. 166-168 |

Example X-380-C

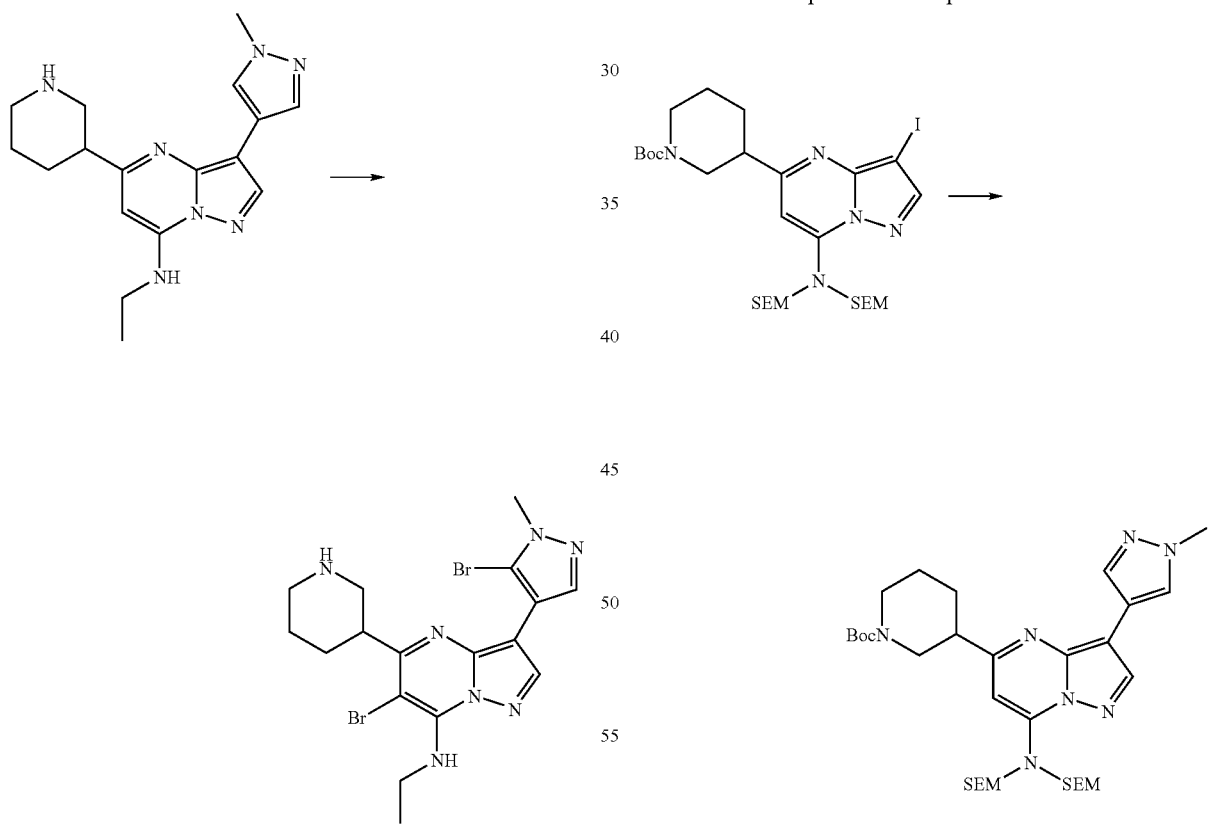

To a mixture of ethyl adduct (65 mg, 0.20 mmol) from Example 24 in CH₃CN (3 mL) at rt was added NBS (32 mg, 0.18 mmol) in a single portion. The resulting mixture was stirred for 1 h, concentrated under reduced pressure, and placed under high vacuum to remove trace volatiles. The crude material was purified by preparative thin-layer chromatography (2×1000 µM plates) using a 10:1 mixture of CH₂Cl₂/MeOH (7M NH₃) as eluent to afford 3 mg (3% yield) of a yellow brown solid. LC-MS=484.3 [M+H]; >80% purity.

Preparative Example X-700-C

A mixture of the product from Preparative Example X-60-C (1.50 g, 2.13 mmol), 1-methyl-4-(4,4,5,5-tetramethyl-1,3,2-dioxaborolan-2-yl)-1H-pyrazole (0.89 g, 4.26 mmol), PdCl₂dppf.CH₂Cl₂ (171 mg, 0.21 mmol), and K₃PO₄ (1.81 g, 8.52 mmol) in 1,2-dimethoxyethane (30 mL) and H₂O (6 mL) was stirred and refluxed under N₂ for 3 hr. The solvents were evaporated and the residue was purified by column chromatography on silica gel with 5:1 CH₂Cl₂/EtOAc as eluent. Yellow wax (1.13 g, 81%) was obtained.

Preparative Example X-710-C

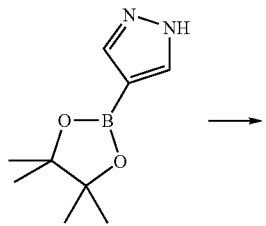

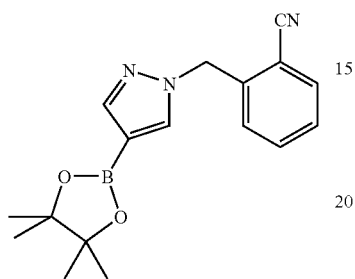

A mixture of 4,4,5,5-tetramethyl-2-(1H-pyrazol-4-yl)-1,3,2-dioxaborolane (0.50 g, 2.58 mmol), 2-(bromomethyl)benzonitrile (0.63 g, 3.21 mmol), and $K_2CO_3$ (1.06 g, 7.68 mmol) in acetonitrile (60 mL) was stirred and refluxed under $N_2$ for 72 hr. The solvents were evaporated and the residue was purified by column chromatography on silica gel with 2:1 $CH_2Cl_2$/EtOAc as eluent. Yellow wax (0.75 g, 94%) was obtained. LC-MS: 310 [M+H].

Preparative Example X720-C-X770-C

By essentially same procedures set forth in Preparative Example X-710-C only using different alkylating agents given in Column 1, compounds given in Column 2 of Table X-100-C were prepared.

TABLE X-100-C

| Ex. X- | Column 1 | Column 2 | Data |
|---|---|---|---|
| 720-C | ethyl 2-chloro-2-phenylacetate | ethyl 2-phenyl-2-(4-(4,4,5,5-tetramethyl-1,3,2-dioxaborolan-2-yl)-1H-pyrazol-1-yl)acetate | LCMS: $MH^+ = 357$ |
| 730-C | 4-(chloromethyl)pyridine·HCl | 4-((4-(4,4,5,5-tetramethyl-1,3,2-dioxaborolan-2-yl)-1H-pyrazol-1-yl)methyl)pyridine | LCMS: $MH^+ = 286$ |
| 740-C | 3-(chloromethyl)pyridine·HCl | 3-((4-(4,4,5,5-tetramethyl-1,3,2-dioxaborolan-2-yl)-1H-pyrazol-1-yl)methyl)pyridine | LCMS: $MH^+ = 286$ |

TABLE X-100-C-continued

| Ex. X- | Column 1 | Column 2 | Data |
|---|---|---|---|
| 750-C | | | LCMS: MH⁺ = 286 |
| 760-C | | | LCMS: MH⁺ = 237 |
| 770-C | | | LCMS: MH⁺ = 280 |

Example X-400-C

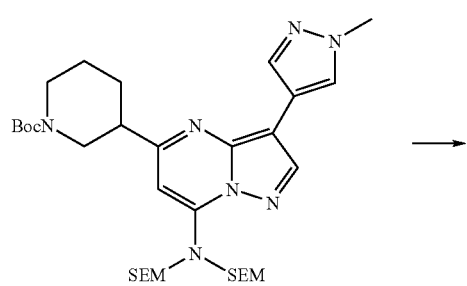

A mixture of the product from Preparative Example X-700-C (1.00 g) and 3N aqueous HCl (20 mL) in EtOH (20 mL) was stirred at 60° C. for 1.5 hr. The solvents were evaporated, $Na_2CO_3$ (2.0 g) and 6:1 mixture of $CH_2Cl_2$/MeOH (20 mL) were added to the residue and the mixture was stirred under $N_2$ for 15 min. Then it was loaded onto a column and it was purified by column chromatography on silica gel with 6:1 $CH_2Cl_2$/7N $NH_3$ in MeOH as eluent. White solid (405 mg, 90%) was obtained. LC-MS: 298 [M+H].

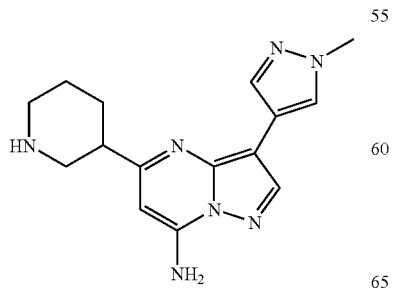

Examples X410-C-X530-C

By essentially same procedures set forth in Preparative Example X-700-C and Example 400-C only using different boron reagents given in Column 1 for the Suzuki couplings with the intermediate from Preparative Example X-60-C, compounds given in Column 2 of Table X-110-C were prepared.

TABLE X-110-C

| Ex. X- | Column 1 | Column 2 | Data |
|---|---|---|---|
| 410-C | | | LCMS: MH$^+$ = 285 Mp = 161-164° C. |
| 420-C | | | LCMS: MH$^+$ = 328 |
| 430-C | | | LCMS: MH$^+$ = 320 |
| 440-C | | | LCMS: MH$^+$ = 295 |
| 450-C | | | LCMS: M$^+$ = 284 waxy solid |
| 460-C | | | LCMS: M$^+$ = 390 |

TABLE X-110-C-continued

| Ex. X- | Column 1 | Column 2 | Data |
|---|---|---|---|
| 470-C | | | LCMS: MH$^+$ = 326 wax |
| 480-C | | | LCMS: MH$^+$ = 375 wax |
| 490-C | | | LCMS: MH$^+$ = 375 |
| 500-C | | | LCMS: MH$^+$ = 375 |
| 510-C | | | LCMS: MH$^+$ = 399 wax |

TABLE X-110-C-continued

| Ex. X- | Column 1 | Column 2 | Data |
|---|---|---|---|
| 520-C | | | LCMS: MH+ = 446 |
| 530-C | | | LCMS: MH+ = 369 wax |

Preparative Example X-770-C

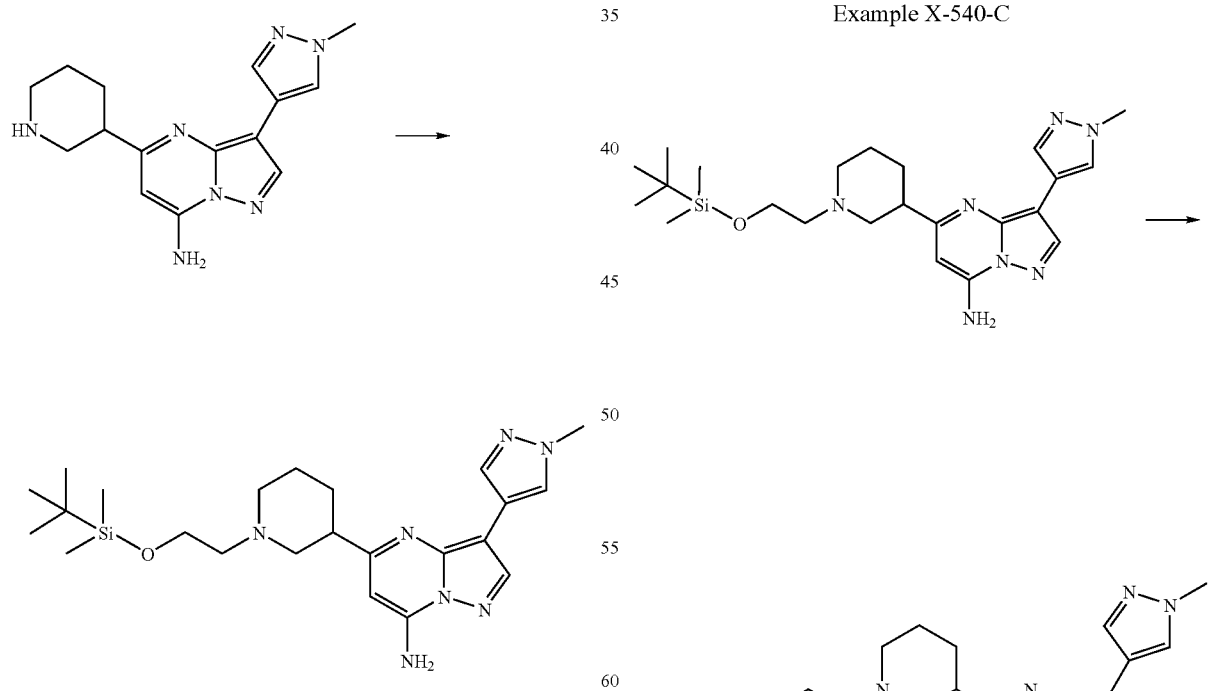

A mixture of the product from Example X-400-C (0.30 g, 1.00 mmol) and (tert-butyldimethylsilyloxy)acetaldehyde (0.17 g, 1.00 mmol) in CH$_2$Cl$_2$ (5 mL) and MeOH (1 mL) was stirred at 25° C. for 18 hr. NaBH(OAc)$_3$ (0.36 g, 1.7 mmol) was then added and the mixture was stirred for 1 hr. The solvents were evaporated and the mixture was purified by column chromatography on silica gel with 10:1 CH$_2$Cl$_2$/MeOH as eluent. Waxy solid (60 mg, 13%) was obtained. LC-MS: 456 [M+].

Example X-540-C

By essentially same procedure set forth in Example X-400-C, starting from compound from Preparative Example X-770-C, the title compound was prepared. Waxy solid. LC-MS: 342 [M+H].

Example X-550-C

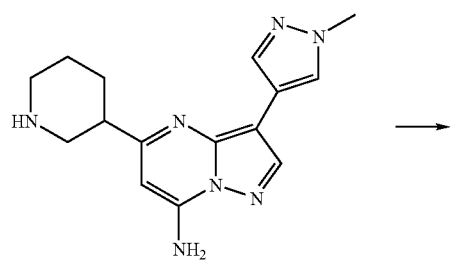

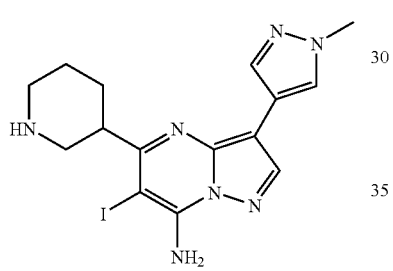

A solution of N-iodosuccinimide (33 mg, 0.15 mmol) in anhydrous CH₃CN (2 mL) was added under N₂ to a stirred solution of the product from Example 400-C (50 mg, 0.17 mmol) in anhydrous CH₃CN (3 mL) and CH₂Cl₂ (5 mL). The mixture was stirred for 1 hr, the solvents were evaporated, and the residue was purified by column chromatography on silica gel with 15:1 CH₂Cl₂/7N NH₃ in MeOH as eluent. White solid (52 mg, 83%) was obtained. LC-MS: 424 [M+H]. Mp=99-101° C.

Preparative Example X-780-C

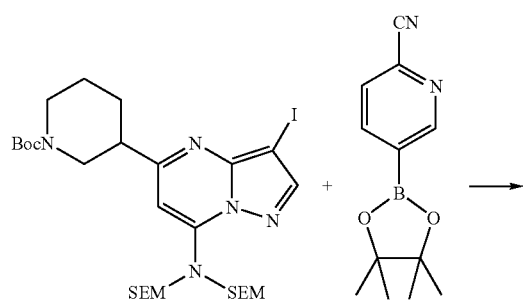

-continued

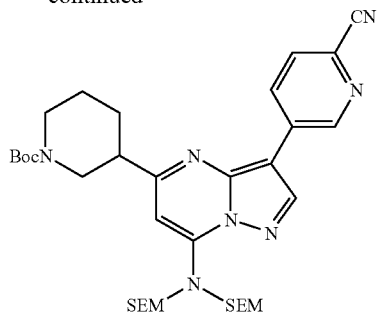

A mixture of the product from Preparative Example X-60-C (703 mg, 1.00 mmol), the boronate (299 mg, 1.30 mmol), PdCl₂dppf·CH₂Cl₂ (82 mg, 0.10 mmol), and K₃PO₄ (848 mg, 4.00 mmol) in 1,2-dimethoxyethane (20 mL) and H₂O (4 mL) was stirred and refluxed under N₂ for 3 hr. The solvents were evaporated and the residue was purified by column chromatography on silica gel with 10:1 CH₂Cl₂/EtOAc as eluent. Yellow wax (430 mg, 63%) was obtained. LC-MS: 680 [M+H].

Example X-560-C

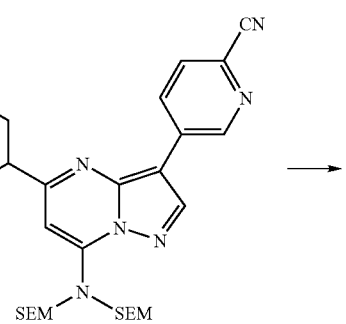

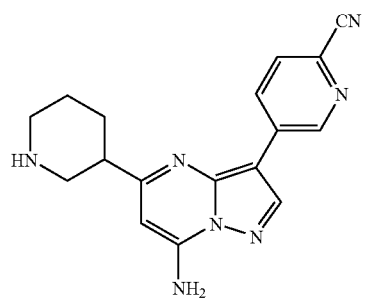

A mixture of the product from Preparative Example X-780-C (200 mg) and TFA (5 mL) in H₂O (5 mL) was stirred at 25° C. for 1.5 hr. The solvents were evaporated, Na₂CO₃ (1.0 g) and 6:1 mixture of CH₂Cl₂/MeOH (3 mL) were added to the residue and the mixture was stirred under N₂ for 15 min. Then it was loaded onto a column and it was purified by column chromatography on silica gel with 6:1 CH₂Cl₂/7N NH₃ in MeOH as eluent. White solid (70 mg, 75%) was obtained. Mp=270-272° C. LC-MS: 320 [M+H].

Example X-570-C

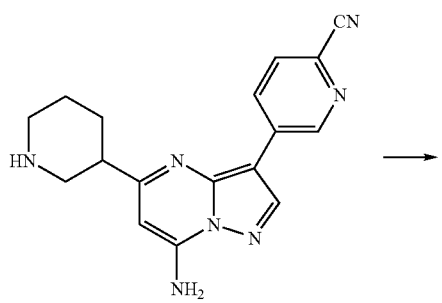

A solution of NBS (32 mg, 0.18 mmol) in anhydrous CH₃CN (3 mL) was added under N₂ to a stirred solution of the product from Example 560-C (65 mg, 0.20 mmol) in anhydrous CH₃CN (3 mL) and MeOH (9 mL). The mixture was stirred for 24 hr, the solvents were evaporated, and the residue was purified by column chromatography on silica gel with 8:1 CH₂Cl₂/7N NH₃ in MeOH as eluent. White solid (27 mg, 38%) was obtained. Mp=200-203° C. LC-MS: 399 [M+H].

Example X-580-C

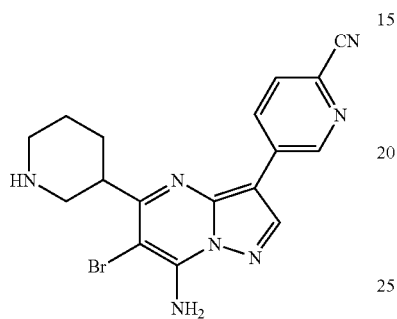

By essentially same procedures set forth in Preparative Example X-570-C, starting from the compound from Example 410-C, the compound above was prepared. Pale yellow solid. Mp=64-67° C. LC-MS: 363 [M+H].

Example X-590-C

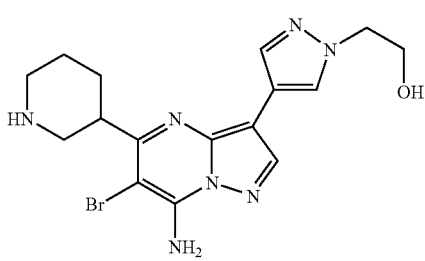

By essentially same procedures set forth in Example X-570-C, starting from the compound from Example 420-C, the compound above was prepared. White solid. Mp=66-69° C. LC-MS: 406 [M+].

Examples X590-C-X630-C

By essentially same procedure set forth in Example X-570-C, starting from the compounds in column 1 of Table X-120C, the compounds in column 2 of Table X-120C were prepared.

TABLE X-120-C

| Ex. X- | Column 1 | Column 2 | Data |
|---|---|---|---|
| 590-C | 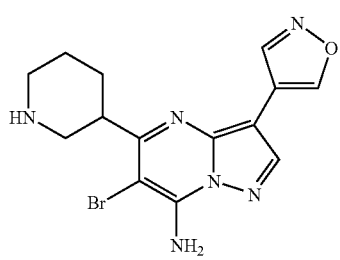 | | LCMS: M⁺ = 398 |

TABLE X-120-C-continued

| Ex. X- | Column 1 | Column 2 | Data |
|---|---|---|---|
| 600-C | | | LCMS: M+ = 390 |
| 610-C | | | LCMS: M+ = 453 wax |
| 620-C | | | LCMS: M+ = 447 Mp = 248-250° C. |
| 630-C | | | LCMS: M+ = 421 wax |

Preparative Example X-790-C

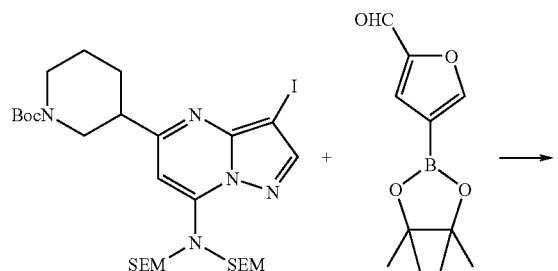

-continued

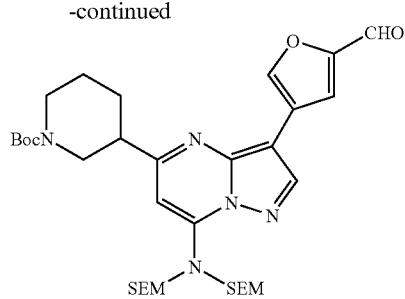

A mixture of the product from Preparative Example X-60-C (1.50 g, 2.13 mmol), the formylfuran pronate (0.732 g, 3.30 mmol), PdCl₂dppf.CH₂Cl₂ (171 mg, 0.21 mmol), and K₃PO₄ (1.81 g, 8.52 mmol) in 1,2-dimethoxyethane (30 mL) and H₂O (6 mL) was stirred and refluxed under N₂ for 3 hr. The solvents were evaporated and the residue was purified by column chromatography on silica gel with 4:1 hexane/EtOAc as eluent. Yellow wax (890 mg, 62%) was obtained. LC-MS: 672 [M+H].

Preparative Example X-800-C

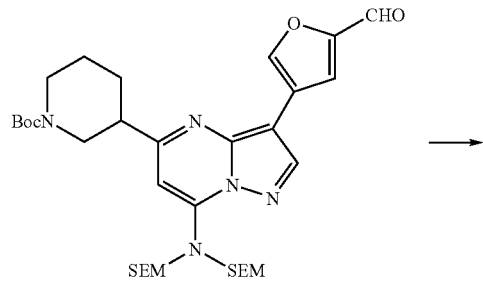 

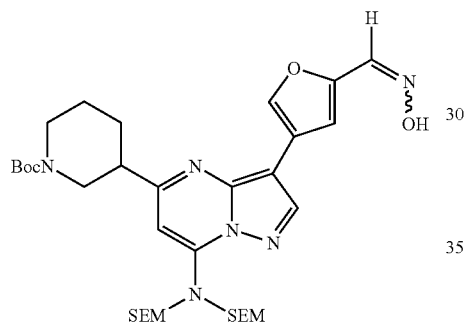

A mixture of the product from Preparative Example X-790-C (440 mg, 0.65 mmol), NH₂OH.HCl (50 mg, 0.72 mmol), and triethylamine (1.0 mL) in 1,2-dichloroethane (3 mL) and MeOH (3 mL) was stirred in a closed flask at 25° C. for 1 hr. The solvent was evaporated and the residue was chromatographed on silica gel with 3:1 hexane/EtOAc as eluent. Slightly yellow wax (310 mg, 69%) was obtained. LC-MS: 687 [M+H].

Preparative Example X-810-C

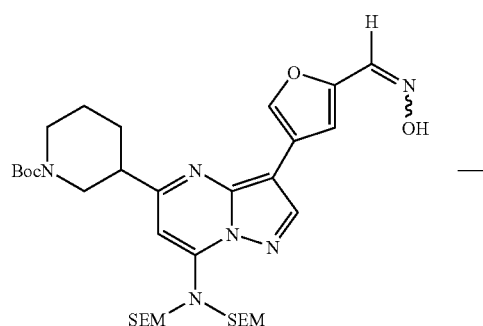

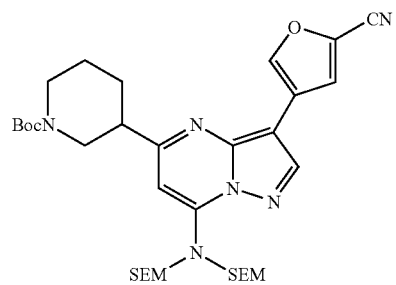

Trifluoroacetic anhydride (92 mg, 0.44 mmol) was added at 0° C. under N₂ to a stirred solution of the product from Preparative Example X-800-C (300 mg, 0.44 mmol) in anhydrous CH₂Cl₂ (5 mL) and triethylamine (0.5 mL). The mixture was stirred for 1.5 hr, then it was poured into saturated aqueous NaHCO₃ solution (50 mL), extracted with CH₂Cl₂ (3×10 mL), dried over Na₂SO₄, and filtered. The solvents were evaporated and the residue was purified by column chromatography on silica gel with 7:1 hexane/EtOAc as eluent. Slightly yellow wax (192 mg, 65%) was obtained. LC-MS: 669 [M+H].

Example X-640-C

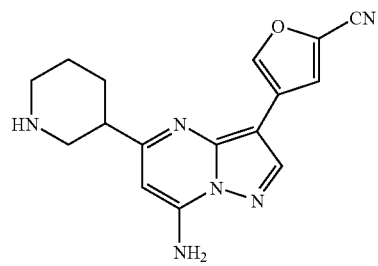

By essentially same procedures set forth in Preparative Example X-780-C, starting from the compound from Preparative Example 810-C, the compound above was prepared. White solid. Mp=188-191° C. LC-MS: 309 [M+H].

Example X-650-C

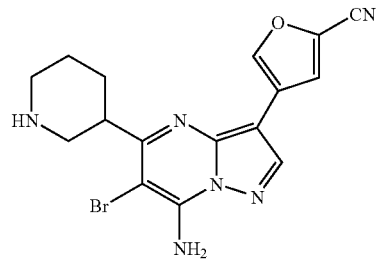

By essentially same procedures set forth in Example X-570-C, starting from the compound from Example 640-C, the compound above was prepared. White solid. LC-MS: 387 [M+H].

Example X-660-C

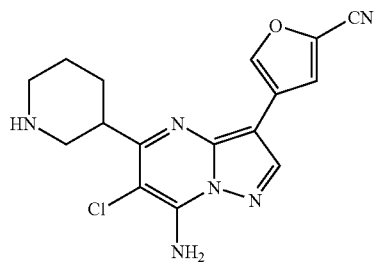

By essentially same procedures set forth in Example X-570-C, starting from the compound from Example X-640-C and using N-chlorosuccinimide instead of N-bromosuccinimide, the compound above was prepared. White solid. LC-MS: 343 [M+H].

Example X-670-C

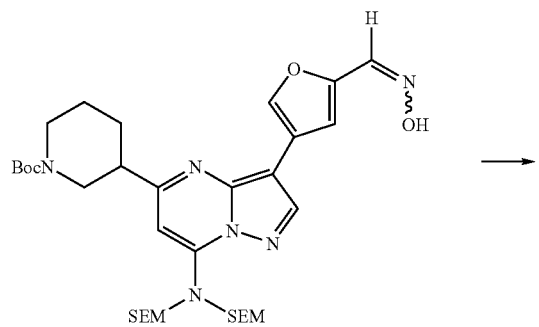

By essentially same procedures set forth in Preparative Example X-560-C, starting from the compound from Pre-parative Example X-800-C, the compound above was prepared. White solid. LC-MS: 327 [M+H].

Example X-680-C

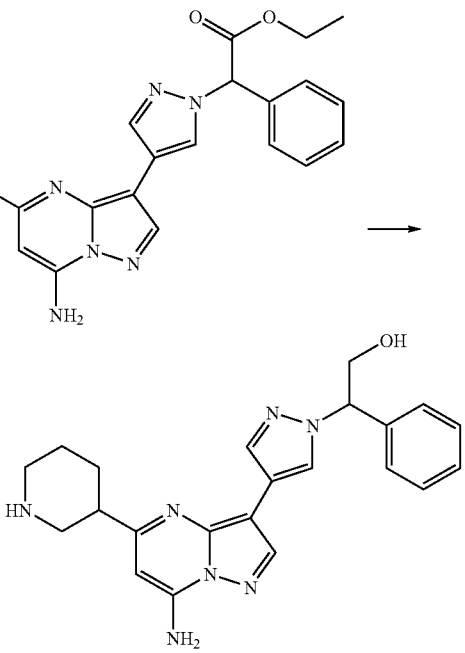

A solution of LiAlH$_4$ (1.0 M, 1.5 mL, 1.5 mmol) in THF was added under N$_2$ to a stirred solution of the product from Preparative Example X-520-C (70 mg, 0.16 mmol) in anhydrous THF (5 mL). The mixture was stirred for 24 hr, and then MeOH (0.5 mL) was added. The solvents were evaporated and the residue was purified by column chromatography on silica gel with 5:1 CH$_2$Cl$_2$/7N NH$_3$ in MeOH as eluent. Yellow wax (22 mg, 35%) was obtained. LC-MS: 404 [M+H].

Preparative Example X-820-C

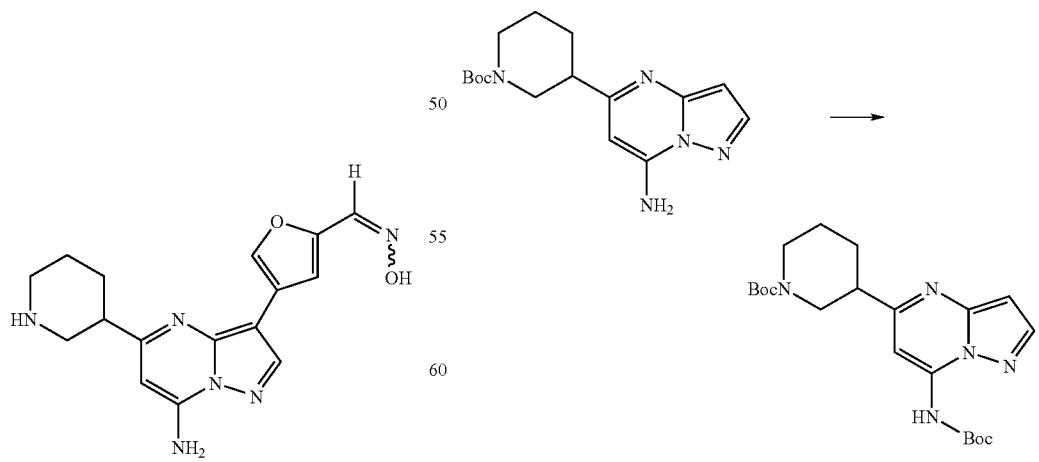

A mixture of the product from Preparative Example X-40-C (1.00 g, 3.15 mmol), Boc$_2$O (0.757 g, 3.47 mmol), 4-dimethylaminopyridine (0.040 g, 0.33 mmol) and TEA (2.0 mL) in dry CH$_2$Cl$_2$ (20 mL) and was stirred under N$_2$ for 2 hr. The mixture was then poured into saturated aqueous NaHCO$_3$ solution (100 mL), extracted with CH$_2$Cl$_2$ (3×30 mL), dried over Na$_2$SO$_4$, and filtered. The solvents were evaporated and the residue was purified by column chromatography on silica gel with 2:1 hexane/EtOAc as eluent. White solid (0.94 g, 71%) was obtained. LC-MS: 418 [M+H].

Preparative Example X-830-C

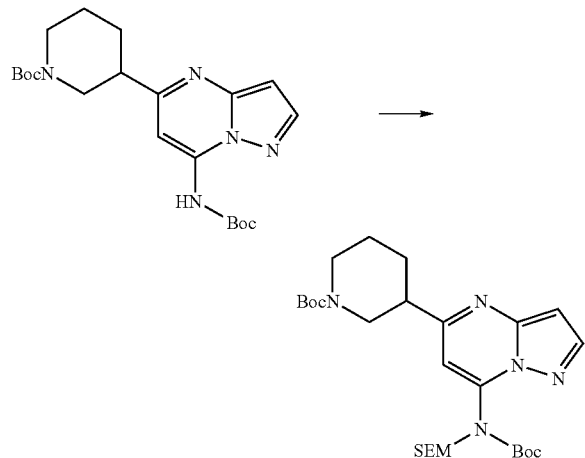

A mixture of the product from Preparative Example X-820-C (460 mg, 1.10 mmol), SEMCI (276 mg, 1.65 mmol), and diisopropylethylamine (426 mg, 3.30 mmol) in dry 1,2-dichloroethane (5 mL) and was stirred and refluxed under N$_2$ for 2 hr. The mixture was then poured into saturated aqueous NaHCO$_3$ solution (50 mL), extracted with CH$_2$Cl$_2$ (3×10 mL), dried over Na$_2$SO$_4$, and filtered. The solvents were evaporated and the residue was purified by column chromatography on silica gel with 2:1 hexane/EtOAc as eluent. Slightly yellow wax (500 mg, 83%) was obtained. LC-MS: 548 [M+H].

Preparative Example X-840-C

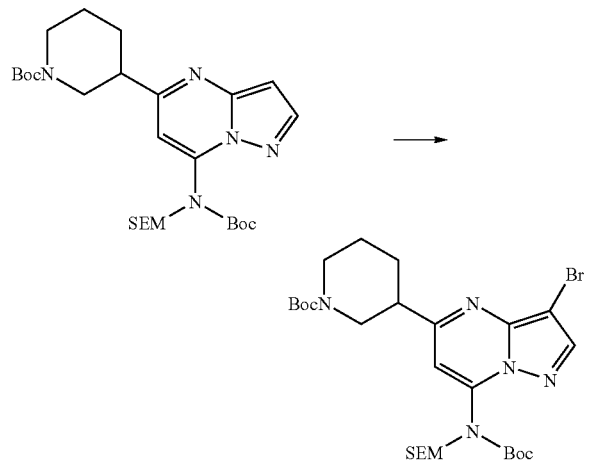

A solution of NBS (71 mg, 0.40 mmol) in anhydrous CH$_3$CN (2 mL) was added under N$_2$ to a stirred solution of the product from Preparative Example X-830-C (240 mg, 0.44 mmol) in anhydrous CH$_3$CN (3 mL). The mixture was stirred for 1 hr, the solvents were evaporated, and the residue was purified by column chromatography on silica gel with 5:1 hexane/EtOAc as eluent. Colorless waxy solid (231 mg, 92%) was obtained. LC-MS: 628 [M+H].

Preparative Example X-850-C

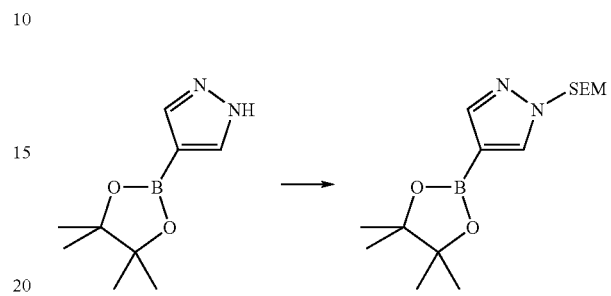

A mixture of 4,4,5,5-tetramethyl-2-(1H-pyrazol-4-yl)-1,3,2-dioxaborolane (5.48 g), SEMCI (5.2 mL), and K$_2$CO$_3$ (5.85 g) in NMP (50 mL) was stirred under N$_2$ for 1 hr. The reaction mixture was diluted with EtOAc, rinsed with H$_2$O, brine, and dried over Na$_2$SO$_4$. The mixture was filtered, the solvents were evaporated and the residue was used directly in the next step.

Preparative Example X-860-C

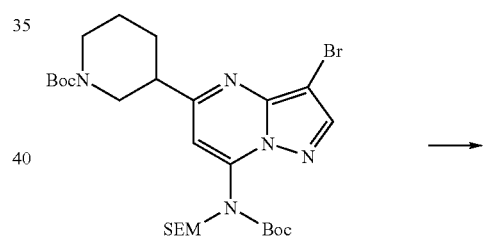

A mixture of the product from Preparative Example X-850-C (774 mg, 1.23 mmol), the boronate from Preparative Example X-1650 (520 mg, 1.60 mmol), PdCl$_2$dppf.CH$_2$Cl$_2$ (100 mg, 0.123 mmol), and K$_3$PO$_4$ (1.04 g, 4.92 mmol) in 1,2-dimethoxyethane (18 mL) and H$_2$O (6 mL) was stirred and refluxed under N$_2$ for 5 hr. The solvents were evaporated and the residue was purified by column chromatography on silica gel with 4:1 hexane/EtOAc as eluent. Yellow wax (528 mg, 58%) was obtained. LC-MS: 744 [M+H].

Example X-690-C

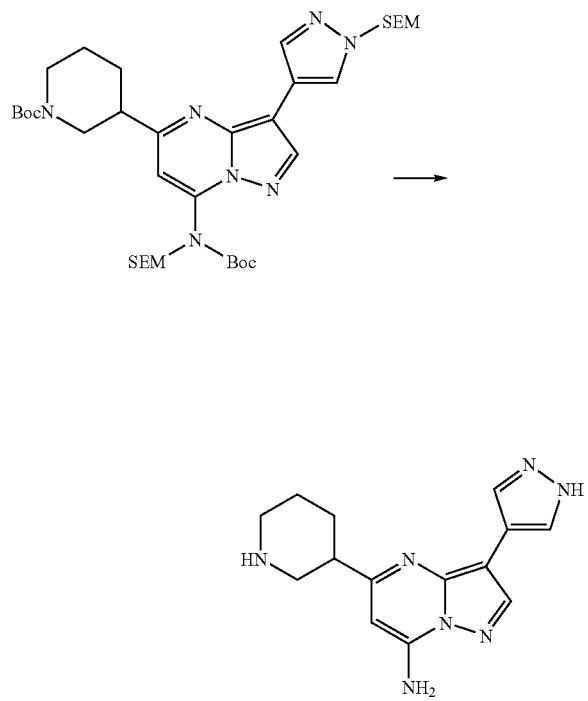

A mixture of the product from Preparative Example X-860-C (520 mg) and 3N aqueous HCl (6 mL) in EtOH (12 mL) was stirred at 60° C. for 1.5 hr. The solvents were evaporated, NaHCO$_3$ (1.0 g) and 6:1 mixture of CH$_2$Cl$_2$/MeOH (10 mL) were added to the residue and the mixture was stirred under N$_2$ for 15 min. Then it was loaded onto a column and it was purified by column chromatography on silica gel with 2:1 CH$_2$Cl$_2$/7N NH$_3$ in MeOH as eluent. White solid (60 mg, 30%) was obtained. LC-MS: 284 [M+H].

Examples X700-C and X710-C

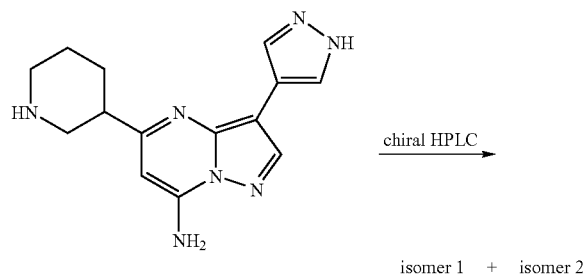

Racemic product from Preparative Example X-690-C was separated on a semipreparative Chiralcel AD column. Chromatography with mobile phase 80:20 hexane/2-propanol with 0.2% diethylamine afforded two isomers: Example 700-C: fast eluting (isomer 1): white solid; LC-MS: 284 [M+H] Example 710-C: slow eluting (isomer 2): white solid; LC-MS: 284 [M+H].

Example X-720-C

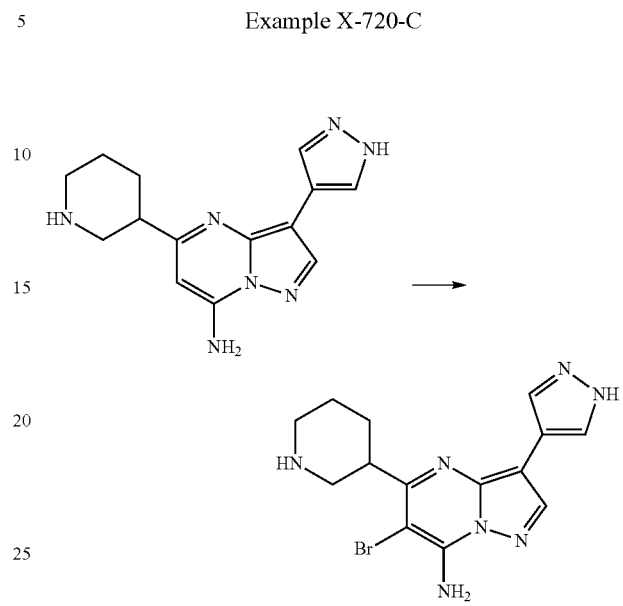

A solution of NBS (3.7 mg, 0.021 mmol) in anhydrous CH$_3$CN (0.2 mL) was added under N$_2$ to a stirred solution of isomer 2 from Example 710-C (7 mg, 0.024 mmol) in anhydrous MeOH (2 mL). The mixture was stirred for 18 hr, the solvents were evaporated, and the residue was purified by preparative thin layer chromatography on silica gel with 7:1 CH$_2$Cl$_2$/7N NH$_3$ in MeOH as eluent. White solid (3.5 mg, 46%) was obtained. LC-MS: 362 [M+H].

Preparative Example X-800-C

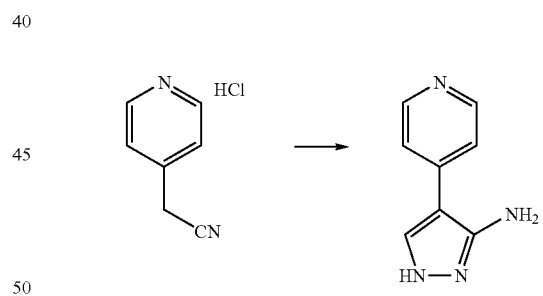

Sodium hydride (60% dispersion in mineral oil, 1.57 g, 39.3 mmol, 3.04 equiv.) was suspended in anhydrous ethyl ether (60 mL) and cooled to 0° C. To this suspension was added ethyl formate (1.55 mL, 19.19 mmol, 1.48 equiv.) and ethanol (1.50 mL, 25.72 mmol, 1.99 equiv.), followed by solid 4-pyridylacetonitrile hydrochloride (2.00 g, 12.95 mmol) in small portions over several minutes. The suspension was then stirred 16 hours, warming to room temperature. Ethanol (3 mL) was added to quench the reaction, and the resulting suspension was filtered and washed with ethyl ether. After drying under vacuum, a light pink solid was obtained (2.7211 g). This solid was suspended in ethanol (30 mL) and acetic acid (3 mL) and hydrazine monohydrate (2.0 mL, 41.23 mmol, 3.18 equiv.) was added. The mixture was then heated to reflux overnight. After cooling, the heterogeneous mixture was concentrated under reduce pressure and the crude solid was suspended in 6.5% methanol-dichloromethane, loaded on a silica gel chromatography column and purified using 6.5% to 20% methanol-dichloromethane. An orange oily solid was obtained (0.645 g, 31% yield).

Preparative Example X-810-C

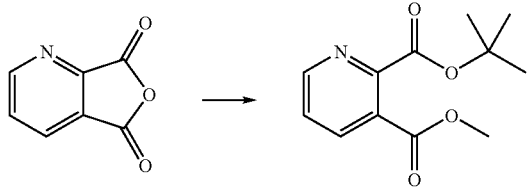

Pyridine-2,3-dicarboxylic anhydride (24 g, 161 mmol) was suspended in anhydrous pyridine (20 mL) and tert-butanol (30 mL) and stirred at 40° C. for 16 hours. After cooling, the suspension was concentrated under reduced pressure at 50° C. for at least 30 minutes, and was then dried under vacuum for 3 hours. The crude intermediate (53 g), which includes pyridine (21 wt %) and tert-butanol (8 wt %), is dissolved in methanol (300 mL) and dichloromethane (100 mL) and treated with trimethylsilyldiazomethane (2M solution in hexanes, 165 mL, 330 mmol, 2.05 equiv.). The resulting orange solution is stirred 16 hours at room temperature, concentrated at reduced pressure (50° C.), and the crude product is dissolved in dichloromethane (120 mL) and purified on an Isco Redisep 330 g chromatography column eluting with 75% ethyl acetate-hexanes. The product, a brown oil (21.3 g, 56% yield), consists of 80% 2-tert-butyl, 3-methylpyridine-2,3-dicarboxylate and 20% 3-tert-butyl, 2-methylpyridine-2,3-dicarboxylate.

Preparative Example X-820-C

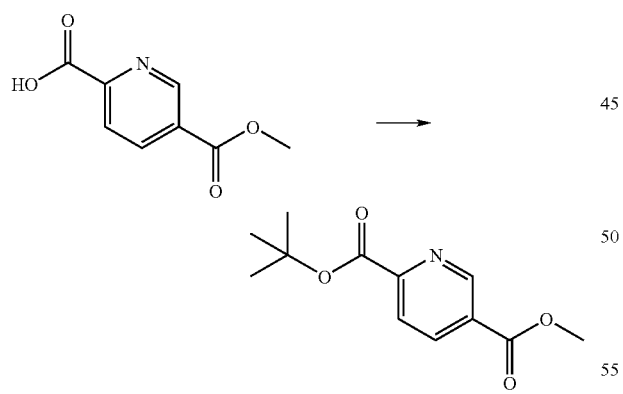

4-(Methoxycarbonyl)pyridine-2-carboxylic acid (24.63 g, 136 mmol) was suspended in tert-butanol (250 mL) and pyridine (75 mL) and cooled in an ice-water bath. 4-Toluenesulfonyl chloride (62.11 g, 326 mmol, 2.39 equiv.) was added in one portion and the mixture was stirred 30 minutes in the ice-water bath then 2 hours at room temperature. The mixture was then slowly poured in a stirring mixture of saturated aqueous sodium bicarbonate (1 L) and ethyl ether (500 mL). The resulting two-phase mixture was then extracted with ethyl ether (3×1 L). The extracts were combined, washed with brine, dried with anhydrous sodium sulfate, filtered and concentrated under reduced pressure. The crude product (25.37 g, 79%) yield was used without further purification.

Preparative Example X-830-C

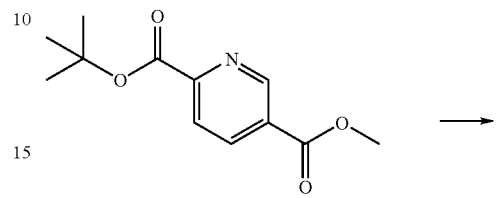

The compound from Preparative Example X-820-C (25.36 g, 107 mmol) was dissolved in glacial acetic acid (120 mL) and hydrogenated at 40-50 psi for 3 days with 10% palladium on carbon catalyst (2.50 g, 2.34 mmol, 0.022 equiv.). The mixture was filtered through a pad of Celite which was then washed with methanol. The combined filtrates were concentrated under reduced pressure until only excess acetic acid remained. The residue was dissolved in water (500 mL) and solid sodium carbonate (55 g) was added to bring the pH to 8. This solution was extracted with dichloromethane (2×500 mL), and the extracts were combined, washed with brine, dried with anhydrous sodium sulfate, filtered and concentrated under reduced pressure to yield a yellow oil (25.98 g, 100% yield).

Preparative Example X-840-C

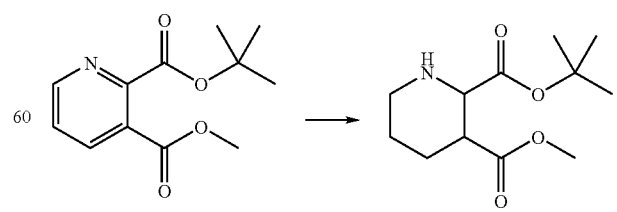

By essentially the same procedure as set forth in Preparative Example X-830-C, only utilizing the compound from Preparative Example 810-C, the above compound was prepared in 96% yield (80:20 mixture of isomers).

Preparative Example X-850-C

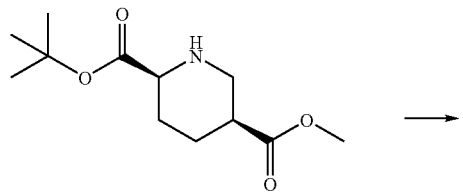

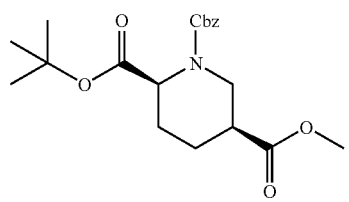

The compound from Preparative Example X-830-C (25.97 g, 106.9 mmol) and triethylamine (20 mL, 143 mmol, 1.34 equiv.) were combined in dichloromethane (200 mL) and cooled to 0° C. Benzyl chloroformate (18.5 mL, 130 mmol, 1.21 equiv.) was slowly added and the mixture was stirred 2 days at room temperature. The mixture was diluted with water (200 mL) and extracted with dichloromethane (2×200 mL). The combined extracts were washed with brine, dried with anhydrous sodium sulfate, filtered and concentrated under reduced pressure. The crude product (41.69 g) was loaded on an Isco Redisep 750-gram chromatography column and purified using the ISCO Combiflash Companion XL system, running a gradient from 10% to 20% ethyl acetate-hexanes. A colorless oil (19.66 g, 49% yield) was obtained.

Preparative Example X-860-C

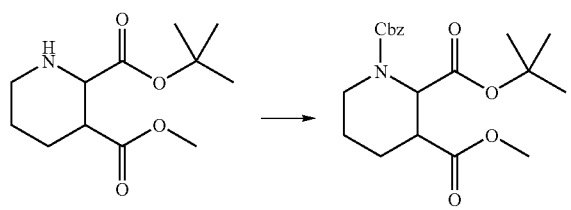

By essentially the same procedure as set forth in Preparative Example X-850-C, only utilizing the compound from Preparative Example X-840-C, the above piperidine was prepared in 82% yield.

Preparative Example X-870-C

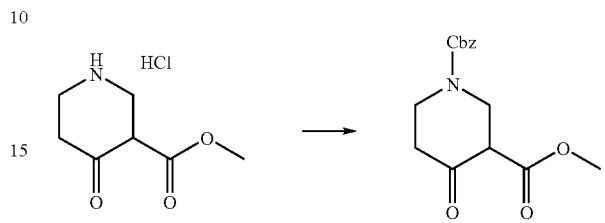

Methyl 4-oxo-piperidinecarboxylate hydrochloride (7.51 g, 38.79 mmol) was suspended in dichloromethane (100 mL) and cooled to 0° C. Triethylamine (19 mL, 136 mmol, 3.5 equiv.) was slowly added followed by benzyl chloroformate (11 mL, 77 mmol, 1.99 equiv.). The mixture was stirred 3 days at room temperature, and was then diluted with water (100 mL) and the two phases were separated. The aqueous phase was then extracted with dichloromethane (100 mL), the two organic extracts were combined and washed with brine, dried with anhydrous sodium sulfate, filtered and concentrated under reduced pressure. The resulting yellow oil was purified by chromatography on an Analogix SF40-240 column using an Analogix Intelliflash 280 system running a gradient from 15% to 30% ethyl acetate-hexanes. The product was obtained as a colorless oil (6.40 g, 57% yield).

Preparative Example X-880-C

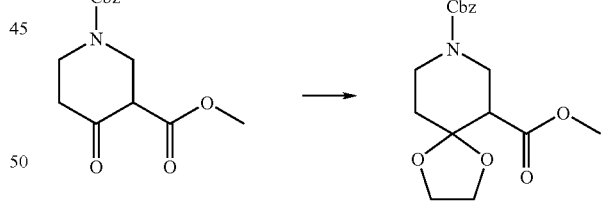

The keto ester from Preparative Example X-870-C (6.39 g, 22.0 mmol), ethylene glycol (12 mL, 215 mmol, 9.8 equiv.) and 4-toluenesulfonic acid monohydrate (0.640 g, 3.36 mmol, 0.15 equiv.) were heated together in benzene (90 mL) at reflux with a Dean-Stark trap for 12 hours. After cooling, saturated aqueous sodium bicarbonate (75 mL) was added and the two phases were mixed and separated. The aqueous phase was extracted with ethyl ether (75 mL), and the ether and benzene layers were combined and washed with brine, dried with anhydrous sodium sulfate, filtered and concen-

Preparative Example X-890-C

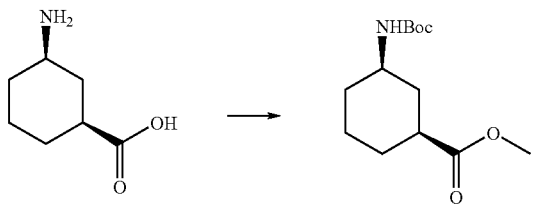

3-Amino-1-cyclohexanecarboxylic acid (1.503 g, 10.50 mmol, 87% cis by NMR) was suspended in anhydrous methanol (20 mL) and thionyl chloride (0.80 mL, 10.99 mmol, 1.05 equiv.) was added dropwise over 3 minutes, resulting in a slightly yellow homogeneous solution. After stirring 1 hour at room temperature, the solution was concentrated under reduced pressure to yield a colorless, viscous oil. This oil was dissolved in anhydrous dichloromethane (20 mL) and triethylamine (3.70 mL, 26.55 mmol, 2.53 equiv.) was added, followed by di-tert-butyldicarbonate (2.78 g, 12.74 mmol, 1.21 equiv.). The resulting suspension was stirred 15 hours at room temperature and was then diluted with water (20 mL), mixed and separated into two phases. The aqueous phase was further extracted with ethyl acetate (2×20 mL). The organic phases were combined, washed with brine, dried with anhydrous sodium sulfate, filtered and concentrated under reduced pressure. The product is obtained as a white solid (2.607 g, 97% yield) which is 90% cis by NMR.

Preparative Example X-900-C

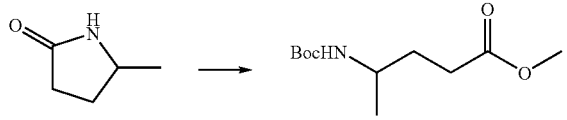

5-Methyl-2-pyrrolidinone (5.09 g, 51.35 mmol) was stirred 15 hours in 6N aqueous hydrochloric acid (75 mL) at 100° C. The solution was concentrated under reduced pressure to yield a white solid that was redissolved in methanol (100 mL) to which thionyl chloride (3.75 mL, 51.54 mmol, 1.00 equiv.) was slowly added. After 1 hour at room temperature, the solution was concentrated under reduced pressure and the resulting crude ester was redissolved in anhydrous dichloromethane (100 mL). Triethylamine (21.5 mL, 154 mmol, 3.00 equiv.) was added, followed by di-tert-butyldicarbonate (16.88 g, 77.3 mmol, 1.51 equiv.), and the resulting solution was stirred 2 days at room temperature. The opaque yellow solution was diluted with water (100 mL), and the two phases were mixed and separated. The aqueous phase was extracted with dichloromethane (2×100 mL), and the combined extracts were washed with brine, dried with anhydrous sodium sulfate, filtered and concentrated under reduced pressure to yield an orange oil (11.13 g, 94% yield.)

Preparative Example X-910-C

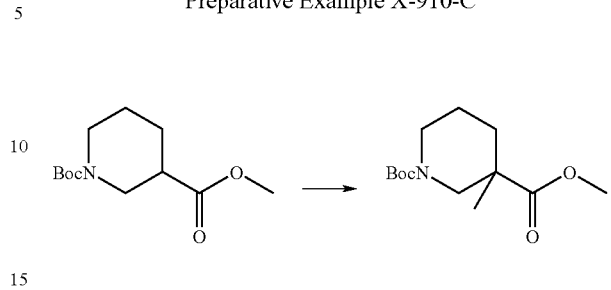

A solution of ester (1.23 g, 5.05 mmol) in THF (20 mL) at −78° C. was treated with LIHMDS (6.1 mL of a 1.0M solution in THF, 1.2 equiv.) dropwise. The solution was stirred at −78° C. for 1 h and treated with $CH_3I$ (0.38 mL, 1.2 equiv.) dropwise. The solution was stirred at −78° C. for 2 h. and at 25° C. for 1 h. The solution was quenched by the addition of saturated $NH_4Cl$ (100 mL). The aqueous layer was extracted with $Et_2O$ (3×25 mL). The combined organic layer was dried ($MgSO_4$), filtered and concentrated under reduced pressure. The residue was purified by an Analogix purification system using a RediSep 40 g column (25% ethyl acetate-hexanes) to provide (1.08 g, 83%) a white solid.

Preparative Examples X920-C-X930-C

By essentially same procedure set forth in Preparative Example X-910-C, the compounds given in Column 2 of Table X-200-C were prepared.

TABLE X-200-C

| Prep. Ex. X- | Column 2 |
| --- | --- |
| 920-C | ![] |
| 930-C | ![] |

Preparative Example X-940-C

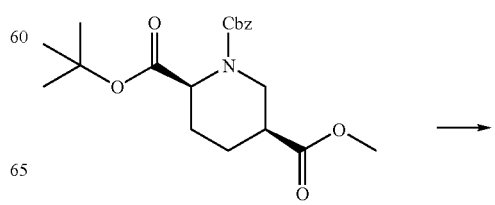

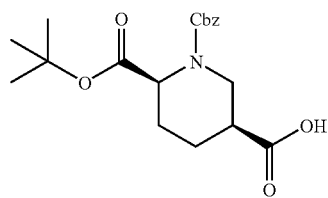

The compound from Preparative Example X-850-C (2.024 g, 5.37 mmol) was stirred 16 hours at room temperature in a mixture of 2N aqueous sodium hydroxide (6.5 mL, 13 mmol, 2.42 equiv.), methanol (8 mL) and tetrahydrofuran (15 mL). 4N aqueous hydrochloric acid (3 mL) was then added to bring the pH to 2-3, the mixture was diluted with water (50 mL) and extracted with ethyl acetate (3×50 mL). The combined extracts were washed with brine, dried with anhydrous sodium sulfate, filtered and concentrated under reduced pressure to yield a light yellow oil (1.857 g, 95% yield).

Preparative Examples X950-C-X980-C

By essentially same procedure set forth in Preparative Example X-940-C, the compounds given in Column 2 of Table X-210-C were prepared.

Preparative Example X-990-C

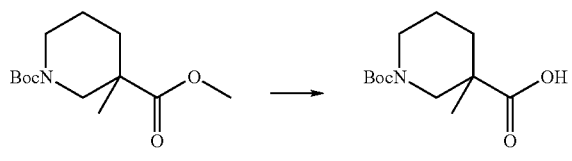

A solution of ester from Preparative Example X-910-C (1.08 g, 4.20 mmol) in EtOH (16.8 mL) at 25° C. was treated with NaOH (0.050 g, 3 equiv.). The solution was heated at 70° C. for 3 h. The solution was cooled to 25° C. and concentrated under reduced pressure. The residue was dissolved in H₂O (50 mL). The aqueous layer was washed with Et₂O (2×30 mL). The aqueous layer was acidified to pH=1 with 1M HCl. The aqueous layer was extracted with Et₂O (2×30 mL) and the organic layer was dried (MgSO₄), filtered and concentrated under reduced pressure. The residue was used directly in the next reaction.

Preparative Examples X1000-C and X1010-C

By essentially same procedure set forth in Preparative Example X-990-C, the compounds given in Column 2 of Table X-220-C were prepared.

TABLE X-210-C

| Prep. Ex. X- | Column 2 |
|---|---|
| 950-C | ![structure] |
| 960-C | ![structure] |
| 970-C | ![structure] |
| 980-C | ![structure] |

TABLE X-220-C

| Prep. Ex. X- | Column 2 |
|---|---|
| 1000-C | ![structure] |
| 1010-C | ![structure] |

Preparative Example X-1020-C

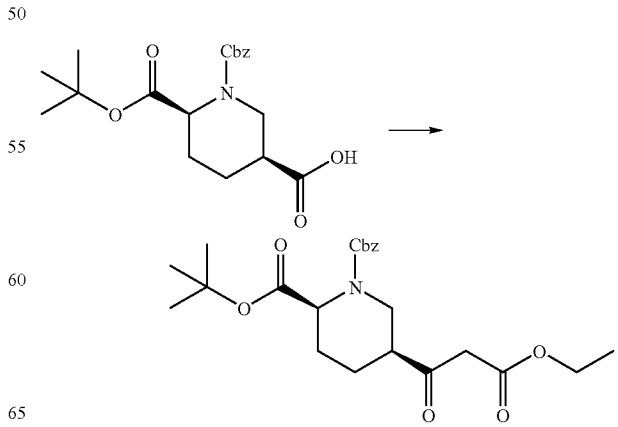

The acid from Preparative Example X-940-C (1.898 g, 5.23 mmol) and 1,1'-carbonyldiimidazole (1.045 g, 6.44 mmol, 1.23 equiv.) were stirred 16 hours room temperature in anhydrous THF (20 mL). In a separate flask, anhydrous ethyl acetate (1.10 mL, 11.26 mmol, 2.15 equiv.) was added drop-wise to a solution of lithium bis(trimethylsilylamide) (11 mL of 1.0M/THF, 11 mmol, 2.10 equiv.) in anhydrous THF (20 mL) at −78° C. After stirring 1 hours at −78° C., the crude acyl imidazole solution was added drop-wise. The solution was stirred four hours, warming to 5° C., and was then quenched with saturated ammonium chloride solution (50 mL) and water (10 mL). This mixture was extracted with ethyl ether (2×60 mL), and the combined extracts were washed with saturated sodium bicarbonate, washed with brine, dried with anhydrous sodium sulfate, filtered, and concentrated under reduced pressure. The crude product (2.17 g) was used without further purification.

Preparative Example X-1030-C

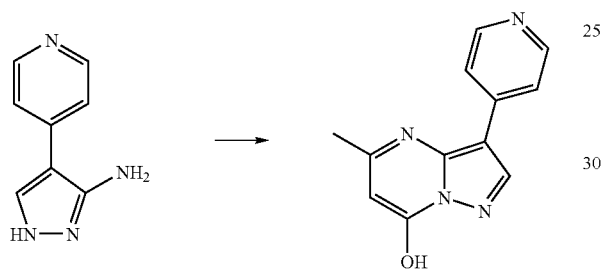

The aminopyrazole from Preparative Example X-800-C (2.39 g, 14.94 mmol) and ethyl acetoacetate (2.50 mL, 19.61 mmol, 1.31 equiv.) were combined in glacial acetic acid (15 mL) and stirred 14 hours at reflux. After cooling, the thick suspension was diluted with ethyl ether, filtered and the resulting solid was washed with additional ethyl ether. After drying under vacuum overnight at 55° C., an orange solid was obtained (2.687 g, 80% yield).

Preparative Example X-1040-C

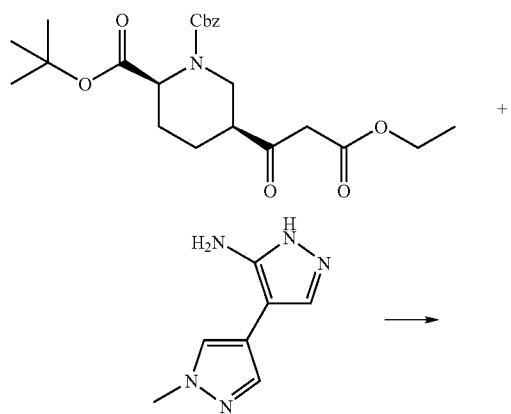

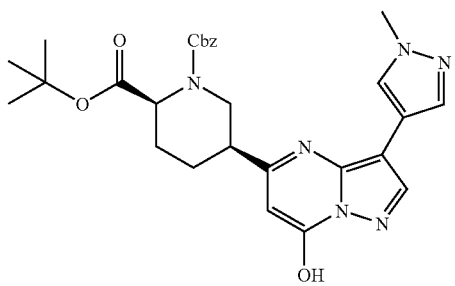

The β-keto ester from Preparative Example X-1020-C (1.516 g, 3.50 mmol) and pyrazole XY (0.457 g, 2.80 mmol) were stirred for 24 hours in a sealed tube heated to 115° C. After cooling to room temperature, the dark brown solution was concentrated under reduced pressure a crude product (1.8434 g, ~80% pure) that was used without purification.

Preparative Example X-1050-C

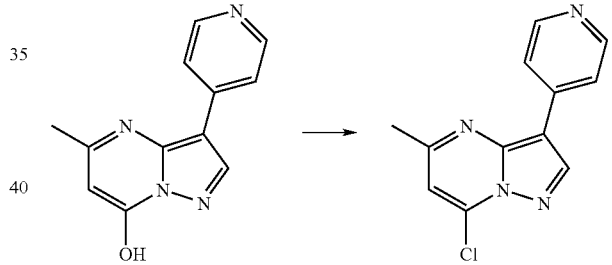

Phosphorus oxychloride (25 mL) was added to the compound from Preparative Example X-1030-C (2.683 g, 11.87 mmol) to give a green suspension, to which N,N-dimethylaniline (6.25 mL, 49.31 mmol, 4.15 equiv.) was added resulting in a yellow-brown suspension. This suspension was heated at 105° C. for 1.5 hours then cooled to room temperature. The reaction was quenched by slowing adding it to a vigorously stirring mixture of ice (200 g), water (100 mL) and sodium carbonate (90 g). After the ice had finished melting, the resulting dark red suspension was extracted with ethyl acetate (200 mL). The organic extract was then washed with water (200 mL) and with brine (100 mL), and then dried with anhydrous sodium sulfate, filtered and concentrated under reduced pressure. The crude red solid thus obtained was dissolved in dichloromethane and purified by chromatography on silica gel using a gradient from 0% to 100% ethyl-acetatedichloromethane followed by 0.5% to 5% methanol-ethyl acetate. A yellow-brown solid (1.014 g, 35% yield) was obtained.

Preparative Example X-1060-C

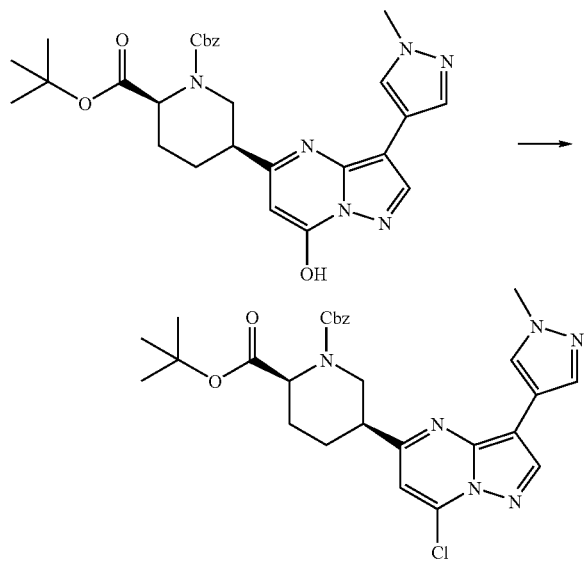

Phosphorus oxychloride (10 mL) was added to crude compound from Preparative Example X-1020-C (0.861 g, 1.40 mmol) to give a green suspension, to which N,N-dimethylaniline (0.55 mL, 4.34 mmol, 3.10 equiv.) was added resulting in a dark brown suspension. This suspension was stirred 2 days at room temperature, and was then diluted with dichloromethane and concentrated under reduced pressure. The residue was redissolved in ethyl acetate (10 mL) and added to a stirring mixture of ice (75 g), 2M aqueous sodium carbonate (75 mL) and ethyl acetate (25 mL). After the ice had finished melting, the resulting dark red suspension was extracted with ethyl acetate (3×100 mL). The combined extracts were then washed with water (200 mL) and with brine (100 mL), and then dried with anhydrous sodium sulfate, filtered and concentrated under reduced pressure. The crude red oil thus obtained was dissolved in dichloromethane and purified by chromatography on silica gel using a gradient from 33% to 100% ethyl-acetate-hexane. An orange oil (0.395 g, 51% yield) was obtained.

Preparative Example X-1070-C

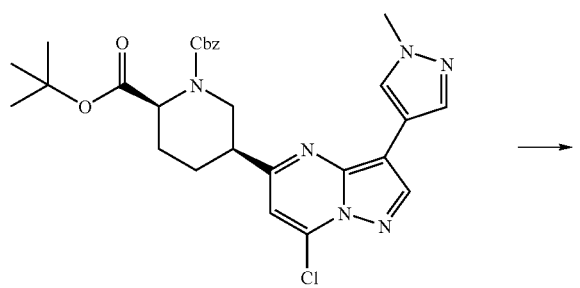

-continued

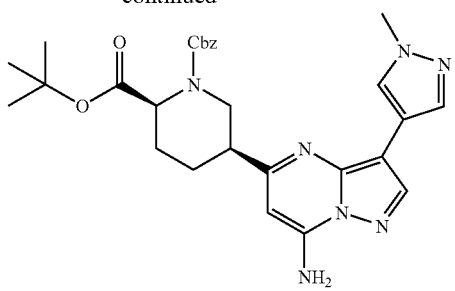

The chloro compound from Preparative Example X-1060-C (0.397 g, 0.721 mmol) in 7N ammonia in methanol (8 mL) was stirred for 16 hours in a sealed tube at 55° C. and then 21 hours at 80° C. Upon cooling, a white precipitate forms and this dissolves upon addition of dichloromethane (5 mL). The solution was concentrated and the resulting yellow solid was dissolved in 20% acetonitrile-dichloromethane and purified by silica gel chromatography using a gradient from 20% to 75% acetonitrile-dichloromethane. A white solid (0.282 g, 74% yield) was obtained.

Preparative Example X-1080-C

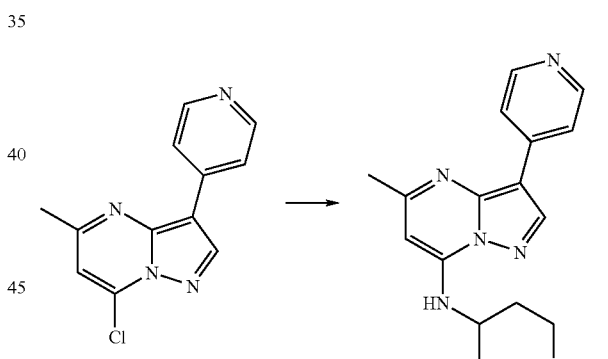

The chloro compound from Preparative Example X-1050-C (0.100 g, 0.410 mmol), 4-amino-1-Boc-piperidine (0.137 g, 0.684 mmol, 1.67 equiv.) and triethylamine (0.25 mL, 1.79 mmol, 4.37 equiv.) were dissolved in anhydrous 1,4-dioxane (5 mL) and the resulting solution was stirred 15 hours at 95° C. After cooling, the solution was concentrated under reduced pressure to yield a yellow solid. This solid was dissolved in dichloromethane and purified by silica gel chromatography using 5% methanol-dichloromethane. A yellow solid (0.1145 g, 68% yield) was obtained. LCMS: 409 [MH$^+$].

$^{13}$C NMR (CDCl$_3$) δ 161.14, 154.58, 149.49, 146.33, 145.27, 141.64, 140.97, 119.79, 105.65, 86.68, 80.10, 67.07, 49.42, 31.72, 28.39, 25.52.

Preparative Example X-1090-C

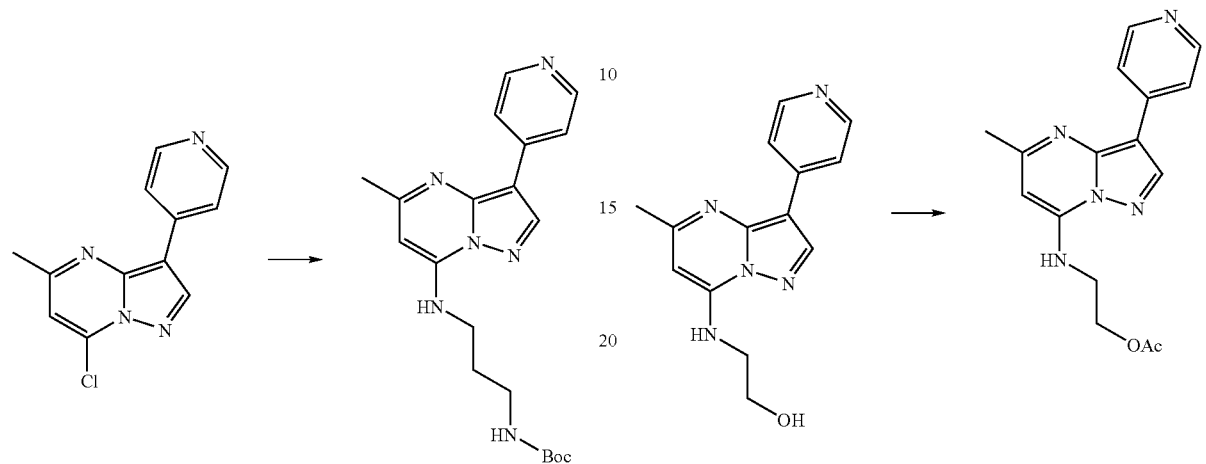

By essentially the same procedure as set forth in Preparative Example X-1080-C, the above was prepared, using N-Boc-propanediamine.

Preparative Examples X1100-C and X1110-C

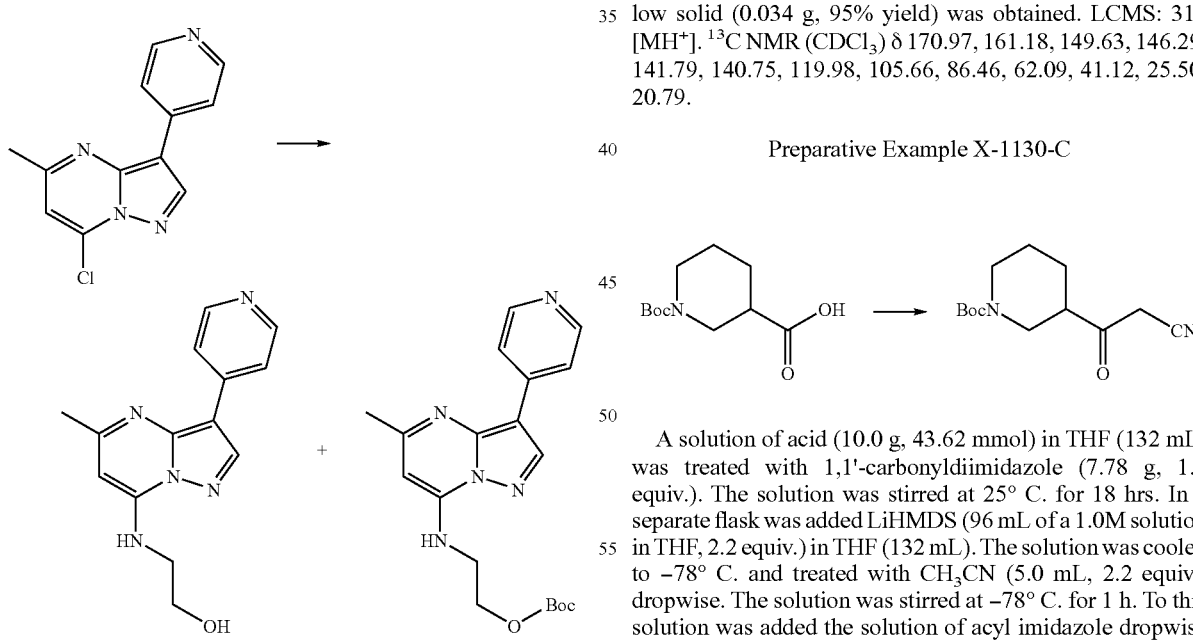

By essentially the same procedure as set forth in Preparative Example X-1080-C, using N-Boc-ethanolamine, the above compounds, Preparative Example 1100-C and Preparative Example X-1110-C were both prepared. X-1100-C: LCMS: 270 [MH$^+$]. $^{13}$C NMR (CD$_3$OD) δ 162.51, 149.43, 148.26, 147.47, 142.95, 121.03, 105.46, 87.73, 60.84, 44.92, 25.33. XXb: LCMS: 370 [MH$^+$]. $^{13}$C NMR (CDCl$_3$) δ 161.25, 153.31, 149.37, 146.32, 141.79, 141.06, 119.91, 105.55, 86.51, 83.13, 64.29, 41.26, 27.66, 25.52.

Preparative Example X-1120-C

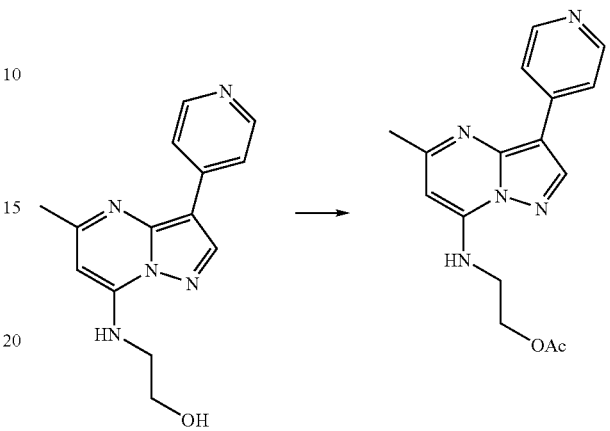

The compound from Preparative Example X-1100-C (0.031 g, 0.115 mmol) was dissolved in anhydrous dichloromethane (3 mL) and triethylamine (0.10 mL, 0.717 mmol, 6.23 equiv.) and acetic anhydride (0.03 mL, 0.32 mmol, 2.78 equiv.) were added. The solution was stirred 2 days at room temperature and was then concentrated under reduced pressure to yield a yellow solid that was dissolved in dichloromethane and purified by silica gel chromatography using a gradient from 5% to 10% methanol-dichloromethane. A yellow solid (0.034 g, 95% yield) was obtained. LCMS: 312 [MH$^+$]. $^{13}$C NMR (CDCl$_3$) δ 170.97, 161.18, 149.63, 146.29, 141.79, 140.75, 119.98, 105.66, 86.46, 62.09, 41.12, 25.50, 20.79.

Preparative Example X-1130-C

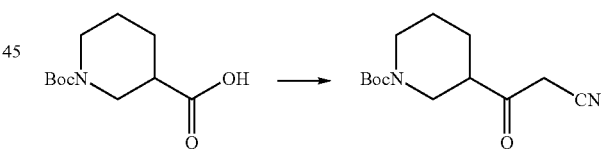

A solution of acid (10.0 g, 43.62 mmol) in THF (132 mL) was treated with 1,1'-carbonyldiimidazole (7.78 g, 1.1 equiv.). The solution was stirred at 25° C. for 18 hrs. In a separate flask was added LiHMDS (96 mL of a 1.0M solution in THF, 2.2 equiv.) in THF (132 mL). The solution was cooled to −78° C. and treated with CH$_3$CN (5.0 mL, 2.2 equiv.) dropwise. The solution was stirred at −78° C. for 1 h. To this solution was added the solution of acyl imidazole dropwise over 10 minutes. The solution was stirred at −78° C. for 2 h. and allowed to warm to 25° C. and stirring was continued for 15 h. The solution was quenched by the addition of saturated NH$_4$Cl (500 mL). The aqueous layer was extracted with Et$_2$O (3×100 mL). The combined organic layer was dried (MgSO$_4$), filtered and concentrated under reduced pressure. The residue was purified by an Analogix purification system using a RediSep 40 g column (0-50% ethyl acetate-hexanes gradient) to provide XX (4.4 g, 40%) as a pale yellow oil.

Preparative Examples X1140-C-X1350-C

By essentially same procedure set forth in Preparative Example X-1130-C, the compounds given in Column 2 of Table X-230-C were prepared.

TABLE X-230-C

| Prep. Ex. X- | Column 2 |
|---|---|
| 1140-C | (structure: piperazine with two NBoc groups, acyl-CH2-CN) |
| 1150-C | (structure: morpholine with BocN, acyl-CH2-CN) |
| 1160-C | (structure: Boc-piperidine with CH(CH3)-C(O)-CH2-CN) |
| 1170-C | (structure: Boc-azetidine-CH2-C(O)-CH2-CN) |
| 1180-C | (structure: NBoc-piperidine-CH2CH2-C(O)-CH2-CN) |
| 1190-C | (structure: BocN-piperidin-4-yl-CH2-C(O)-CH2-CN) |
| 1200-C | (structure: Boc-piperidin-2-yl-CH2-C(O)-CH2-CN) |
| 1210-C | (structure: Boc-pyrrolidin-3-yl-CH2-C(O)-CH2-CN) |
| 1220-C | (structure: BocHN-CH(CH3)-CH2-C(O)-CH2-CN) |
| 1230-C | (structure: BocN-piperidin-3-yl-CH2-C(O)-CH2-CN) |
| 1240-C | (structure: BocHN-(CH2)3-C(O)-CH2-CN) |

TABLE X-230-C-continued

| Prep. Ex. X- | Column 2 |
|---|---|
| 1250-C | (structure: BocHN-(CH2)4-C(O)-CH2-CN) |
| 1260-C | (structure: Boc-piperidine with 3-methyl, C(O)-CH2-CN) |
| 1270-C | (structure: Boc-piperidine with 3-F, C(O)-CH2-CN) |
| 1280-C | (structure: piperidin-3-yl (NBoc) CH(CH3)-C(O)-CH2-CN) |
| 1290-C | (structure: Cbz-piperidine with tBuO2C and C(O)-CH2-CN) |
| 1300-C | (structure: Cbz-piperidine spiro dioxolane with C(O)-CH2-CN) |
| 1310-C | (structure: Cbz-piperidine with CO2tBu and C(O)-CH2-CN) |
| 1320-C | (structure: NHBoc-cyclohexyl-C(O)-CH2-CN) |

TABLE X-230-C-continued

| Prep. Ex. X- | Column 2 |
|---|---|
| 1330-C | BocHN-cyclopentyl-C(O)CH2CN |
| 1340-C | BocHN-cyclopentyl-C(O)CH2CN |
| 1350-C | BocHN-CH(CH3)-CH2CH2-C(O)-CH2CN |

Preparative Example X-1360-C

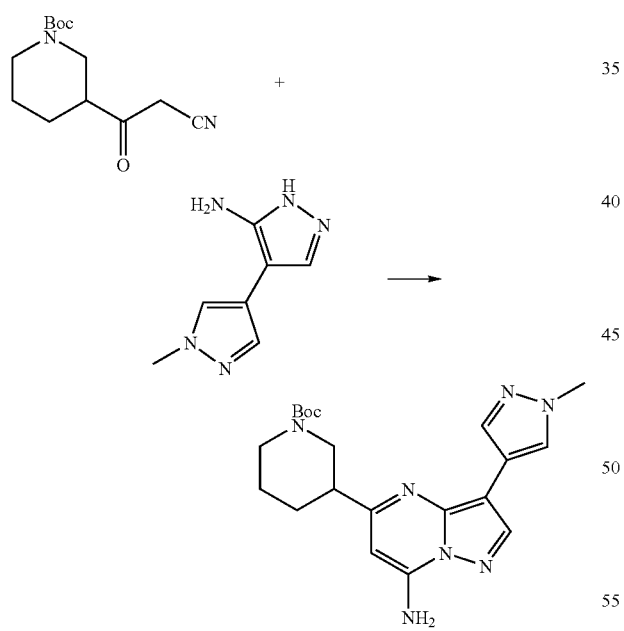

A solution of beta-ketonitrile from Preparative Example X-1130-C (7.96 g, 22.11 mmol) and bispyrazole from Preparative Example X-490-C (3.87 g, 23.73 mmol) in toluene (50 mL) was heated at 115° C. for 40 h. The solution was cooled to 25° C. and MeOH was added to solubilize the precipitate. The solution was concentrated under reduced pressure. Purification by an Analogix purification system using an Analogix SF40-240 g column (0-50% acetone-CH$_2$Cl$_2$ grad)ent) afforded (7.17 g, 82%) a pale yellow solid.

Preparative Examples X1370-C-X1540-C

By essentially same procedure set forth in Preparative Example X-1360-C, the compounds given in Column 2 of Table X-240-C were prepared.

TABLE X-240-C

| Prep. Ex. X- | Column 2 |
|---|---|
| 1370-C | (structure) |
| 1380-C | (structure) |
| 1390-C | (structure) |
| 1400-C | (structure) |
| 1410-C | (structure) |

TABLE X-240-C-continued

| Prep. Ex. X- | Column 2 |
|---|---|
| 1420-C | (structure) |
| 1430-C | (structure) |
| 1440-C | (structure) |
| 1450-C | (structure) |
| 1460-C | (structure) |
| 1470-C | (structure) |
| 1480-C | (structure) |
| 1490-C | (structure) |
| 1500-C | (structure) |
| 1510-C | (structure) |
| 1520-C | (structure) |

TABLE X-240-C-continued

| Prep. Ex. X- | Column 2 |
|---|---|
| 1530-C | 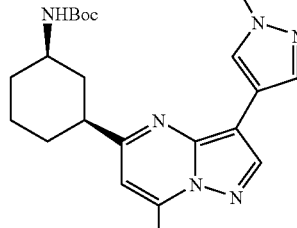 |
| 1540-C | 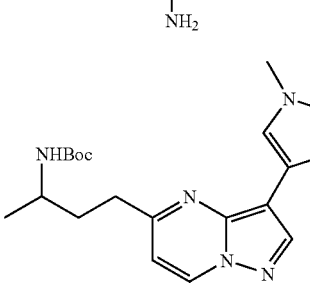 |

Preparative Example X-1550-C

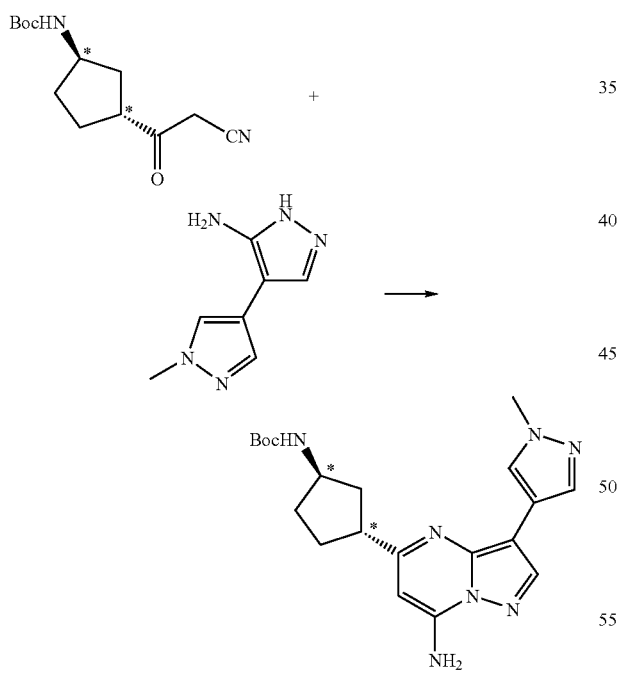

The β-Keto nitrile from Preparative Example X-1330-C (0.638 g, 2.53 mmol), bispyrazole from Preparative Example X-490-C (0.414 g, 2.54 mmol, 1.00 equiv.), and anhydrous magnesium sulfate (0.4965 g, 4.14 mmol, 1.63 equiv.) were combined in methanol (5 mL) and the resulting suspension was stirred vigorously for two days at room temperature. The suspension was then diluted with dichloromethane, filtered to remove the magnesium sulfate, and the filtrate was concentrated under reduced pressure to yield a tan solid. This was suspended in dichloromethane and loaded on an Isco Redisep RS-40 column using an Analogix DASI-65-Si-50 silica module to retain the undissolved solids from the column. The product was purified using an Analogix Intelliflash 280 system running a gradient from 10% to 70% acetone-dichloromethane. The product was obtained as an off-white solid (0.725 g, 72% yield).

Preparative Example X1560-C and X1570-C

Using essentially the same procedure as set forth in Preparative Example X-1550-C only substituting the appropriate β-keto nitriles, the compounds shown in Column 2 of Table X-250-C were prepared.

TABLE X-250-C

| Prep. Ex. X- | Column 2 |
|---|---|
| 1560-C |  |
| 1570-C |  |

Example X-800-C

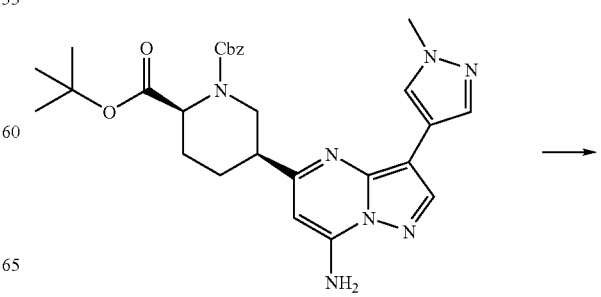

-continued

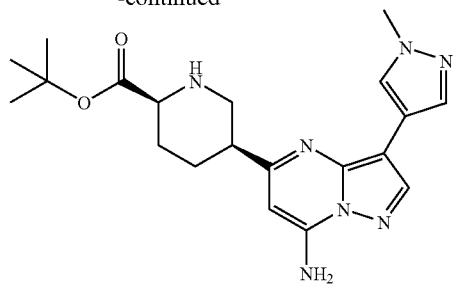

The compound from Preparative Example X-1500-C (0.116 g, 0.218 mmol) was dissolved in 50% ethanol-ethyl acetate (5 mL) and hydrogenated using the Thales Nanotechnology H-Cube hydrogenation reactor with a 10% palladium-on-carbon catalyst cartridge at 1 mL/minute, 50 bar hydrogen pressure and room temperature. The product solution was concentrated and purified by silica gel chromatography using a gradient from 4% to 7.5% 7N ammonia in methanol-dichloromethane. A white solid (0.040 g, 46% yield) is obtained. LCMS: 398 [MH+]. $^{13}$C NMR (CDCl$_3$) δ 172.61, 164.07, 147.21, 144.47, 140.72, 135.93, 127.30, 113.39, 101.40, 87.21, 81.50, 57.10, 46.98, 40.44, 38.44, 27.96, 27.85, 25.28.

Example X-810-C

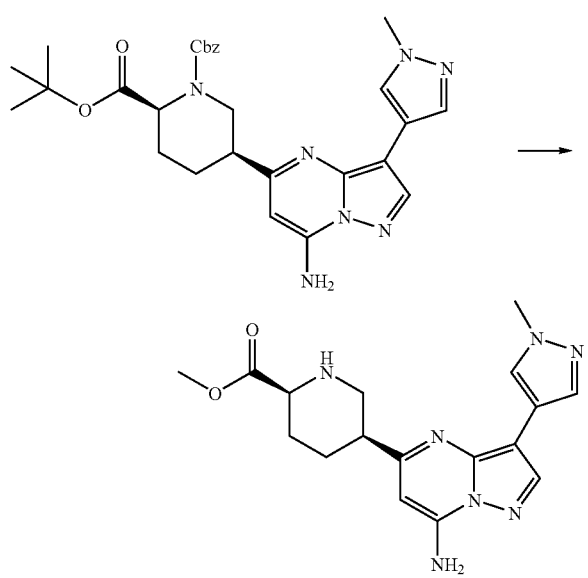

The compound from Preparative Example X-1500-C (0.120 g, 0.226 mmol) was stirred in 1.25 M HCl/methanol (10 mL) in a sealed tube at 85° C. for 24 hours. After cooling, the solution was concentrated and the resulting oil was redissolved in methanol (4 mL). Half of this solution was then diluted with glacial acetic acid (0.5 mL) and hydrogenated using the Thales Nanotechnology H-Cube hydrogenation reactor with a 10% palladium-on-carbon catalyst cartridge at 1 mL/minute, 50 bar hydrogen pressure and room temperature. The product solution was concentrated and the residue was redissolved in 7N ammonia in methanol (5 mL) and concentrated again. The resulting white solid was loaded on an Isco Redisep 5-gram chromatography column and purified using an Analogix Intelliflash 280 system running a gradient from 0% to 10% methanol-dichloromethane followed by 5% to 15% 7N ammonia in methanol-dichloromethane. The product was a colorless oil (0.018 g, 46% yield). LCMS: 356 [MH+]. $^{13}$C NMR (CDCl$_3$) δ 171.15, 162.63, 147.89, 143.87, 141.23, 136.15, 127.26, 112.96, 101.37, 87.03, 55.95, 52.63, 46.45, 38.43, 37.77, 27.35, 23.67.

Preparative Example X-1580-C

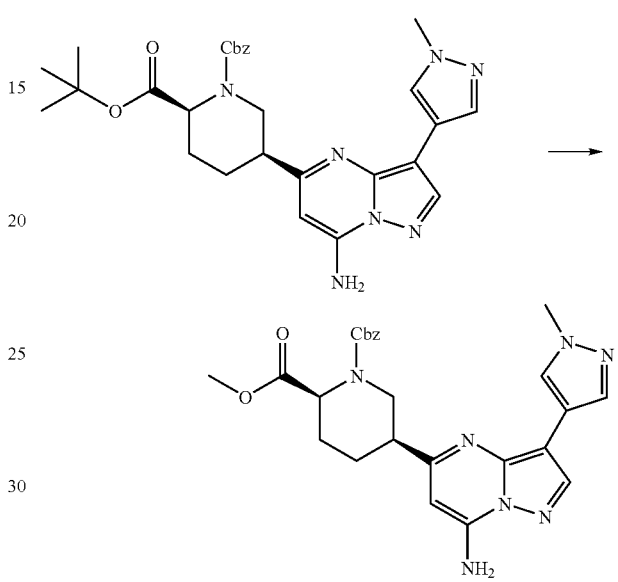

The compound from Preparative Example X-1500-C (2.33 g, 4.39 mmol) was dissolved in 1.25 M HCl in methanol solution (30 mL) and stirred 16 hours at 85° C. in a sealed tube. After cooling, the solution was concentrated under reduced pressure and the resulting oil was redissolved in a mixture of 7N ammonia in methanol and dichloromethane. After stirring for a few minutes, the resulting white suspension was loaded on an Analogix SF40-115 g column using a DASI-65-frit module to trap the insoluble inorganic matter from the column body. The column was run using an Analogix Intelliflash-280 system running a gradient from 0% to 5% methanol-dichloromethane. The product was obtained as a light brown solid (1.838 g, 85% yield).

Preparative Example X-1590-C

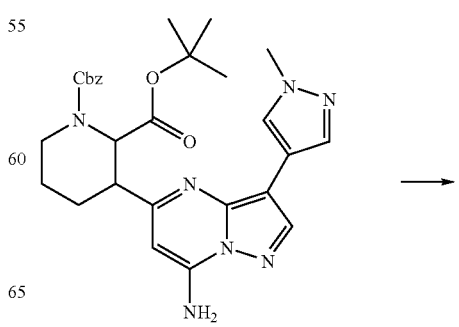

-continued

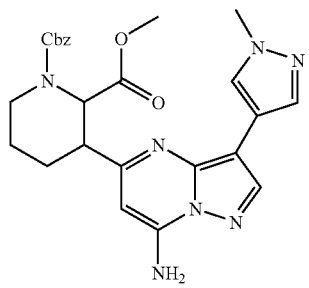

By essentially the same procedure as set forth in Preparative Example X-1580-C, only substituting the methyl ester from Preparative Example X-1520-C the tert-butyl ester was prepared in 70% yield.

Preparative Example X-1600-C

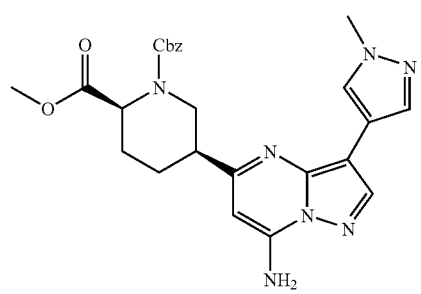

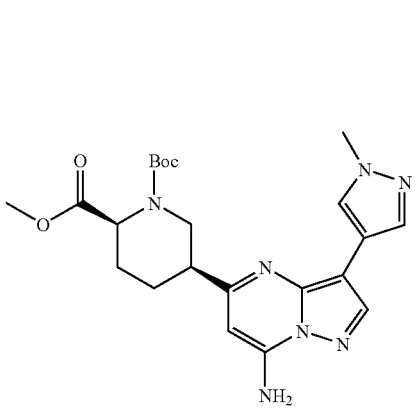

The compound from Preparative Example X-1520-C (1.894 g, 3.874 mmol) was dissolved in methanol (75 mL) to which di-tert-butyldicarbonate (2.535 g, 11.62 mmol, 3.00 equiv.) and 10% palladium on carbon (1.220 g, 1.15 mmol, 0.30 equiv.) were then added. The mixture was hydrogenated in a Parr vessel for 3 days at 52 psi. After filtering through Celite and washing with methanol then dichloromethane, the combined filtrates were combined and concentrated under reduced pressure. The residue was dissolved in methanol and purified on an Analogix SF40-150 column using the Analogix Intelliflash-280 running a gradient from 0% to 10% methanol-dichloromethane. The product was obtained as a yellow solid (1.510 g, 86% yield).

Preparative Example X-1610-C

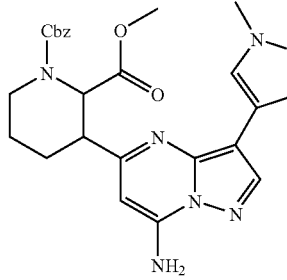

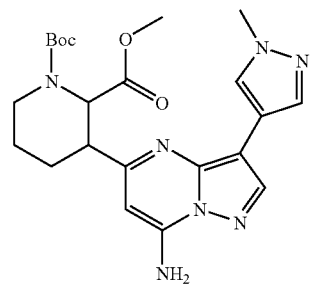

By essentially the same procedure as set forth in Preparative Example X-1600-C, only substituting the methyl ester from Preparative Example X-1590-C the above compound was prepared in 81% yield.

Preparative Example X-1620-C

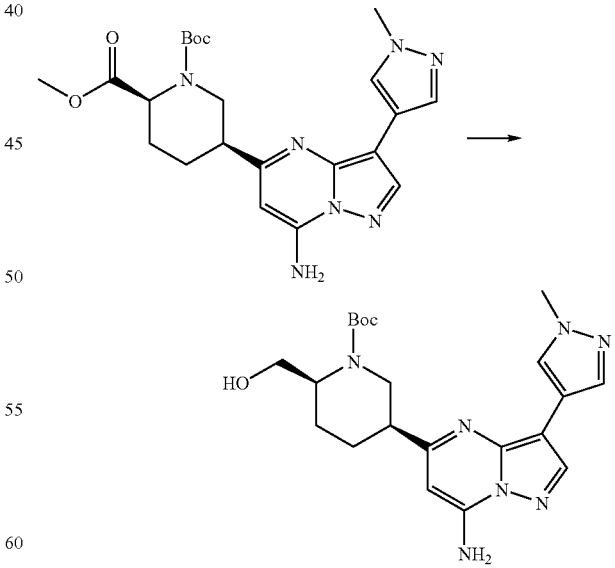

The ester from Preparative Example X-1600-C (0.356 g, 0.781 mmol) in anhydrous THF (6 mL) was treated with lithium triethylborohydride (1M solution in THF, 4.6 mL, 4.6 mmol, 5.89 equiv.) and stirred 14 hours at room temperature. The solution was then diluted with methanol and concentrated. The residue was suspended in dichloromethane, loaded on an Isco Redisep-40 gram column and purified with an Analogix Intelliflash-280 system running a gradient from 0% to 5% methanol-dichloromethane. The product is obtained as a white solid (0.282 g, 85% yield).

Preparative Example X-1630-C

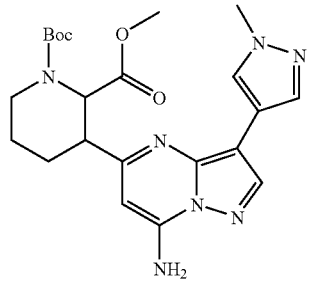

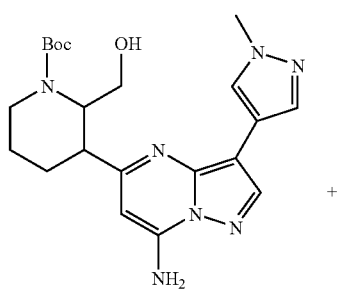

By essentially the same procedure as set forth in Preparative Example X-1620-C, two products were obtained from the methyl ester from Preparative Example X-1610-C. The alcohol (53% yield) was obtained as a mixture of cis and trans isomers, while the cyclic carbamate (18% yield) consisted only of trans isomer. LCMS 354 [MH$^+$]. $^1$H NMR (CDCl$_3$) δ 8.16 (s, 1H), 7.93 (s, 1H), 7.86 (s, 1H), 5.99 (s, 1H), 5.96 (s, 2H), 4.48 (t, J=8.8 Hz, 1H), 4.25 (m, 1H), 4.06 (m, 1H), 3.98 (s, 3H), 3.95 (m, 1H), 2.90 (m, 1H), 2.65 (m, 1H), 2.18 (m, 1H), 1.6-1.9 (m, 3H).

Preparative Example X-1640-C

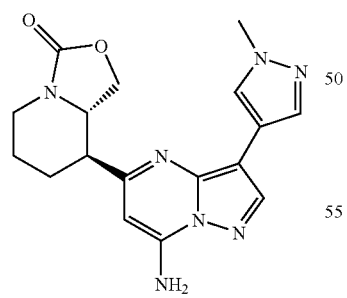

The ester from Preparative Example X-1600-C (0.182 g, 0.400 mmol), di-tert-butyl dicarbonate (0.263 g, 1.20 mmol, 3 equiv.) and N,N-dimethylaminopyridine (0.149 g, 1.22 mmol, 3 equiv.) were stirred together in THF (2 mL) at room temperature for 14 hours. The resulting solution was then concentrated under reduced pressure, and the residue was dissolved in dichloromethane and purified by chromatography on an Isco Redisep-12 gram column using an Analogix Intelliflash 280 system running 1% methanol-dichloromethane. A yellow oil (0.245 g, 94% yield) was obtained.

Preparative Example X-1650-C

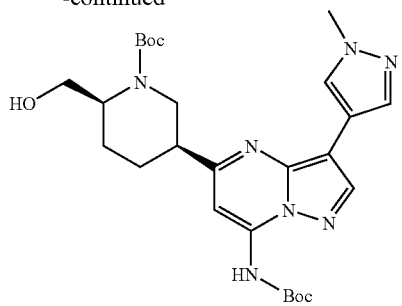

The ester from Preparative Example X-1640-C (0.255 g, 0.374 mmol) in anhydrous THF (5 mL) was treated with lithium triethylborohydride (1M solution in THF, 2.5 mL, 2.5 mmol, 6.68 equiv.) and stirred 14 hours at room temperature. The solution was then diluted with saturated aqueous ammonium chloride (10 mL) and water (1 mL) and extracted with ethyl acetate (2×15 mL). The combined extracts were washed with brine, dried with anhydrous sodium sulfate, filtered and concentrated under reduced pressure. The resulting yellow solid was suspended in dichloromethane, loaded on an Isco Redisep-4 gram column and purified using an Analogix Intelliflash-280 system running a gradient from 0% to 30% methanol-dichloromethane. The product is obtained as a yellow oil (0.172 g, 87% yield).

Preparative Example X-1660-C

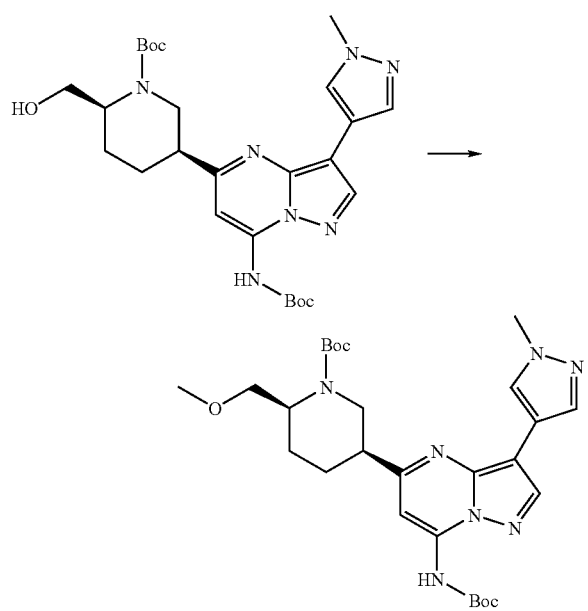

The alcohol from Preparative Example X-1650-C (0.086 g, 0.162 mmol) was dissolved in anhydrous THF (1 mL) and sodium hydride (60% dispersion in mineral oil, 0.019 g, 0.475 mmol, 2.93 equiv.) was added. The resulting suspension was stirred 1.5 hours at room temperature, then iodomethane (0.11 mL, 0.161 mmol, 0.99 equiv.) was added, the mixture was stirred 16 hours at room temperature. Water (3 mL) and brine (1 mL) were added, and the mixture was extracted with ethyl acetate (3×3 mL). The combined extracted were concentrated under reduced pressure, and the residue was dissolved in dichloromethane and purified by chromatography on an Analogix SF12-4 column using an Analogix Intelliflash 280 system running a gradient from 10% to 50% acetone-dichloromethane. The product was obtained as a yellow oil (0.018 g, 21% yield).

Preparative Example X-1670-C

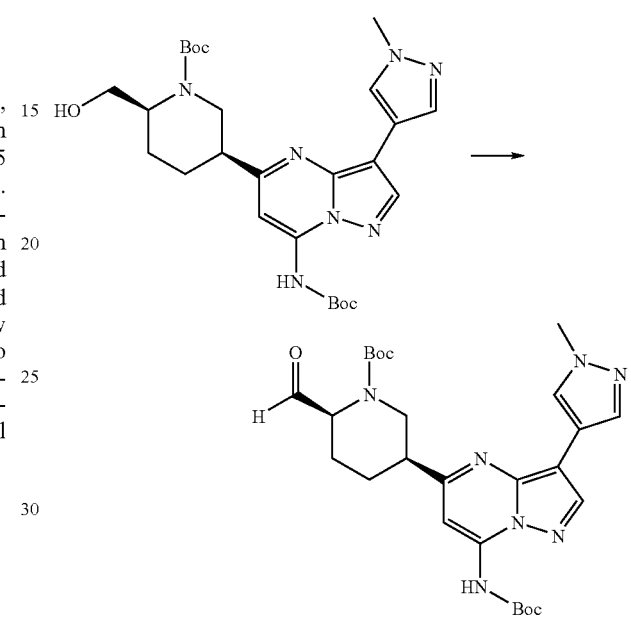

The alcohol from Preparative Example X-1660-C (0.160 g, 0.298 mmol) in dichloromethane (5 mL) was slowly added to a suspension Dess-Martin periodinane (0.267 g, 0.629 mmol, 2.11 equiv.) in dichloromethane (2 mL). The resulting solution was stirred 2.5 hours at room temperature before it was quenched by adding 2N aqueous sodium hydroxide (10 mL) and ethyl ether (10 mL). The two-phase mixture was stirred vigorously for 1 hour, and then the two layers were separated, and the aqueous phase was extracted with ethyl ether (10 mL). The ether extracts were combined, washed with brine, dried with anhydrous sodium sulfate, filtered, and concentrated under reduced pressure to yield a yellow solid (0.091 g, 57% yield) which was used without further purification.

Preparative Example X-1680-C

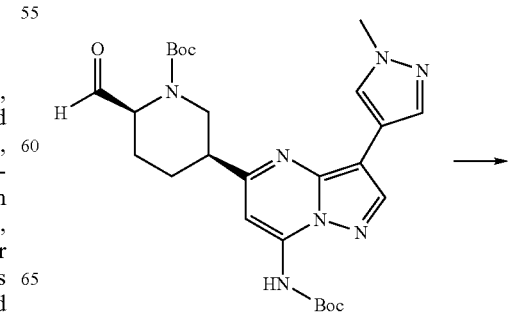

-continued

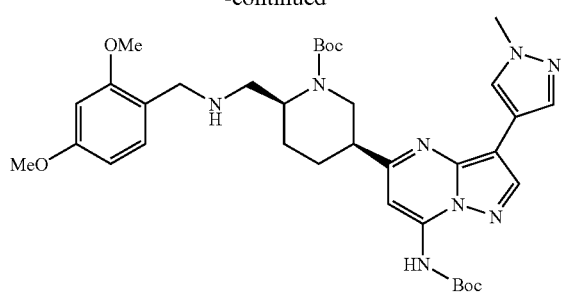

The aldehyde from Preparative Example X-1670-C (0.086 g, 0.164 mmol), 2,4-dimethoxybenzylamine (0.05 mL, 0.333 mmol, 2.03 equiv.), and sodium cyanoborohydride (0.031 g, 0.493 mmol, 3.01 equiv.) were combined in methanol (2 mL) and acetic acid (0.025 mL, 0.440 mmol, 2.66 equiv.) was added to achieve a pH of 5 to 6. The resulting solution was stirred 3 days at room temperature. Water (10 mL) and saturated aqueous potassium carbonate (1 mL) were added, and the mixture was extracted with dichloromethane (3×10 mL). The extracts were combined and concentrated under reduced pressure to yield a crude oil that was purified by chromatography on an Isco Redisep 4-gram column using an Analogix Intelliflash 280 system running a gradient from 0% to 10% methanol-dichloromethane. The product was obtained as a yellow oil (0.090 g, 82% yield)

Preparative Example X-1690-C

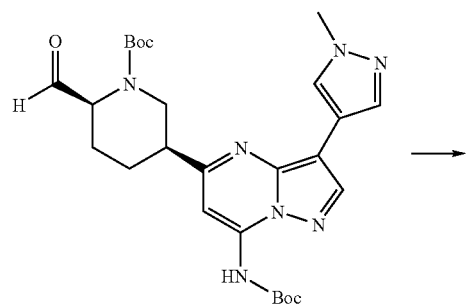

By essentially the same procedure set forth in Preparative Example X-1680-C, the above secondary amine was prepared using methylamine (2M solution in THF, 3.67 equiv.). The product was obtained as a yellow solid (0.014 g, 22% yield).

Preparative Example X-1700-C

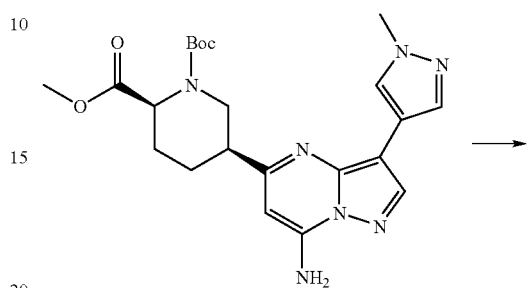

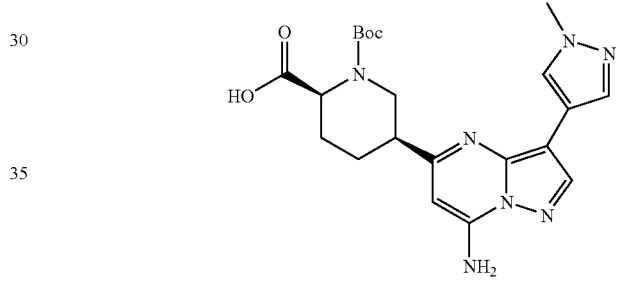

The ester from Preparative Example X-1600-C (0.125 g, 0.275 mmol) was stirred for 4.5 hours at room temperature in a mixture of THF (2 mL), methanol (1 mL) and 2N aqueous sodium hydroxide (0.50 mL, 1.0 mmol, 3.6 equiv.). After adding 2N aqueous hydrochloric acid (0.50 mL) and water (5 mL), the mixture was extracted with ethyl acetate (6×5 mL). The combined extracts were dried with anhydrous sodium sulfate, filtered and concentrated under reduced pressure to yield a yellow solid (0.116 g, 92% yield).

Preparative Example X-1710-C

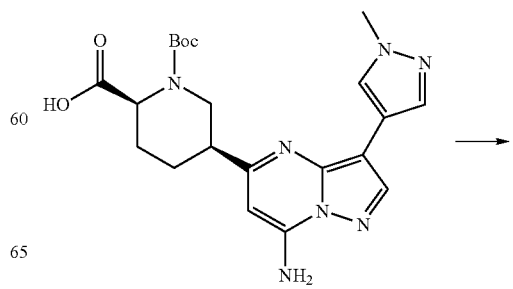

-continued

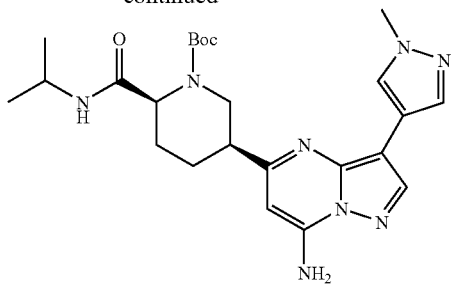

The acid from Preparative Example X-1700-C (0.114 g, 0.258 mmol), N-(3-dimethylaminopropyl)-N'-ethylcarbodiimide hydrochloride (0.075 g, 0.391 mmol, 1.52 equiv.), 1-hydroxybenzotriazole (0.056 g, 0.411 mmol, 1.59 equiv.), triethylamine (0.12 mL, 0.861 mmol, 3.34 equiv.) and isopropylamine (0.04 mL, 0.467 mmol, 1.81 equiv.) were combined in anhydrous dichloromethane (5.0 mL) and anhydrous DMF (0.12 mL) and stirred at room temperature for 16 hours. The crude reaction mixture was then loaded directly on an Isco Redisep 4-gram chromatography column and purified using an Analogix Intelliflash 280 system running a gradient from 0% to 3% methanol-dichloromethane. The product was obtained as a yellow oil (0.100 g, 81% yield).

Preparative Examples X1720-C-X1760-C

By essentially the same procedure as set forth in Preparative Example X-1710-C, the compounds given in Column 2 of Table X-260-C were prepared.

TABLE X-260-C

| Prep. Ex. X- | Column 2 |
|---|---|
| 1720-C | |
| 1730-C | |
| 1740-C | |
| 1750-C | |

TABLE X-260-C-continued

| Prep. Ex. X- | Column 2 |
|---|---|
| 1760-C | 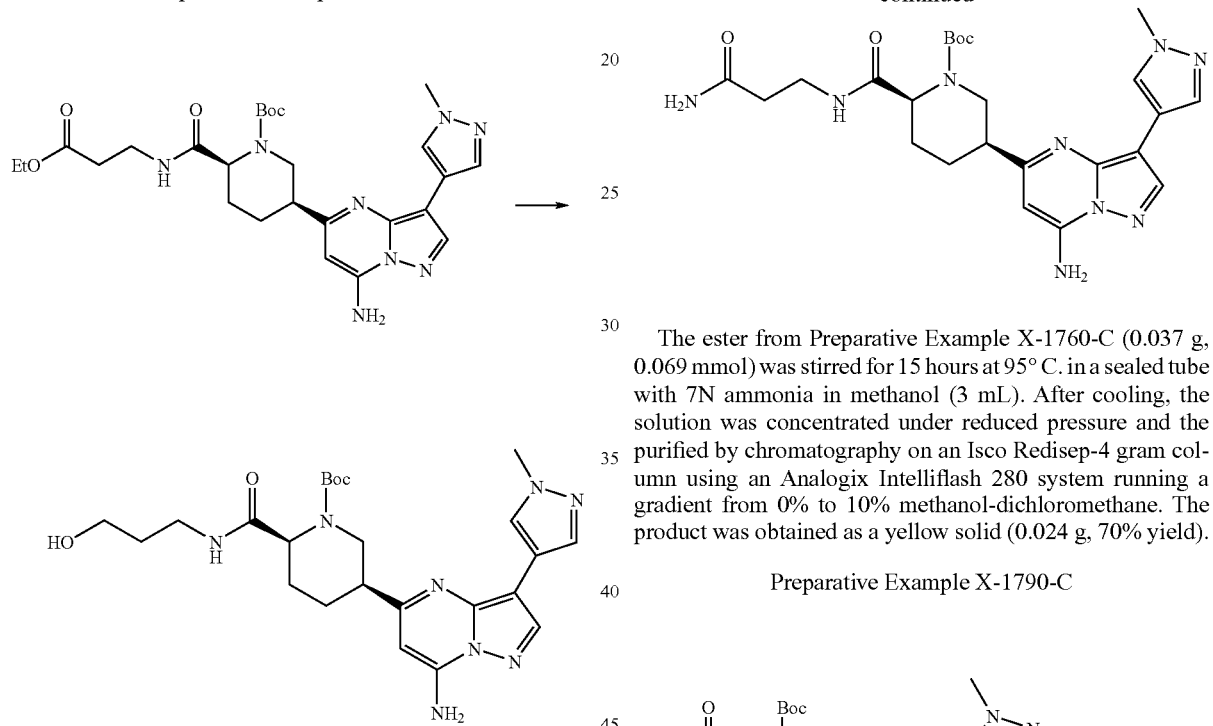 |

Preparative Example X-1770-C

By essentially the same procedure as set forth in Preparative Example X-1620-C, only utilizing the compound from Preparative Example X-1760-C (0.037 g, 0.069 mmol) the above alcohol was obtained as a colorless oil (0.025 g, 72% yield).

Preparative Example X-1780-C

-continued

The ester from Preparative Example X-1760-C (0.037 g, 0.069 mmol) was stirred for 15 hours at 95° C. in a sealed tube with 7N ammonia in methanol (3 mL). After cooling, the solution was concentrated under reduced pressure and the purified by chromatography on an Isco Redisep-4 gram column using an Analogix Intelliflash 280 system running a gradient from 0% to 10% methanol-dichloromethane. The product was obtained as a yellow solid (0.024 g, 70% yield).

Preparative Example X-1790-C

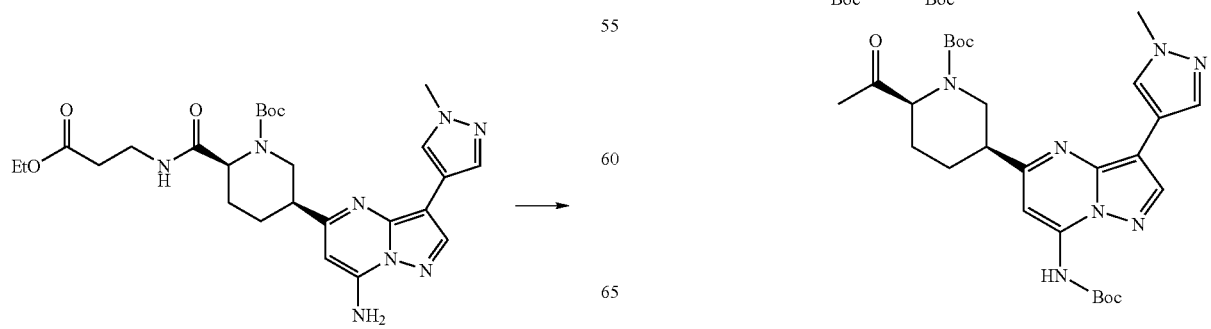

The ester from Preparative Example X-1640-C (0.211 g, 0.322 mmol) was dissolved anhydrous THF (3.5 mL) and cooled to −20° C. N,O-dimethylhydroxylamine hydrochloride (0.043 g, 0.441 mmol, 1.37 equiv.) in one portion followed by methylmagnesium chloride (3M solution in THF, 0.35 mL, 1.05 mmol, 3.26 equiv.) slowly via syringe. After stirring for 1 hour, warming to −5° C., additional methylmagnesium chloride (3M solution in THF, 0.70 mL, 2.10 mmol, 6.52 equiv.) was added, and the mixture was stirred 15 hours warming to room temperature. At this point, TLC (20% methanol-dichloromethane) indicated the continued presence of starting material. An additional portion of N,O-dimethylhydroxylamine hydrochloride (0.052 g, 0.533 mmol, 1.66 equiv.) followed by methylmagnesium chloride (3M solution in THF, 0.40 mL, 1.20 mmol, 3.73 equiv.). After stirring 1.5 hours at room temperature, additional methylmagnesium chloride (3M solution in THF, 0.70 mL, 2.10 mmol, 6.52 equiv.) was added. The mixture was stirred 3 hours at room temperature and was then quenched with saturated aqueous ammonium chloride (10 mL) and water (2 mL) and extracted with ethyl acetate (3×15 mL). The combined extracts were washed with brine, dried with anhydrous sodium sulfate, filtered and concentrated. The crude material was purified by chromatography on an Isco Redisep-12 g column using an Analogix Intelliflash 280 system running a gradient from 0% to 20% acetone-dichloromethane. The product was obtained as an partially solidified yellow oil (0.113 g, 66% yield).

Preparative Example X-1800-C

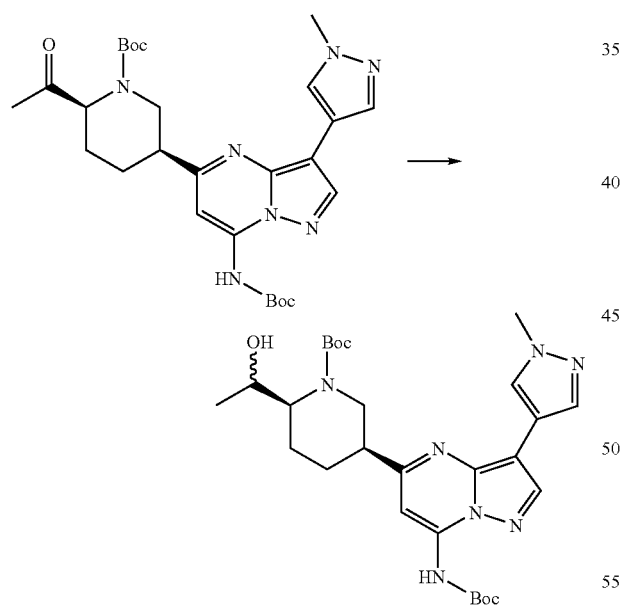

The ketone from Preparative Example X-1790-C (0.056 g, 0.104 mmol) in anhydrous THF (3 mL) was treated with lithium triethylborohydride (1M solution in THF, 0.35 mL, 0.35 mmol, 3.37 equiv.) and stirred 15 hours at room temperature. Water was then added (2 mL) and the resulting solution was concentrated under reduced pressure. The resulting oily residue was dissolved in methanol and concentrated again to yield a yellow solid. This was suspended in 10% methanol-dichloromethane (1.5 mL), loaded on an Isco Redisep-4 g chromatography column and purified using an Analogix Intelliflash 280 system running a gradient from 0% to 35% acetone-dichloromethane. The product was obtained as a yellow oil (0.048 g, 85% yield).

Preparative Example X-1810-C

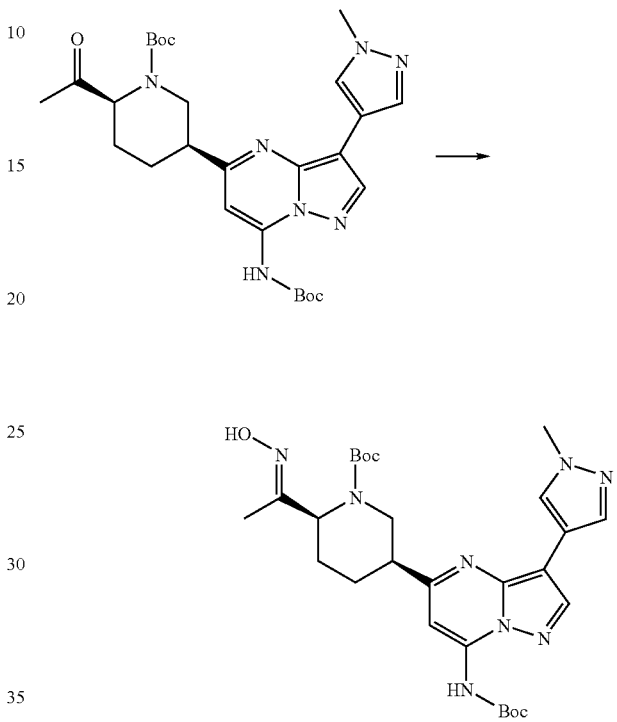

The ketone from Preparative Example X-1790-C (0.066 g, 0.122 mmol), hydroxylamine hydrochloride (0.023 g, 0.334 mmol, 2.74 equiv.) and sodium acetate (0.023 g, 0.274 mmol, 2.25 equiv.) were stirred 15 hours in ethanol (5 mL) at 70° C. After cooling, the mixture was concentrated under reduced pressure, and the crude solid was suspended in dichloromethane and purified by chromatography on an Isco Redisep-4 g column using an Analogix Intelliflash 280 system running gradient from 0% to 20% acetone-dichloromethane. The product was obtained as a yellow oil (0.0566 g total, 84% yield) in an E:Z ratio of 87:13, of which 0.037 g was obtained as pure E isomer.

Preparative Example X-1820-C

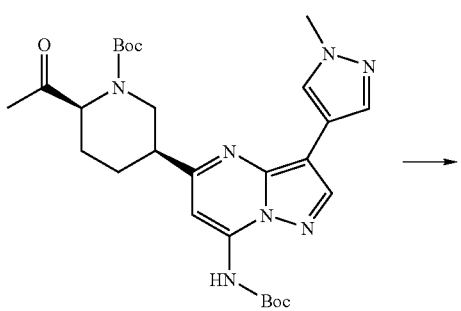

321

-continued

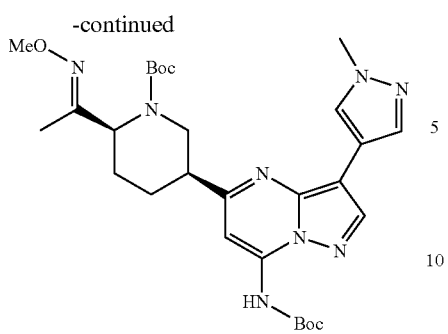

By essentially the same procedure set forth in Preparative Example X-1810-C, methyl oxime was prepared using methoxylamine hydrochloride. The product was obtained as a yellow oil in 81% yield that consisted of a 90:10 ratio of E to Z product. This mixture was used without further purification in the next step.

Example X-820-C

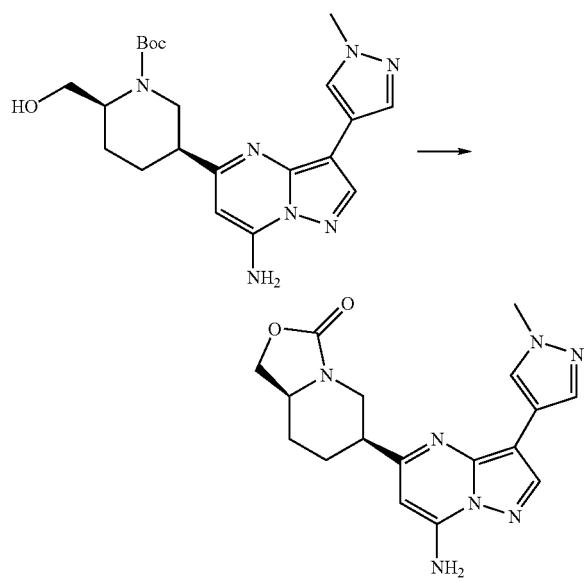

The alcohol from Preparative Example X-1650-C (0.067 g, 0.156 mmol) in anhydrous dichloromethane (2 mL) was treated with triethylamine (0.025 mL, 0.179 mmol, 1.15 equiv.) and methanesulfonyl chloride (0.03 mL, 0.388 mmol, 2.49 equiv.) and stirred 14 hours at room temperature. The resulting yellow-white suspension was treated with additional triethylamine (0.10 mL, 0.717 mmol, 4.60 equiv.), at which point it became homogenous, and was then heated for 4 hours at 40° C. After cooling, the solution was diluted with water (7 mL) and extracted with ethyl acetate (3×7 mL). The combined extracts were dried with anhydrous sodium sulfate, filtered and concentrated under reduced pressure. The crude orange solid was dissolved in dichloromethane and purified by chromatography on an Isco Redisep 4-gram column using an Analogix Intelliflash 280 system running 5% methanol-dichloromethane. The product was obtained as a yellow oil (0.023 g, 41% yield). LCMS: 354 [MH$^+$]. $^{13}$C NMR (CDCl$_3$)

322

δ 161.74, 157.61, 147.16, 144.96, 136.56, 127.12, 113.82, 102.53, 86.95, 69.05, 54.49, 43.62, 42.79, 38.76, 30.67, 26.68.

Preparative Example X-1830-C

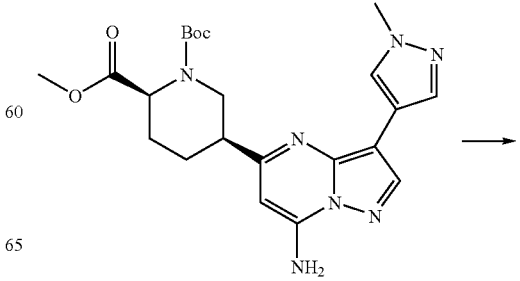

The alcohol from Preparative Example X-1650-C (0.050 g, 0.117 mmol) was dissolved in anhydrous dichloromethane (1 mL) and triethylamine (0.04 mL, 0.287 mmol, 2.45 equiv.) and acetic anhydride (0.015 mL, 0.159 mmol, 1.35 equiv.) were added. The solution was 15 hours at room temperature. The solution was then concentrated under reduced pressure to yield a yellow solid that was dissolved in dichloromethane and purified by chromatography on an Isco Redisep 4-gram column using an Analogix Intelliflash 280 system running a gradient from 0% to 5% methanol-dichloromethane. A yellow oil (0.051 g, 94% yield) was obtained.

Example X-830-C

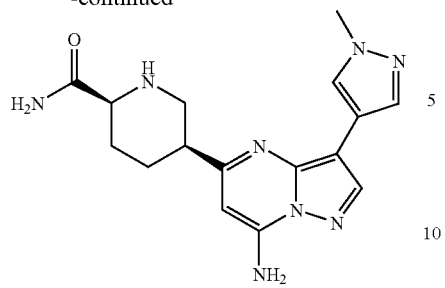

The ester from Preparative Example X-1640-C (0.103 g, 0.227 mmol) was dissolved in 7N ammonia in methanol (10 mL) in a sealed tube and stirred 15 hours at 120° C. followed by 22 hours at 160° C. After cooling, the solution was concentrated under reduced pressure to yield an orange gummy solid which was dissolved in 25% acetonitrile-water (1.0 mL) and purified by reverse-phase HPLC on a Waters PrepLC 25 mm column running a gradient from 5% to 50% acetonitrile-water. The product was obtained as a yellow oil (0.024 g, 26% yield). LCMS 341 [MH$^+$]. $^{13}$C NMR (CD$_3$OD) δ 161.70, 149.97, 146.25, 142.43, 137.51, 128.49, 115.42, 102.33, 87.25, 58.67, 47.92, 41.75, 38.87, 30.35, 28.61.

Example X-840-C

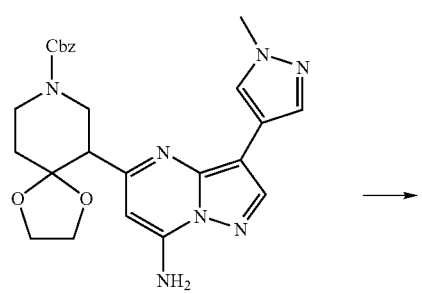

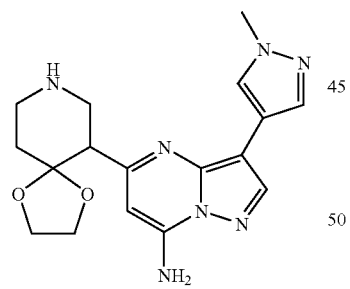

The ketal from Preparative Example X-1510-C (0.075 g, 0.153 mmol) hydrogenated at 55 psi for 20 hours in methanol (20 mL) with 10% palladium on carbon (0.055 g, 0.052 mmol, 0.34 equiv.) added. The suspension was filtered through Celite, the Celite was washed with methanol and dichloromethane, and the combined filtrates were concentrated under reduced pressure. The crude residue was dissolved in 5% methanol-dichloromethane and purified by chromatography on an Isco Redisep-4 g column using an Analogix Intelliflash 280 system running a gradient from 0% to 10% 7N ammonia in methanol-dichloromethane. The product was obtained as a colorless oil (0.0125 g, 23% yield). LCMS: 356 [MH$^+$]. $^{13}$C NMR (CDCl$_3$) δ 160.09, 146.21, 144.36, 140.83, 136.27, 126.88, 113.56, 108.44, 101.81, 89.65, 64.82, 64.52, 51.60, 49.33, 48.49, 44.10, 38.81.

Preparative Example X-1840-C

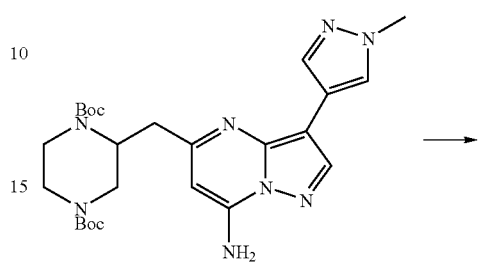

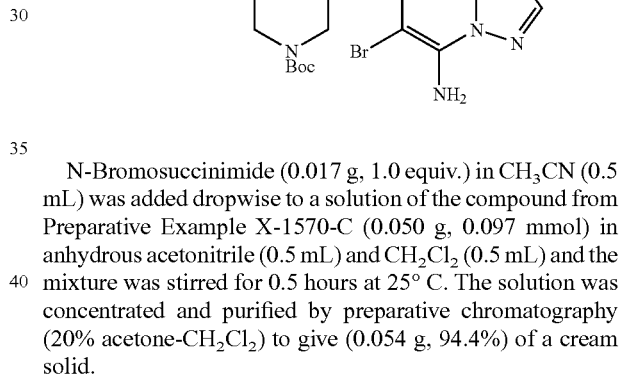

N-Bromosuccinimide (0.017 g, 1.0 equiv.) in CH$_3$CN (0.5 mL) was added dropwise to a solution of the compound from Preparative Example X-1570-C (0.050 g, 0.097 mmol) in anhydrous acetonitrile (0.5 mL) and CH$_2$Cl$_2$ (0.5 mL) and the mixture was stirred for 0.5 hours at 25° C. The solution was concentrated and purified by preparative chromatography (20% acetone-CH$_2$Cl$_2$) to give (0.054 g, 94.4%) of a cream solid.

Preparative Examples X1850-C-X2030-C

By essentially the same procedure as set forth in Preparative Example X-1840-C, the compounds given in Column 2 of Table X-270-C were prepared.

TABLE X-270-C

| Prep. Ex. X- | Column 2 |
|---|---|
| 1850-C | 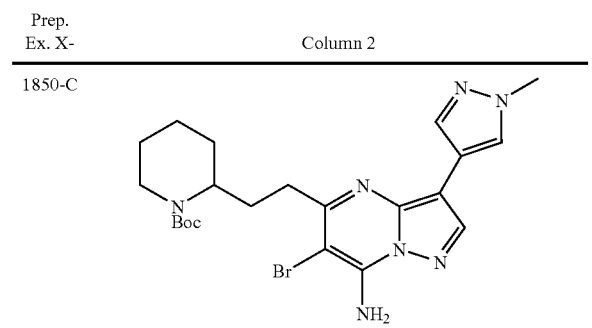 |

TABLE X-270-C-continued
| Prep. Ex. X- | Column 2 |
|---|---|
| 1860-C | 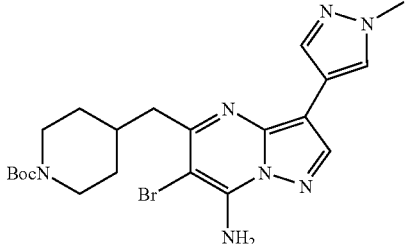 |
| 1870-C | 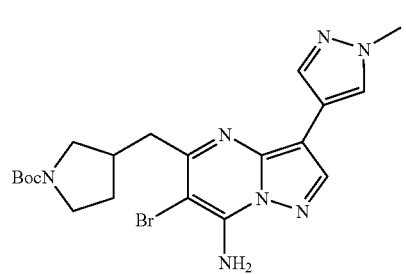 |
| 1880-C | 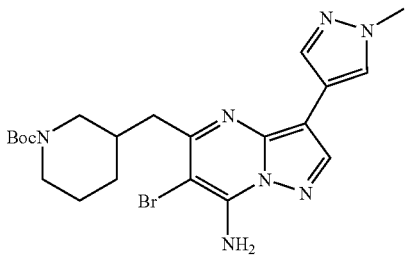 |
| 1890-C | 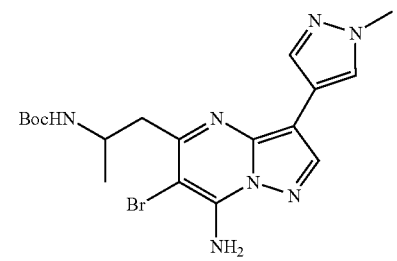 |
| 1900-C | 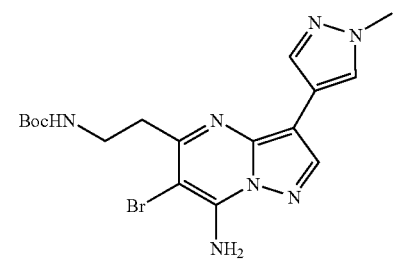 |
| 1910-C | 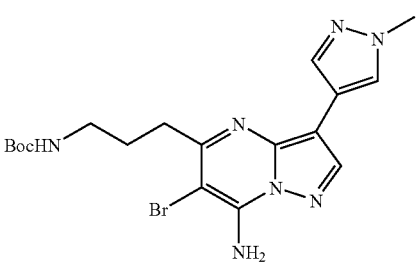 |
| 1920-C | 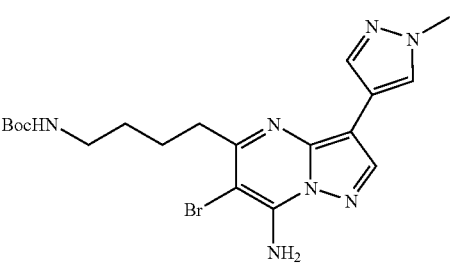 |
| 1930-C | 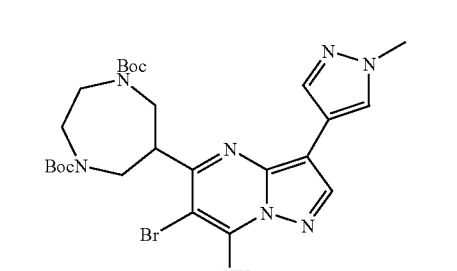 |
| 1940-C | 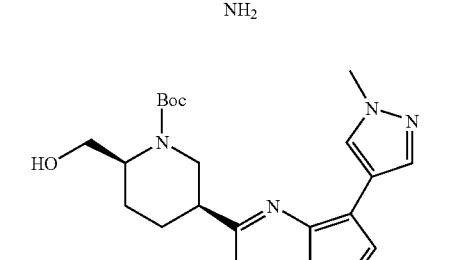 |
| 1950-C | 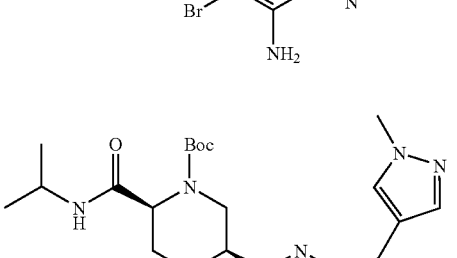 |
| 1960-C | 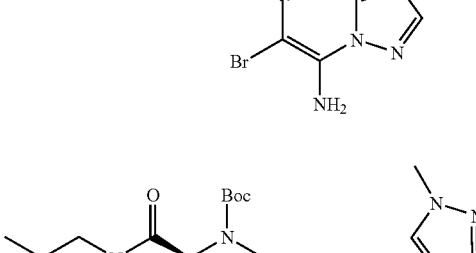 |

TABLE X-270-C-continued

| Prep. Ex. X- | Column 2 |
|---|---|
| 1970-C | |
| 1980-C | |
| 1990-C | |
| 2000-C | |
| 2010-C | |
| 2020-C | |
| 2030-C | |

Example X-850-C

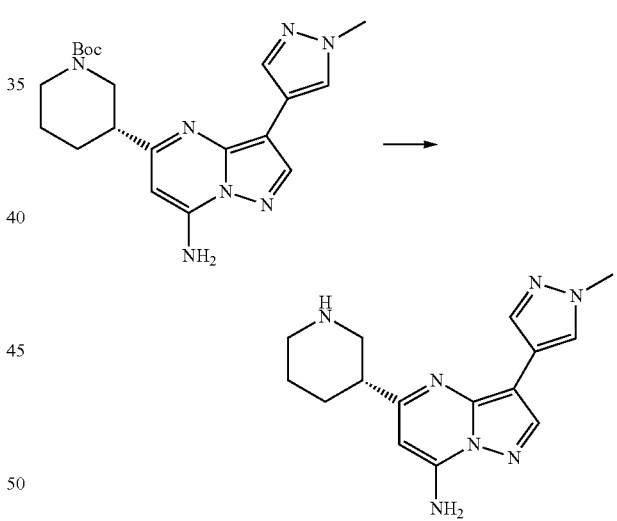

A solution of the compound from Preparative Example X-1360-C (0.25 g, 0.63 mmol) in CH$_2$Cl$_2$ (6 mL) and trifluoroacetic acid (2 ml) was stirred at 25° C. for 1 h. The solution was concentrated under reduced pressure and the residue was diluted with CH$_2$Cl$_2$ (10 mL), 1N NaOH (1 mL) and saturated aqueous K$_2$CO$_3$ (30 mL). The aqueous layer was further extracted with CH$_2$Cl$_2$ (3×10 mL). The combined organic layer was dried (Na$_2$SO$_4$), filtered and concentrated under reduced pressure. Purification by preparative thin layer chromatography (10% 7N NH$_3$ in MeOH—CH$_2$Cl$_2$) afforded XX (0.16 g, 85%) as a white solid. $^1$H NMR (CD$_3$OD) δ 8.20 (s, 1H), 8.05 (s, 1H), 7.96 (s, 1H), 6.06 (s, 1H), 3.94 (s, 3H), 3.29-3.22 (m, 1H), 3.10-3.03 (m, 1H), 2.99-2.93 (m, 1H), 2.88-2.80 (m, 1H), 2.73-2.66 (m, 1H), 2.14-2.09 (m, 1H), 1.89-1.79 (m, 2H), 1.71-1.60 (m, 1H); MH$^+$=298.

Examples X860-C-X1600-C

By essentially the same procedure as set forth in Example X-850-C, the compounds given in Column 2 of Table X-280-C were prepared.

TABLE X-280-C

| Ex. | Column 2 | $^1$H or $^{13}$C NMR, LCMS [MH$^+$] |
|---|---|---|
| 860-C | | $^{13}$C NMR (DMSO-d$_6$) δ 160.45, 149.53, 146.17, 145.56, 141.76, 140.34, 118.94, 103.43, 86.67, 49.72, 44.98, 32.30, 24.85; MH$^+$ = 309 |
| 870-C | | $^{13}$C NMR (DMSO-d$_6$) δ 160.30, 149.51, 146.54, 146.03, 141.85, 140.38, 118.91, 103.37, 86.30, 31.36, 24.86; MH$^+$ = 283 |
| 880-C | | $^1$H NMR (CD$_3$OD) δ 8.20 (s, 1H), 8.07 (s, 1H), 7.95 (s, 1H), 3.95 (s, 3H), 3.48-3.39 (m, 1H), 3.07-2.86 (m, 6H), 2.81-2.75 (m, 1H), 2.65-2.60 (m, 1H); MH$^+$ = 391/393. |
| 890-C | | $^1$H NMR (CD$_3$OD) δ 8.21 (s, 1H), 8.08 (s, 1H), 7.96 (s, 1H), 4.25-4.19 (m, 1H), 3.95 (s, 3H), 3.88-3.84 (m, 1H), 3.70-3.63 (m, 1H), 3.23-3.17 (m, 1H), 3.07-2.96 (m, 2H), 2.89-2.78 (m, 2H), 2.73-2.67 (m, 1H); MH$^+$ = 392/394. |

TABLE X-280-C-continued

| Ex. | Column 2 | $^1$H or $^{13}$C NMR, LCMS [MH$^+$] |
|---|---|---|
| 900-C | | $^1$H NMR (CD$_3$OD) δ 8.19 (s, 1H), 8.05 (s, 1H), 7.92 (s, 1H), 6.10 (s, 1H), 4.03-3.96 (m, 1H), 3.94 (s, 3H), 3.85-3.82 (m, 1H), 3.65-3.58 (m, 1H), 2.99-2.95 (m, 1H), 2.88-2.75 (m, 4H), 2.65-2.59 (m, 1H); MH$^+$ = 314. |
| 1000-C | | $^1$H NMR (CD$_3$OD) δ 8.19 (s, 1H), 8.05 (s, 1H), 7.95 (s, 1H), 6.03 (s, 1H), 3.94 (s, 3H), 3.04-3.01 (m, 1H), 2.87-2.84 (m, 1H), 2.61-2.55 (m, 1H), 2.42-2.36 (m, 1H), 2.12-2.09 (m, 1H), 2.02-1.94 (m, 1H), 1.83-1.79 (m, 1H), 1.64-1.54 (m, 1H), 1.33-1.17 (m, 4H); MH$^+$ = 326. |
| 1010-C | isomer 2 | $^1$H NMR (CD$_3$OD) δ 8.19 (s, 1H), 8.04 (s, 1H), 7.96 (s, 1H), 6.04 (s, 1H), 3.94 (s, 3H), 3.38-3.34 (m, 1H), 3.07-3.04 (m, 1H), 2.681-2.50 (m, 3H), 2.03-1.98 (m, 1H), 1.72-1.64 (m, 2H), 1.55-1.45 (m, 1H), 1.34-1.28 (m, 4H); MH$^+$ = 326. |
| 1020-C | | $^1$H NMR (CD$_3$OD) δ 8.19 (s, 1H), 8.01 (s, 1H), 7.94 (s, 1H), 6.02 (s, 1H), 3.94 (s, 3H), 3.92-3.88 (m, 2H), 3.73-3.69 (m, 2H), 3.39-3.33 (m, 1H), 3.05-3.03 (d, J = 8.05 Hz, 2H); MH$^+$ = 284. |
| 1030-C | | $^1$H NMR (CD$_3$OD) δ 8.19 (s, 1H), 8.05 (s, 1H), 7.95 (s, 1H), 3.93 (s, 3H), 3.03-3.00 (m, 3H), 2.61-2.55 (m, 2H), 1.91-1.76 (m, 4H), 1.62-1.59 (m, 1H), 1.51-1.33 (m, 2H), 1.25-1.15 (m, 1H); MH$^+$ = 404/406. |

TABLE X-280-C-continued

| Ex. | Column 2 | ¹H or ¹³C NMR, LCMS [MH⁺] |
|---|---|---|
| 1040-C | | ¹H NMR (CD₃OD) δ 8.18 (s, 1H), 8.03 (s, 1H), 7.93 (s, 1H), 6.07 (s, 1H), 3.94 (s, 3H), 3.06-3.04 (m, 1H), 2.81-2.77 (m, 2H), 2.66-2.60 (m, 2H), 1.93-1.80 (m, 4H), 1.65-1.62 (m, 1H), 1.52-1.15 (m, 2H), 0.91-0.85 (m, 1H); MH⁺ = 326. |
| 1050-C | | ¹H NMR (CD₃OD) δ 8.19 (s, 1H), 8.03 s, 1H), 7.96 (s, 1H), 3.94 (s, 3H), 3.10-3.04 (m, 2H), 2.90-2.88 (d, J = 6.59 Hz, 2H), 2.67-2.60 (m, 2H), 2.24-2.13 (m, 1H), 1.831-1.75 (m, 2H), 1.42-1.31 (m, 2H); MH⁺ = 390/392. |
| 1060-C | | ¹H NMR (CD₃OD) δ 8.18 (s, 1H), 8.01 (s, 1H), 7.92 (s, 1H), 6.04 (s, 1H), 3.94 (s, 3H), 3.11-3.08 (m, 2H), 2.70-2.64 (m, 4H), 2.10-2.01 (m, 1H), 1.83-1.76 (m, 2H), 1.38-1.28 (m, 2H); MH⁺ = 312. |
| 1070-C | | ¹H NMR (CD₃OD) δ 8.19 (s, 1H), 8.03 (s, 1H), 7.93 (s, 1H), 6.04 (s, 1H), 3.93 (s, 3H), 3.10-3.02 (m, 2H), 2.77-2.75 (m, 2H), 2.68-2.62 (m, 1H), 1.83-1.73 (m, 2H), 1.66-1.62 (m, 1H), 1.54-1.24 (m, 3H); MH⁺ = 312. |
| 1080-C | | ¹H NMR (CD₃OD) δ 8.18 (s, 1H), 8.03 (s, 1H), 7.91 (s, 1H), 6.02 (s, 1H), 3.94 (s, 3H), 3.05-2.97 (m, 2H), 2.60-2.52 (m, 3H), 2.41-2.35 (m, 1H), 2.14-2.02 (m, 1H), 1.89-1.86 (m, 1H), 1.73-1.68 (m, 1H), 1.59-1.47 (m, 1H), 1.30-1.18 (m, 1H); MH⁺ = 312. |
| 1090-C | | ¹H NMR (CD₃OD) δ 8.19 (s, 1H), 8.05 (s, 1H), 7.94 (s, 1H), 3.94 (s, 3H), 3.09-3.06 (m, 1H), 2.99-2.96 (m, 1H), 2.88-2.78 (m, 2H), 2.60-2.53 (m, 1H), 2.43 (t, J = 11 Hz, 1H), 2.27-2.17 (m, 1H), 1.98-1.87 (m, 1H), 1.74-1.69 (m, 1H), 1.60-1.48 (m, 1H), 1.34-1.24 (m, 1H); MH⁺ = 390/392. |

TABLE X-280-C-continued

| Ex. | Column 2 | ¹H or ¹³C NMR, LCMS [MH⁺] |
|---|---|---|
| 1100-C | | ¹H NMR (CD₃OD) δ 8.19 (s, 1H), 8.03 (s, 1H), 7.96 (s, 1H), 3.94 (s, 3H), 3.24-3.19 (m, 1H), 3.11-2.95 (m, 4H), 2.88-2.81 (m, 1H), 2.77-2.72 (m, 1H), 2.14-2.06 (m, 1H), 1.70-1.61 (m, 1H); MH⁺ = 376/378. |
| 1110-C | | ¹H NMR (CD₃OD) δ 8.19 (s, 1H), 8.02 (s, 1H), 7.94 (s, 1H), 6.07 (s, 1H), 3.94 (s, 3H), 3.27-3.23 (m, 1H), 3.19-3.13 (m, 1H), 3.08-3.01 (m, 1H), 2.88-2.71 (m, 4H), 2.14-2.06 (m, 1H), 1.71-1.62 (m, 1H); MH⁺ = 298. |
| 1120-C | | ¹H NMR (CD₃OD) δ 8.18 (s, 1H), 8.03 (s, 1H), 7.92 (s, 1H), 6.07 (s, 3H), 3.94 (s, 3H), 2.79-2.74 (m, 4H), 2.00-1.93 (m, 2H); MH⁺ = 272. |
| 1130-C | | ¹H NMR (CD₃OD) δ 8.19 (s, 1H), 8.05 (s, 1H), 7.95 (s, 1H), 3.94 (s, 3H), 3.00 (t, J = 6.6 Hz, 1H), 2.80 (t, J = 6.6 Hz, 1H), 2.05 (m, 1H); MH⁺ = 350/352. |
| 1140-C | | ¹H NMR (CD₃OD) δ 8.21 (s, 1H), 8.05 (s, 1H), 7.94 (s, 1H), 3.94 (s, 3H), 3.67-3.59 (m, 1H), 3.06 (dd, J = 15.2 Hz, J = 4.8 Hz, 1H), 2.91 (dd, J = 15.2 Hz, J = 8.4 Hz, 1H), 1.25 (d, J = 6.6 Hz, 3H); MH⁺ = 350/352. |

TABLE X-280-C-continued

| Ex. | Column 2 | ¹H or ¹³C NMR, LCMS [MH⁺] |
|---|---|---|
| 1150-C | | ¹H NMR (CD₃OD) δ 8.20 (s, 1H), 8.05 (s, 1H), 7.94 (s, 1H), 3.94 (s, 3H), 2.97 (t, J = 7.3 Hz, 2H), 2.75 (t, J = 7.3 Hz, 1H), 1.92-1.85 (m, 2H), 1.69-1.61 (m, 2H); MH⁺ = 364/366. |
| 1160-C | | ¹H NMR (CD₃OD) δ 8.19 (s, 1H), 8.05 (s, 1H), 7.95 (s, 1H), 3.94 (s, 3H), 2.19 (t, J = 5.8 Hz, 2H), 2.75 (t, J = 5.8 Hz, 2H); MH⁺ = 336/338. |
| 1170-C | | ¹H NMR (CD₃OD) δ 8.17 (s, 1H), 8.03 (s, 1H), 7.91 (s, 1H), 6.06 (s, 1H), 3.94 (s, 3H), 2.75-2.67 (m, 4H), 1.86-1.79 (m, 2H), 1.61-1.54 (m, 2H); MH⁺ = 286. |
| 1180-C | | ¹H NMR (CD₃OD) δ 8.23 (s, 1H), 8.03 (s, 1H), 7.96 (s, 1H), 6.23 (s, 1H), 3.93 (s, 3H), 3.87-3.84 (m, 1H), 2.99-2.94 (m, 1H), 2.74-2.65 (m, 2H), 2.39-2.30 (m, 1H), 1.93 (s, 3H), 1.80-1.73 (m, 1H), 1.62-1.56 (m, 1H), 1.44-1.32 (m, 1H); MH⁺ = 312. |
| 1190-C | | ¹H NMR (CD₃OD) δ 8.25 (s, 1H), 8.05 (s, 1H), 7.96 (s, 1H), 6.39 (d, J = 2.2 Hz, 1H), 3.95 (s, 3H), 3.43-3.34 (m, 1H), 3.15-3.07 (m, 2H), 2.85-2.74 (m, 1H), 2.47-2.30 (m, 1H), 2.11-2.06 (m, 1H), 2.00-1.88 (m, 4H), 1.74-1.69 (m, 1H); MH⁺ = 316. |
| 1200-C | | ¹H NMR (CD₃OD) δ 8.12 (s, 1H), 8.01 (s, 1H), 7.89 (s, 1H), 6.20 (s, 1H), 5.93-5.80 (br s, 2H), 3.96 (s, 3H), 3.75-3.72 (m, 1H), 3.29-3.27 (m, 2H), 2.85-2.79 (m, 1H), 2.55-2.38 (m, 3H), 2.04-1.93 (m, 1H), 1.68-1.51 (m, 4H); MH⁺ = 298. |

TABLE X-280-C-continued

| Ex. | Column 2 | ¹H or ¹³C NMR, LCMS [MH⁺] |
|---|---|---|
| 1210-C | | ¹H NMR (CD₃OD) δ 8.25 (s, 1H), 8.24 (s, 1H), 7.99 (s, 1H), 4.25-4.21 (m, 1H), 3.96 (s, 3H), 3.35-3.31 (m, 1H), 2.88-2.82 (m, 1H), 2.18-2.13 (m, 1H), 1.78-1.59 (m, 2H), 1.49-1.39 (m, 1H); M⁺ = 376/378. |
| 1220-C | | ¹H NMR (CD₃OD) δ 8.23 (s, 1H), 8.17 (s, 1H), 7.98 (s, 1H), 6.16 (s, 1H), 3.94 (s, 3H), 3.87-3.84 (m, 1H), 3.27-3.23 (m, 1H), 3.16-3.09 (m, 1H), 2.98-2.91 (m, 2H), 2.85-2.78 (m, 2H); MH⁺ = 299. |
| 1230-C | | ¹H NMR (CD₃OD) δ 8.23-8.21 (m, 1H), 8.02-8.01 (m, 1H), 7.95-7.94 (m, 1H), 6.20-6.19 (m, 1H), 4.00-3.98 (m, 1H), 3.93-3.92 (m, 3H), 3.69-3.62 (m, 1H), 3.58-3.53 (m, 1H), 3.48-3.42 (m, 1H), 3.31-3.30 (m, 1H), 3.18-3.07 (m, 1H), 2.92-2.85 (m, 1H); MH⁺ = 332. |
| 1240-C | isomer 2 | ¹H NMR (CD₃OD) δ 8.20-8.18 (m, 1H), 7.99-7.98 (m, 1H), 7.95-7.92 (m, 1H), 6.17-6.13 (m, 1H), 3.91-3.90 (m, 3H), 3.88-3.85 (m, 1H), 3.60-3.3 (m, 2H), 3.35-3.28 (m, 1H), 3.15-2.99 (m, 2H), 2.86-2.80 (m, 1H); MH⁺ = 332. |
| 1250-C | | ¹H NMR (CD₃OD) δ 8.26 (s, 1H), 8.04 (s, 1H), 7.95 (s, 1H), 6.33 (s, 1H), 4.36-3.32 (m, 1H), 3.95 (s, 3H), 3.75-3.69 (m, 1H), 3.62-3.57 (m, 1H), 3.44-3.35 (m, 3H), 3.21-3.15 (m, 1H); MH⁺ = 348. |

TABLE X-280-C-continued

| Ex. | Column 2 | ¹H or ¹³C NMR, LCMS [MH⁺] |
|---|---|---|
| 1260-C | | ¹H NMR (CD₃OD) δ 8.20 (s, 1H), 8.05 (s, 1H), 7.93 (s, 1H), 3.94 (s, 3H), 3.79-3.72 (m, 1H), 3.38-3.33 (m, 2H), 3.23-3.17 (m, 2H), 3.05-2.97 (m, 4H); MH⁺ = 391/393. |
| 1270-C | | ¹³C NMR (DMSO-d₆) δ 147.83, 143.91, 140.64, 135.60, 126.38, 113.24, 100.26, 86.18, 62.20, 56.05, 46.56, 38.43, 26.71, 23.42; MH⁺ = 328. |
| 1280-C | | ¹³C NMR (CD₃OD) δ 160.54, 148.14, 143.80, 143.10, 137.94, 129.35, 114.28, 103.23, 83.34, 62.38, 58.71, 47.86, 38.94, 36.41, 26.47, 22.13; MH⁺ = 406/408. |
| 1290-C | | ¹³C NMR (CD₃OD) δ 171.99, 163.62, 150.60, 144.98, 143.20, 137.46, 128.69, 115.13, 102.28, 64.65, 56.51, 48.20, 39.01, 37.10, 28.55, 22.27, 19.97; MH⁺ = 370. |
| 1300-C | | ¹³C NMR (CD₃OD) δ 164.20, 150.50, 144.92, 143.23, 137.59, 129.63, 114.46, 102.70, 87.83, 58.92, 47.34, 38.85, 37.07, 28.70, 26.40, 24.64; MH⁺ = 355. |

TABLE X-280-C-continued

| Ex. | Column 2 | $^1$H or $^{13}$C NMR, LCMS [MH$^+$] |
|---|---|---|
| 1310-C | | $^{13}$C NMR (CD$_3$OD) δ 171.65, 164.17 150.54, 144.88, 143.24, 137.78, 129.40, 114.55, 102.61, 87.84, 58.92, 47.39, 38.93, 38.30, 36.90, 28.69, 24.38; MH$^+$ = 385. |
| 1320-C | | $^{13}$C NMR (CD$_3$OD) δ 170.35, 164.24 150.43, 144.90, 143.14, 137.53, 129.61, 114.46, 102.65, 87.85, 58.95, 47.29, 42.33, 38.83, 37.14, 28.73, 24.84, 23.61, 11.70; MH$^+$ = 383. |
| 1330-C | | $^{13}$C NMR (CD$_3$OD) δ 171.52, 162.70, 149.90, 146.32, 142.12, 137.51, 128.47, 115.47, 102.23, 87.27, 58.60, 43.85, 42.32, 38.86, 30.58, 29.47, 25.31, 23.63, 11.68; MH$^+$ = 383. |
| 1340-C | | $^{13}$C NMR (CD$_3$OD) δ 169.33, 164.22, 150.46, 144.88, 143.17, 137.54, 129.66, 114.44, 102.68, 87.86, 58.98, 58.98, 47.25, 43.00, 68.83, 37.01, 28.72, 24.72, 22.50; MH$^+$ = 383. |
| 1350-C | | $^{13}$C NMR (CD$_3$OD) δ 170.08, 164.43, 150.47, 144.89, 143.20, 137.55, 129.88, 114.39, 102.74, 87.87, 57.19, 47.16, 38.83, 36.94, 36.85, 35.96, 28.58, 23.07. MH$^+$ = 369. |

TABLE X-280-C-continued
| Ex. | Column 2 | $^1$H or $^{13}$C NMR, LCMS [MH$^+$] |
|---|---|---|
| 1360-C | 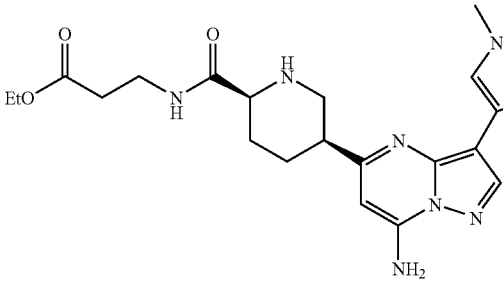 | $^{13}$C NMR (CD$_3$OD) δ 173.25, 171.02, 164.42, 150.38, 145.02, 143.08, 137.52, 129.56, 114.54, 102.63, 87.85, 61.79, 58.83, 47.44, 38.89, 37.60, 36.53, 24.86, 28.77, 24.97, 14.48; MH$^+$ = 441. |
| 1370-C | 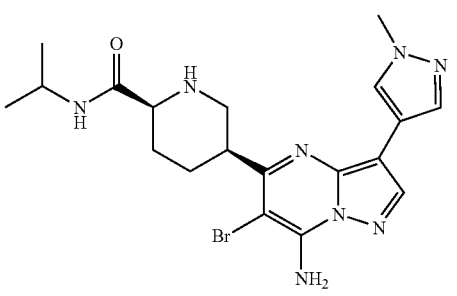 | $^{13}$C NMR (CD$_3$OD) δ 169.19, 160.32, 148.04, 143.66, 142.87, 137.76, 129.86, 113.87, 103.38, 58.75, 47.15, 42.99, 38.89, 35.95, 26.44, 24.65, 22.53; MH$^+$ = 461/463. |
| 1380-C | 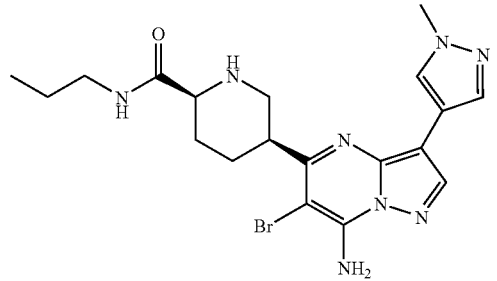 | $^{13}$C NMR (CD$_3$OD) δ 170.07, 160.36, 148.12, 143.73, 142.93, 137.82, 129.86, 113.92, 103.41, 83.39, 58.79, 47.21, 42.36, 38.89, 35.99, 26.47, 24.71, 23.59, 11.70; MH$^+$ = 461/463. |
| 1390-C | 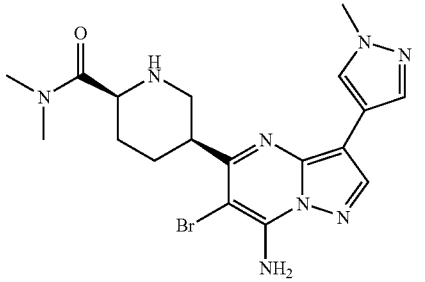 | $^{13}$C NMR (CD$_3$OD) δ 169.97, 160.54, 148.11, 143.74, 142.90, 137.82, 130.10, 113.84, 103.46, 83.39, 56.97, 47.13, 38.89, 36.95, 35.97, 35.78, 26.28, 22.99; MH$^+$ = 447/449. |
| 1400-C | 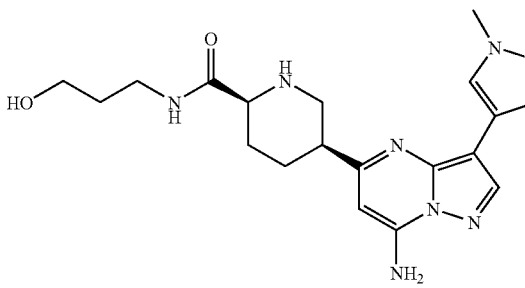 | $^{13}$C NMR (CD$_3$OD) δ 170.46, 164.24, 150.46, 144.93, 143.18, 137.56, 129.62, 114.46, 102.68, 87.85, 60.33, 58.91, 47.30, 38.88, 37.68, 37.14, 33.13, 28.73, 24.78; MH$^+$ = 399. |

TABLE X-280-C-continued
| Ex. | Column 2 | $^1$H or $^{13}$C NMR, LCMS [MH$^+$] |
|---|---|---|
| 1410-C | 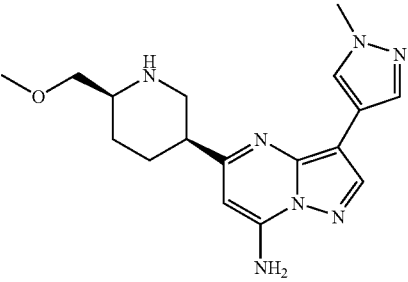 | $^{13}$C NMR (CD$_3$OD) δ 163.89, 150.50, 145.03, 143.22, 137.72, 128.81, 115.02, 102.38, 87.60, 72.82, 59.55, 57.04, 47.82, 38.98, 37.17, 28.71, 22.35; MH$^+$ = 342. |
| 1420-C | 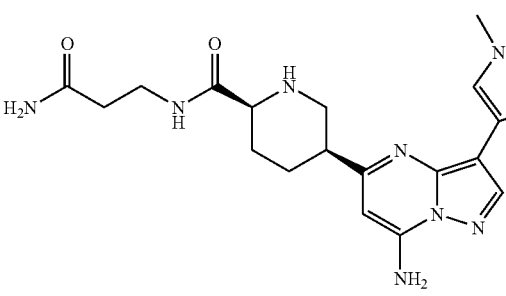 | $^{13}$C NMR (CD$_3$OD) δ 193.34, 170.43, 164.21, 150.48, 144.91, 143.20, 137.58, 129.69, 114.44, 102.68, 87.84, 58.84, 47.28, 38.91, 37.05, 37.03, 35.75, 28.70, 24.73; MH$^+$ = 412. |
| 1430-C | 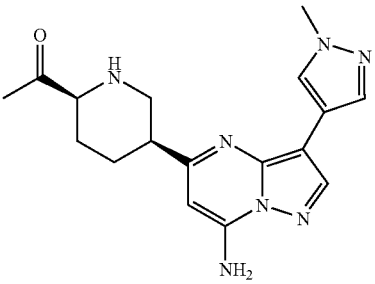 | $^{13}$C NMR (CD$_3$OD) δ 205.83, 164.03, 150.53, 144.87, 143.23, 137.60, 129.10, 114.54, 102.47, 87.85, 64.38, 47.35, 38.95, 37.05, 28.85, 22.95; MH$^+$ = 340. |
| 1440-C | 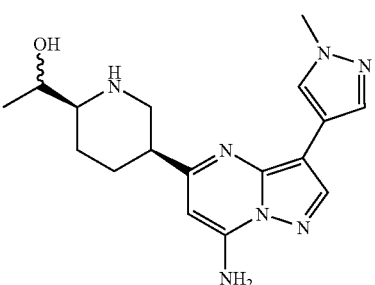 | $^{13}$C NMR (CD$_3$OD) δ 163.90, 150.48, 145.09, 143.16, 137.66, 129.00, 114.88, 102.41, 87.65, 68.07, 62.83, 47.82, 38.93, 37.43, 28.53, 23.23, 20.54; MH$^+$ = 342. |
| 1450-C | 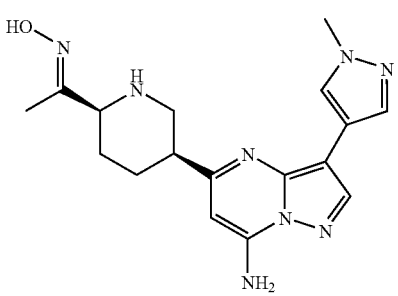 | $^{13}$C NMR (CD$_3$OD) δ 164.29, 154.15, 150.54, 143.32, 137.79, 128.94, 114.99, 87.78, 59.95, 48.19, 39.06, 37.39, 29.12, 25.14, 11.68; MH$^+$ = 355. |

TABLE X-280-C-continued

| Ex. | Column 2 | ¹H or ¹³C NMR, LCMS [MH⁺] |
|---|---|---|
| 1460-C | | ¹³C NMR (CD₃OD) δ 8.24 (s, 1H), 8.00 (s, 1H), 7.95 (s, 1H), 6.13 (s, 1H), 3.94 (s, 3H), 3.75 (m, 1H), 3.25 (m, 2H), 3.13 (m, 1H), 2.85-2.95 (m, 2H), 2.53 (s, 3H), 2.05-2.12 (m, 2H), 1.58-1.80 (m, 2H); MH⁺ = 341. |
| 1470-C | | ¹³C NMR (CD₃OD) δ 160.51, 154.07, 148.14, 143.74, 143.09, 137.83, 129.24, 114.47, 102.97, 83.42, 59.73, 48.14, 39.10, 36.52, 26.84, 25.13, 11.73; MH⁺ = 433/435. |
| 1480-C | | ¹³C NMR (CD₃OD) δ 163.77, 154.83, 150.57, 144.95, 143.25, 137.73, 128.81, 115.05, 102.47, 87.59, 62.45, 59.16, 47.75, 38.99, 37.14, 29.20, 25.30, 12.32; MH⁺ = 368. |
| 1490-C | | ¹³C NMR (CD₃OD) δ 160.15, 154.81, 148.24, 143.76, 143.01, 137.80, 129.03, 114.58, 103.16, 83.21, 62.41, 59.11, 48.02, 39.04, 36.63, 26.77, 25.51, 12.40; MH⁺ = 447/449. |
| 1500-C | | ¹³C NMR (CD₃OD) δ 170.23, 161.12, 150.05, 145.97, 142.52, 137.50, 128.61, 115.33, 102.43, 87.43, 61.11, 53.46, 45.63, 45.05, 38.87, 29.78, 22.78; MH⁺ = 356. |

TABLE X-280-C-continued

| Ex. | Column 2 | ¹H or ¹³C NMR, LCMS [MH⁺] |
|---|---|---|
| 1510-C | | ¹³C NMR (CD₃OD) δ 161.79, 149.98, 146.40, 142.54, 137.47, 128.59, 115.37, 102.26, 88.25, 61.78, 60.99, 45.39, 44.98, 38.86, 31.16, 23.50; MH⁺ = 383. |
| 1520-C | | ¹³C NMR (CD₃OD) δ 158.35, 153.81, 149.08, 141.20, 136.81, 133.15, 100.35, 86.30, 56.24, 55.52, 43.77, 42.08, 39.23, 21.26, 19.35; MH⁺ = 383. |
| 1530-C | | ¹³C NMR (CD₃OD) δ 165.74, 149.84, 146.31, 142.37, 137.58, 128.53, 115.57, 101.90, 87.07, 51.53, 45.47, 38.86, 36.94, 32.44, 31.54, 25.12; MH⁺ = 312. |
| 1540-C | | ¹³C NMR (CD₃OD) δ 161.51, 146.99, 144.33, 142.42, 137.51, 128.39, 115.22, 102.84, 84.24, 51.45, 43.67, 38.92, 35.99, 31.61, 31.47, 25.09; MH⁺ = 390/392. |
| 1550-C | | ¹³C NMR (CD₃OD) δ 165.58, 149.58, 146.48, 142.26, 137.47, 128.36, 115.64, 101.92, 87.46, 53.14, 46.43, 38.86, 37.79, 32.38, 32.58; MH⁺ = 298. |

TABLE X-280-C-continued

| Ex. | Column 2 | $^1$H or $^{13}$C NMR, LCMS [MH$^+$] |
|---|---|---|
| 1560-C | | $^{13}$C NMR (CD$_3$OD) δ 166.79, 150.01, 146.48, 143.54, 138.11, 129.14, 115.05, 101.47, 88.00, 53.49, 46.64, 38.97, 38.23, 32.44, 32.83; MH$^+$ = 298. |
| 1570-C | | $^{13}$C NMR (CD$_3$OD) δ 161.77, 146.95, 144.09, 142.47, 137.39, 128.34, 115.19, 102.83, 84.45, 53.23, 44.97, 38.92, 37.04, 32.14, 31.43; MH$^+$ = 376/378. |
| 1580-C | | $^{13}$C NMR (CD$_3$OD) δ 162.23, 147.26, 144.21, 143.26, 137.93, 128.94, 114.79, 102.59, 84.41, 53.38, 45.53, 38.97, 37.31, 31.87, 31.51; MH$^+$ = 376/378. |
| 1590-C | | $^{13}$C NMR (CD$_3$OD) δ 161.79, 150.40, 144.83, 143.41, 137.92, 129.11, 114.54, 101.53, 88.56, 48.69, 38.92, 34.78, 34.05, 18.71; MH$^+$ = 286. |
| 1600-C | | $^{13}$C NMR (CD$_3$OD) δ 158.88, 147.07, 144.17, 142.66, 137.57, 128.61, 115.01, 102.73, 84.48, 48.62, 38.91, 34.37, 33.46, 18.78; MH$^+$ = 364/366. |

Examples X1610-C and X1620-C

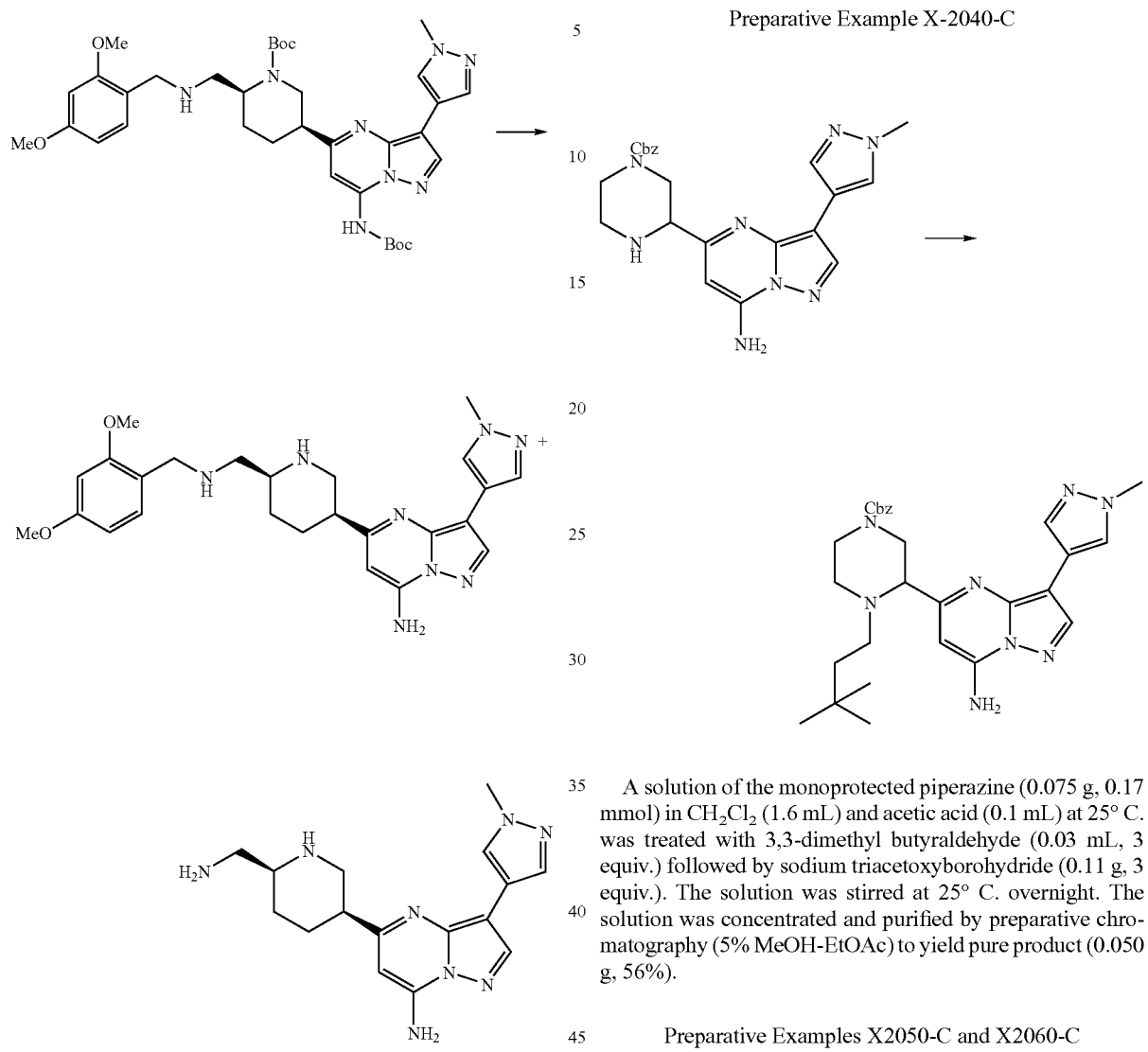

The compound from Preparative Example X-1680-C (0.094 g, 0.139 mmol) was stirred 15 hours at room temperature in dichloromethane (3 mL) and trifluoroacetic acid (3 mL). A portion of this solution (0.4 mL) was removed, concentrated under reduced pressure and purified by reverse-phase HPLC on a Waters PrepLC 25 mm column running a gradient from 5% to 50% acetonitrile-water. Example X-1610-C, the DMB-protected amine, was obtained as a yellow oil (0.012 g, 18% yield). LCMS 477 [MH$^+$]. $^{13}$C NMR (CD$_3$OD) δ 163.71, 163.03, 160.26, 150.27, 145.53, 142.89, 137.63, 132.48, 128.70, 116.99, 115.20, 105.75, 102.40, 99.46, 87.46, 55.99, 55.10, 49.93, 47.39, 38.96, 28.14, 24.93.

The remainder of the deprotection reaction was heated to 60° C. for 15 hours with an additional quantity of trifluoroacetic acid (2 mL) added. After cooling, this solution was also concentrated and purified by reverse-phase HPLC as above. Example X-1620-C, the fully deprotected amine, was obtained as a yellow oil (0.026 g, 57% yield). LCMS 327 [MH$^+$]. $^{13}$C NMR (CD$_3$OD) δ 162.30, 150.42, 145.51, 142.96, 137.59, 128.83, 115.12, 102.45, 87.24, 54.77, 47.50, 42.50, 41.64, 38.94, 38.16, 27.13, 24.51.

Preparative Example X-2040-C

A solution of the monoprotected piperazine (0.075 g, 0.17 mmol) in CH$_2$Cl$_2$ (1.6 mL) and acetic acid (0.1 mL) at 25° C. was treated with 3,3-dimethyl butyraldehyde (0.03 mL, 3 equiv.) followed by sodium triacetoxyborohydride (0.11 g, 3 equiv.). The solution was stirred at 25° C. overnight. The solution was concentrated and purified by preparative chromatography (5% MeOH-EtOAc) to yield pure product (0.050 g, 56%).

Preparative Examples X2050-C and X2060-C

By essentially the same procedure as set forth in Preparative Example X-2040-C, the compounds given in Column 2 of Table X-300-C were prepared.

TABLE X-300-C

| Prep. Ex. X- | Column 2 |
|---|---|
| 2050-C | |

TABLE X-300-C-continued

| Prep. Ex. X- | Column 2 |
|---|---|
| 2060-C | 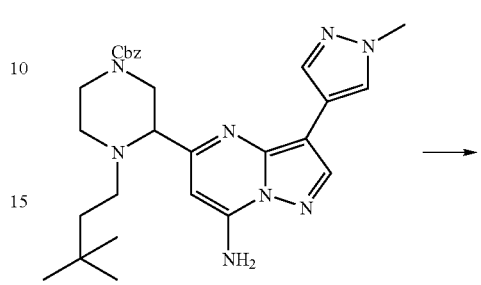 |

Preparative Example X-2070-C

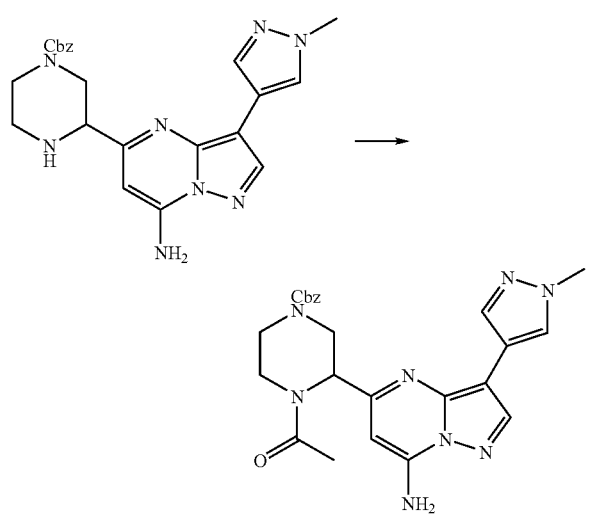

A solution of the monoprotected piperazine (0.067 g, 0.15 mmol) in THF (1.5 mL) at 25° C. was treated with triethylamine (0.043 mL, 2.0 equiv.) followed by acetyl chloride (0.014 mL, 1.3 equiv.). The solution was stirred at 25° C. overnight. The solution was concentrated and purified by preparative chromatography (5% MeOH-EtOAc) to give pure product (0.058 g, 79%).

Example X-1630-C

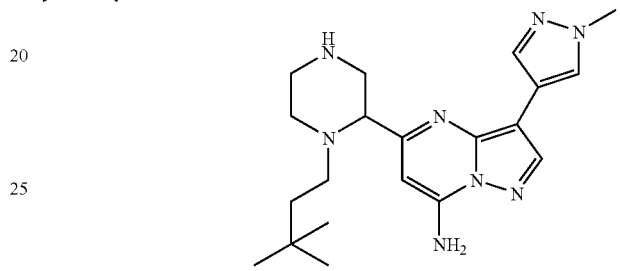

A mixture of the compound from Preparative Example X-2040-C (0.050 g, 0.097 mmol) in EtOAc (1 ml) and MeOH (1 mL) was treated with Pd/C and stirred under a hydrogen atmosphere overnight. The mixture was filtered through a pad of Celite and concentrated. Purification by preparative chromatography (10% 7N $NH_3$ in MeOH-EtOAc) yielded product (0.032 g, 87%). $^1$H NMR ($CD_3OD$) δ 8.22 (s, 1H), 8.14 (s, 1H), 7.96 (s, 1H), 6.31 (s, 1H), 3.94 (s, 3H), 3.39 (dd, J=10.2 Hz, J=2.9 Hz, 1H), 3.16-2.78 (m, 5H), 2.65-2.58 (m, 1H), 2.35-2.28 (m, 1H), 2.21-2.13 (m, 1H), 1.62-1.54 (m, 1H), 1.40-1.33 (m, 1H), 0.75 (s, 9H); $MH^+$=383.

Examples X1640-C-X1660-C

By essentially the same procedure as set forth in Example X-1630-C, the compounds given in Column 2 of Table X-310-C were prepared.

TABLE X-310-C

| Ex. X- | Column 2 | $^1$H or $^{13}$C NMR, LCMS [$MH^+$] |
|---|---|---|
| 1640-C |  | $^1$H NMR ($CD_3OD$) δ 8.21 (s, 1H), 8.13 (s, 1H), 7.94 (s, 1H), 6.31 (s, 1H), 3.94 (s, 3H), 3.37 (dd, J = 10.4 Hz, J = 3.7 Hz, 1H), 3.17-2.81 (m, 5H), 2.70-2.61 (m, 1H), 2.34-2.18 (m, 1H), 1.05 (t, J = 6.6 Hz, 3H); $MH^+$ = 327. |

TABLE X-310-C-continued

| Ex. X- | Column 2 | $^1$H or $^{13}$C NMR, LCMS [MH$^+$] |
|---|---|---|
| 1650-C | 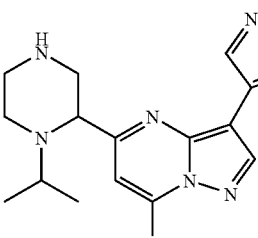 | $^1$H NMR (CD$_3$OD) δ 8.21 (s, 1H), 8.10 (s, 1H), 7.95 (s, 1H), 6.33 (s, 1H), 3.94 (s, 3H), 3.72-3.69 (m, 1H), 3.09-2.83 (m, 6H), 2.53-2.46 (m, 1H), MH$^+$ = 341. |
| 1660-C | | |

Examples X1670-C-X1700-C

By essentially the same procedure as set forth in Preparative Example X-2040-C, only utilizing the appropriate amine, the compounds given in Column 2 of Table X-320-C were prepared.

TABLE X-320-C

| Ex. X- | Column 2 | $^1$H or $^{13}$C NMR, LCMS [MH$^+$] |
|---|---|---|
| 1670-C | 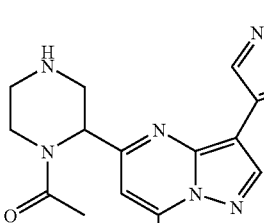 | |
| 1680-C | | $^1$H NMR (CDCl$_3$) δ 8.11 (s, 1H), 7.96 (s, 1H), 7.92 (s, 1H), 6.06 (br s, 2H), 3.97 (s, 3H), 3.21-2.73 (m, 11H), 1.12-1.08 (m, 12H); MH$^+$ = 475/477. |

TABLE X-320-C-continued

| Ex. X- | Column 2 | $^1$H or $^{13}$C NMR, LCMS [MH$^+$] |
|---|---|---|
| 1690-C | | $^1$H NMR (CD$_3$OD) δ 8.21 (s, 1H), 8.03 (s, 1H), 7.96 (s, 1H), 3.94 (s, 3H), 3.20-3.17 (m, 4H), 3.06-2.99 (m, 1H), 1.15 (s, 3H), 1.14 (s, 3H); M$^+$ = 378/380. |
| 1700-C | | $^1$H NMR (CD$_3$OD) δ 8.21 (s, 1H), 8.03 (s, 1H), 7.96 (s, 1H), 3.94 (s, 3H), 3.26-3.17 (m, 5H), 1.99-1.90 (m, 2H), 1.743-1.53 (m, 4H), 1.44-1.35 (m, 2H); M$^+$ = 404/406. |

Example X-1710-C

By essentially the same procedure as set forth in Example X-2070-C, the compounds given in Column 2 of Table X-330-C were prepared.

TABLE 330-C

| Ex. X- | Column 2 | $^1$H or $^{13}$C NMR, LCMS [MH$^+$] |
|---|---|---|
| 1710-C | | |

Example X-1720-C

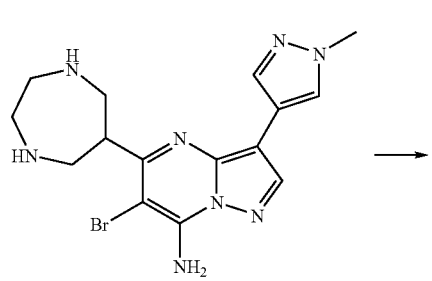

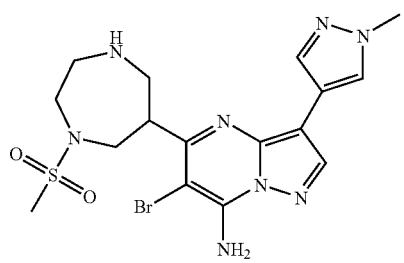

-continued

A solution of the compound from Example X-1260-C (0.075 g, 0.19 mmol) in DMF (3.8 mL) was treated with triethylamine (0.054 mL, 2.0 equiv.) followed by methanesulfonyl chloride 0.015 mL, 1.0 equiv.). The solution was stirred at 25° C. for 19 h. The solution was concentrated under reduced pressure and purified by preparative chromatography (10% 7N NH$_3$ in MeOH—CH$_2$Cl$_2$) to yield product (0.0135 g, 14%).

Example X-1730-C

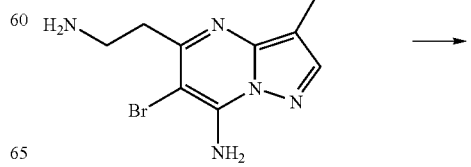

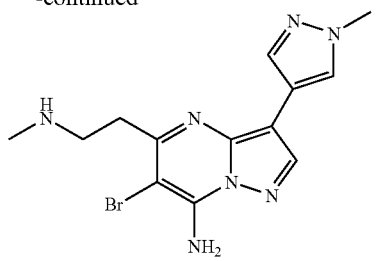

A solution of the compound from Example X-1150-C (0.050 g, 0.14 mmol) in CH$_2$Cl$_2$ (0.75 mL) and MeOH (0.75 mL) was stirred at 25° C. for 3 h. NaBH$_4$ (0.01 g, 1.1. equiv.) was added and stirring was continued for 17 h. The solution was concentrated and purified by preparative chromatography (10% 7N NH$_3$ in MeOH—CH$_2$Cl$_2$) to yield (0.035 g, 65%) a light orange solid. $^1$H NMR (CD$_3$OD) δ 8.21 (s, 1H), 8.03 (s, 1H), 7.96 (s, 1H), 3.94 (s, 3H), 3.19-3.17 (m, 4H), 2.75 (q, J=15.4 Hz, J=6.8 Hz, 2H), 1.92-1.85 (t, J=7.2 Hz, 3H); MH$^+$=364/366.

Examples X1740-C-X1770-C

By essentially the same procedure as set forth in Example X-1730-C, the compounds given in Column 2 of Table X-400-C were prepared.

TABLE X-400-C

| Ex. X- | Column 2 | $^1$H NMR, LCMS [MH$^+$] |
|---|---|---|
| 1740-C | | $^1$H NMR (CD$_3$OD) δ 8.21 (s, 1H), 8.04 (s, 1H), 7.96 (s, 1H), 3.94 (s, 3H), 3.19-3.17 (m, 4H), 2.76-2.70 (m, 2H), 1.47-1.41 (m, 2H), 0.92 (s, 9H); M$^+$ = 420/422. |
| 1750-C | | $^1$H NMR (CD$_3$OD) δ 8.20 (s, 1H), 8.02 (s, 1H), 7.94 (s, 1H), 7.41-7.40 (m, 1H), 6.34-6.33 (m, 1H), 6.28-6.27 (d, J = 3.2 Hz, 1H) 3.92 (s, 3H), 3.87 (s, 2H), 3.15-3.13 (m, 4H); M$^+$ = 416/418. |
| 1760-C | | $^1$H NMR (CD$_3$OD) δ 8.21 (s, 1H), 8.03 (s, 1H), 7.96 (s, 1H), 3.94 (s, 3H), 3.17-3.14 (m, 4H), 2.70 (t, J = 7.2 Hz, 2H), 1.61-1.50 (m, 2H), 0.93 (t, J = 7.2 Hz, 1H); M$^+$ = 378/380. |
| 1770-C | | $^1$H NMR (CD$_3$OD) δ 8.20 (s, 1H), 7.97 (s, 1H), 7.93 (s, 1H), 7.38-7.33 (m,, 5H), 4.05-4.00 (m, 2H), 3.89 (s, 3H), 3.38-3.23 (m, 4H); M$^+$ = 426/428. |

Example X1780-C and X1790-C

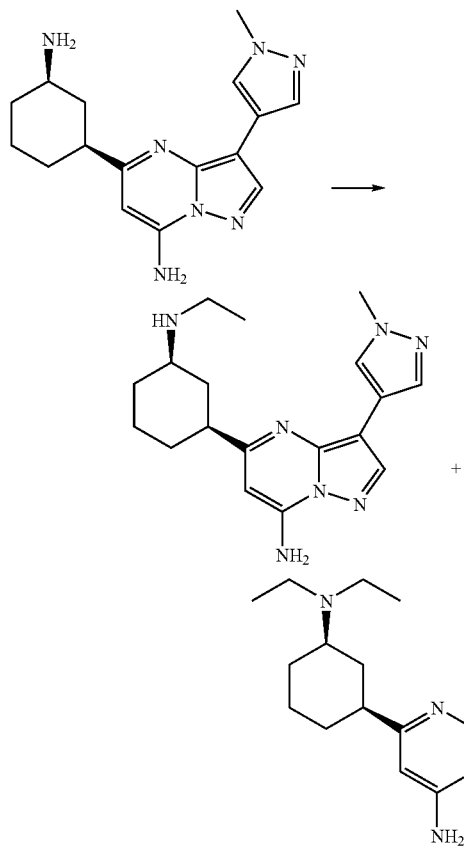

The compound from Example Compound X-1530-C (0.047 g, 0.151 mmol), sodium cyanoborohydride (0.019 g, 0.302 mmol, 2 equiv.) and acetaldehyde (0.01 mL, 0.178 mmol, 1.18 equiv.) were dissolved in methanol (5 mL), and acetic acid (2 drops) was added to reach a pH of about 6. The mixture was stirred 15 hours at room temperature in a sealed vial. The mixture was concentrated under a stream of nitrogen to a volume of about 1 mL, diluted with dichloromethane (6 mL) and loaded on an Isco Redisep 12-gram column, and partially purified using an Analogix Intelliflash 280 running a gradient from 5% to 50% 7N ammonia in methanol-dichloromethane. Fractions containing the products were combined, concentrated under reduced pressure then purified by reverse-phase HPLC on a Waters PrepLC 25 mm column running a gradient from 5% to 20% acetonitrile-water. Example X-1780-C (0.031 g, 61% yield) and Example X-1790-C (0.015 g, 26% yield) were obtained as colorless oils. LCMS 340 [MH+], $^{13}$C NMR (CD$_3$OD) δ 165.74, 149.77, 146.51, 142.31, 137.56, 128.48, 115.57, 101.94, 87.15, 57.89, 45.52, 41.09, 38.89, 35.52, 32.64, 29.99, 25.10, 11.82; and LCMS 368 [MH+], $^{13}$C NMR (CD$_3$OD) δ 165.63, 149.82, 146.49, 142.38, 128.56, 115.52, 101.97, 87.05, 63.16, 46.60, 46.00, 38.88, 33.30, 32.43, 27.36, 25.44, 10.70, respectively.

Examples X1800-C and X1810-C

By essentially the same procedure as set forth in Example X-1780-C, the compounds in Column 2 of Table X-410-C were prepared from compound BOB by employing acetone and 2-(tert-butyldimethylsilyloxy)acetaldehyde, respectively.

TABLE X-410-C

| Ex. X- | Column 2 | $^{13}$C NMR and LCMS [MH+] |
|---|---|---|
| 1800-C | ![structure] | $^{13}$C NMR (CD$_3$OD) δ 165.75, 149.79, 146.52, 142.32, 137.59, 128.45, 115.61, 101.93, 87.10, 55.00, 48.12, 45.50, 38.87, 35.59, 32.70, 30.02, 25.11, 19.39; MH+ = 354. |
| 1810-C | ![structure with TBDMS] | $^{13}$C NMR (CD$_3$OD) δ 166.90, 158.24, 149.74, 142.26, 137.52, 128.61, 115.54, 101.85, 86.98, 62.01, 58.11, 48.90, 46.32, 38.86, 38.13, 33.08, 32.21, 26.41, 25.68, 5.17, −5.24; MH+ = 470. |

Example X-1820-C

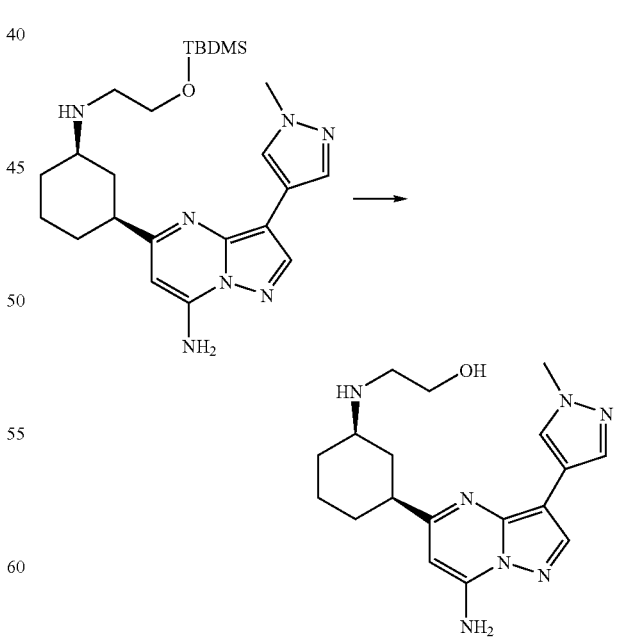

The compound from Example X-1810-C (0.060 g, 0.128 mmol) in anhydrous THF (3 mL) was treated with tetrabutylammonium fluoride (1M solution in THF, 0.25 mL, 0.25 mmol, 1.95 equiv.) and the solution was stirred 12 hours at room temperature. The solution was then diluted with methanol and dichloromethane and concentrated under reduced pressure. The colorless oil that resulted was purified reverse-phase HPLC on a Waters PrepLC 25 mm column running a gradient from 5% to 20% acetonitrile-water. The product was obtained as a white solid (0.038 g, 83% yield). LCMS 356 [MH$^+$]. $^{13}$C NMR (CD$_3$OD) δ 165.80, 149.78, 146.50, 142.29, 137.55, 128.51, 115.55, 101.94, 87.08, 58.22, 58.18, 47.84, 45.66, 38.87, 35.33, 32.63, 29.78, 25.20.

The preparation of the compounds in copending application Ser. No. 11/542,833 is illustrated below:

Preparative Example Y-10-C

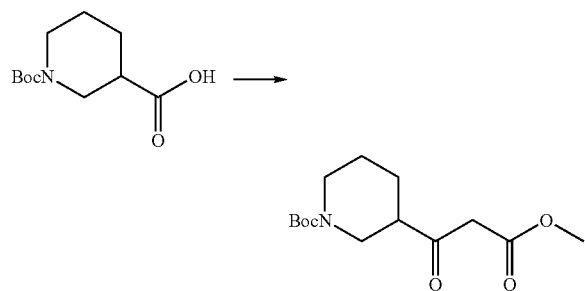

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (60 mL). The mixture was stirred at 25° C. for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, filtered, and the solvent was evaporated. The residue was dissolved in MeOH (580 mL), and the mixture was refluxed for 4 hr. The solvent was evaporated and the residue was purified by column chromatography on silica gel with 10:1 CH$_2$Cl$_2$/EtOAc as eluent. Pale yellow oil (26.5 g, 43%) was obtained.

Preparative Example Y-20-C

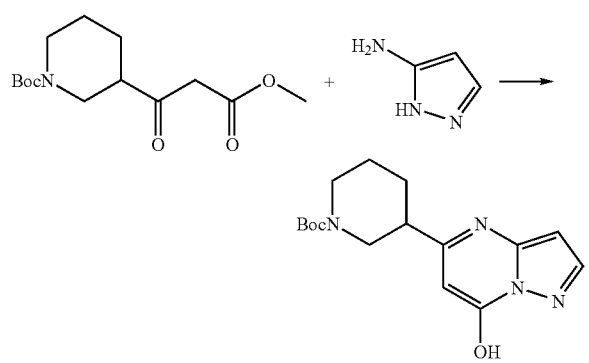

A mixture of the β-ketoester from Preparative Example Y-10-C (20.0 g, 70.1 mmol) and 3-aminopyrazole (5.40 g, 65.0 mmol) in anhydrous toluene (60 mL) was stirred and refluxed under N$_2$ for 24 hr. The solvent was evaporated and the residue was purified by column chromatography on silica gel with 20:1 CH$_2$Cl$_2$/MeOH as eluent. White solid (15.0 g, 73%) was obtained.

Preparative Example Y-30-C

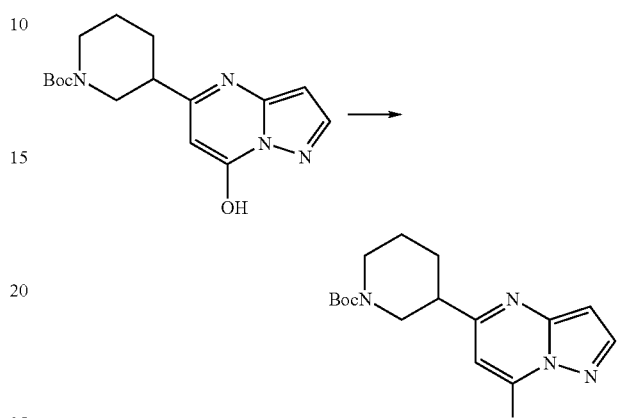

A mixture of the product from Preparative Example Y-20-C (12.50 g, 39.3 mmol), N,N-dimethylaniline (15.5 mL), and POCl$_3$ (125 mL) was stirred at 25° C. for 4 days. Excess of POCl$_3$ was evaporated and the residue was poured into saturated aqueous NaHCO$_3$ (600 mL). The mixture was extracted with CH$_2$Cl$_2$ (3×200 mL), the combined extracts were dried over Na$_2$SO$_4$, filtered, and the solvent was evaporated. The residue was purified by column chromatography on silica gel with 8:1 CH$_2$Cl$_2$/EtOAc as eluent. Pale yellow wax (9.41 g, 71%) was obtained.

Preparative Example Y-40-C

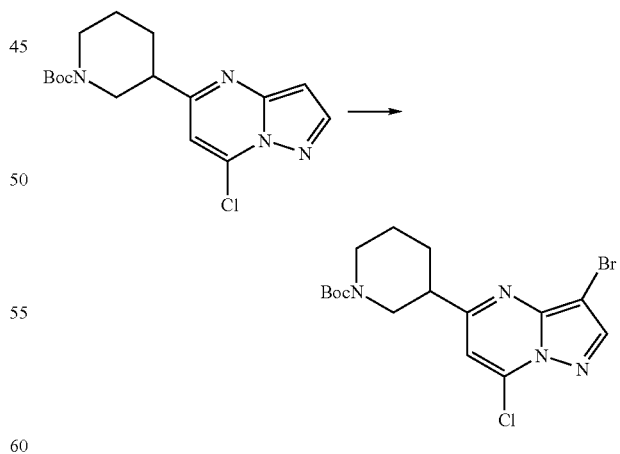

A solution of NBS (4.03 g, 22.7 mmol) in anhydrous CH$_3$CN (40 mL) was added under N$_2$ to a stirred solution of the product from Preparative Example 30-C (7.63 g, 22.7 mmol) in anhydrous CH$_3$CN (60 mL) and CH$_2$Cl$_2$ (20 mL). The mixture was stirred for 2 hr, the solvents were evaporated, and the residue was purified by column chromatography on silica gel with 20:1 CH$_2$Cl$_2$/EtOAc as eluent. Pale yellow solid foam (9.20 g, 97%) was obtained.

Preparative Example Y-50-C

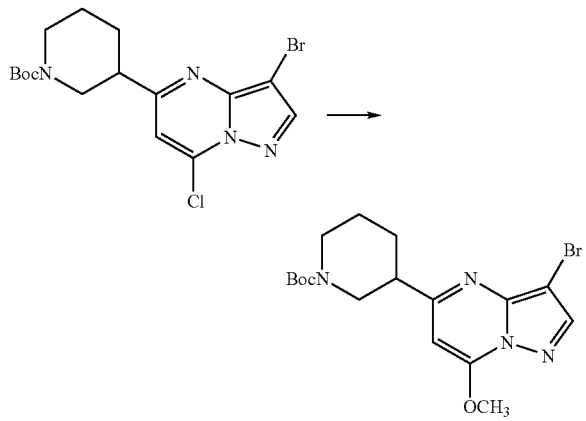

A mixture of the product from Preparative Example Y-40-C (8.00 g, 19.3 mmol) and NaOMe (2.16 g, 40.0 mmol) in anhydrous MeOH (100 mL) was stirred for 20 hr. CH$_2$Cl$_2$ (200 mL) was then added, the mixture was filtered through Celite, the solvent was evaporated, and the residue was purified by column chromatography on silica gel with 2:1 CH$_2$Cl$_2$/EtOAc as eluent. White solid (7.75 g, 98%) was obtained.

Preparative Example Y-60-C

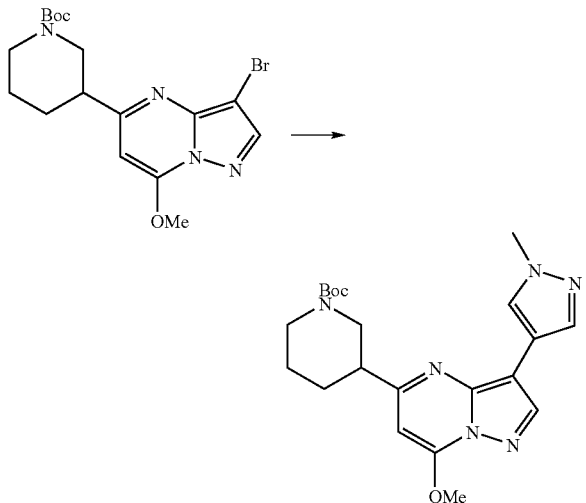

To a mixture of Boc derivative (3.0 g, 7.3 mmol) from Preparative Example Y-50-C in DME/H$_2$O (16 mL/4 mL) was added 1-methyl-4-(4,4,5,5-tetramethyl-1,3,2-dioxaborolan-2-yl)-1H-pyrazole (2.8 g, 13.5 mmol) and Na$_2$CO$_3$ (3.9 g, 36.4 mmol). N$_2$ was bubbled thru the solution for 20 min with stirring whereupon PdCl$_2$(PPh$_3$)$_2$ (0.39 g, 0.47 mmol) was added. The mixture was heated to 110° C. and was stirred for 12 h. The mixture was cooled to rt, concentrated under reduced pressure and placed under high vacuum. The crude product was purified by flash chromatography using a 30:1 mixture of CH$_2$Cl$_2$/MeOH as eluent to afford 1.57 g (52% yield) as an orange/brown solid. LC-MS:=413.2 [M+H] 97% purity.

Preparative Example Y-70-C

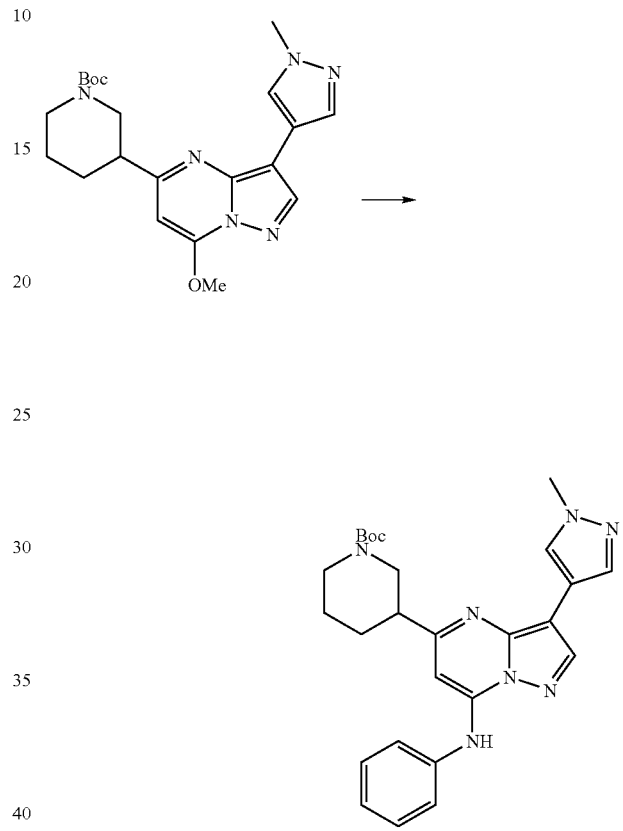

To a solution of aniline (0.044 mL, 0.49 mmol) in dry DMSO (2 mL) at rt was added 60% NaH in oil (20 mg, 0.49 mmol) in one portion. The resulting mixture was stirred for 30 min at rt where upon the 7-methoxy adduct (0.10 g, 0.24 mmol) from Preparative Example Y-60-C was added in a single portion. The mixture was stirred for 12 h at rt, cooled to rt, and quenched with sat. aq. NH$_4$Cl (2 mL). The mixture was extracted with a mixture of 10% IPA/CH$_2$Cl$_2$ (3×10 ml) and the organic layers were combined. The organic layer was washed with brine (1×5 mL), dried (Na$_2$SO$_4$), filtered and concentrated under reduced pressure. The crude product was purified by preparative thin-layer chromatography (6×1000 μM plates) using a 12:1 mixture of CH$_2$Cl$_2$/MeOH as eluent to afford (60 mg, 53% yield) as a yellow semisolid. LC-MS:=474.4 [M+H] 94% purity.

Preparative Examples Y-80-C-Y90-C

Following the procedure set forth in Preparative Example Y-70-C but utilizing the commercially available heteroaryl amines (as indicated) in Table Y-10-C with the 7-methoxy adduct from Preparative Example Y-60-C, the substituted pyrazolo[1,5-a]pyrimidine adducts were prepared (Products).

TABLE Y-10-C

| Prep. Ex. | Amine | Product | 1. Yield (%) 2. LC-MS |
|---|---|---|---|
| 80-C | 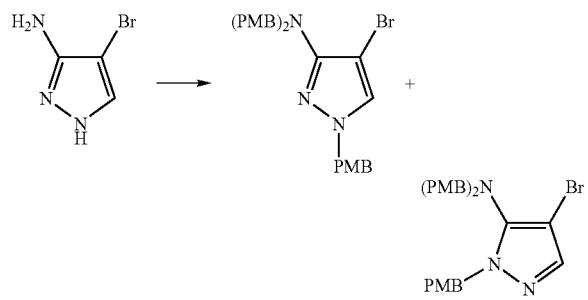 | | 1. 32 2. 518.3 |
| 90-C | | | 1. 42 2. 545.3 |

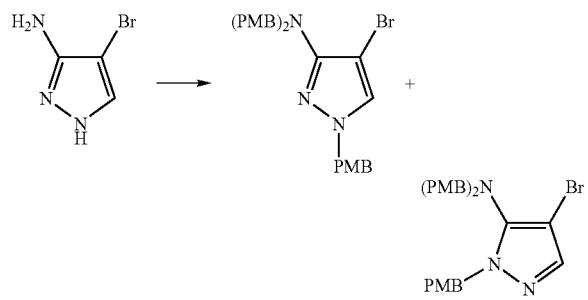

Preparative Example Y-100-C uct, a white solid, is obtained as a 60:40 mixture of the 1-benzylated-1H product and the 2-benzylated-2H product (14.96 g total, 93% yield).

Preparative Example Y-110-C

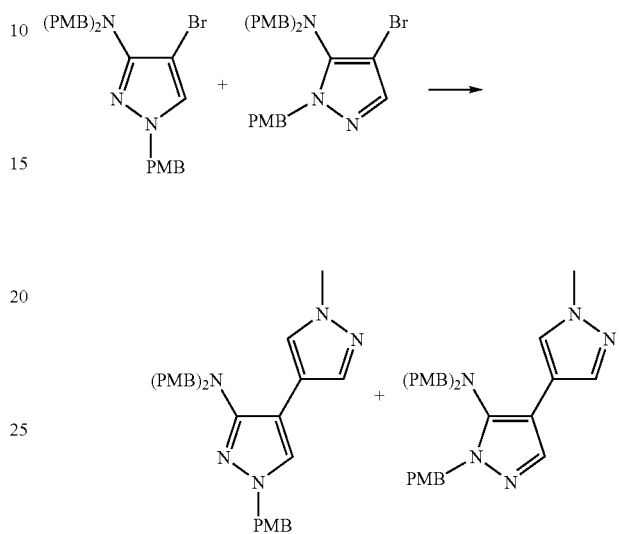

The compound from Preparative Example Y-100-C (10 g, 19.15 mmol) and 1-methyl-4-(4,4,5,5-tetramethyl-1,3,2-dioxaborolan-2-yl)-1H-pyrazole (11.95 g, 57.42 mmol, 3.0 equiv.) were combined in 120 mL dimethoxyethane. 2M sodium carbonate solution (30 mL, 60 mmol, 3.1 equiv.) was added followed by tetrakis(triphenylphosphine)palladium(0) (2.36 g, 2.04 mmol, 0.11 equiv.). The mixture was stirred 16 hours at 90° C. After cooling to room temperature, water (200 mL) and brine (50 mL) were added and the mixture was extracted with ethyl acetate (2×200 mL). The extracts were combined, washed with brine, dried over anhydrous sodium sulfate and concentrated under reduced pressure. The crude product was dissolved in dichloromethane and purified by silica gel chromatography using a gradient from 33% to 66% ethyl acetate-hexanes. The 1-benzylated-1H product ($R_f$=0.27 in 66% ethyl acetate-hexanes) elutes first, followed by the 2-benzylated-2H-product ($R_f$=0.19 in 66% ethyl acetate-hexanes). The product is obtained as a yellow solid (5.60 g total, 56% yield) with an isomeric ratio of 62:38.

Preparative Example Y-120-C

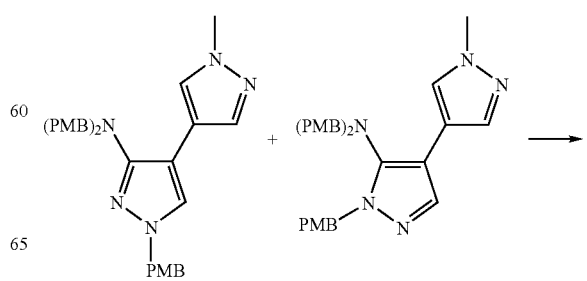

3-Amino-4-bromopyrazole (5 g, 30.9 mmol) and 4-methoxybenzyl chloride (21 g, 134 mmol, 4.3 equiv.) were combined in anhydrous DMF (25 mL) and added dropwise to a stirred suspension of sodium hydride (60% dispersion in mineral oil, 6.25 g, 156 mmol, 5 equiv.) in anhydrous DMF (50 mL). The resulting suspension was stirred 2 days at room temperature. Water (300 mL) was added slowly and the resulting mixture was extracted with ether (4×350 mL). The organic layers were combined, washed with brine, dried over anhydrous sodium sulfate and concentrated under reduced pressure. The crude product was dissolved in dichloromethane and purified by silica gel chromatography using a gradient from 10% to 20% ethyl acetate-hexanes. The prod- -continued

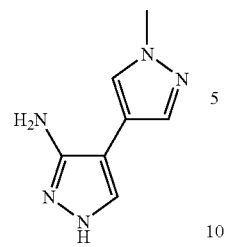

The compound from Preparative Example Y-110-C (4.3 g, 8.22 mmol) was dissolved in trifluoroacetic acid (70 mL) and stirred 17 hours at reflux. After cooling, the trifluoroacetic acid was removed under reduced pressure. The resulting residue was dissolved in tetrahydrofuran (100 mL), methanol (50 mL) and 4N aqueous sodium hydroxide solution (25 mL, 100 mmol, 12 equiv.). The mixture was stirred 4 hours at 70° C. then cooled to room temperature. The mixture was concentrated and the residue was suspended in brine (100 mL) and water (40 mL). This mixture was extracted with 20% isopropanol in ethyl acetate (8×100 mL). The extracts were combined, dried over anhydrous sodium sulfate, filtered and concentrated under reduced pressure. The crude product was dissolved in 10% methanol in dichloromethane and purified by silica gel chromatography using 10% methanol-dichloromethane followed by 10% 7N ammonia in methanol-dichloromethane. The product is obtained as a tan to brown solid (1.03 g, 77% yield).

Preparative Example Y-130-C

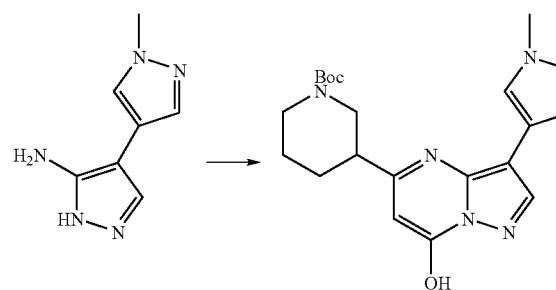

To a solution of aminopyrazole (0.74 g, 4.5 mmol) from Preparative Example Y-120-C in toluene (40 mL) in a pressure tube at rt was added β-keto ester (1.5 g, 5.0 mmol) from Preparative Example 1. The pressure tube was capped and heated to 110° C. and was stirred for 12 h. The mixture was cooled to rt and was concentrated under reduced pressure. The material was taken on crude to the next transformation. LC-MS:=399.2 [M+H]; 70% purity.

Preparative Example Y-140-C

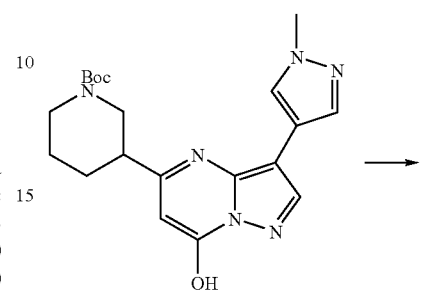

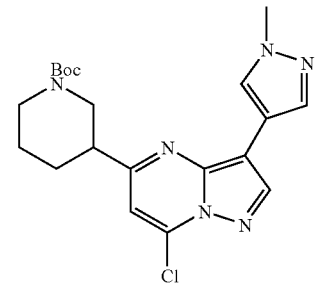

To a solution of 7-hydroxyl adduct (1.84 g, 4.5 mmol) from Preparative Example Y-130-C in POCl$_3$ (13 mL, 0.14 mol) at rt was added N,N-dimethylaniline (2 mL, 15.8 mmol). The resulting solution was stirred at rt for 12 h (until complete by TLC) and was concentrated under reduced pressure. The crude material was cooled to 0° and was treated with CH$_2$Cl$_2$ (50 mL) and sat. aq. NaHCO$_3$ (10 mL). The layers were separated and the aqueous layer was extracted with CH$_2$Cl$_2$ (2×50 mL). The organic layers were combined, dried (Na$_2$SO$_4$), filtered, and concentrated under reduced pressure. The crude product was purified by flash chromatography using a 1:1 mixture of hexanes/CH$_2$Cl$_2$ as eluent to afford 1.4 g (96% yield) of a brown semisolid. LC-MS:=317.2 [M+H]; 95% purity.

Preparative Example Y-150-C

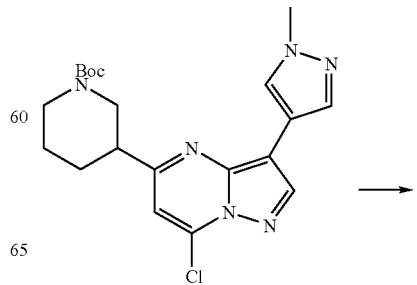

-continued

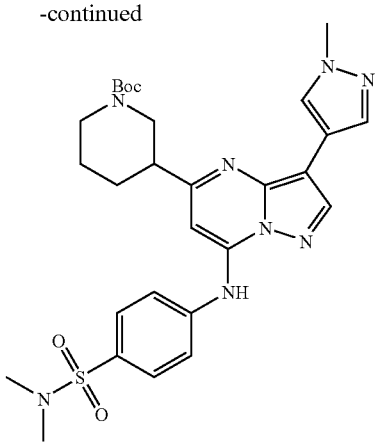

To a solution of 4-amino-N,N-dimethylbenzenesulfonamide (96 mg, 0.48 mmol) in dry DMSO (2 mL) at rt was added 60% NaH in oil (20 mg, 0.49 mmol) in one portion. The resulting mixture was stirred for 20 min at rt where upon the 7-chloro adduct (0.10 g, 0.24 mmol) from Preparative Example Y-140-C was added in a single portion. The mixture was stirred for 12 h at rt, cooled to rt, and quenched with sat. aq. NH$_4$Cl (2 mL). The mixture was extracted with a mixture of 10% IPA/CH$_2$Cl$_2$ (3×10 ml) and the organic layers were combined. The organic layer was washed with brine (1×5 mL), dried (Na$_2$SO$_4$), filtered and concentrated under reduced pressure. The crude product was diluted with water (10 mL) and the resultant solid was filtered off and washed with water (50 mL). The resultant ppt was placed under high vacuum to afford 0.13 g (98% yield) of a dark yellow solid. LC-MS:=581.3 [M+H] 90% purity.

Preparative Examples Y150-C-Y190-C

Following the procedure set forth in Preparative Example Y-150-C but utilizing the commercially available heteroaryl amines (as indicated) in Table Y-20-C with the 7-chloro adduct from Preparative Example Y-140-C, the substituted pyrazolo[1,5-a]pyrimidine adducts were prepared (Products).

TABLE Y-20-C

| Prep. Ex. | Amine | Product | 1. Yield (%) 2. LC-MS |
|---|---|---|---|
| 150-C | | | 1. 53 2. 552.3 |
| 160-C | | | 1. 44 2. 581.5 |

TABLE Y-20-C-continued

| Prep. Ex. | Amine | Product | 1. Yield (%) 2. LC-MS |
|---|---|---|---|
| 170-C | | | 1. 51 2. 552.5 |
| 180-C | | | 1. 47 2. 615.5 |
| 190-C | | | 1. 90 2. 538.3 |

Example Y-10-C

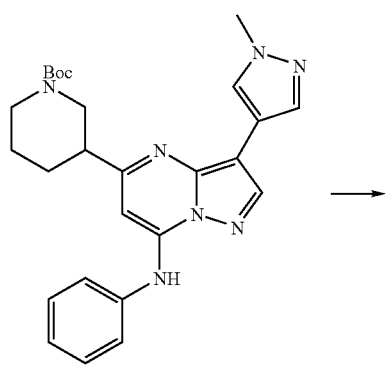

To a solution of Boc adduct (60 mg, 0.13 mmol) from Preparative Example Y-70-C in $CH_2Cl_2$ (3 mL) at rt was added was added TFA (1 mL). The resulting solution was stirred at rt for 5 h (until complete by TLC) and was concentrated under reduced pressure. The crude material was taken up in 2M $NH_3$ in MeOH (3 mL) and stirred for 12 h. The mixture was concentrated under reduced pressure and was purified by preparative thin-layer chromatography (4×1000 μM plates) using a 6:1 mixture of $CH_2Cl_2$/MeOH (7M $NH_3$) as eluent to afford (5 mg, 10% yield) as a yellow solid. mp 131-134° C.; LC-MS:=374.2 [M+H]>90% purity.

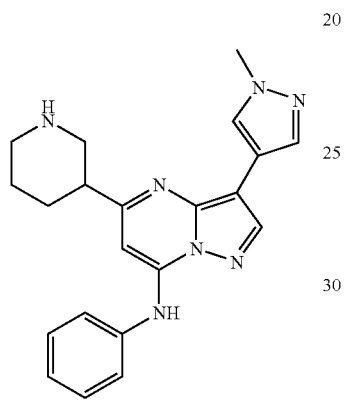

Examples Y20-C-Y90-C

Following the procedure set forth in Example Y-10-C utilizing the appropriate Boc derivatives shown in Column 2 of Table Y-30-C, the final substituted pyrazolo[1,5-a]pyrimidine adducts were prepared (Products).

TABLE Y-30-C

| Ex. Y Y- | Column 2 | Product | 1. Yield (%) 2. LC-MS 3. mp (° C.) |
|---|---|---|---|
| 20-C | | | 1. 28 2. 418.2 3. 106-108 |

TABLE Y-30-C-continued

| Ex. Y Y- | Column 2 | Product | 1. Yield (%) 2. LC-MS 3. mp (° C.) |
|---|---|---|---|
| 30-C | | | 1. 98 2. 445.2 |
| 40-C | | | 1. 91 2. 481.2 3. 168-171 |
| 50-C | | | 1. 63 2. 452.2 3. 139-141 |

TABLE Y-30-C-continued
| Ex. Y Y- | Column 2 | Product | 1. Yield (%) 2. LC-MS 3. mp (° C.) |
|---|---|---|---|
| 60-C | 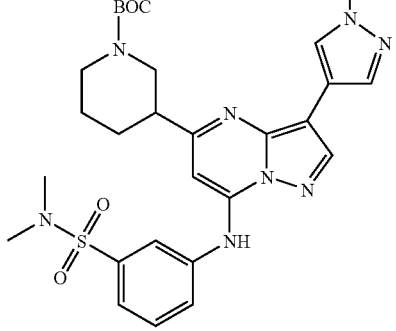 | 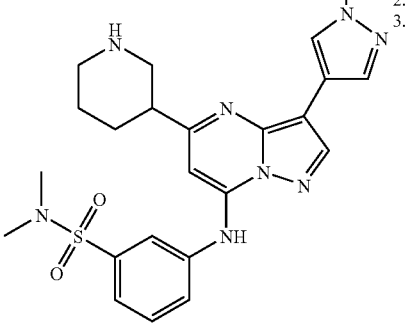 | 1. 66 2. 481.3 3. 145-148 |
| 70-C | 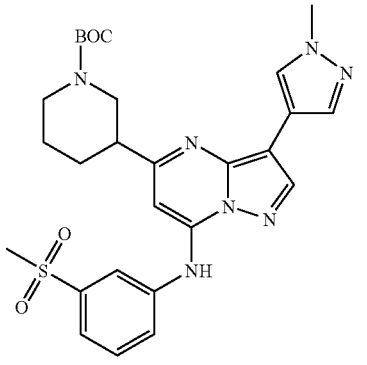 | 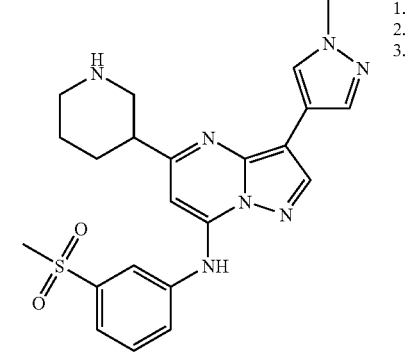 | 1. 81 2. 452.2 3. 156-158 |
| 80-C | 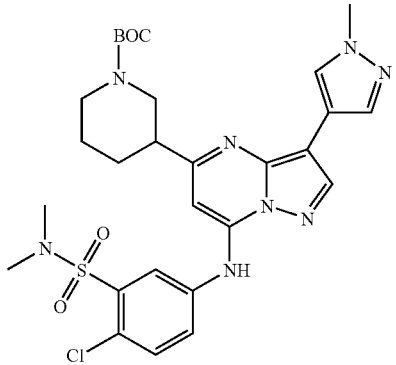 | 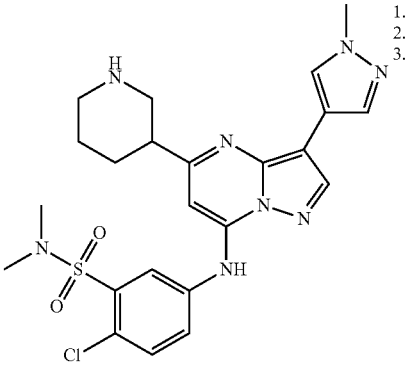 | 1. 47 2. 515.3 3. 167-169 |
| 90-C | 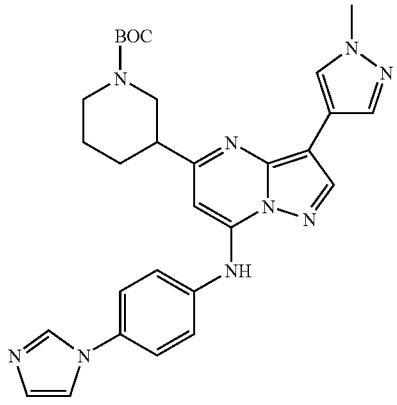 | 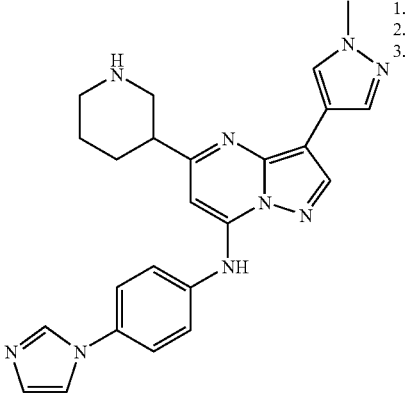 | 1. 64 2. 440.2 3. 110-112 |

The preparation of the compounds in copending application Ser. No. 11/543,182 is illustrated below:

Preparative Example Z-10-C

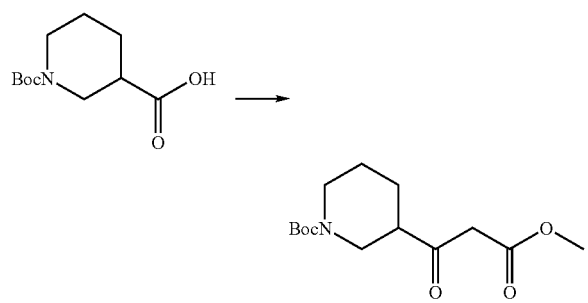

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (60 mL). The mixture was stirred at 25° C. for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, filtered, and the solvent was evaporated. The residue was dissolved in MeOH (580 mL), and the mixture was refluxed for 4 hr. The solvent was evaporated and the residue was purified by column chromatography on silica gel with 10:1 CH$_2$Cl$_2$/EtOAc as eluent. Pale yellow oil (26.5 g, 43%) was obtained.

Preparative Example Z-20-C

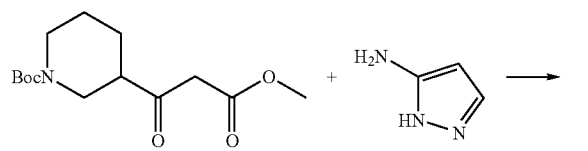

A mixture of the β-ketoester from Preparative Example Z-10-C (20.0 g, 70.1 mmol) and 3-aminopyrazole (5.40 g, 65.0 mmol) in anhydrous toluene (60 mL) was stirred and refluxed under N$_2$ for 24 hr. The solvent was evaporated and the residue was purified by column chromatography on silica gel with 20:1 CH$_2$Cl$_2$/MeOH as eluent. White solid (15.0 g, 73%) was obtained.

Preparative Example Z-30-C

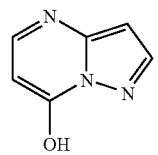

The known compound was prepared according to the procedure documented in *J. Heterocyclic Chem.* 1986, 23, 349.

Preparative Example Z-40-C

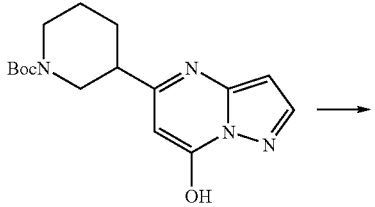

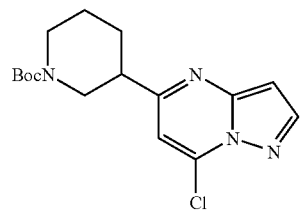

A mixture of the product from Preparative Example Z-20-C (12.50 g, 39.3 mmol), N,N-dimethylaniline (15.5 mL), and POCl$_3$ (125 mL) was stirred at 25° C. for 4 days. Excess of POCl$_3$ was evaporated and the residue was poured into saturated aqueous NaHCO$_3$ (600 mL). The mixture was extracted with CH$_2$Cl$_2$ (3×200 mL), the combined extracts were dried over Na2SO4, filtered, and the solvent was evaporated. The residue was purified by column chromatography on silica gel with 8:1 CH$_2$Cl$_2$1EtOAc as eluent. Pale yellow wax (9.41 g, 71%) was obtained.

Preparative Example Z-50-C

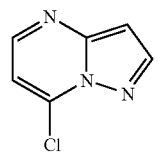

The known compound was prepared according to the procedure documented in *J. Med. Chem.* 1981, 24(5), 610-613.

Preparative Example Z-60-C

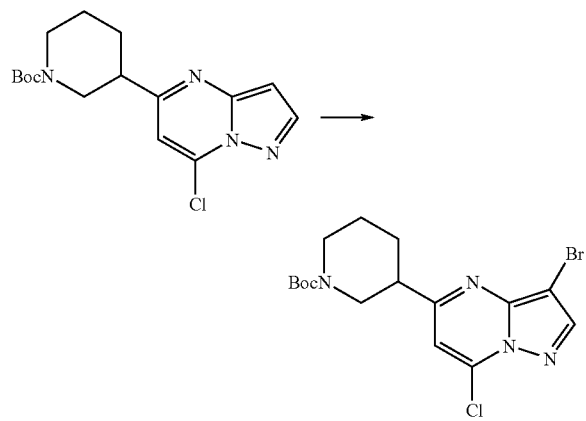

A solution of NBS (4.03 g, 22.7 mmol) in anhydrous CH₃CN (40 mL) was added under N₂ to a stirred solution of the product from Preparative Example Z-40-C (7.63 g, 22.7 mmol) in anhydrous CH₃CN (60 mL) and CH₂Cl₂ (20 mL). The mixture was stirred for 2 hr, the solvents were evaporated, and the residue was purified by column chromatography on silica gel with 20:1 CH₂Cl₂/EtOAc as eluent. Pale yellow solid foam (9.20 g, 97%) was obtained.

Preparative Example Z-70-C

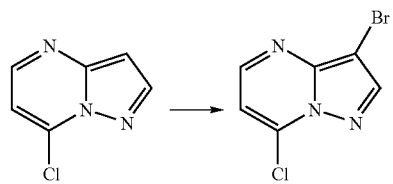

By essentially same procedure set forth in Preparative Example Z-60-C, the 7-chloro adduct (1.2 g, 7.5 mmol) from Preparative Example 50-C was treated with NBS (1.5 g, 8.2 mmol) to afford 1.2 g (69% yield) of a yellow solid. MS=233.9 [M+H].

Preparative Example Z-80-C

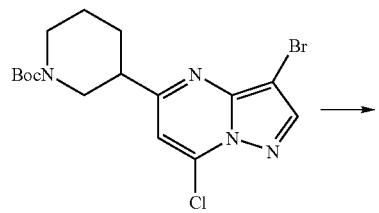

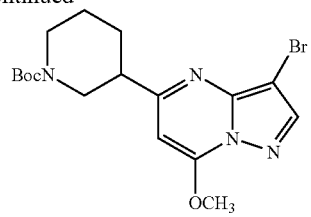

A mixture of the product from Preparative Example Z-60-C (8.00 g, 19.3 mmol) and NaOMe (2.16 g, 40.0 mmol) in anhydrous MeOH (100 mL) was stirred for 20 hr. CH₂Cl₂ (200 mL) was then added, the mixture was filtered through Celite, the solvent was evaporated, and the residue was purified by column chromatography on silica gel with 2:1 CH₂Cl₂/EtOAc as eluent. White solid (7.75 g, 98%) was obtained.

Preparative Example Z-90-C

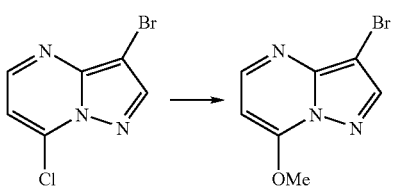

By essentially same procedure set forth in Preparative Example Z-80-C, the 7-chloro adduct (1.6 g, 6.9 mmol) from Preparative Example 70-C was treated with NaOMe (0.74 g, 13.8 mmol) to afford 1.5 g (95% yield) of a yellow/orange solid. LC-MS=228.1 [M+H]; 97% purity.

Preparative Example Z-100-C

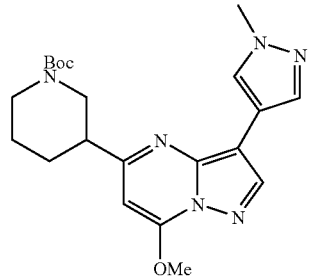

To a mixture of Boc derivative (3.0 g, 7.3 mmol) from Preparative Example Z-80-C in DME/H₂O (16 mL/4 mL) was added 1-methyl-4-(4,4,5,5-tetramethyl-1,3,2-dioxaborolan-2yl)-1H-pyrazole (2.8 g, 13.5 mmol) and Na₂CO₃ (3.9 g, 36.4 mmol). N₂ was bubbled thru the solution for 20 min with stirring whereupon PdCl$_2$(PPh$_3$)$_2$ (0.39 g, 0.47 mmol) was added. The mixture was heated to 110° C. and was stirred for 12 h. The mixture was cooled to rt, concentrated under reduced pressure and placed under high vacuum. The crude product was purified by flash chromatography using a 30:1 mixture of CH$_2$Cl$_2$/MeOH as eluent to afford 1.57 g (52% yield) as an orange/brown solid. LC-MS:=413.2 97% purity.

Preparative Example Z-110-C

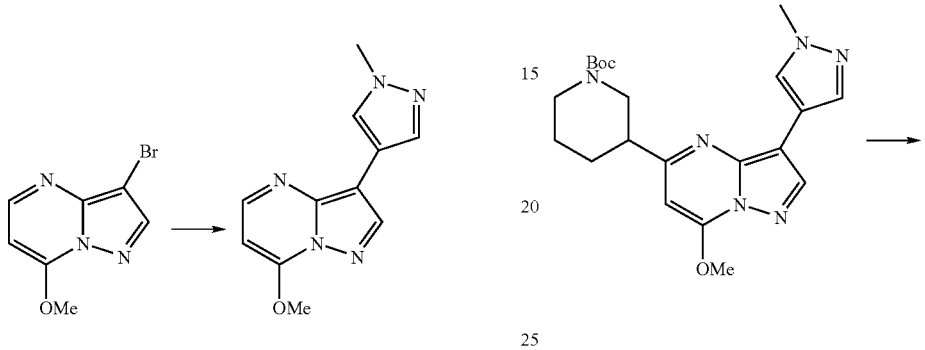

By essentially same procedure set forth in Preparative Example Z-100-C, the 7-methoxy adduct (0.80 g, 3.5 mmol) from Preparative Example 90-C was converted to 0.68 g (84% yield) of an orange solid. MS=230.2. [M+H].

Preparative Example Z-120-C

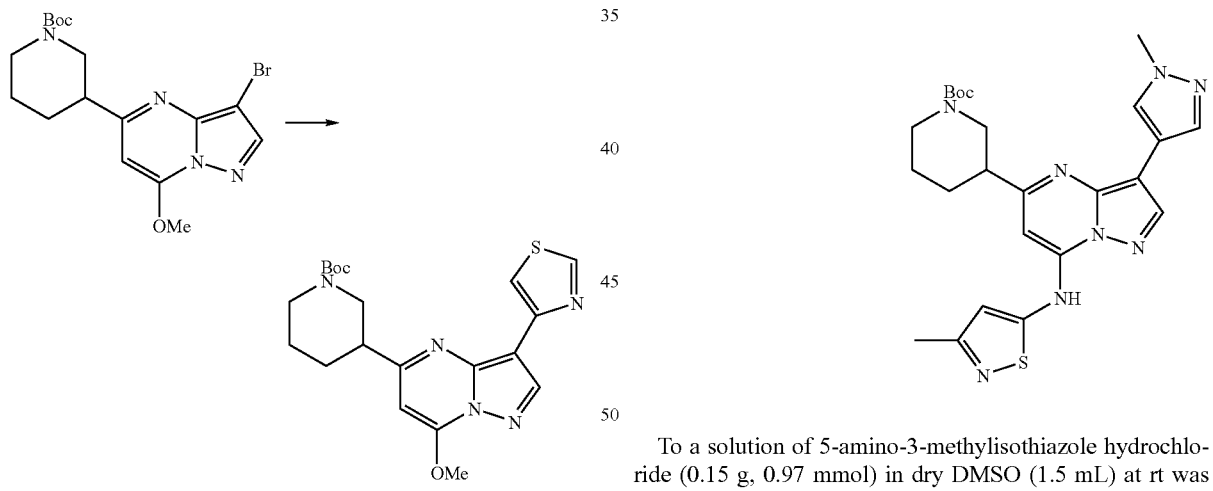

To a solution of 3-Br adduct (0.27 g, 0.67 mmol) from Preparative Example Z-80-C in CH$_3$CN (4 mL) at rt was 4-tributylstannylthiazole (0.50 g, 1.34 mmol) followed by PdCl$_2$(PPh$_3$)$_2$ (47 mg, 0.067 mmol). The resulting mixture was degassed under aspirator vacuum and filled with N$_2$ six times. The mixture was fitted with a condenser and was heated to 85° C. The mixture was stirred for 12 h, cooled to rt, and diluted with EtOAc (10 mL). The mixture was filtered thru a Celite pad which was washed with EtOAc (3×5 mL), CH$_2$Cl$_2$ (1×5 mL) and MeOH (1×5 mL). The resulting filtrate was concentrated under reduced pressure and was placed under high vacuum. The crude product was purified by preparative thin-layer chromatography (6×1000 μM plates) using a 20:1 mixture of CH$_2$Cl$_2$/MeOH as eluent to afford 0.26 g (93% yield) as an orange oil. LC-MS:=416.2 [M+H] 61% purity.

Preparative Example Z-130-C

To a solution of 5-amino-3-methylisothiazole hydrochloride (0.15 g, 0.97 mmol) in dry DMSO (1.5 mL) at rt was added 60% NaH in oil (46 mg, 1.94 mmol) in one portion. The resulting mixture was stirred for 15 min at rt where upon the 7-methoxy adduct (0.20 g, 0.48 mmol) from Preparative Example Z-100-C was added in a single portion. The mixture was stirred for 12 h at rt, cooled to rt, and quenched with sat. aq. NH$_4$Cl (3 mL). The mixture was extracted with a mixture of 10% IPA/CH$_2$Cl$_2$ (3×20 ml) and the organic layers were combined. The organic layer was washed with brine (1×10 mL), dried (Na$_2$SO$_4$), filtered and concentrated under reduced pressure. The crude product was diluted with water (2 mL) and the resultant ppt was filtered and washed with water (2×1 mL). The ppt was dried under high vacuum to afford 0.22 g (93% yield) of a red/orange solid. LC-MS: =495.3 [M+H] 99% purity.

391
Preparative Example Z-140-C

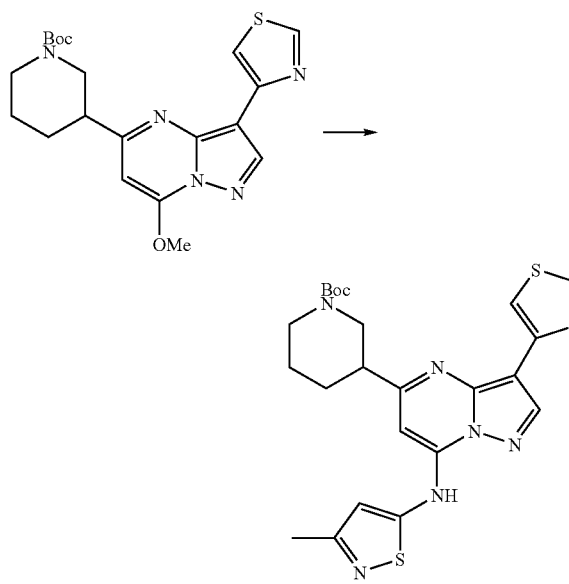

By essentially same procedure set forth in Preparative Example Z-130-C, the 7-methoxy adduct (0.28 g, 0.69 mmol) from Preparative Example Z-120-C was converted to 70 mg (20% yield) of an orange semisolid. MS=498.1 [M+H].

392
Example Z-10-C

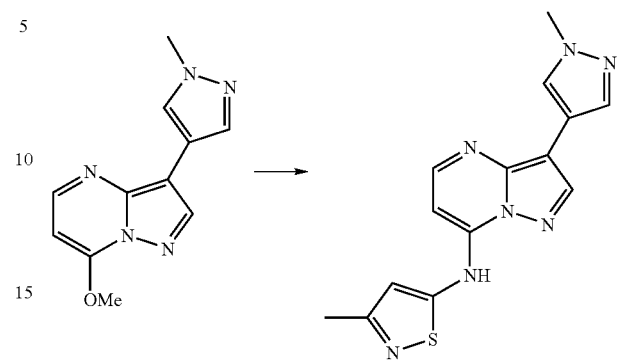

By essentially same procedure set forth in Preparative Example Z-130-C, the 7-methoxy adduct (0.15 g, 0.66 mmol) from Preparative Example Z-110-C was converted to 56 mg (27% yield) of a yellow solid. mp 152-155° C.; LC-MS=312.2. [M+H]; 85% purity.

Preparative Examples Z150-C-Z230-C

Following the procedure set forth in Preparative Example Z-130-C but utilizing the commercially available heteroaryl amines (as indicated) in Table Z-10-C with the 7-methoxy adduct from Preparative Example Z-100-C, the substituted pyrazolo[1,5-a]pyrimidine adducts were prepared (Products).

TABLE Z-10-C

| Prep. Ex. Z- | Amine | Product | 1. Yield (%) 2. LC-MS |
|---|---|---|---|
| 150-C | [2-aminopyridine structure] | [Boc-piperidinyl pyrazolopyrimidine with pyridin-2-ylamino and N-methylpyrazole structure] | 1. 58 2. 475.3 |
| 160-C | [3-aminopyridine structure] | [Boc-piperidinyl pyrazolopyrimidine with pyridin-3-ylamino and N-methylpyrazole structure] | 1. 48 2. 475.3 |

TABLE Z-10-C-continued

| Prep. Ex. Z- | Amine | Product | 1. Yield (%) 2. LC-MS |
|---|---|---|---|
| 170-C | 4-aminopyridine | Boc-piperidinyl pyrazolo[1,5-a]pyrimidine with 1-methylpyrazole and 4-pyridylamino | 1. 67 2. 475.3 |
| 180-C | 5-amino-3-methylisoxazole | Boc-piperidinyl pyrazolo[1,5-a]pyrimidine with 1-methylpyrazole and 3-methylisoxazol-5-ylamino | 1. 98 2. 479.3 |
| 190-C | 2-aminopyrazine | Boc-piperidinyl pyrazolo[1,5-a]pyrimidine with 1-methylpyrazole and pyrazin-2-ylamino | 1. 33 2. 476.3 |
| 200-C | 2-amino-5-bromopyrimidine | Boc-piperidinyl pyrazolo[1,5-a]pyrimidine with 1-methylpyrazole and 5-bromopyrimidin-2-ylamino | 1. 56 2. 556.3 |

TABLE Z-10-C-continued

| Prep. Ex. Z- | Amine | Product | 1. Yield (%) 2. LC-MS |
|---|---|---|---|
| 210-C | | | 1. 98 <br> 2. 492.3 |
| 220-C | | | 1. 66 <br> 2. 482.3 |
| 230-C | | | 1. 90 <br> 2. 479.3 |

Preparative Example Z-231-C

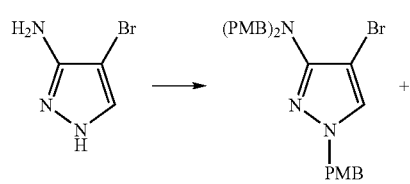

-continued

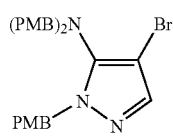

3-Amino-4-bromopyrazole (5 g, 30.9 mmol) and 4-methoxybenzyl chloride (21 g, 134 mmol, 4.3 equiv.) were combined in anhydrous DMF (25 mL) and added dropwise to a stirred suspension of sodium hydride (60% dispersion in mineral oil, 6.25 g, 156 mmol, 5 equiv.) in anhydrous DMF (50 mL). The resulting suspension was stirred 2 days at room temperature. Water (300 mL) was added slowly and the resulting mixture was extracted with ether (4×350 mL). The organic layers were combined, washed with brine, dried over anhydrous sodium sulfate and concentrated under reduced pressure. The crude product was dissolved in dichloromethane and purified by silica gel chromatography using a gradient from 10% to 20% ethyl acetate-hexanes. The product, a white solid, is obtained as a 60:40 mixture of the 1-benzylated-1H product and the 2-benzylated-2H product (14.96 g total, 93% yield).

Preparative Example Z-232-C

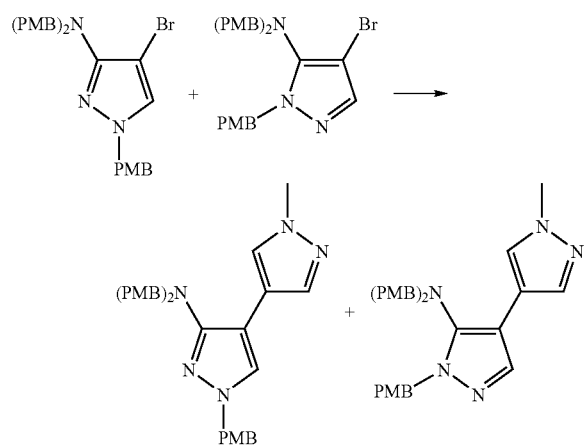

The compound from Preparative Example Z-231-C (10 g, 19.15 mmol) and 1-methyl-4-(4,4,5,5-tetramethyl-1,3,2-dioxaborolan-2-yl)-1H-pyrazole (11.95 g, 57.42 mmol, 3.0 equiv.) were combined in 120 mL dimethoxyethane. 2M sodium carbonate solution (30 mL, 60 mmol, 3.1 equiv.) was added followed by tetrakis(triphenylphosphine)palladium(0) (2.36 g, 2.04 mmol, 0.11 equiv.). The mixture was stirred 16 hours at 90° C. After cooling to room temperature, water (200 mL) and brine (50 mL) were added and the mixture was extracted with ethyl acetate (2×200 mL). The extracts were combined, washed with brine, dried over anhydrous sodium sulfate and concentrated under reduced pressure. The crude product was dissolved in dichloromethane and purified by silica gel chromatography using a gradient from 33% to 66% ethyl acetate-hexanes. The 1-benzylated-1H product ($R_f$=0.27 in 66% ethyl acetate-hexanes) elutes first, followed by the 2-benzylated-2H-product ($R_f$=0.19 in 66% ethyl acetate-hexanes). The product is obtained as a yellow solid (5.60 g total, 56% yield) with an isomeric ratio of 62:38.

Preparative Example Z-233-C

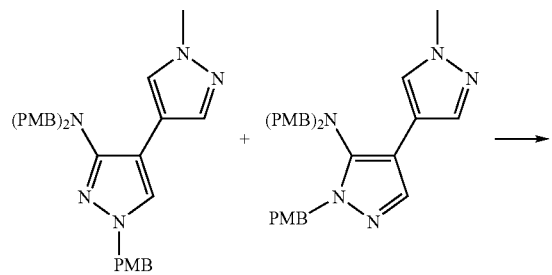

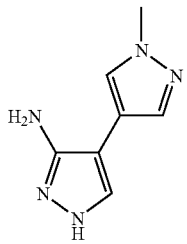

The compound from Preparative Example Z-232-C (4.3 g, 8.22 mmol) was dissolved in trifluoroacetic acid (70 mL) and stirred 17 hours at reflux. After cooling, the trifluoroacetic acid was removed under reduced pressure. The resulting residue was dissolved in tetrahydrofuran (100 mL), methanol (50 mL) and 4N aqueous sodium hydroxide solution (25 mL, 100 mmol, 12 equiv.). The mixture was stirred 4 hours at 70° C. then cooled to room temperature. The mixture was concentrated and the residue was suspended in brine (100 mL) and water (40 mL). This mixture was extracted with 20% isopropanol in ethyl acetate (8×100 mL). The extracts were combined, dried over anhydrous sodium sulfate, filtered and concentrated under reduced pressure. The crude product was dissolved in 10% methanol in dichloromethane and purified by silica gel chromatography using 10% methanol-dichloromethane followed by 10% 7N ammonia in methanol-dichloromethane. The product is obtained as a tan to brown solid (1.03 g, 77% yield).

Preparative Example Z-240-C

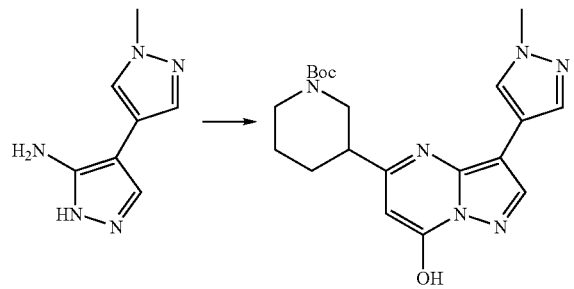

To a solution of aminopyrazole (0.74 g, 4.5 mmol) from Preparative Example Z-233-C in toluene (40 mL) in a pressure tube at rt was added β-keto ester (1.5 g, 5.0 mmol) from Preparative Example Z-10-C. The pressure tube was capped and heated to 110° C. and was stirred for 12 h. The mixture was cooled to rt and was concentrated under reduced pressure. The material was taken on crude to the next transformation. LC-MS:=399.2 [M+H]; 70% purity.

Preparative Example Z-250-C

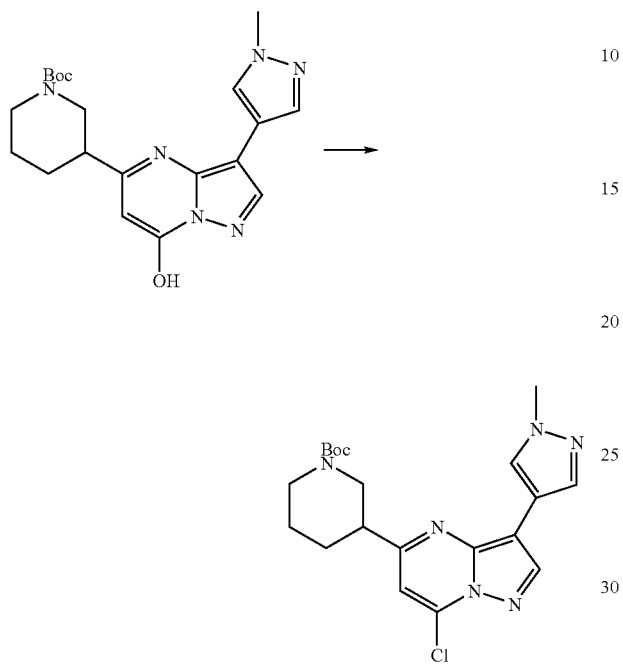

To a solution of 7-hydroxyl adduct (1.84 g, 4.5 mmol) from Preparative Example Z-240-C in POCl₃ (13 mL, 0.14 mol) at rt was added N,N-dimethylaniline (2 mL, 15.8 mmol). The resulting solution was stirred at rt for 12 h (until complete by TLC) and was concentrated under reduced pressure. The crude material was cooled to 0° C. and was treated with CH₂Cl₂ (50 mL) and sat. aq. NaHCO₃ (10 mL). The layers were separated and the aqueous layer was extracted with CH₂Cl₂ (2×50 mL). The organic layers were combined, dried (Na₂SO₄), filtered, and concentrated under reduced pressure. The crude product was purified by flash chromatography using a 1:1 mixture of hexanes/CH₂Cl₂ as eluent to afford 1.4 g (96% yield) of a brown semisolid. LC-MS:=317.2 [M+H]; 95% purity.

Preparative Example Z-251-C

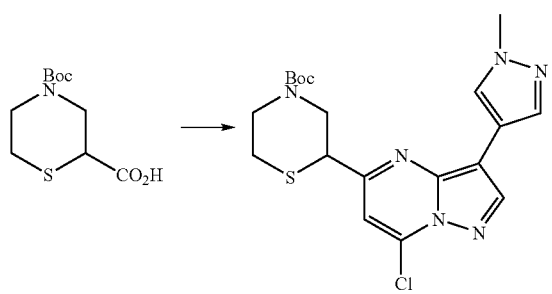

By essentially the same procedures set forth to make the compound from Preparative Example Z-250-C only starting with thiomorpholine carboxylic acid, the above compound was prepared.

Preparative Example Z-260-C

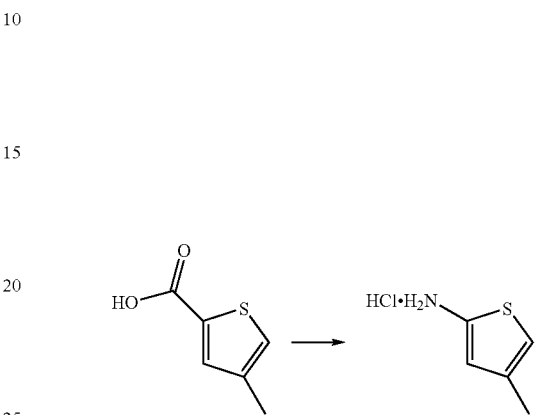

To a solution of 4-methylthiophene-2-carboxylic acid (5.0 g, 35.2 mmol) in t-BuOH (60 mL) was added DPPA (7.6 mL, 35.2 mmol) and Et₃N (4.9 mL, 35.2 mmol). The resulting mixture was heated to reflux and stirred for 48 h. The mixture was cooled to rt and was concentrated under reduced pressure. The crude material was purified by flash chromatography using a 3:1 mixture of hexanes/CH₂Cl₂ as eluent to afford 4.2 g (56% yield) as an orange oil.

The Boc derivative from above step (0.5 g, 2.3 mmol) was treated with 4M HCl/dioxane (25 mL) and was heated to 70° C. The mixture was stirred for 12 h, cooled to rt, and concentrated under reduced pressure to afford 0.32 g (93% yield) of the title compound. This material was used directly in subsequent coupling reactions.

Preparative Example Z-270-C

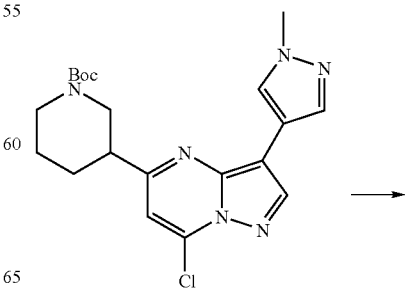

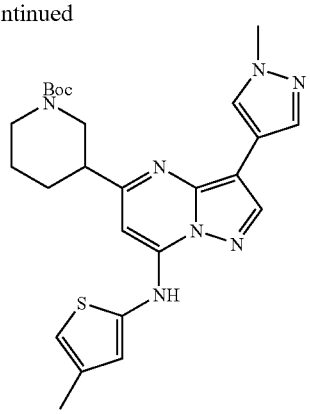

By essentially same procedure set forth in Preparative Example Z-130-C, the 7-chloro adduct (0.15 g, 0.35 mmol) from Preparative Example 250-C was treated with 2-amino-4-methyl thiophene hydrochloride (0.32 g, 2.1 mmol) from Preparative Example Z-260-C to afford 110 mg (64% yield) of a yellow semisolid. LC-MS=494.3 [M+H]; 80% purity.

Preparative Example Z-280-C

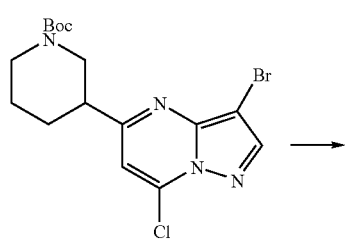

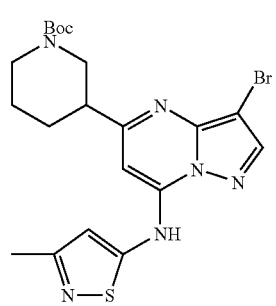

By essentially same procedure set forth in Preparative Example Z-130-C, the 7-chloro adduct (0.40 g, 0.96 mmol) from Preparative Example Z-60-C was treated with 5-amino-3-methylisothiazole hydrochloride (0.28 g, 1.9 mmol) to afford 430 mg (91% yield) of a yellow semisolid. LC-MS=495.3 [M+H]; 80% purity.

Example Z-20-C

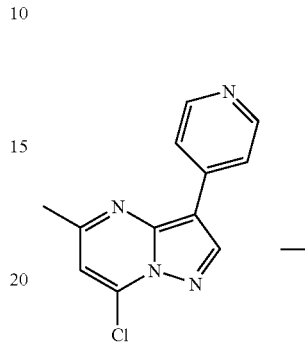

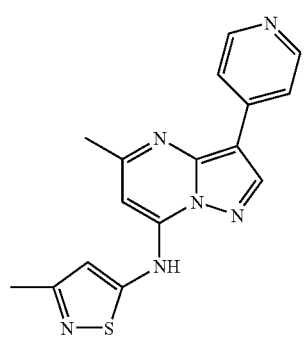

By essentially same procedure set forth in Preparative Example Z-130-C, the 7-chloro adduct (0.12 g, 0.49 mmol) from was treated with 5-amino-3-methylisothiazole hydrochloride (0.15 g, 0.98 mmol) to afford 38 mg (24% yield) of an orange solid. mp 165-167° C.; LC-MS=323.2 [M+H]; 98% purity.

Preparative Example Z-290-C

Following the procedure set forth in Preparative Example Z-130-C but utilizing the commercially available heteroaryl amines (as indicated) in Table 20-C with the 7-chloro adduct from Preparative Example Z-250-C, the substituted pyrazolo[1,5-a]pyrimidine adducts were prepared (Products).

TABLE Z-20-C

| Prep. Ex. Z- | Amine | Product | 1. Yield (%) 2. LC-MS |
|---|---|---|---|
| 290-C | | | 1. 53 2. 557.3 |
| 291-C | | | |

Preparative Example Z-300-C

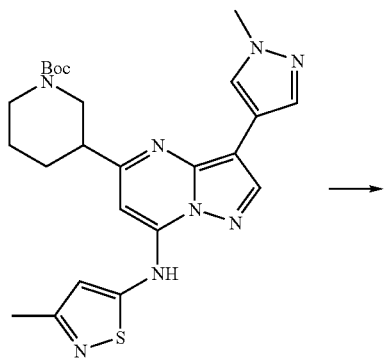

→

-continued

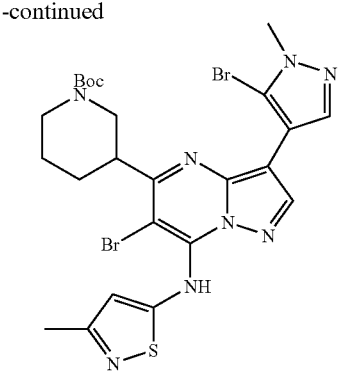

To a solution of Boc adduct (54 mg, 0.11 mmol) from Preparative Example Z-130-C in $CH_2Cl_2$ (5 mL) at rt was added t-BuNH$_2$ (0.41 mL, 3.9 mmol). The mixture was stirred for 15 min whereupon Br$_2$ (5 µL, 0.099 mmol) was added dropwise and the reaction was stirred for 1.5 h (until complete by TLC). The mixture was concentrated to dryness and the crude product was purified by preparative thin-layer chromatography using 4×1000 µM plates with a 24:1 mixture of $CH_2Cl_2$/MeOH as eluent to afford 25 mg (35% yield) of the title compound. LC-MS=653.4 [M+H]; 99% purity.

Example Z-30-C

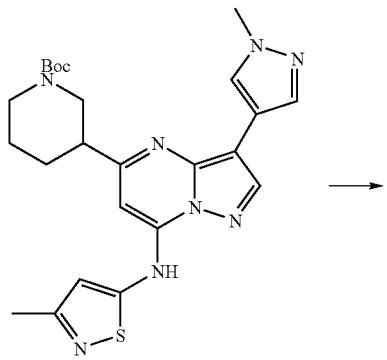

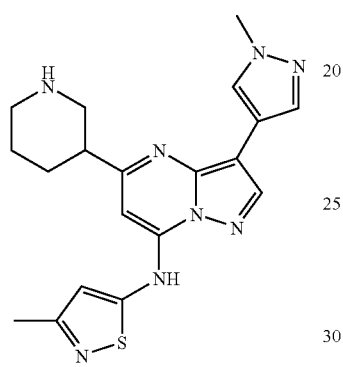

To a mixture of pyrazole adduct (120 mg, 0.24 mmol) from Preparative Example Z-130-C in $CH_2Cl_2$ (2 mL) at 0° C. was added TFA (0.6 mL) dropwise. The resulting mixture was stirred for 3 h at rt and concentrated under reduced pressure. The crude material was dissolved in 7M $NH_3$ in MeOH (3 mL) and was stirred for 2 h. The mixture was concentrated under reduced pressure and placed under high vacuum. The crude product was purified by preparative thin-layer chromatography (4×1000 μM plates) using a 10:1 mixture of $CH_2Cl_2$/MeOH (7M $NH_3$) as eluent to afford 20 mg (21% yield) as maize solid. mp 167-170° C.: LC-MS:=395.2 [M+H] 95% purity.

Examples Z-40-C-Z170-C

Following the procedure set forth in Example Z-30-C utilizing the appropriate Boc derivatives shown in Column 2, the substituted pyrazolo[1,5-a]pyrimidine adducts were prepared (Products) in Table Z-30-C.

TABLE Z-30-C

| Ex. Z- | Column 2 | Product | 1. Yield (%) 2. LC-MS 3. mp (° C.) |
|---|---|---|---|
| 40-C | (structure) | (structure) | 1. 38 2. 375.2 3. 124-126 |
| 50-C | (structure) | (structure) | 1. 26 2. 375.2 3. 169-171 |

TABLE Z-30-C-continued

| Ex. Z- | Column 2 | Product | 1. Yield (%) 2. LC-MS 3. mp (° C.) |
|---|---|---|---|
| 60-C | | | 1. 36 2. 375.2 3. 200-202 |
| 70-C | | | 1. 78 2. 379.2 3. 180-182 |
| 80-C | | | 1. 92 2. 376.2 3. 119-121 |
| 90-C | | | 1. 71 2. 454.1 3. 157-159 |

TABLE Z-30-C-continued

| Ex. Z- | Column 2 | Product | 1. Yield (%) 2. LC-MS 3. mp (° C.) |
|---|---|---|---|
| 100-C | | | 1. 98  2. 392.2  3. 171-174 |
| 110-C | | | 1. 33  2. 382.2  3. 130-132 |
| 120-C | | | 1. 70  2. 379.2  3. 118-121 |
| 130-C | | | 1. 46  2. 457.3  3. 172-175 |

TABLE Z-30-C-continued

| Ex. Z- | Column 2 | Product | 1. Yield (%) 2. LC-MS 3. mp (° C.) |
|---|---|---|---|
| 140-C | | | 1. 34 2. 394.2 3. 121-123 |
| 150-C | | | 1. 27 2. 398.2 3. 156-158 |
| 160-C | | | 1. 42 2. 395.2 3. 168-171 |
| 170-C | | | 1. 32 2. 563.3 |

TABLE Z-30-C-continued

| Ex. Z- | Column 2 | Product | 1. Yield (%) 2. LC-MS 3. mp (° C.) |
|---|---|---|---|
| 171-C | (BOC-thiomorpholine-pyrazolopyrimidine structure) | (thiomorpholine-pyrazolopyrimidine structure) | $^1$H NMR (DMSO) δ 8.46 (s, 1H), 8.11 (s, 1H), 7.96 (s, 1H), 7.13 (s, 1H), 6.72 (s, 1H), 4.13–4.10 (m, 1H), 3.89 (s, 3H), 3.50–3.46 (m, 1H), 3.30–3.15 (m, 2H), 2.95–2.88 (m, 1H), 2.83–2.77 (m, 1H), 2.69–2.65 (m, 1H), 2.38 (s, 3H); MH$^+$ = 413. |

Examples Z180-C and Z190-C

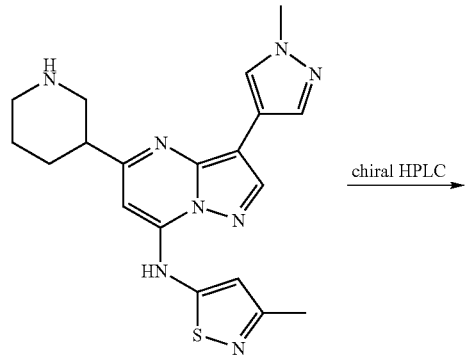

chiral HPLC →

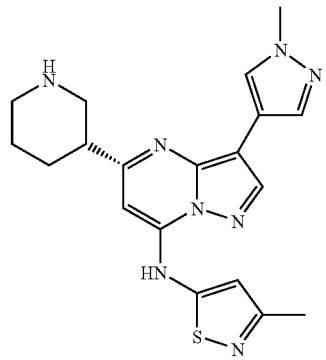

isomer 2

20 mg of Example 30-C was injected on a semipreparative Chiralcel AD column. Chromatography with mobile phase 70:30 hexane/2-propanol with 0.2% diethylamine afforded two isomers: fast eluting (isomer 1) Example Z-180-C: 7 mg, yellow solid; LC-MS: 395.2 [M+H]; purity 99% and a slower eluting (isomer 2) Example 190-C: 8 mg, yellow solid; LC-MS: 395.2 [M+H]; purity 99%.

Examples Z200-C and Z210-C

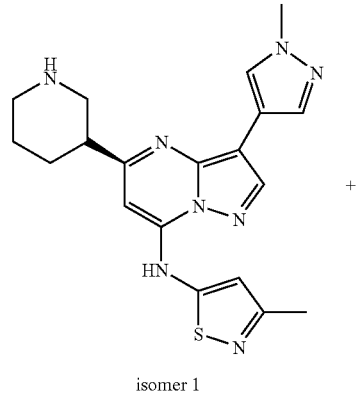

isomer 1

+

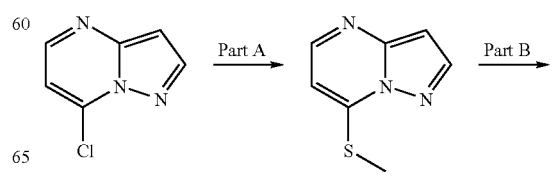

Part A → Part B →

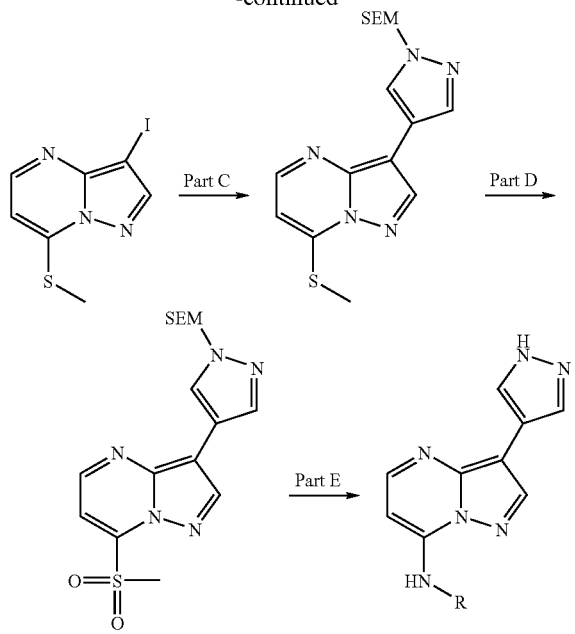

Part A

To a solution of 7-chloro-pyrazolo[1,5-a]pyrimidine (0.66 g) in DMSO (10 mL) was added sodium methanethiolate (0.45 g) in one portion. The resulting suspension was heated at 90° C. for 16 hr, allowed to cool and then was extracted with ethyl acetate (3×50 mL). The organic phase was washed with water, brine and then dried (sodium sulfate). Chromatographic purification (silica gel, 25% ethyl acetate in hexanes) afforded the title compound as a yellow orange solid (0.42 g). $^1$H-NMR (400 MHz, DMSO-$d_6$) δ 8.81 (dd, 1H), 8.08 (dd, 1H), 6.90 (d, 1H), 6.50 (dd, 1H), 2.55 (s, 3H). LCMS: MH$^+$=166.

Part B

To a solution of 7-methylsulfanyl-pyrazolo[1,5-a]pyrimidine (0.42 g, 2.54 mmol, 1.00 equiv) in acetonitrile (12 mL) at rt was added N-iodosuccinimide (0.6 g, 2.7 mmol, 1.05 equiv) in one portion. After 30 min at rt, the reaction was concentrated affording the title compound as a yellow orange solid. The product was used in the next step without purification. $^1$H-NMR (400 MHz, DMSO-$d_6$) δ 8.83 (d, 1H, J=8.0 Hz), 8.17 (s, 1H), 6.98 (d, 1H, J=8.0 Hz), 2.55 (s, 3H). LCMS: MH$^+$=292.

Part C

A mixture of 3-iodo-7-methylsulfanyl-pyrazolo[1,5-a]pyrimidine (0.21 g, 0.73 mmol, 1.00 equiv), boronate (0.31 g, 0.95 mmol, 1.3 equiv), PdCl$_2$(dppf) (0.059 g, 0.07 mmol, 10 mol %) and potassium phosphate monohydrate (0.34 g, 1.5 mmol, 2.0 equiv) in 1,2-DME (6 mL) and water (1 mL) was stirred under Argon at 100° C. for 12 hr. The mixture was allowed to cool to rt and then was partitioned between ethyl acetate and water, washed with brine and dried (sodium sulfate). Chromatographic purification (silica gel, 20% ethyl acetate in hexanes) afforded 0.2 g of the title compound. LCMS: MH$^+$=362.

Part D

To a solution of 7-methylsulfanyl-3-[1-(2-trimethylsilanyl-ethoxymethyl)-1H-pyrazol-4-yl]-pyrazolo[1,5-a]pyrimidine (0.2 g, 0.55 mmol, 1.00 equiv) in DCM (10 mL) at rt was added m-CPBA (0.25 g, 1.1 mmol, 2.0 equiv) in one portion. The resulting mixture was allowed to stir for 30 min at rt and then was concentrated. The residue was partitioned between ethyl acetate and water and the organic phase was washed with aq. sodium bicarbonate (2×), brine and dried (sodium sulfate). Concentration afforded the title compound as an orange solid that was used directly in the next step.

Part E

To a solution of isothiazole (1.15 equiv) in DMSO (2 mL) was added NaH (2.65 equiv). The resulting suspension was stirred 5 min, then sulfone (1 equiv) from Part D was added. The reaction was quenched with saturated aq. NH$_4$Cl and extracted with ethyl acetate. The crude residue was treated with 2N HCl dioxane at 50° C. for 10 min, concentrated, purified by Prep-LC and then converted to a hydrochloric salt.

By the procedures outlined in Part A-E, the compounds shown Column 2 of Table Z-40-C were prepared.

TABLE Z-40-C

| Example Z- | Column 2 | Exact mass | MS m/z (M + H) | HPLC MS $t_R$ |
|---|---|---|---|---|
| 200-C | 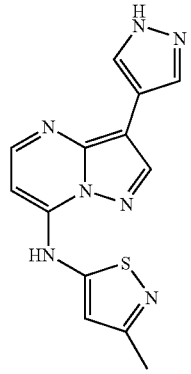 | 297.1 | 298.1 | 0.96 |
| 210-C | 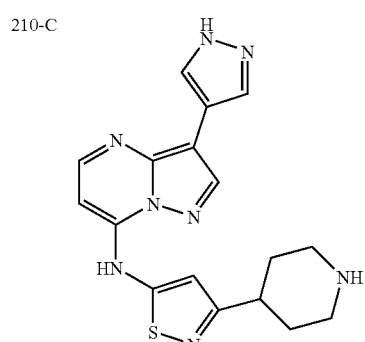 | 366.1 | 367.1 | 0.79 |

Preparative Example Z-310-C

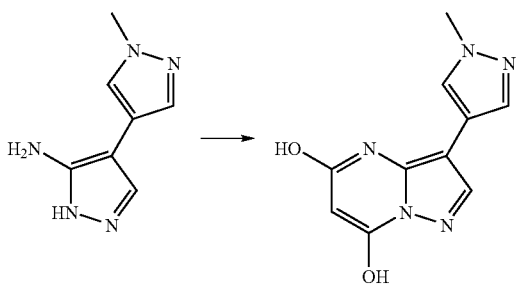

To a suspension of pyrazole from Preparative Example Z-233-C (4.0 g, 24.5 mmol, 1.00 equiv), dimethylmalonate (3.1 mL, 27.0 mmol, 1.1 equiv) in EtOH (74 mL) at rt was added 25% NaOMe in MeOH (11.2 mL). The mixture was heated at reflux overnight (16 h), allowed to cool to rt and then concentrated. The residue was dissolved in a minimum amount of water (~100 mL) and then was treated with 1N HCl until the pH was ~0.2-3. The resulting ppt was collected by filtration and dried affording the title compound as a tan solid (4.9 g, 87%). LCMS: $MH^+=232$.

Example Z-320-C

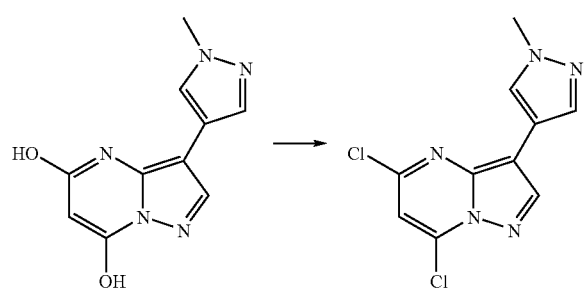

A suspension of 5,7-dihydroxypyrazolopyrimidine from Preparative Example Z-310-C (4.2 g, 18.2 mmol, 1.00 equiv), N,N-diethylaniline (9 mL) and $PCl_5$ (1.94 g, 9.32 mmol, 0.5 equiv) in $POCl_3$ (170 mL was heated at 120° C. in a sealed vessel for 20 h. After the solution was allowed to cool, volatiles were removed under reduced pressure. The residue was dissolved in DCM and then carefully added to aq. sodium bicarbonate. The organic phase was rinsed with water, brine and dried. Concentration and purification by flash chromatography (silica gel) afforded the title compound as a bright yellow solid (3.7 g, 76%). LCMS: $MH^+=268$.

Preparative Example Z-330-C

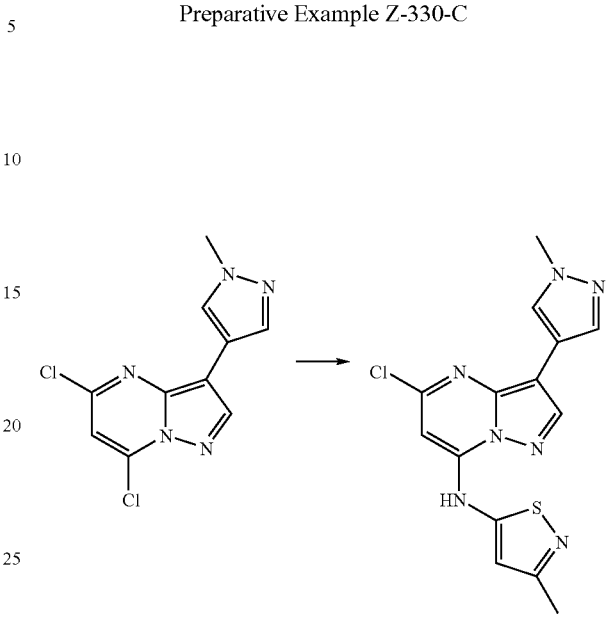

To a solution of aminoisothiazole (0.66 g, 2.0 equiv) in DMSO (30 mL) at rt was added NaH (0.29 g of 60% dispersion in oil, 2.5 equiv) in one portion. After ca. 10 min, the compound from Preparative Example Z-320-C (0.78 g, 1.00 equiv) was added in one portion. After 30 min at rt, the reaction was quenched with sat. aq. ammonium chloride and then extracted with 10% IPA/DCM (twice). The combined organic layers were washed with water, brine and dried (sodium sulfate). After concentration the residue was purified by column chromatography (silica gel, 80% EtOAc/hexane→EtOAc) to give the title compound 2 as a yellow solid 0.85 g (86%). $^1$H-NMR (400 MHz, DMSO-$d_6$) δ 11.63 (bs, 1H), 8.59 (s, 1H), 8.11 (s, 1H), 7.91 (d, 1H), 7.32 (s, 1H), 6.63 (s, 1H), 3.91 (s, 3H) and 2.41 (s, 3H). HPLC-MS $t_R$=1.64 Min ($UV_{254nm}$). Mass calculated for formula C14H12ClN7S 345.06, observed LC/MS m/z 346.0 (M+H).

Preparative Example Z-340-C

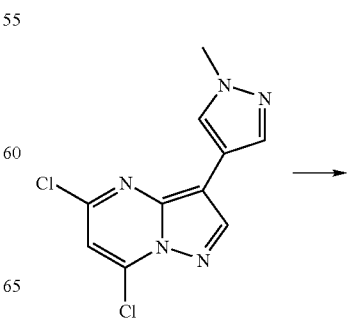

-continued

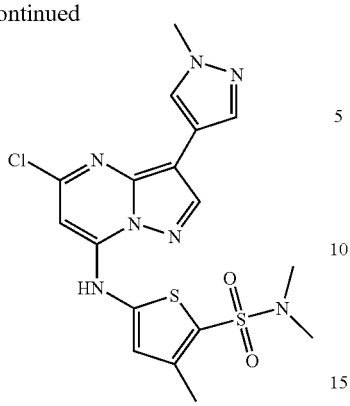

By essentially the same procedure set forth in Preparative Example Z-330-C, the compound shown above was prepared.

Example Z-220-C

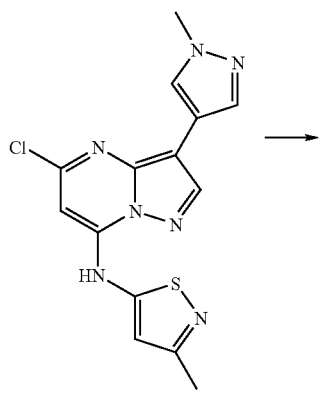

-continued

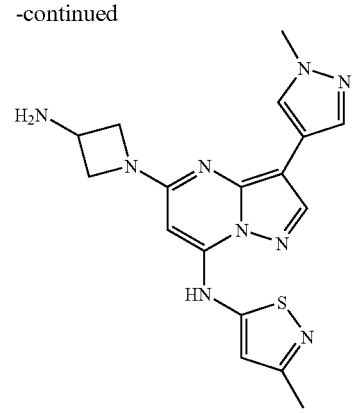

To a solution of the compound from Preparative Example Z-330-C (0.03 g, 0.087 mmol) in DMSO (1 mL) in a sealed tube vessel was added 3-aminoazetidine (3 equiv) and triethylamine (5 equiv). The tube was sealed and heated via a microwave at 125° C. for 60 min. LC-MS analysis indicated the reaction was complete. Purification by Prep-LC and conversion to a hydrochloric salt afforded compound 2. HPLC-MS $t_R$=2.58 Min ($UV_{254nm}$). Mass calculated for formula C17H19N9S 381.15, observed LC/MS m/z 382.1 (M+H).

Examples Z230-C-Z430-C

By essentially the same procedure outline in Example Z-220-C only substituting the appropriate amine, the compounds shown in Column 2 of Table Z-50-C were prepared.

TABLE Z-50-C

| Example Z- | Column 2 | Exact mass | MS m/z (M + H) | HPLC MS $t_R$ |
|---|---|---|---|---|
| 230-C | 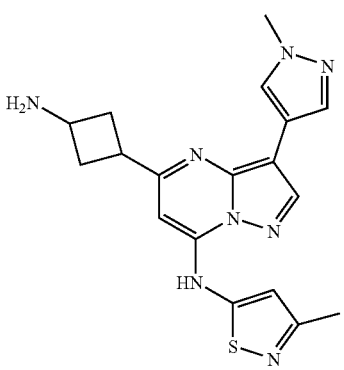 | 381.15 | 382.1 | 2.58 |

TABLE Z-50-C-continued

| Example Z- | Column 2 | Exact mass | MS m/z (M + H) | HPLC MS $t_R$ |
|---|---|---|---|---|
| 240-C | | 395.16 | 396.1 | 1.94 |
| 250-C | | 409.18 | 410.1 | 2.08 |
| 260-C | | 409.18 | 410.1 | 2.12 |
| 270-C | | 395.16 | 396.1 | 1.98 |

TABLE Z-50-C-continued

| Example Z- | Column 2 | Exact mass | MS m/z (M + H) | HPLC MS $t_R$ |
|---|---|---|---|---|
| 280-C | | 424.18 | 425.2 | 3.72 |
| 290-C | | 410.16 | 411.1 | 3.21 |
| 300-C | | 409.18 | 410.2 | 2.75 |
| 310-C | | 407.16 | 408.1 | 2.67 |

TABLE Z-50-C-continued

| Example Z- | Column 2 | Exact mass | MS m/z (M + H) | HPLC MS $t_R$ |
|---|---|---|---|---|
| 320-C | | 395.16 | 396.1 | 2.62 |
| 330-C | | 423.2 | 424.1 | 3.31 |
| 340-C | | 423.2 | 424.1 | 2.85 |
| 350-C | | 423.2 | 424.1 | 2.92 |

TABLE Z-50-C-continued

| Example Z- | Column 2 | Exact mass | MS m/z (M + H) | HPLC MS $t_R$ |
|---|---|---|---|---|
| 360-C | | 395.16 | 396.1 | 2.62 |
| 370-C | | 439.19 | 440.2 | 2.76 |
| 380-C | | 515.19 | 516.1 | 3.38 |

TABLE Z-50-C-continued

| Example Z- | Column 2 | Exact mass | MS m/z (M + H) | HPLC MS t_R |
|---|---|---|---|---|
| 390-C | | 487.16 | 488.2 | 3.06 |
| 400-C | | 501.17 | 502.1 | 3.48 |
| 410-C | | 515.19 | 516.1 | 3.68 |

TABLE Z-50-C-continued
| Example Z- | Column 2 | Exact mass | MS m/z (M + H) | HPLC MS $t_R$ |
|---|---|---|---|---|
| 420-C | | 513.17 | 514.2 | 3.27 |
| 430-C | | 412.13 | 413.0 | 3.12 |
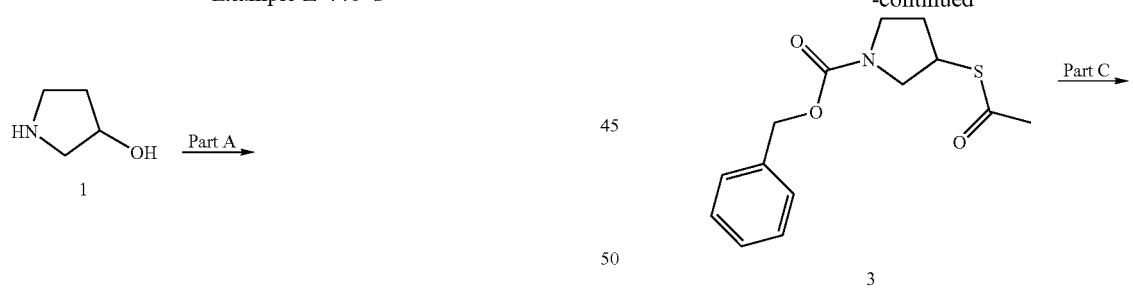
Example Z-440-C
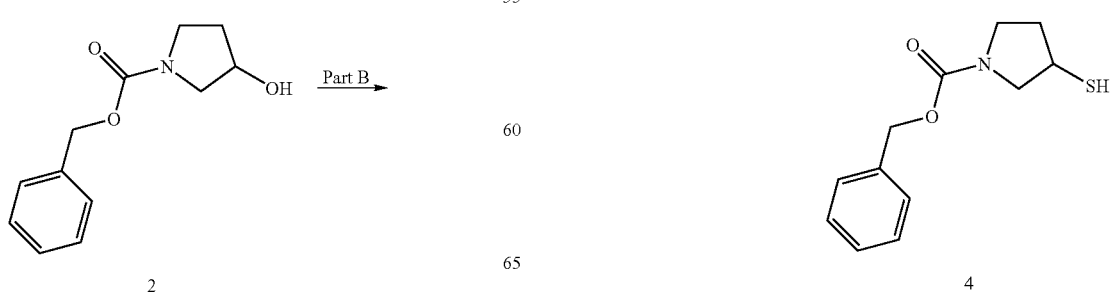

-continued

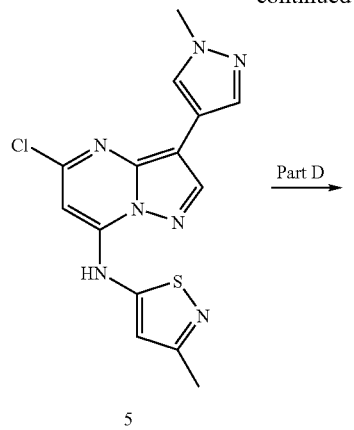

5

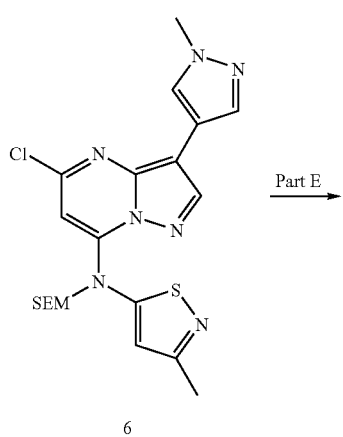

6

7

-continued

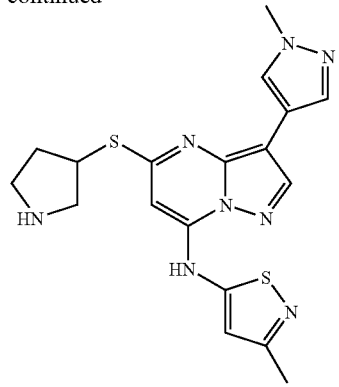

8

Part A:
To compound 1 (2.1 g, 24.1 mmol) in DCM (150 mL) was added triethylamine (1.2 equiv). The resulting solution was cooled to 0° C. (ice-bath) and stirred at 0° C. for 10 min, then added benzyl chloroformate (1.2 equiv). The reaction mixture was stirred at 0° C. for 60 min at which time LC-MS analysis indicate that the reaction was complete. After concentration the residue was purified by column chromatography (SiO$_2$, 60% ethyl acetate/hexanes) afforded compound 2 as a clear oil 4.0 g (75%).

Part B:
A solution of compound 2 (1 g, 4.52 mmol) and triphenyphosphine (1.1 equiv) in anh. THF (30 mL) was treated at 0° C. with diisopropyl azodicarboxylate (1.1 equiv) for 10 min, thioacetic acid (1.1 equiv) was added and the reaction mixture allowed to slowly warm to rt. The reaction mixture was stirred at rt overnight. After concentration the residue was purified by column chromatography (SiO$_2$, 40% ethyl acetate/hexanes) afforded compound 3 as a clear oil 1.2 g (95%).

Part C:
A solution of compound 3 (1.2 g, 4.26 mmol) in methanol (30 mL) was treated with potassium carbonate (1.2 equiv). The resulting solution was stirred at rt for 16 h, at which time LC-MS analysis indicated that the reaction was complete. After concentration the residue was purified by column chromatography (SiO$_2$, 40% ethyl acetate/hexanes) afforded compound 4 as a clear oil 0.26 g (26%).

Part D:
Compound 5 was synthesized via the synthetic method described in Preparative example 3 (Part A).
To compound 5 (0.29 g, 0.84 mmol) in dichloroethane (10 mL) was added DIEA (1.2 equiv) at rt. The resulting solution was stirred at rt for 10 min, and then added 2-(trimethylsilyl)-ethoxymethyl chloride (1.2 equiv). The resulting mixture was stirred at rt for 4 h at which time LC-MS analysis indicated the reaction was complete. After concentration the residue was purified by column chromatography (SiO$_2$, 80% ethyl acetate/hexanes) afforded compound 6 as an orange oil 0.17 g (43%).

Part E:
A mixture of compound 7 (35 mgs, 0.074 mmol, 1 equivalent), compound 4 (1.4 equivalent), PdCl$_2$(dppf) (0.07 equiv), sodium t-butoxide (1.1 equiv) in 1,2-dimethoxyethane (1 ml) was stirred at 85 C under Ar for 16 h. The reaction mixture was cooled to rt, filtered through celite and the filtrate concentrated. The residue was taken back up in ethyl acetate and washed with water, brine, dried over anhydrous sodium sulfate and concentrated to afford crude compound 7, which was used in the next step directly without further purification.

Part F:

To a solution of compound 7 in THF (2 mL) was added 4N HCl in dioxane (2 mL) at rt. The resulting solution was heated at 60° C. for 60 min at which time LC-MS analysis indicated the reaction was complete. The mixture was cooled to 25° C. and concentrated. Purification by Prep-LC and conversion to a hydrochloric salt afforded compound 8, Example 440-C. HPLC-MS $t_R$=3.10 Min (UV$_{254nm}$). Mass calculated for formula C18H20N8S2 412.13, observed LC/MS m/z 413.0 (M+H).

Preparative Example Z-631-C

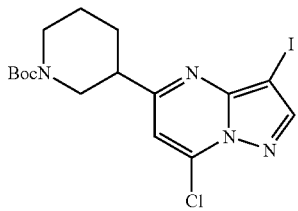

By essentially same procedure set forth in Preparative Example Z-60-C, using N-iodosuccinimide instead of N-bromosuccinimide, the title compound was prepared.

Preparative Example Z-641-C

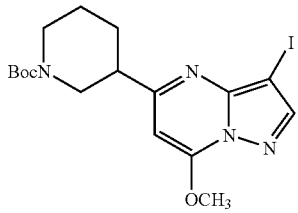

By essentially same procedure set forth in Preparative Example Z-80-C, starting from the compound from Preparative Example Z-631-C, the title compound was prepared.

Preparative Example Z-645-C

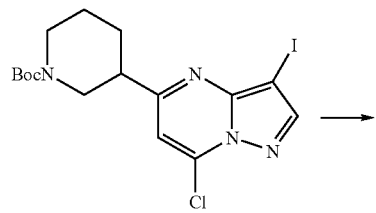

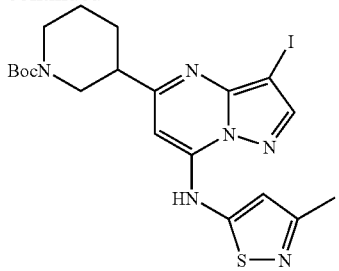

A mixture of the product from Preparative Example Z-631-C (2.40 g, 5.20 mmol), 5-amino-3-methylisothiazole hydrochloride (1.01 g, 6.70 mmol) and K$_2$CO$_3$ (2.15 g, 15.60 mmol) in anhydrous CH$_3$CN (30 mL) was stirred and refluxed under N$_2$ for 72 hr. CH$_2$Cl$_2$ (200 mL) was then added, the mixture was filtered through Celite, the solvent was evaporated, and the residue was purified by column chromatography on silica gel with 10:1 CH$_2$Cl$_2$/EtOAc as eluent. Canary yellow solid (580 mg, 21%) was obtained. LC-MS: 541 [M+H].

Preparative Example Z-646-C

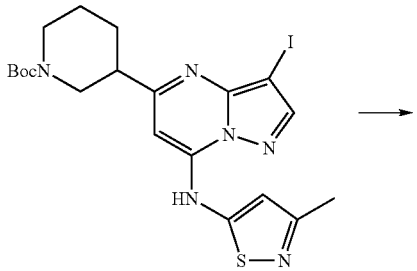

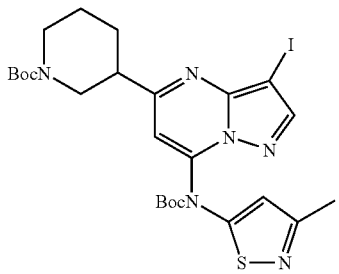

Boc$_2$O (305 mg, 1.40 mmol) was added to a stirred solution of the product from Preparative Example Z-645-C (580 mg, 1.07 mmol) and 4-dimethylamino pyridine (146 mg, 1.20 mmol) in anhydrous CH$_2$Cl$_2$ (10 mL). The mixture was stirred at 25° C. for 2 hr, then it was poured into saturated aqueous NaHCO$_3$ solution (60 mL), extracted with CH$_2$Cl$_2$ (3×10 mL), dried over Na$_2$SO$_4$, and filtered. The solvents were evaporated and the residue was purified by column Preparative Example Z-647-C

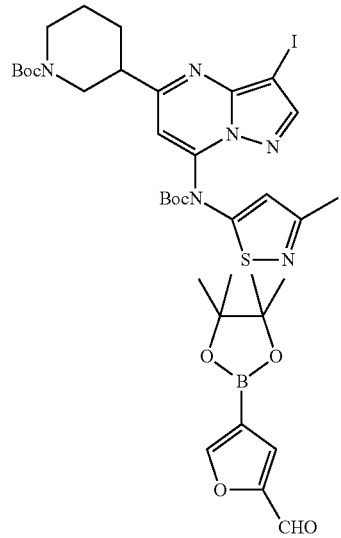

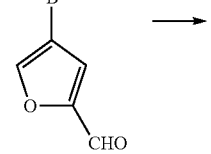

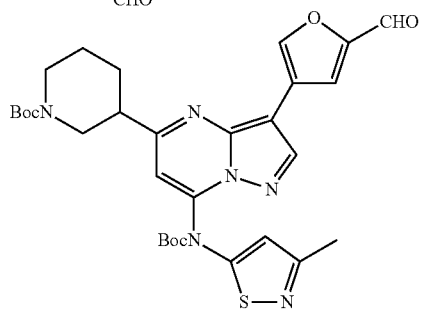

A mixture of the product from Preparative Example Z-646-C (400 mg, 0.63 mmol), the boronate (208 mg, 0.94 mmol), PdCl₂dppf.CH₂Cl₂ (49 mg, 0.06 mmol), and K₃PO₄ (530 mg, 2.50 mmol) in 1,2-dimethoxyethane (10 mL) and H₂O (2 mL) was stirred and refluxed under N₂ for 2 hr. The solvents were evaporated and the residue was purified by column chromatography on silica gel with 2:1 hexane/EtOAc as eluent. Pale yellow solid (42 mg, 11%) was obtained. LC-MS: 609 [M+H].

Preparative Example Z-648-C

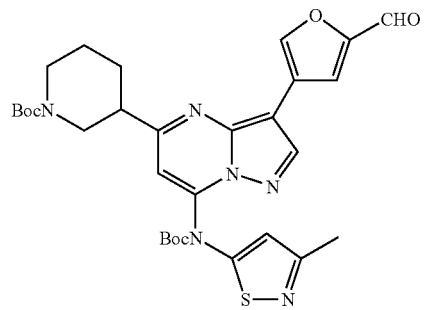

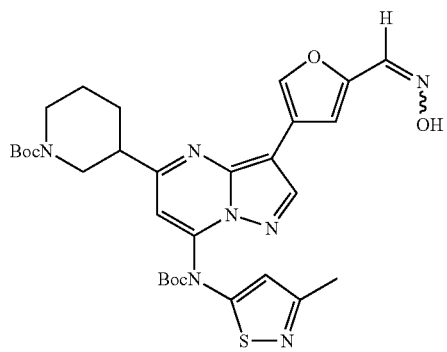

A mixture of the product from Preparative Example Z-647-C (42 mg, 0.069 mmol), NH₂OH.HCl (7 mg, 0.10 mmol), and triethylamine (0.2 mL) in CH₂Cl₂ (1 mL) and MeOH (1 mL) was stirred in a closed flask at 25° C. for 4 hr. The solvent was evaporated and the residue was chromatographed on silica gel with 2:1 hexane/EtOAc as eluent. Yellow solid (30 mg, 70%) was obtained.

Preparative Example Z-650-C

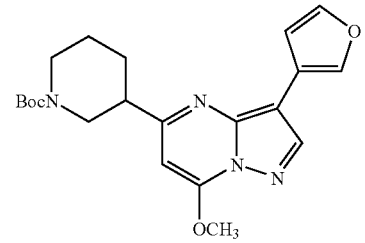

A mixture of the product from Preparative Example Z-641-C (300 mg, 0.66 mmol), 3-furylboronic acid (110 mg, 0.98 mmol), PdCl₂dppf.CH₂Cl₂ (54 mg, 0.06 mmol), and K₃PO₄ (560 mg, 2.64 mmol) in 1,2-dimethoxyethane (10 mL) and H₂O (2 mL) was stirred and refluxed under N₂ for 5 hr. The solvents were evaporated and the residue was purified by column chromatography on silica gel with 25:1 CH₂Cl₂/MeOH as eluent. Pale yellow solid (175 mg, 67%) was obtained. LC-MS: 399 [M+H].

Preparative Examples Z651-C-Z652-C

By essentially same procedure set forth in Preparative Example Z-650-C, only using different boron reagents given in Column 1 for the Suzuki couplings with the intermediate from preparative Example Z-641-C, compounds given in Column 2 of Table Z-100-C were prepared.

TABLE Z-100-C

| Prep. Ex. Z- | Column 1 | Column 2 | Data |
|---|---|---|---|
| 651-C | | | LCMS: MH⁺ = 435 |
| 652-C | | | LCMS: MH⁺ = 427 |

Preparative Example Z-655-C

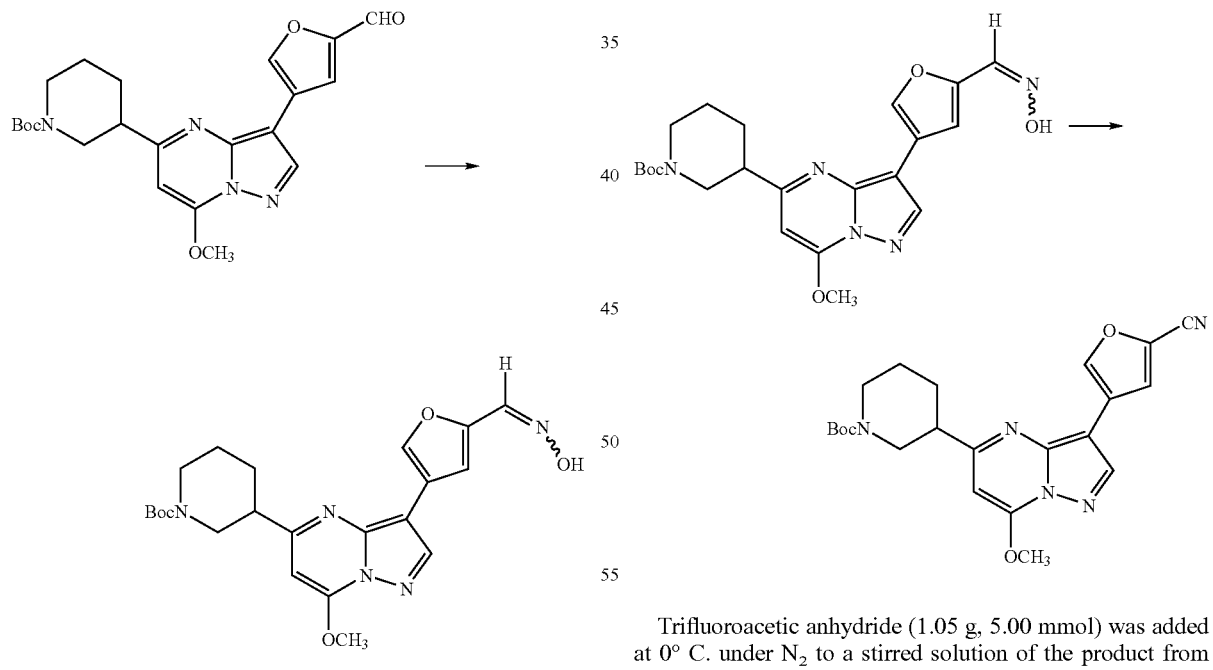

Preparative Example Z-656-C

A mixture of the product from Preparative Example Z-652-C (3.82 g, 9.00 mmol), NH₂OH.HCl (750 mg, 10.76 mmol), and triethylamine (4.0 mL) in CH₂Cl₂ (30 mL) and MeOH (30 mL) was stirred in a closed flask at 25° C. for 3 hr. The solvent was evaporated and the residue was chromatographed on silica gel with 20:1 CH₂Cl₂/MeOH as eluent. Slightly yellow solid (2.20 g, 56%) was obtained. LC-MS: 442 [M+H].

Trifluoroacetic anhydride (1.05 g, 5.00 mmol) was added at 0° C. under N₂ to a stirred solution of the product from Preparative Example Z-655-C (2.20 g, 5.00 mmol) in anhydrous CH₂Cl₂ (30 mL) and triethylamine (4 mL). The mixture was stirred for 2 hr, then it was poured into saturated aqueous NaHCO₃ solution (200 mL), extracted with CH₂Cl₂ (3×40 mL), dried over Na₂SO₄, and filtered. The solvents were evaporated and the residue was purified by column chromatography on silica gel with 50:1 CH₂Cl₂/MeOH as eluent. Slightly yellow solid (1.66 g, 79%) was obtained. LC-MS: 424 [M+H].

Preparative Example Z-660-C

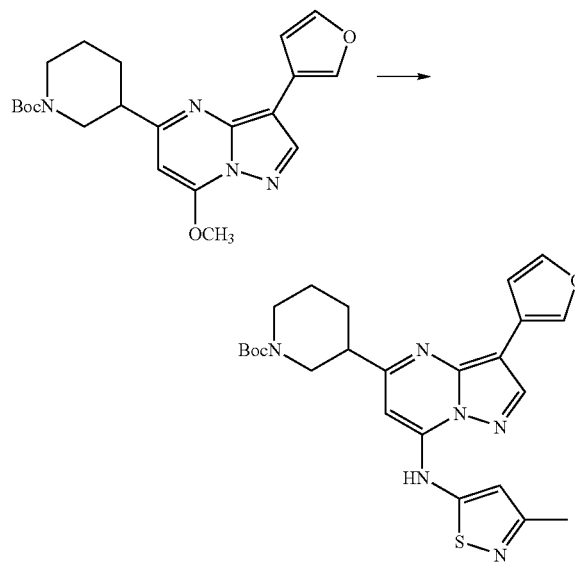

Anhydrous DMSO (2 mL) was added under $N_2$ to a mixture of 5-amino-3-methylisothiazole hydrochloride (58 mg, 0.38 mmol) and 60% NaH (30 mg, 0.76 mmol). The mixture was stirred at 25° C. for 0.5 hr, then a solution of the product from Preparative Example Z-650-C (170 mg, 0.42 mmol) was added and the resulting mixture was stirred at 25° C. for 18 hr. The mixture was poured into brine (100 mL), extracted with 10:1 EtOAc/$CH_2Cl_2$ mixture (3×30 mL), washed with brine (2×50 mL), dried over $Na_2SO_4$, and filtered. The solvents were evaporated and the residue was purified by column chromatography on silica gel with 20:1 $CH_2Cl_2$/MeOH as eluent. Yellow solid (74 mg, 48%) was obtained. LC-MS: 481 [M+H].

Preparative Example Z661-C and Z662-C

By essentially same procedure set forth in Preparative Example Z-660-C, only using different starting materials given in Column 1, compounds given in Column 2 of Table Z-110-C were prepared.

TABLE Z-110-C

| Prep. Ex. Z- | Column 1 | Column 2 | Data |
|---|---|---|---|
| 661-C | (structure) | (structure) | LCMS: $MH^+ = 517$ |
| 662-C | (structure) | (structure) | LCMS: $MH^+ = 506$ |

Example Z-500-C

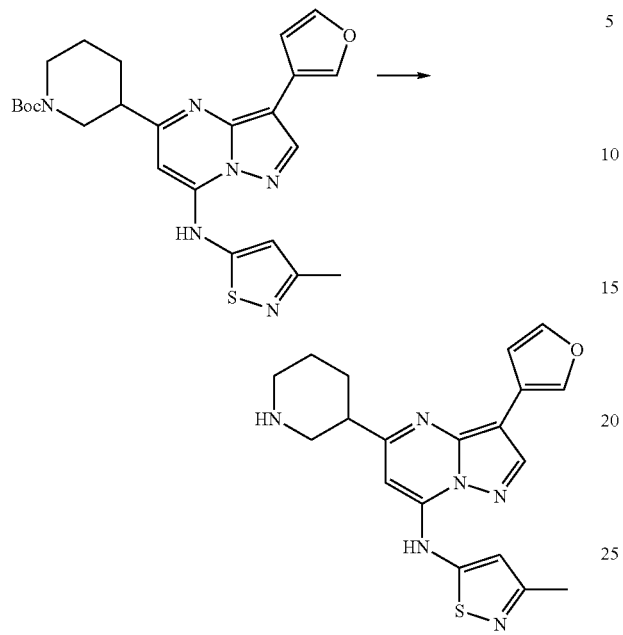

A mixture of the product from Preparative Example Z-660-C (74 mg) in TFA (21 mL) and H$_2$O (2 mL) was stirred at 25° C. under N$_2$ for 5 hr. The solvents were evaporated, to the residue was added NaHCO$_3$ (200 mg) and 6:1 CH$_2$Cl$_2$/MeOH (1 mL), and the mixture was stirred at 25° C. under N$_2$ for 0.5 hr. The mixture was loaded onto a column and was purified by column chromatography on silica gel with 4:1 CH$_2$Cl$_2$/7N NH$_3$ in MeOH as eluent. Pale yellow solid (30 mg, 51%) was obtained. LC-MS: 381 [M+H]. Mp=115-118° C.

Example Z510-C-Z530-C

By essentially same procedure set forth in Example Z-500-C, only using different starting materials given in Column 1, compounds given in Column 2 of Table Z-120-C were prepared.

TABLE Z-120-C

| Ex. Z- | Column 1 | Column 2 | Data |
|---|---|---|---|
| 510-C | 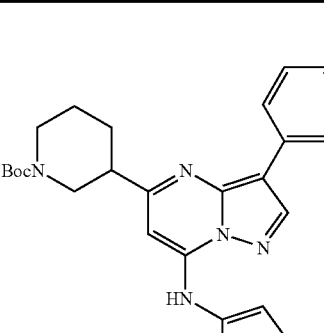 | 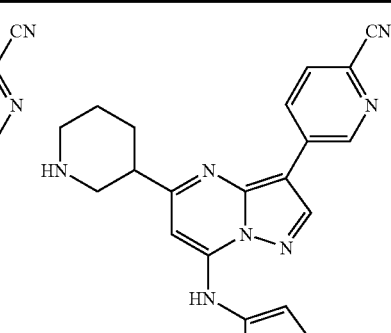 | LCMS: MH$^+$ = 417 wax |
| 520-C | | | LCMS: MH$^+$ = 406 waxy solid |

TABLE Z-120-C-continued

| Ex. Z- | Column 1 | Column 2 | Data |
|---|---|---|---|
| 530-C | 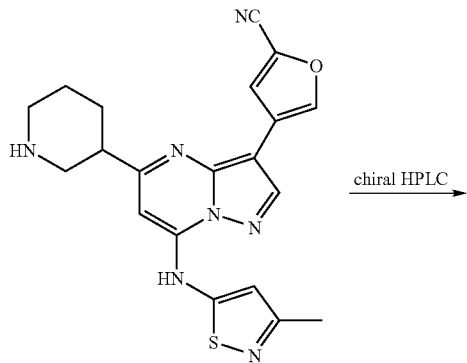 | 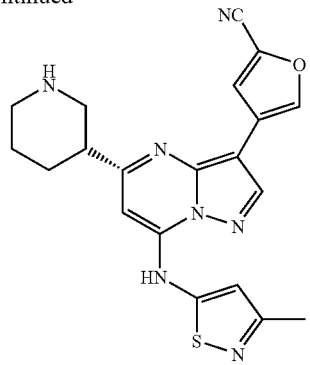 | LCMS: MH+ = 424 waxy solid |

Example Z540-C and Z550-C

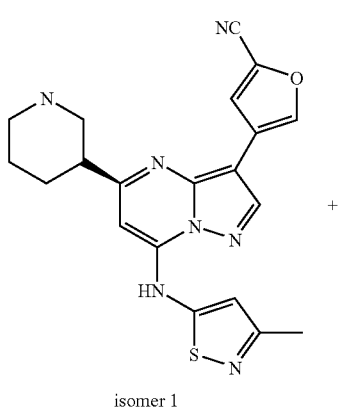

isomer 1 chiral HPLC ⟶ isomer 2

20 mg of the product from Example Z-520-C was dissolved in warm 2-propanol (3 mL), the solution was allowed to cool to 25° C., hexane (1 mL) was added, the solution was filtered and the filtrate was injected on a semipreparative Chiralcel AD column. Chromatography with mobile phase 75:25 hexane/2-propanol with 0.2% diethylamine afforded two isomers: fast eluting (isomer 1): 5 mg, pale yellow solid; LC-MS: 406 [M+H]; Mp=188-190° C. and slow eluting (isomer 2): 5 mg, pale yellow solid; LC-MS: 406 [M+H]; Mp=187-190° C.

Assays:

CHK1 SPA Assay

An in vitro assay was developed that utilizes recombinant His-CHK1 expressed in the baculovirus expression system as an enzyme source and a biotinylated peptide based on CDC25C as substrate (biotin-RSGLYRSPSMPENLNRPR).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 µg/mL, stored at −80° C.
3) D-PBS (without CaCl and MgCl): GIBCO, Cat.#14190-144
4) SPA beads: Amersham, Cat.#SPQ0032: 500 mg/vial Add 10 mls of D-PBS to 500 mg of SPA beads to make a working concentration of 50 mg/ml. Store at 4° C. Use within 2 week after hydration.

5) 96-Well White Microplate with Bonded GF/B filter: Packard, Cat.#6005177

6) Top seal-A 96 well Adhesive Film: Perkin Elmer, Cat.#6005185

7) 96-well Non-Binding White Polystyrene Plate: Corning, Cat. #6005177

8) $MgCl_2$: Sigma, Cat.#M-8266

9) DTT: Promega, Cat.#V3155

10) ATP, stored at 4° C.: Sigma, Cat.#A-5394

11) $\gamma^{33}$P-ATP, 1000-3000 Ci/mMol: Amersham, Cat.#AH9968

12) NaCl: Fisher Scientific, Cat.#BP358-212

13) $H_3PO_4$ 85% Fisher, Cat.#A242-500

14) Tris-HCL pH 8.0: Bio-Whittaker, Cat. #16-015V

15) Staurosporine, 100 µg: CALBIOCHEM, Cat. #569397

16) Hypure Cell Culture Grade Water, 500 mL: HyClone, Cat.#SH30529.02

Reaction Mixtures:

1) Kinase Buffer: 50 mM Tris pH 8.0; 10 mM $MgCl_2$; 1 mM DTT

2) His-CHK1, In House Lot P976, MW ~30 KDa, stored at −80° C.

6 nM is required to yield positive controls of ~5,000 CPM. For 1 plate (100 rxn): dilute 8 µL of 235 µg/mL (7.83 µM) stock in 2 mL Kinase Buffer. This makes a 31 nM mixture. Add 20 µL/well. This makes a final reaction concentration of 6 nM.

3) CDC25C Biotinylated peptide.

Dilute CDC25C to 1 mg/mL (385 µM) stock and store at −20° C. For 1 plate (100 rxn): dilute 10 µL of 1 mg/mL peptide stock in 2 ml Kinase Buffer. This gives a 1.925 µM mix. Add 20 µL/rxn. This makes a final reaction concentration of 385 nM.

4) ATP Mix.

For 1 plate (100 rxn): dilute 10 µL of 1 mM ATP (cold) stock and 2 µL fresh P33-ATP (20 uCi) in 5 ml Kinase Buffer. This gives a 2 µM ATP (cold) solution; add 50 µl/well to start the reaction. Final volume is 100 µl/rxn so the final reaction concentrations will be 1 µM ATP (cold) and 0.2 µCi/rxn.

5) Stop Solution:

For 1 plate add: To 10 mL Wash Buffer 2 (2M NaCl 1% $H_3PO_4$): 1 mL SPA bead slurry (50 mg); Add 100 µL/well 6) Wash buffer 1: 2 M NaCl 7) Wash buffer 2: 2 M NaCl, 1% $H_3PO_4$ Assay Procedure:

| Assay Component | Final Concentration | Volume |
|---|---|---|
| CHK1 | 6 nM | 20 µl/rxn |
| Compound (10% DMSO) | — | 10 µl/rxn |
| CDC25C | 0.385 µM | 20 µl/rxn |
| $\gamma^{33}$P-ATP | 0.2 µCi/rxn | 50 µl/rxn |
| Cold ATP | 1 µM | |
| Stop solution SPA beads | 0.5 mg/rxn | 100 µl/rxn* |
| | | 200 µl/rxn** |

*Total reaction volume for assay.
**Final reaction volume at termination of reaction (after addition of stop solution).

1) Dilute compounds to desired concentrations in water/10% DMSO - this will give a final DMSO concentration of 1% in the rxn. Dispense 10 µl/rxn to appropriate wells. Add 10 µL 10% DMSO to positive (CHK1 + CDC25C + ATP) and negative (CHK1 + ATP only) control wells.
2) Thaw enzyme on ice -- dilute enzyme to proper concentration in kinase buffer (see Reaction Mixtures) and dispense 20 µl to each well.
3) Thaw the Biotinylated substrate on ice and dilute in kinase buffer (see Reaction Mixtures). Add 20 µl/well except to negative control wells. Instead, add 20 µL Kinase Buffer to these wells.
4) Dilute ATP (cold) and P33-ATP in kinase buffer (see Reaction Mixtures). Add 50 µL/well to start the reaction.
5) Allow the reaction to run for 2 hours at room temperature.
6) Stop reaction by adding 100 µL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 ml each wash; 1X with 2M NaCl; 1X with 2M NaCl/1% $H_3PO_4$
11) Allow filter plate to dry 15 min.
12) Put TopSeal-A adhesive on top of filter plate.
13) Run filter plate in Top Count
Settings: Data mode: CPM
Radio nuclide: Manual SPA: P33
Scintillator: Liq/plast
Energy Range: Low $IC_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

The $IC_{50}$ values for a non-limiting list of illustrative compounds useful in the methods of the present invention determined according to the above method are shown earlier. Several compounds useful in the present invention exhibited not only excellent Checkpoint kinase (e.g., CHK-1) inhibitory activity but also surprisingly high ratio of Checkpoint kinase (e.g., CHK-1) inhibition versus cyclin dependent kinase (such as, for example CDK1 or CDK2) inhibition showing a high selectivity in targeting the kinase. Thus, for example, several compounds exhibited CHK-1 inhibition at least five-fold (five times) their respective CDK (e.g. CDK2) inhibition. Several compounds exhibited CHK-1 inhibition at least ten-fold their respective CDK (e.g. CDK2) inhibition. Several compounds exhibited CHK-1 inhibition at least fifty-fold their respective CDK (e.g. CDK2) inhibition. Certain pyrazolopyrimidines compounds exhibited CHK-1 inhibition at least five-fold their respective CDK (e.g. CDK2) inhibition. Certain pyrazolopyrimidines exhibited CHK-1 inhibition at least ten-fold their respective CDK (e.g. CDK2) inhibition. Certain pyrazolopyrimidine compounds exhibited CHK-1 inhibition at least fifty-fold their respective CDK (e.g. CDK2) inhibition. The CDK (e.g., CDK1 and CDK2) activities of the various compounds useful in the methods of the present invention are disclosed in the afore-mentioned published and co-pending patent applications, including, for example, U.S. application Nos. 11/542,921 and 11/542,920 that are incorporated by reference thereto. One skilled in the art would find such high selectivities desirable under certain circumstances.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

Therefore, we claim:

1. A method of inhibiting a Checkpoint kinase in a patient, comprising administering to the patient a therapeutically effective amount of a compound of formula:

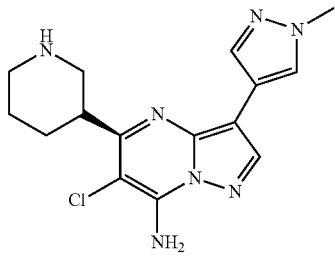

or a pharmaceutically acceptable salt thereof.

2. A method of inhibiting a Checkpoint kinase in a patient, comprising administering to the patient a therapeutically effective amount of a compound of formula:

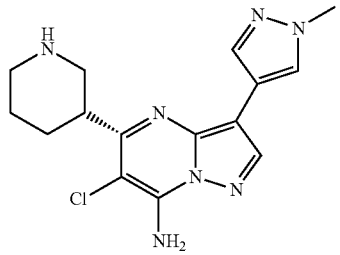

or a pharmaceutically acceptable salt thereof.

* * * * *